(12) United States Patent
Kakiuchi et al.

(10) Patent No.: US 8,030,438 B2
(45) Date of Patent: Oct. 4, 2011

(54) THIOPHENE COMPOUND HAVING PHOSPHORIC ESTER AND PROCESS FOR PRODUCING THE SAME

(75) Inventors: Nobuyuki Kakiuchi, Funabashi (JP); Hitoshi Furusho, Funabashi (JP); Naoki Otani, Funabashi (JP); Tohru Minami, Munakata (JP); Tatsuo Okauchi, Kitakyusyu (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 649 days.

(21) Appl. No.: 11/919,552

(22) PCT Filed: May 16, 2006

(86) PCT No.: PCT/JP2006/309692
§ 371 (c)(1),
(2), (4) Date: Mar. 21, 2008

(87) PCT Pub. No.: WO2006/109895
PCT Pub. Date: Oct. 19, 2006

(65) Prior Publication Data
US 2010/0019229 A1    Jan. 28, 2010

(30) Foreign Application Priority Data

May 19, 2005  (JP) ................................ 2005-146882
Apr. 14, 2006  (JP) ................................ 2006-112179

(51) Int. Cl.
C08G 75/00    (2006.01)
(52) U.S. Cl. .......... 528/377; 528/380; 528/373; 257/40; 257/E51.027; 205/419; 549/6
(58) Field of Classification Search .................. 528/377, 528/380, 373; 257/40, E51.027; 205/49; 549/6
See application file for complete search history.

(56) References Cited

U.S. PATENT DOCUMENTS

| | | | |
|---|---|---|---|
| 4,356,429 A | 10/1982 | Tang | |
| 5,720,903 A | 2/1998 | Wessling et al. | |
| 2002/0077450 A1 | 6/2002 | Kirchmeyer et al. | |
| 2003/0171531 A1 | 9/2003 | Ong et al. | |
| 2005/0209388 A1* | 9/2005 | Hsu et al. ...................... | 524/457 |
| 2007/0088149 A1 | 4/2007 | Ong et al. | |

FOREIGN PATENT DOCUMENTS

| | | |
|---|---|---|
| JP | 2002-206022 A | 7/2002 |
| JP | 2003-221434 A | 8/2003 |
| WO | WO 03/074169 A2 | 9/2003 |
| WO | WO 2004/058740 A1 | 7/2004 |

OTHER PUBLICATIONS

R. H. Partridge, *Polymer*, 1983, vol. 24, pp. 748-754.

S. Hayashi et al., *Japanese Journal of Applied Physics*, 1986, vol. 25, No. 9, pp. L773-L775.
C. W. Tang et al., *Applied Physics Letters*, 1987, vol. 51, No. 12, pp. 913-915.
Electrochemistry and Industrial Physicochemistry, 1986, vol. 54, pp. 306-311 (with English abstract).
S. Tanaka et al., *Synthetic Metals*, U.S.A. 1995, vol. 69, pp. 599-600.
M. Karikomi et al., *Journal of the American Chemical Society*, 1995, vol. 117, No. 25, pp. 6791-6792.
NEDO Book Archive, Report of the Results of Studies and Developments of Conductive Polymer Materials, Mar. 1988, pp. 218-251 (with English translation).
K. Takabashi, Heterocycles, 1996, vol. 43, No. 9, pp. 1927-1935.
Y. Goldberg et al., *J. Org. Chem.*, 1993, vol. 58, pp. 3072-3075.
M. Sainsbury, *Tetrahedron*, 1980, vol. 36, pp. 3327-3359.
Bachman, Werner E and Roger A. Hoffman, Organic Reactions vol. II, Chapter 6, New York, John Wiley & Sons, Inc. 1944.
Heck, Richard F., Organic Reactions vol. 27, Chapter 2, New York, John Wiley & Sons, Inc. 1982.
K. Sonogashira et al., *Tetrahedron Letters*, 1975, No. 50, pp. 4467-4470.
M. Kumada et al., *Organic Syntheses, Coll.*, vol. 6, pp. 407 (1988), vol. 58, p. 127 (1978).
G. M. Kosolapoff et al., Journal of Chemical Society, 1959, vol. 73, pp. 3950-3953.
P. C. Crofts et al., Journal of American Chemical Society, 1953, pp. 3379-3383.
Fild, Manfred and Reinhard Schmutzler, Organic Phosphorus Compounds vol. 4, Chapter 9, New York, Wiley Interscience,1972.
Crofts, P. C., Organic Phosphorus Compounds vol. 6, Chapter 14, New York, Wiley Interscience, 1973.
Worms, K. H. and M. Schmidt-Dunker, Organic Phosphorus Compounds vol. 7, Chapter 189, New York, Wiley Interscience,1976.
Y. Hatanaka et al., *Tetrahedron*, 1994, vol. 50, No. 28, pp. 8301-8316.

(Continued)

*Primary Examiner* — Randy Gulakowski
*Assistant Examiner* — Shane Fang
(74) *Attorney, Agent, or Firm* — Birch, Stewart, Kolasch & Birch, LLP

(57) ABSTRACT

A thiophene compound having a phosphate group, for example, one represented by the formula [1]. The compound has high resistance to heat and oxidation and can be improved in solubility or dispersibility in various solvents.

[1]

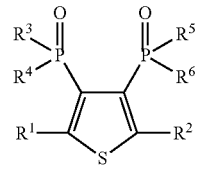

(In the formula, $R^1$ and $R^2$ each independently represents, e.g., hydrogen, halogeno, cyano, or phenyl optionally substituted by W; and $R^3$ to $R^6$ each independently represents —$OR^7$, $SR^8$, or —$NR^9{}_2$, provided that $R^7$ to $R^9$ each independently represents hydrogen, $C_{1-10}$ alkyl, or phenyl optionally substituted by W and W represents halogeno, cyano, nitro, hydroxyl, mercapto, amino, formyl, carboxy, $C_{1-10}$ alkyl, etc.)

25 Claims, No Drawings

OTHER PUBLICATIONS

J. K. Stille et al., *Organic Syntheses Coll.*, vol. 9, p. 553 (1998), vol. 71, p. 97 (1993).

Beckmann et a., "31P-13C Shift Correlated 2D NMR Spectra of the AA'X Spin System: Determination of P-P Coupling Constants and Tehir Relative Signs in Symmetrical Diphosphonates," Magnetic Resonance in Chemistry, vol. 30, No. 9, 1992, pp. 860-864, XP002588895.

EP 06 74 6406; European Search Report, Aug. 5, 2010, 11 pages.

Erker et al., "Synthesis of Nitrated Thienylphosphonates via Michaelis-Arbuzov-Type Rearrangement," Synthesis, No. 5, Feb. 19, 2004, pp. 668-670, XP002588896.

Kielbasinski et al., "Asymmetric synthesis of alpha-sulfinyphosphonates in the thiolane series," Tetrahedron: Asymmetry vol. 16, 2005, pp. 651-655., XP002588897.

Kruglov et al., "Synthesis of Symmetrical and Mixed Diphophonic Esters," Journal of General Chemistry USSR, vol. 43, No. 7, Jul. 1973, pp. 1470-1478, XP008087621.

McCullough, "The Chemistry of Conducting Polythiopenes," Advanced Materials, Wiley VCH Verlang, vol. 10, No. 2, Jan. 22, 1998, pp. 93-116, XP000727852.

Pollok et al., "2,3-Bis(Diphenylphosphinyl)-1,3-Butadiene Via A Double [2,3]-Sigmatropic Rearrangement. A Reinvestigation of the Reaction of 2-Butyne-1, 4-Diol with Chlorodiphenylphosphine," Tetrahedron Letters, vol. 28, No. 10, pp. 1085-1088, 1987, XP002588894.

Pudovik et al., "Acetylene-Allene-Diene Rearrangements of Diphosphites with a Beta Gamma-Acetylene Linkage in a Common Ester Radical," J. Gen. Chem. USSR, vol. 33, 1963, pp. 702, XP009135188.

Gerbier, Philippe et al., Journal of Materials Chemistry, 1999, 9(10), pp. 2559-2565.

Huche, Michel et al., Tetrahedron Letters, 1973, (44), pp. 4291-4242.

Benincori, Tiziana et al., Journal of Organic Chemistry, 2005, 70 (14), pp. 5436-5441.

* cited by examiner

THIOPHENE COMPOUND HAVING PHOSPHORIC ESTER AND PROCESS FOR PRODUCING THE SAME

TECHNICAL FIELD

This invention relates to a thiophene compound having a phosphoric ester and a process for producing the same and more particularly, to thiophene monomers, oligomers and polymers each having a phosphoric ester and also to processes for producing the same.

BACKGROUND ART

In recent years, aromatic compounds and heterocyclic compounds having a π-conjugated system have been utilized in various types of electronic devices such as organic electroluminescent devices, cells, semiconductors and the like by use of their emission characteristic and electron or hole transport characteristic.

Organic electroluminescent devices are broadly classified into a polymer device and a low molecular weight device. Especially, with a low molecular weight device, an appropriate degree of carrier mobility and fluorescence emission characteristic are required, which, in turn, requires to freely change a band gap in the development of derivatives of π-conjugated compounds. Moreover, importance is placed on film characteristics of these compounds and, especially, it is required for the compounds to form a stable amorphous film (see Non-patent Document 1, Non-patent Document 2, Non-patent Document 3, and Patent Document 1).

Upon use as a cell, it is required that a compound be controlled in redox potential (see, for example, Non-patent Document 4). Especially, an electrode active substance used in a cell should have a redox potential within a decomposition voltage of a liquid electrolyte, for which it has been accepted as important how to control a redox potential.

With semiconductors, consideration has been generally given to π-conjugated compounds in order to achieve a narrow band gap thereof. However, π-conjugated compounds are ordinarily unlikely to handle because of the low solubility in solvents along with a problem in that structural control is difficult.

Another approach of narrowing a band gap is one wherein π-conjugated systems are two-dimensionally extended (see Non-patent Document 5, Non-patent Document 6). However, these materials are also insoluble in solvents, thus involving inconvenience in handling.

Further, although ordinary π-conjugated polymers behave as an impurity semiconductor by doping, a difficulty is involved in stably preparing semiconductors of both n type and p type from one material.

For a conductive polymer, polymers of aniline and aniline derivatives have been generally in wide use. These polymers are usually synthesized according to an electrolytic polymerization process or chemical polymerization process, and Lewis acid or the like is doped for imparting conductivity thereto. It has been reported (see Patent Document 2) that the aniline polymer obtained in this way is dispersed in water or an organic solvent to provide a varnish, which is coated such as on a substrate by spin coating to provide a thin film, thereby exhibiting very high electric conductivity.

However, aniline polymer is not resistant to oxidation with oxygen in air, with the attendant drawback that the electric conductivity is significantly impaired depending on the degree of oxidation. Additionally, it has been pointed out that upon polymerization, benzidine that is a carcinogenic compound is incorporated as a side product (see Non-patent Document 5, Non-patent Document 7).

Although a polymer of pyrrole is also known as a conductive polymer, this also has a problem in that a difficulty is involved in film formation owing to its insolubility and infusibility, like the aniline polymer.

On the other hand, polythiophene compounds are generally poor in dispersability and solubility in organic or aqueous solvents, with a difficulty in forming a polymer film, dispersion and solution. From a process aspect, these facts present a serious problem in the case of applications as a conductive polymer material.

To cope with this, a hydrocarbon group is introduced into a thiophene monomer at the 3-position thereof, thereby improving solubility in organic solvents of corresponding polythiophene (see Patent Document 3).

According to Bayer, it has been reported that (3,4-ethylenedioxy)thiophene and derivatives thereof are subjected to oxidation polymerization by use of polystyrenesulfonic acid as a dopant to provide a water-solubilized conductive polymer varnish (Patent Document 4).

However, polythiophene-based conductive polymers are very low in solid concentration enabling stable dispersion, with a problem that control in film thickness is difficult.

In this way, hitherto known conductive polymers, respectively, have different problems on the formation of conductive thin films in respect of physical properties. Thus, a novel type of conductive polymer having the possibility of solving these problems has been demanded.

Non-Patent Document 1:
Polymer, Britain, 1983, Vol. 24, p. 748
Non-Patent Document 2:
Japanese Journal of Applied Physics, 1986, Vol. 25, p. 775
Non-Patent Document 3:
Applied Physics Letters, United States of America, 1987, Vol. 51, p. 913
Non-Patent Document 4:
Electrochemistry and Industrial Physicochemistry 1986, Vol. 54, p. 306
Non-Patent Document 5:
Synthetic Metals, United States of America, 1995, Vol. 69, pp. 599-600
Non-Patent Document 6:
Journal of the American Chemical Society, United States of America, 1995, Vol. 117, No. 25, pp. 6791-6792
Non-Patent Document 7:
NEDO Book Archive, Report of the Results of Studies and Developments of Conductive Polymer Materials, March, 1988, pp. 218-251
Patent Document 1:
U.S. Pat. No. 4,356,429
Patent Document 2:
U.S. Pat. No. 5,720,903
Patent Document 3:
JP-A 2003-221434
Patent Document 4:
JP-A 2002-206022

DISCLOSURE OF THE INVENTION

Problems to be Solved by the Invention

The invention has been made under these circumstances and has for its object the provision of thiophene compounds having a phosphoric ester which have high resistances to heat and oxidation and are able to improve solubility and dispersability in various solvents and processes for producing the same.

Means for Solving the Problems

In order to achieve the above object, we paid attention to a thiophene skeleton having high resistances to heat and oxidation, and investigated and studied thiophene compounds having a novel molecular structure for the purpose of improving solubility or dispersability in various solvent, with the result that a thiophene compound having a phosphoric ester group in the molecule and a useful production process thereof have been found, thus arriving at completion of the invention.

More particularly, the invention provides:
1. A bisphosphorylthiophene compound, characterized by being represented by the formula [1]

[Chemical Formula 1]

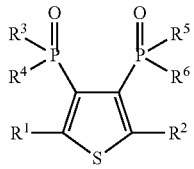

[1]

(wherein $R^1$ and $R^2$ each independently a hydrogen atom, a halogen atom, a cyano group, a phenyl group which may be substituted with W, a naphthyl group which may be substituted with W, an anthranil group which may be substituted with W, a hydroxyl group, an amino group, a formyl group, a carboxyl group, an alkyl group having 1-10 carbon atoms, a haloalkyl group having 1-10 carbon atoms, a monoalkylamino group having 1-10 carbon atoms, a dialkylamino group having 1-10 carbon atoms, a trialkylstannyl group having 1-10 carbon atoms, or a trialkylsilyl group having 1-10 carbon atoms, $R^3$-$R^6$ each independently represent —$OR^7$, —$SR^8$ or —$NR^9_2$; $R^7$-$R^9$ each independently represent a hydrogen atom, an alkyl group having 1-10 carbon atoms, or a phenyl group which may be substituted with W; W represents a halogen atom, a cyano group, a nitro group, a hydroxyl group, a mercapto group, an amino group, a formyl group, a carboxyl group, an alkyl group having 1-10 carbon atoms, a haloalkyl group having 1-10 carbon atoms, an alkenyl group having 1-10 carbon atoms, an alkynyl group having 1-10 carbon atoms, an alkoxy group having 1-10 carbon atoms, an alkylthio group having 1-10 carbon atoms, a monoalkylamino group having 1-10 carbon atoms, a dialkylamino group having 1-10 carbon atoms, a diphenylamino group which may be substituted with W', a dinaphthylamino group which may be substituted with W', a dianthranilamino group which may be substituted with W', an N-phenyl-N-napthylamino group which may be substituted with W', an N-phenyl-N-anthranilamino group which may be substituted with W', an N-naphthyl-N-anthranilamino group which may be substituted with W', a trialkylsilyl group having 1-10 carbon atoms, an alkylcarbonyl group having 1-10 carbon atoms, an alkoxycarbonyl group having 1-10 carbon atoms, or a phenyl group which may be substituted with W'; and W' represents an alkyl group having 1-10 carbon atoms, a haloalkyl group having 1-10 carbon atoms or an alkoxy group having 1-10 carbon atoms);

2. A monophosphorylthiophene compound, characterized by being represented by the formula [2]

[Chemical Formula 2]

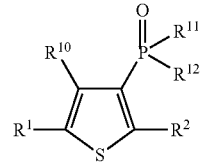

[2]

(wherein $R^1$ and $R^2$ have the same meanings as defined above; $R^{10}$ represents a hydrogen atom, a halogen atom, a cyano group, a nitro group, a hydroxyl group, a mercapto group, an amino group, a formyl group, a carboxyl group, an alkyl group having 1-10 carbon atoms, a haloalkyl group having 1-10 carbon atoms, an alkenyl group having 1-10 carbon atoms, an alkynyl group having 1-10 carbon atoms, an alkoxy group having 1-10 carbon atoms, an alkylthio group having 1-10 carbon atoms, a monoalkylamino group having 1-10 carbon atoms, a dialkylamino group having 1-10 carbon atoms, or a phenyl group which may be substituted with W; $R^{11}$ and $R^{12}$ represent —$SR^8$ or —$NR^9_2$; and $R^8$, $R^9$ and W have the same meanings as defined above);

3. A phosphorylthiophene oligomer, characterized by being represented the formula [3]

[Chemical Formula 3]

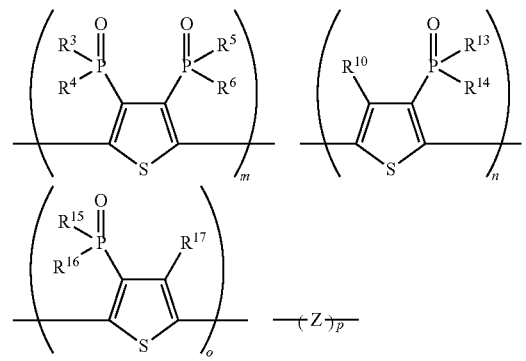

[3]

(wherein $R^3$-$R^6$ have the same meanings as defined above; $R^{10}$ has the same meaning as defined above; $R^{13}$-$R^{16}$ each independently represent —$OR^7$, —$SR^8$ or —$NR^9_2$; $R^7$-$R^9$ have the same meanings as defined above; $R^{17}$ each independently represents a hydrogen atom, a halogen atom, a cyano group, a nitro group, a hydroxyl group, a mercapto group, an amino group, a formyl group, a carboxyl group, an alkyl group having 1-10 carbon atoms, a haloalkyl group having 1-10 carbon atoms, an alkenyl group having 1-10 carbon atoms, an alkynyl group having 1-10 carbon atoms, an alkoxy group having 1-10 carbon atoms, an alkylthio group having 1-10 carbon atoms, a monoalkylamino group having 1-10 carbon atoms, a dialkylamino group having 1-10 carbon atoms, or a phenyl group which may be substituted with W; W has the same meaning as defined above; m, n and o each independently represent 0 or an integer of 1 or over; p is an integer of 1 or over provided that m+n+o≧1 and 2≦m+n+o+

$p \leqq 50$ are satisfied; and Z represents at least one divalent organic group selected from those of the following formulas [4] to [12]

[Chemical Formula 4]

[4]
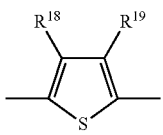

[5]
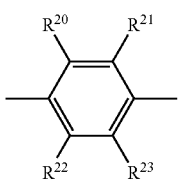

[6]
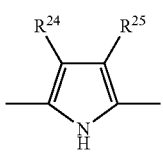

[7]
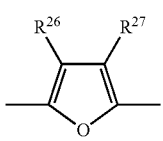

[8]
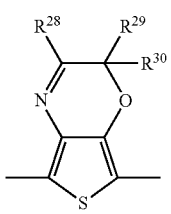

[9]
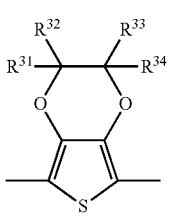

[10]
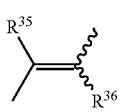

[11]

[12]
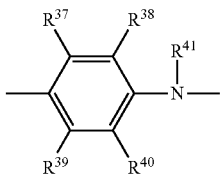

wherein $R^{18}$-$R^{40}$ each independently represent a hydrogen atom, an alkyl group having 1-10 carbon atoms, a haloalkyl group having 1-10 carbon atoms, an alkoxy group having 1-10 carbon atoms, an alkylthio group having 1-10 carbon atoms, a dialkylamino group having 1-10 carbon atoms, or a phenyl group which may be substituted with W; W has the same meaning as defined above; $R^{41}$ represents a hydrogen atom, an alkyl group having 1-10 carbon atoms, a haloalkyl group having 1-10 carbon atoms, an alkoxy group having 1-10 carbon atoms, or a phenyl group which may be substituted with W'; W' has the same meaning as defined above; and opposite terminal ends of the phosphorylthiophene polymer compound are each independently a hydrogen atom, a halogen atom, a monoalkylamino group having 1-10 carbon atoms, a dialkylamino group having 1-10 carbon atoms, a phenyl group which may be substituted with W, a naphthyl group which may be substituted with W, an anthranil group which may be substituted with W, a trialkylstannyl group having 1-10 carbon atoms or a trialkylsilyl group having 1-10 carbon atoms);

4. A phosphorylthiophene compound of 3, characterized in that Z is represented said formula [4];

5. A phosphorylthiophene polymer compound, characterized by being represented by the formula [29]

[Chemical Formula 5]

[29]
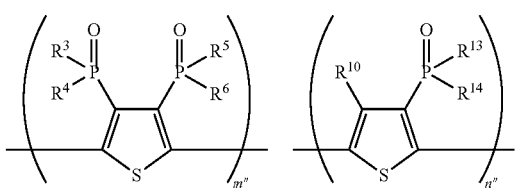
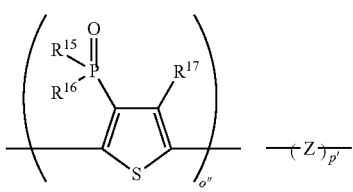

(wherein $R^3$-$R^6$, $R^{13}$-$R^{16}$, $R^{10}$ and $R^{17}$ have the same meanings as defined above, m", n" and o" each independently represent 0 or an integer of 1 or over, p' is 0 or an integer of 1 or over provided that $m"+n"+o" \geqq 1$ and $50 < m"+n"+o"+p" < 5000$, Z has the same meaning as defined above provided that opposite terminal ends of the phosphorylthiophene oligomer compound are each independently a hydrogen atom, a halogen atom, a monoalkylamino group having 1-10 carbon atoms, a dialkylamino group having 1-10 carbon atoms, a phenyl group which may be substituted with W, a naphthyl group which may be substituted with W, an anthranil group which may be substituted with W, a trialkylstannyl group having 1-10 carbon atoms or a trialkylsilyl group having 1-10 carbon atoms wherein W has the same meaning as defined above);

6. A sulfonylthiophene polymer compound of 5, characterized in that Z is a divalent organic group represented by said formula [4];

7. A phosphorylthiophene oligomer compound, characterized by being represented by the formula [13]

[Chemical Formula 6]

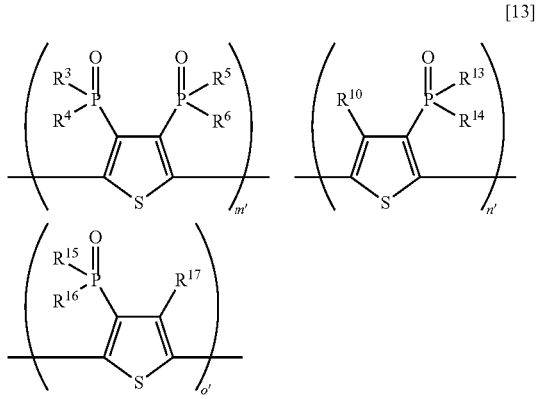

[13]

(wherein $R^3$-$R^6$, $R^{13}$-$R^{16}$, $R^{10}$ and $R^{17}$ have the same meanings as defined above, m', n' and o' each independently represent 0 or an integer of 1 or over provide that $2 \leq m'+n'+o' \leq 50$ is satisfied, opposite terminal ends of the phosphorylthiophene polymer compound being each independently a hydrogen atom, a halogen atom, a monoalkylamino group having 1-10 carbon atoms, a dialkylamino group having 1-10 carbon atoms, a phenyl group which may be substituted with W, a naphthyl group which may be substituted with W, an anthranil group which may be substituted with W, a trialkylstannyl group having 1-10 carbon atoms or a trialkylsilyl group having 1-10 carbon atoms wherein W has the same meaning as defined above);

8. A phosphorylthiophene polymer compound, characterized by being represented by the formula [30]

[Chemical Formula 7]

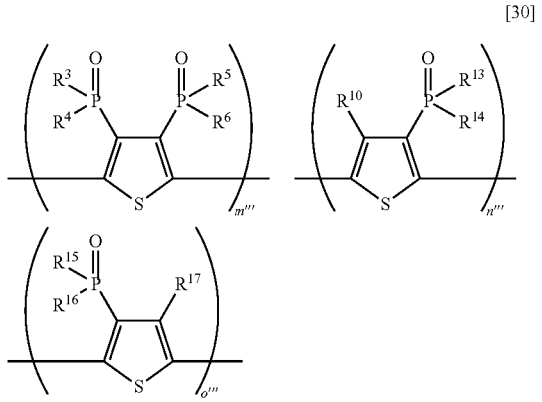

[30]

(wherein $R^3$-$R^6$, $R^{13}$-$R^{16}$, $R^{10}$ and $R^{17}$ have the same meanings as defined above, m''', n''' and o''' each independently represent 0 or an integer of 1 or over and $50 < m'''+n'''+o''' \leq 5000$ is satisfied, provided that opposite terminal ends of the phosphorylthiophene polymer compound are each independently a hydrogen atom, a halogen atom, a monoalkylamino group having 1-10 carbon atoms, a dialkylamino group having 1-10 carbon atoms, a phenyl group which may be substituted with W, a naphthyl group which may be substituted with W, an anthranil group which may be substituted with W, a trialkylstannyl group having 1-10 carbon atoms or a trialkylsilyl group having 1-10 carbon atoms wherein W has the same meaning as defined above);

9. A phosphorylthiophene polymer compound obtained by electrolytic oxidation polymerization or chemical oxidation polymerization of at least one selected from the phosphorylthiophene oligomers of 3 and 7;

10. A process for producing a phosphorylthiophene polymer compound including electrolytic oxidation polymerization or chemical oxidation polymerization of at least one selected from the phosphorylthiophene oligomers of 3 and 7;

11. A phosphorylthiophene polymer compound obtained by catalytic polymerization of the bisphosphorylthiophene polymer of 1, the monophosphorylthiophene compound of 2 or at least one selected from the phosphorylthiophene oligomers of 3 and 7;

12. A process for producing a phosphorylthiophene polymer compound comprising catalytic polymerization of the bisphosphorylthiophene polymer of 1, the monophosphorylthiophene compound of 2 or at least one selected from the phosphorylthiophene oligomers of 3 and 7;

13. A process for producing a bisphosphorylbutadiene compound, the process including reacting a butynediol compound represented by the formula [14]

[Chemical Formula 8]

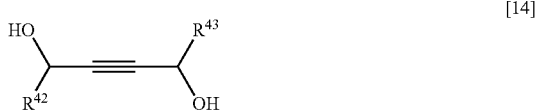

[14]

(wherein $R^{42}$ and $R^{43}$ each independently represent a hydrogen atom, a halogen atom, a cyano group, a phenyl group which may be substituted with W'', an alkyl group having 1-10 carbon atoms or an haloalkyl group having 1-10 carbon atoms; W'' represents a halogen atom, a cyano group, a nitro group, an alkyl group having 1-10 carbon atoms, a haloalkyl group having 1-10 carbon atoms, an alkenyl group having 1-10 carbon atoms, an alkynyl group having 1-10 carbon atoms, an alkoxy group having 1-10 carbon atoms, or a phenyl group) with a butynediol compound represented by the formula [15]

[Chemical Formula 9]

$P(OR^{44})_2 X$    [15]

(wherein $R^{44}$ represents a hydrogen atom, an alkyl group having 1-10 carbon atoms or a phenyl group which may be substituted with W''; X represents a halogen atom; and W'' has the same meaning as defined above) in the presence of a base, thereby producing a bisphosphorylbutadiene compound of the formula [16]

[Chemical Formula 10]

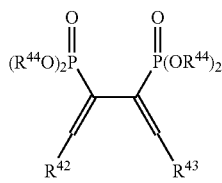

[16]

(wherein $R^{42}$, $R^{43}$ and $R^{44}$ have the same meanings as define above);

14. A process for producing a 3,4-bisphosphorylthiolane compound, the process including reacting a bisphosphorylbutadiene compound of the formula [16]

[Chemical Formula 11]

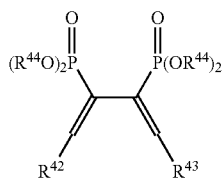

[16]

(wherein $R^{42}$, $R^{43}$ and $R^{44}$ have the same meanings as defined above) with a metal sulfide, thereby producing a bisphosphorylbutadiene compound of the formula [17]

[Chemical Formula 12]

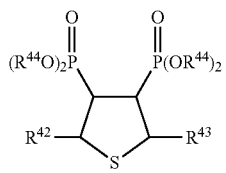

[17]

(wherein $R^{42}$, $R^{43}$ and $R^{44}$ have the same meanings as defined above);

15. A process for producing a 3,4-bisphosphorylsulfurane, the process including reacting a 3,4-bisphosphorylthiolane compound represented by the formula [17]

[Chemical Formula 13]

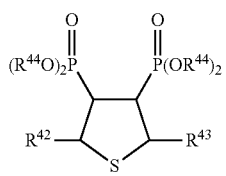

[17]

(wherein $R^{42}$, $R^{43}$ and $R^{44}$ have the same meanings as defined above) with an inorganic oxidizing agent, thereby producing a 3,4-bisphosphorylsulfurane compound represented by the formula [18]

[Chemical Formula 14]

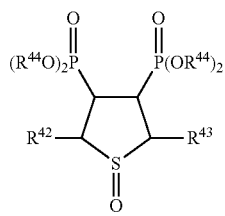

[18]

(wherein $R^{42}$, $R^{43}$ and $R^{44}$ have the same meanings as defined above);

16. A process for producing a 3,4-bisphosphoryldihydrothiophene compound, the process including reacting a 3,4-bisphosphorylsulfurane compound represented by the formula [18]

[Chemical Formula 15]

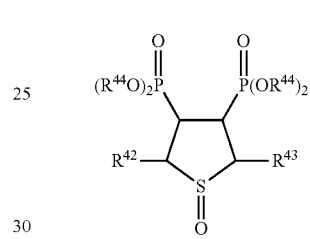

[18]

(wherein $R^{42}$, $R^{43}$ and $R^{44}$ have the same meanings as defined above) with an organic acid anhydride in the presence of an organic acid catalyst, thereby producing a 3,4-bisphosphoryldihydrothiophene represented by the formula [19]

[Chemical Formula 16]

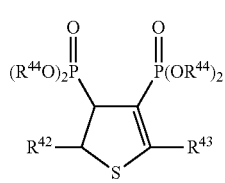

[19]

(wherein $R^{42}$, $R^{43}$ and $R^{44}$ have the same meanings as defined above);

17. A process for producing a 3,4-bisphosphorylthiophene compound, the process including oxidizing a 3,4-bisphosphoryldihydrothiophene compound represented by the formula [19]

[Chemical Formula 17]

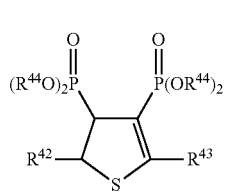

[19]

(wherein $R^{42}$, $R^{43}$ and $R^{44}$ have the same meanings as defined above) with an inorganic oxidizing agent, thereby producing a 3,4-bisphosphorylthiophene represented by the formula [20]

[Chemical Formula 18]

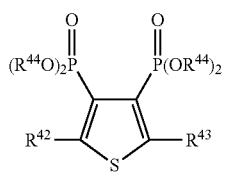
[20]

(wherein $R^{42}$, $R^{43}$ and $R^{44}$ have the same meanings as defined above);

18. A process for producing a phosphorylthiophene compound, the process including reacting a thiophene compound represented by the formula [21]

[Chemical Formula 19]

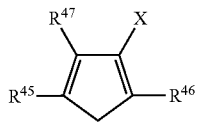
[21]

(wherein X has the same meaning as defined above; $R^{45}$ and $R^{46}$ each independently represent a hydrogen atom, a cyano group, a phenyl group which may be substituted with W''', a hydroxyl group, an amino group, a formyl group, a carboxyl group, an alkyl group having 1-10 carbon atoms, a haloalkyl group having 1-10 carbon atoms, a monoalkylamino group having 1-10 carbon atoms, or a dialkylamino group having 1-10 carbon atoms; $R^{47}$ represents a hydrogen atom, a halogen atom, a cyano group, a nitro group, a phenyl group which may be substituted with W''', a hydroxyl group, a mercapto group, an amino group, a formyl group, a carboxyl group, an alkyl group having 1-10 carbon atoms, a haloalkyl group having 1-10 carbon atoms, a monoalkylamino group having 1-10 carbon atoms, a dialkylamino group having 1-10 carbon atoms or —P(O)(OR$^{48}$)$_2$; $R^{48}$ represents a hydrogen atom, an alkyl group having 1-10 carbon atoms or a phenyl group which may be substituted with W''', W''' represents a cyano group, a nitro group, a hydroxyl group, a mercapto group, an amino group, a formyl group, a carboxyl group, an alkyl group having 1-10 carbon atoms, a haloalkyl group having 1-10 carbon atoms, an alkenyl group having 1-10 carbon atoms, an alkynyl group having 1-10 carbon atoms, an alkoxy group having 1-10 carbon atoms, an alkylthio group having 1-10 carbon atoms, a monoalkylamino group having 1-10 carbon atoms, a dialkylamino group having 1-10 carbon atoms, an alkylcarbonyl group having 1-10 carbon atoms, an alkoxycarbonyl group having 1-10 carbon atoms, or a phenyl group) with a phosphite compound represented by the formula [22]

[Chemical Formula 20]

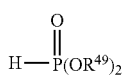
[22]

(wherein $R^{49}$ represents an alkyl group having 1-10 carbon atoms or a phenyl group which may be substituted with W'''; W''' has the same meaning as defined above) in the presence of a metal catalyst and a base, thereby producing a phosphorylthiophene compound represented by the formula [23]

[Chemical Formula 21]

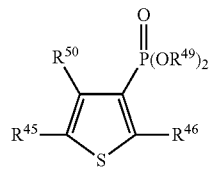
[23]

(wherein $R^{45}$ and $R^{46}$ have the same meanings as defined above; $R^{50}$ represents a hydrogen atom, a halogen atom, a cyano group, a nitro group, a phenyl group which may be substituted with W''', a hydroxyl group, a mercapto group, an amino group, a formyl group, a carboxyl group, an alkyl group having 1-10 carbon atoms, a haloalkyl group having 1-10 carbon atoms, a monoalkyl group having 1-10 carbon atoms, a dialkylamino group having 1-10 carbon atoms, —P(O)(OR$^{48}$)$_2$ or —P(O)(OR$^{49}$)$_2$; W''', $R^{48}$ and $R^{49}$ have the same meanings as defined above);

19. A process for producing a phosphorylthiophene compound, the process including reacting a thiophene compound of the formula [21]

[Chemical Formula 22]

[21]

(wherein X, $R^{45}$, $R^{46}$ and $R^{47}$ have the same meanings as defined above) with a phosphite compound represented by the formula [24]

[Chemical Formula 23]

$P(OR^{49})_3$ [24]

(wherein $R^{49}$ has the same meaning as defined above) in the presence of a metal catalyst, thereby producing a phosphorylthiophene compound represented by the formula [23]

[Chemical Formula 24]

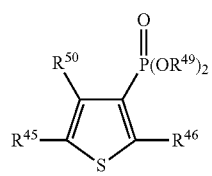
[23]

(wherein $R^{45}$, $R^{46}$, $R^{49}$ and $R^{50}$ have the same meanings as defined above);

20. A bisphosphorylbutadiene compound represented by the formula (16)

[Chemical Formula 25]

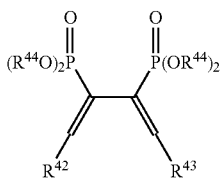
[16]

(wherein $R^{42}$, $R^{43}$ and $R^{44}$ have the same meanings as defined above);

21. A 3,4-bisphosphorylthiolane compound represented by the formula [17]

[Chemical Formula 26]

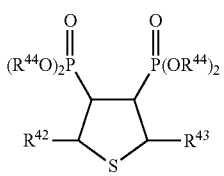
[17]

(wherein $R^{42}$, $R^{43}$ and $R^{44}$ have the same meanings as defined above);

22. A 3,4-bisphosphorylsulfuran compound represented by the formula [18]

[Chemical Formula 27]

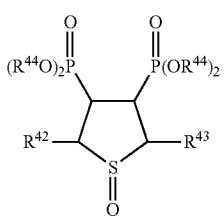
[18]

(wherein $R^{42}$, $R^{43}$ and $R^{44}$ have the same meanings as defined above);

23. A 3,4-bisphosphoryldihydrothiophene compound represented by the formula [19]

[Chemical Formula 28]

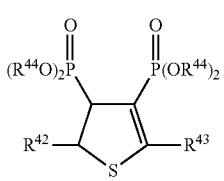
[19]

(wherein $R^{42}$, $R^{43}$ and $R^{44}$ have the same meanings as defined above);

24. A 3,4-bisphosphorylthiophene compound represented by the formula [20]

[Chemical Formula 29]

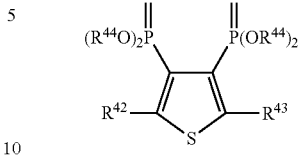
[20]

(wherein $R^{42}$, $R^{43}$ and $R^{44}$ have the same meanings as defined above);

25. A 3,3',4,4'-tetrakisphosphorylbithiophene compound represented by the formula [25]

[Chemical Formula 30]

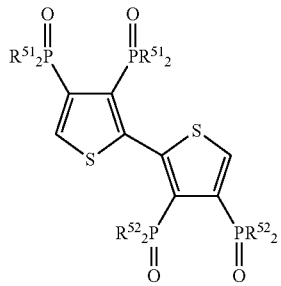
[25]

(wherein $R^{51}$ and $R^{52}$ each independently represent a halogen atom, —$OR^7$, —$SR^8$ or —$NR^9{}_2$; and $R^7$-$R^9$ have the same meanings as defined above);

26. A 3,3'-bisphosphorylbithiophene compound represented by the formula [26]

[Chemical Formula 31]

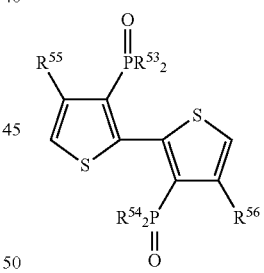
[26]

(wherein $R^{53}$ and $R^{54}$ each independently represent a halogen atom, —$OR^7$, —$SR^8$ or —$NR^9{}_2$; $R^7$-$R^9$ have the same meanings as defined above; $R^{55}$ and $R^{56}$ each independently represent a hydrogen atom, a halogen atom, a cyano group, a nitro group, a hydroxyl group, a mercapto group, a amino group, a formyl group, a carboxyl group, an alkyl group having 1-10 carbon atoms, a haloalkyl group having 1-10 carbon atoms, an alkenyl group having 1-10 carbon atoms, an alkynyl group having 1-10 carbon atoms, an alkoxy group having 1-10 carbon atoms, an alkylthio group having 1-10 carbon atoms, a monoalkylamino group having 1-10 carbon atoms, a dialkylamino group having 1-10 carbon atoms or a phenyl group which may be substituted with W; and W has the same meaning as defined above);

27. A 4,4'-bisphosphorylbithiophene compound represented by the formula [27]

[Chemical Formula 32]

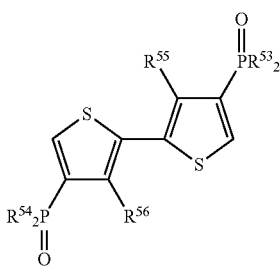

[27]

(wherein $R^{53}$, $R^{54}$, $R^{55}$ and $R^{56}$ have the same meanings as defined above);

28. A 3,4'-bisphosphorylbithiophene compound represented by the formula [28]

[Chemical Formula 33]

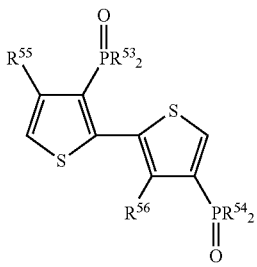

[28]

(wherein $R^{53}$, $R^{54}$, $R^{55}$ and $R^{56}$ have the same meanings as defined above);

29. An active substance for cell including one selected from the phosphorylthiophene oligomer compound defined in any one of 3, 4 and 7 and the phosphorylthiophene polymer compounds of 5, 6 and 8;

30. An electrode material including one selected from the phosphorylthiophene oligomer compound defined in any one of 3, 4 and 7 and the phosphorylthiophene polymer compounds of 5, 6 and 8;

31. An organic electroluminescent material including one selected from the phosphorylthiophene oligomer compound defined in any one of 3, 4 and 7 and the phosphorylthiophene polymer compounds of 5, 6 and 8;

32. A p-type semiconductor obtained by oxidizing at least one selected from the phosphorylthiophene oligomer compound defined in any one of 3, 4 and 7 and the phosphorylthiophene polymer compounds of 5, 6 and 8 with an oxidizing agent or by electrochemical doping;

33. An n-type semiconductor obtained by reducing at least one selected from the phosphorylthiophene oligomer compound defined in any one of 3, 4 and 7 and the phosphorylthiophene polymer compounds of 5, 6 and 8 with a reducing agent or by electrochemical doping;

34. A semiconductor device making use of at least one selected from the phosphorylthiophene oligomer compound defined in any one of 3, 4 and 7 and the phosphorylthiophene polymer compounds of 5, 6 and 8;

35. An organic electroluminescent device making use of at least one selected from the phosphorylthiophene oligomer compound defined in any one of 3, 4 and 7 and the phosphorylthiophene polymer compounds of 5, 6 and 8;

36. A total solid-state organic solar cell making use of at least one selected from the phosphorylthiophene oligomer compound defined in any one of 3, 4 and 7 and the phosphorylthiophene polymer compounds of 5, 6 and 8;

37. A dye-sensitized solar cell making use of any one of at least one selected from the phosphorylthiophene oligomer compound defined in any one of 3, 4 and 7 and the phosphorylthiophene polymer compounds of 5, 6 and 8;

38. A capacitor electrode including one selected from the phosphorylthiophene oligomer compound defined in any one of 3, 4 and 7 and the phosphorylthiophene polymer compounds of 5, 6 and 8;

39. An actuator making use of at least one selected from the phosphorylthiophene oligomer compound defined in any one of 3, 4 and 7 and the phosphorylthiophene polymer compounds of 5, 6 and 8;

40. A solid electrolyte for capacitor including one selected from the phosphorylthiophene oligomer compound defined in any one of 3, 4 and 7 and the phosphorylthiophene polymer compounds of 5, 6 and 8;

41. An antenna material including one selected from the phosphorylthiophene oligomer compound defined in any one of 3, 4 and 7 and the phosphorylthiophene polymer compounds of 5, 6 and 8;

42. A sensor making use of at least one selected from the phosphorylthiophene oligomer compound defined in any one of 3, 4 and 7 and the phosphorylthiophene polymer compounds of 5, 6 and 8; and 43. A fuel cell separator including one selected from the phosphorylthiophene oligomer compound defined in any one of 3, 4 and 7 and the phosphorylthiophene polymer compounds of 5, 6 and 8.

EFFECTS OF THE INVENTION

According to the invention, there can be provided practical processes for producing thiophene monomers and oligomers having a phosphoric acid ester group as being expected for use as conductive polymers that have an excellent resistance to heat and better solubility or dispersability in water or organic solvents than existing counterparts and also a practical process for producing polymers derived therefrom.

The thiophene compounds or polythiophene compounds having a phosphoric ester exhibit an excellent resistance to heat and are better than existing counterparts with respect to solubility or dispersability in water or organic solvents, enable easy control of an electrochemical redox potential, and are so small in band gap of the compound itself along with intense fluorescence-emitting characteristics. Moreover, these thiophene compounds have both an electron donative group and an electron acceptive group, thus exhibiting p-type and n-type semiconductive characteristics.

These compounds can be readily thinned by vacuum deposition, spin coating, dipping, casting or screen printing and can be applied as an active substance or electrode material for cells, an electroluminescent device material, a p-type or n-type semiconductor, a semiconductor device, a non-linear optical material and the like. Further, the phosphorylthiophene compounds of the invention can be conveniently used for sensors, fluorescent filters, organic electronic devices, organic electroluminescent devices, organic electro chromic devices, total solid-state solar cells, dye-sensitized solar cells, capacitor electrodes, actuators, fuel cell separators, solid electrolytes for capacitor, electromagnetic shield films, antistatic films, IR cut films, UV cut films, antenna materials, non-linear optical materials and the like.

BEST MODE FOR CARRYING OUT THE INVENTION

The invention is now described in more detail.

It will be noted that in the present specification, "n" means normal, "I" iso, "s" secondary, "t" tertiary, "c" cyclo, "o" ortho, "m" meta, and "p" para, and "Me" means methyl group, "Et" ethyl group, "Pr" propyl group, "Bu" butyl group, and "p" phenyl group, respectively.

The phosphorylthiophene compounds of the invention are represented by the above formulas [1] and [2]. In the formulas [1] and [2], $R^1$ and $R^2$ each independently represent a hydrogen atom, a halogen atom, a cyano group, a phenyl group which may be substituted with W, a naphthyl group which may be substituted with W, an anthranil group which may be substituted with W, a hydroxyl group, an amino group, a formyl group, a carboxyl group, an alkyl group having 1-10 carbon atoms, a haloalkyl group having 1-10 carbon atoms, a monoalkylamino group having 1-10 carbon atoms, a dialkylamino group having 1-10 carbon atoms, a trialkylstannyl group having 1-10 carbon atoms, or a trialkylsilyl group having 1-10 carbon atoms.

For a halogen atom, mention is made of a fluorine atom, a chlorine atom, a bromine atom or an iodine atom.

Specific examples of the alkyl group having 1-10 carbon atoms include methyl, ethyl, n-propyl, i-propyl, c-propyl, n-butyl, i-butyl, s-butyl, t-butyl, c-butyl, n-pentyl, 1-methyl-n-butyl, 2-methyl-n-butyl, 3-methyl-n-butyl, 1,1-dimethyl-n-propyl, c-pentyl, 2-methyl-c-butyl, n-hexyl, 1-methyl-n-pentyl, 2-methyl-n-pentyl, 1,1-dimethyl-n-butyl, 1-ethyl-n-butyl, 1,1,2-trimethyl-n-propyl, c-hexyl, 1-methyl-c-pentyl, 1-ethyl-c-butyl, 1,2-dimethyl-c-butyl, n-heptyl, n-octyl, n-nonyl, n-decyl and the like.

Specific examples of the haloalkyl group having 1-10 carbon atoms include $CH_2F$, $CHF_2$, $CF_3$, $CH_2CH_2F$, $CH_2CHF_2$, $CH_2CF_3$, $CH_2CH_2CH_2F$, $CH_2CH_2CHF_2$, $CH_2CH_2CF_3$, $CH_2Cl$, $CHCl_2$, $CCl_3$, $CH_2CH_2Cl$, $CH_2Br$, $CHBr_2$, $CBr_3$, $CH_2CH_2Br$ and the like.

Specific examples of the monoalkylamino group having 1-10 carbon atoms include NHMe, NHEt, NHPr-n, NHPr-i, NHBu-n, NHBu-i, NHBu-s, NHBu-t, NHPen-n, $NHCHEt_2$, NHHex-n and the like.

Specific examples of the dialkylamino group having 1-10 carbon atoms include $NMe_2$, $NEt_2$, $N(Pr-n)_2$, $N(Pr-i)_2$, $N(Bu-n)_2$, $N(Bu-i)_2$, $N(Bu-s)_2$, $N(Bu-t)_2$, $N(Pen-n)_2$, $N(CHEt_2)_2$, $N(Hex-n)_2$ and the like.

Specific examples of the trialkylstannyl group having 1-10 carbon atoms include $SnMe_3$, $SnEt_3$, $Sn(Pr-n)_3$, $Sn(Pr-i)_3$, $Sn(Bu-n)_3$, $Sn(Bu-i)_3$, $Sn(Bu-s)_3$, $Sn(Bu-t)_3$ and the like.

For the trialkylsilyl group having 1-10 carbon atoms, mention is made of $SiMe_3$, $SiEt_3$, $Si(Pr-n)_3$, $Si(Pr-i)_3$, $Si(Bu-n)_3$, $Si(Bu-i)_3$, $Si(Bu-s)_3$, $Si(Bu-t)_3$ and the like.

W represents a halogen atom, a cyano group, a nitro group, a hydroxyl group, a mercapto group, an amino group, a formyl group, a carboxyl group, an alkyl group having 1-10 carbon atoms, a haloalkyl group having 1-10 carbon atoms, an alkenyl group having 1-10 carbon atoms, an alkynyl group having 1-10 carbon atoms, an alkoxy group having 1-10 carbon atoms, an alkylthio group having 1-10 carbon atoms, a monoalkylamino group having 1-10 carbon atoms, a dialkylamino group having 1-10 carbon atoms, a diphenylamino group which may be substituted with W', a dinaphthylamino group which may be substituted with W', a dianthranilamino group which may be substituted with W', an N-phenyl-N-naphthylamino group which may be substituted with W', an N-phenyl-N-anthranilamino group which may be substituted with W', an N-naphthyl-N-anthranilamino group which may be substituted with W', a trialkylsilyl group having 1-10 carbon atoms, an alkylcarbonyl group having 1-10 carbon atoms, an alkoxycarbonyl group having 1-10 carbon atoms, or a phenyl group which may be substituted with W'. W' represents an alkyl group having 1-10 carbon atoms, a haloalkyl group having 1-10 carbon atoms or an alkoxy group having 1-10 carbon atoms.

In this case, specific examples of the alkenyl group having 1-10 carbon atoms include $CH=CH_2$, $CH=CHMe$, $CH=CHEt$, $CH=CMe_2$, $CH=CEt_2$, $CMe=CH_2$, $CMe=CHMe$, $CMe=CMe_2$, $CH_2CH=CH_2$, $CH_2CH=CHMe$, $CH_2CH=CHEt$, $CH_2CMe=CH_2$, $CH_2CH_2CH=CH_2$, $CH_2CH_2CH=CHMe$, $CH_2CH=CMe_2$, $CHMeCH=CH_2$, $CH_2CMe=CHMe$, $CHMeCH=CHMe$, $CH_2CMe=CHEt$, $CH_2CH_2CH=CMe_2$, $CH_2CMe=CMe_2$, $CH=C=CH_2$ and the like.

Specific examples of the alkynyl group having 1-10 carbon atoms include $C\equiv CMe$, $C\equiv CEt$, $CH_2C\equiv CH$, $CH_2C\equiv CMe$, $CH_2C\equiv CEt$, $CH_2CH_2C\equiv CH$, $CH_2CH_2C\equiv CMe$, $CHMeC\equiv CH$, $CHMeC\equiv CMe$ and the like.

Specific examples of the alkoxy group having 1-10 carbon atoms include OMe, OEt, OPr-n, OPr-i, OBu-n, OBu-i, OBu-s, OBu-t, OPen-n, $OCHEt_2$, OHex-n, OCHMe(Pr-n), OCHMe(Bu-n), OCHEt(Pr-n), $OCH_2CH_2CHMe_2$ and the like.

Specific examples of the alkylthio group having 1-10 carbon atoms include SMe, SEt, SPr-n, SPr-i, SBu-n, SBu-i, SBu-s, SBu-t, SPen-n, $SCHEt_2$, SHex-n, SCHMe(Pr-n), SCHMe(Bu-n), SCHEt(Pr-n), $SCH_2CH_2CHMe_2$ and the like.

Specific examples of the alkylcarbonyl group having 1-10 carbon atoms include C(O)Me, C(O)Et, C(O)Pr-n, C(O)Pr-i, C(O)Bu-n, C(O)Bu-i, C(O)Bu-s, C(O)Bu-t, C(O)Pen-n, $C(O)CHEt_2$, C(O)Hex-n and the like.

Specific examples of the alkoxycarbonyl group having 1-10 carbon atoms include OC(O)Me, OC(O)Et, OC(O)Pr-n, OC(O)Pr-i, OC(O)Bu-n, OC(O)Bu-i, OC(O)Bu-s, OC(O)Bu-t, OC(O)Pen-n, $OC(O)CHEt_2$, OC(O)Hex-n and the like.

Specific examples of the phenyl group which may be substituted with W include phenyl, o-methylphenyl, m-methylphenyl, p-methylphenyl, o-trifluoromethylphenyl, m-trifluoromethylphenyl, p-trifluoromethylphenyl, p-ethylphenyl, p-i-propylphenyl, p-t-butylphenyl, o-chlorophenyl, m-chlorophenyl, p-chlorophenyl, o-bromophenyl, m-bromophenyl, p-bromophenyl, o-fluorophenyl, p-fluorophenyl, o-methoxyphenyl, m-methoxyphenyl, p-methoxyphenyl, o-trifluoromethoxyphenyl, p-trifluoromethoxyphenyl, o-nitrophenyl, m-nitrophenyl, p-nitrophenyl, o-dimethylaminophenyl, m-dimethylaminophenyl, p-dimethylaminophenyl, p-cyanophenyl, 3,5-dimethylphenyl, 3,5-bistrifluoromethylphenyl, 3,5-dimethoxyphenyl, 3,5-bistrifluoromethoxyphenyl, 3,5-diethylphenyl, 3,5-di-i-propylphenyl, 3,5-dichlorophenyl, 3,5-dibromophenyl, 3,5-difluorophenyl, 3,5-dinitrophenyl, 3,5-dicyanophenyl, 2,4,6-trimethylphenyl, 2,4,6-tristrifluoromethylphenyl, 2,4,6-trimethoxyphenyl, 2,4,6-tristrifluoromethoxylphenyl, 2,4,6-trichlorophenyl, 2,4,6-tribromophenyl, 2,4,6-trifluorophenyl, o-biphenylyl, m-biphenylyl, p-biphenylyl and the like.

Specific examples of the naphthyl group which may be substituted with W include 1-naphthyl, 2-naphthyl, 2-butyl-1-naphthyl, 3-butyl-1-naphthyl, 4-butyl-1-naphthyl, 5-butyl-1-naphthyl, 6-butyl-1-naphthyl, 7-butyl-1-naphthyl, 8-butyl-1-naphthyl, 1-butyl-2-naphthyl, 3-butyl-2-naphthyl, 4-butyl-2-naphthyl, 5-butyl-2-naphthyl, 6-butyl-2-naphthyl, 7-butyl- 2-naphthyl, 8-butyl-2-naphthyl, 2-hexyl-1-naphthyl, 3-hexyl-1-naphthyl, 4-hexyl-1-naphthyl, 5-hexyl-1-naphthyl, 6-hexyl-1-naphthyl, 7-hexyl-1-naphthyl, 8-hexyl-1-naphthyl, 1-hexyl-2-naphthyl, 3-hexyl-2-naphthyl, 4-hexyl-2-naphthyl, 5-hexyl-2-naphthyl, 6-hexyl-2-naphthyl, 7-hexyl-2-naphthyl, 8-hexyl-2-naphthyl, 2-octyl-1-naphthyl, 3-octyl-1-naphthyl, 4-octyl-1-naphthyl, 5-octyl-1-naphthyl, 6-octyl-1-naphthyl, 7-octyl-1-naphthyl, 8-octyl-1-naphthyl, 1-octyl-2-naphthyl, 3-octyl-2-naphthyl, 4-octyl-2-naphthyl, 5-octyl-2-naphthyl, 6-octyl-2-naphthyl, 7-octyl-2-naphthyl, 8-octyl-2-naphthyl, 2-phenyl-1-naphthyl, 3-phenyl-1-naphthyl, 4-phenyl-1-naphthyl, 5-phenyl-1-naphthyl, 6-phenyl-1-naphthyl, 7-phenyl-1-naphthyl, 8-phenyl-1-naphthyl, 1-phenyl-2-naphthyl, 3-phenyl-2-naphthyl, 4-phenyl-2-naphthyl, 5-phenyl-2-naphthyl, 6-phenyl-2-naphthyl, 7-phenyl-2-naphthyl, 8-phenyl-2-naphthyl, 2-methoxy-1-naphthyl, 3-methoxy-1-naphthyl, 4-methoxy-1-naphthyl, 5-methoxy-1-naphthyl, 6-methoxy-1-naphthyl, 7-methoxy-1-naphthyl, 8-methoxy-1-naphthyl, 1-methoxy-2-naphthyl, 3-methoxy-2-naphthyl, 4-methoxy-2-naphthyl, 5-methoxy-2-naphthyl, 6-methoxy-2-naphthyl, 7-methoxy-2-naphthyl, 8-methoxy-2-naphthyl, 2-ethoxy-1-naphthyl, 3-ethoxy-1-naphthyl, 4-ethoxy-1-naphthyl, 5-ethoxy-1-naphthyl, 6-ethoxy-1-naphthyl, 7-ethoxy-1-naphthyl, 8-ethoxy-1-naphthyl, 1-ethoxy-2-naphthyl, 3-ethoxy-2-naphthyl, 4-ethoxy-2-naphthyl, 5-ethoxy-2-naphthyl, 6-ethoxy-2-naphthyl, 7-ethoxy-2-naphthyl, 8-ethoxy-2-naphthyl, 2-butoxy-1-naphthyl, 3-butoxy-1-naphthyl, 4-butoxy-1-naphthyl, 5-butoxy-1-naphthyl, 6-butoxy-1-naphthyl, 7-butoxy-1-naphthyl, 8-butoxy-1-naphthyl, 1-butoxy-2-naphthyl, 3-butoxy-2-naphthyl, 4-butoxy-2-naphthyl, 5-butoxy-2-naphthyl, 6-butoxy-2-naphthyl, 7-butoxy-2-naphthyl, 8-butoxy-2-naphthyl, 2-amino-1-naphthyl, 3-amino-1-naphthyl, 4-amino-1-naphthyl, 5-amino-1-naphthyl, 6-amino-1-naphthyl, 7-amino-1-naphthyl, 8-amino-1-naphthyl, 1-amino-2-naphthyl, 3-amino-2-naphthyl, 4-amino-2-naphthyl, 5-amino-2-naphthyl, 6-amino-2-naphthyl, 7-amino-2-naphthyl, 8-amino-2-naphthyl, 2-(N,N-dimethylamino)-1-naphthyl, 3-(N,N-dimethylamino)-1-naphthyl, 4-(N,N-dimethylamino)-1-naphthyl, 5-(N,N-dimethylamino)-1-naphthyl, 6-(N,N-dimethylamino)-1-naphthyl, 7-(N,N-dimethylamino)-1-naphthyl, 8-(N,N-dimethylamino)-1-naphthyl, 1-(N,N-dimethylamino)-2-naphthyl, 3-(N,N-dimethylamino)-2-naphthyl, 4-(N,N-dimethylamino)-2-naphthyl, 5-(N,N-dimethylamino)-2-naphthyl, 6-(N,N-dimethylamino)-2-naphthyl, 7-(N,N-dimethylamino)-2-naphthyl, 8-(N,N-dimethylamino)-2-naphthyl, 2-(N,N-diphenylamino)-1-naphthyl, 3-(N,N-diphenylamino)-1-naphthyl, 4-(N,N-diphenylamino)-1-naphthyl, 5-(N,N-diphenylamino)-1-naphthyl, 6-(N,N-diphenylamino)-1-naphthyl, 7-(N,N-diphenylamino)-1-naphthyl, 8-(N,N-diphenylamino)-1-naphthyl, 1-(N,N-diphenylamino)-2-naphthyl, 3-(N,N-diphenylamino)-2-naphthyl, 4-(N,N-diphenylamino)-2-naphthyl, 5-(N,N-diphenylamino)-2-naphthyl, 6-(N,N-diphenylamino)-2-naphthyl, 7-(N,N-diphenylamino)-2-naphthyl, 8-(N,N-diphenylamino)-2-naphthyl and the like.

Specific examples of the anthranil group which may be substituted with W include 1-anthranil, 2-anthranil, 9-anthranil, 2-butyl-1-anthranil, 3-butyl-1-anthranil, 4-butyl-1-anthranil, 5-butyl-1-anthranil, 6-butyl-1-anthranil, 7-butyl-1-anthranil, 8-butyl-1-anthranil, 9-butyl-1-anthranil, 10-butyl-1-anthranil, 1-butyl-2-anthranil, 3-butyl-2-anthranil, 4-butyl-2-anthranil, 5-butyl-2-anthranil, 6-butyl-2-anthranil, 7-butyl-2-anthranil, 8-butyl-2-anthranil, 9-butyl-2-anthranil, 10-butyl-2-anthranil, 1-butyl-9-anthranil, 2-butyl-9-anthranil, 3-butyl-9-anthranil, 4-butyl-9-anthranil, 10-butyl-9-anthranil, 2-hexyl-1-anthranil, 3-hexyl-1-anthranil, 4-hexyl-1-anthranil, 5-hexyl-1-anthranil, 6-hexyl-1-anthranil, 7-hexyl-1-anthranil, 8-hexyl-1-anthranil, 9-hexyl-1-anthranil, 10-hexyl-1-anthranil, 1-hexyl-2-anthranil, 3-hexyl-2-anthranil, 4-hexyl-2-anthranil, 5-hexyl-2-anthranil, 6-hexyl-2-anthranil, 7-hexyl-2-anthranil, 8-hexyl-2-anthranil, 9-hexyl-2-anthranil, 10-hexyl-2-anthranil, 1-hexyl-9-anthranil, 2-hexyl-9-anthranil, 3-hexyl-9-anthranil, 4-hexyl-9-anthranil, 10-hexyl-9-anthranil, 2-octyl-1-anthranil, 3-octyl-1-anthranil, 4-octyl-1-anthranil, 5-octyl-1-anthranil, 6-octyl-1-anthranil, 7-octyl-1-anthranil, 8-octyl-1-anthranil, 9-octyl-1-anthranil, 10-octyl-1-anthranil, 1-octyl-2-anthranil, 3-octyl-2-anthranil, 4-octyl-2-anthranil, 5-octyl-2-anthranil, 6-octyl-2-anthranil, 7-octyl-2-anthranil, 8-octyl-2-anthranil, 9-octyl-2-anthranil, 10-octyl-2-anthranil, 1-octyl-9-anthranil, 2-octyl-9-anthranil, 3-octyl-9-anthranil, 4-octyl-9-anthranil, 10-octyl-9-anthranil, 2-phenyl-1-anthranil, 3-phenyl-1-anthranil, 4-phenyl-1-anthranil, 5-phenyl-1-anthranil, 6-phenyl-1-anthranil, 7-phenyl-1-anthranil, 8-phenyl-1-anthranil, 9-phenyl-1-anthranil, 10-phenyl-1-anthranil, 1-phenyl-2-anthranil, 3-phenyl-2-anthranil, 4-phenyl-2-anthranil, 5-phenyl-2-anthranil, 6-phenyl-2-anthranil, 7-phenyl-2-anthranil, 8-phenyl-2-anthranil, 9-phenyl-2-anthranil, 10-phenyl-2-anthranil, 1-phenyl-9-anthranil, 2-phenyl-9-anthranil, 3-phenyl-9-anthranil, 4-phenyl-9-anthranil, 10-phenyl-9-anthranil, 2-methoxy-1-anthranil, 3-methoxy-1-anthranil, 4-methoxy-1-anthranil, 5-methoxy-1-anthranil, 6-methoxy-1-anthranil, 7-methoxy-1-anthranil, 8-methoxy-1-anthranil, 9-methoxy-1-anthranil, 10-methoxy-1-anthranil, 1-methoxy-2-anthranil, 3-methoxy-2-anthranil, 4-methoxy-2-anthranil, 5-methoxy-2-anthranil, 6-methoxy-2-anthranil, 7-methoxy-2-anthranil, 8-methoxy-2-anthranil, 9-methoxy-2-anthranil, 10-methoxy-2-anthranil, 1-methoxy-9-anthranil, 2-methoxy-9-anthranil, 3-methoxy-9-anthranil, 4-methoxy-9-anthranil, 10-methoxy-9-anthranil, 2-ethoxy-1-anthranil, 3-ethoxy-1-anthranil, 4-ethoxy-1-anthranil, 5-ethoxy-1-anthranil, 6-ethoxy-1-anthranil, 7-ethoxy-1-anthranil, 8-ethoxy-1-anthranil, 9-ethoxy-1-anthranil, 10-ethoxy-1-anthranil, 1-ethoxy-2-anthranil, 3-ethoxy-2-anthranil, 4-ethoxy-2-anthranil, 5-ethoxy-2-anthranil, 6-ethoxy-2-anthranil, 7-ethoxy-2-anthranil, 8-ethoxy-2-anthranil, 9-ethoxy-2-anthranil, 10-ethoxy-2-anthranil, 1-ethoxy-9-anthranil, 2-ethoxy-9-anthranil, 3-ethoxy-9-anthranil, 4-ethoxy-9-anthranil, 10-ethoxy-9-anthranil, 2-butoxy-1-anthranil, 3-butoxy-1-anthranil, 4-butoxy-1-anthranil, 5-butoxy-1-anthranil, 6-butoxy-1-anthranil, 7-butoxy-1-anthranil, 8-butoxy-1-anthranil, 9-butoxy-1-anthranil, 10-butoxy-1-anthranil, 1-butoxy-2-anthranil, 3-butoxy-2-anthranil, 4-butoxy-2-anthranil, 5-butoxy-2-anthranil, 6-butoxy-2-anthranil, 7-butoxy-2-anthranil, 8-butoxy-2-anthranil, 9-butoxy-2-anthranil, 10-butoxy-2-anthranil, 1-butoxy-9-anthranil, 2-butoxy-9-anthranil, 3-butoxy-9-anthranil, 4-butoxy-9-anthranil, 10-butoxy-9-anthranil, 2-amino-1-anthranil, 3-amino-1-anthranil, 4-amino-1-anthranil, 5-amino-1-anthranil, 6-amino-1-anthranil, 7-amino-1-anthranil, 8-amino-1-anthranil, 9-amino-1-anthranil, 10-amino-1-anthranil, 1-amino-2-anthranil, 3-amino-2-anthranil, 4-amino-2-anthranil, 5-amino-2-anthranil, 6-amino-2-anthranil, 7-amino-2-anthranil, 8-amino-2-anthranil, 9-amino-2-anthranil, 10-amino-2-anthranil, 1-amino-9-anthranil, 2-amino-9-anthranil, 3-amino-9-anthranil, 4-amino-9-anthranil, 10-amino-9-anthranil, 2-(N,N-dimethylamino)-1-anthranil, 3-(N,N-dimethylamino)-1-anthranil, 4-(N,N-dimethylamino)-1-anthranil, 5-(N,N-dimethylamino)-1-anthranil, 6-(N,N-dimethylamino)-1-anthranil, 7-(N,N-dimethylamino)-1-anthranil, 8-(N,N-dimethylamino)-1-anthranil, 9-(N,N-dimethylamino)-1-anthranil, 10-(N,N-dimethylamino)-1-anthranil, 1-(N,N-dimethylamino)-2- anthranil, 3-(N,N-dimethylamino)-2-anthranil, 4-(N,N-dimethylamino)-2-anthranil, 5-(N,N-dimethylamino)-2-anthranil, 6-(N,N-dimethylamino)-2-anthranil, 7-(N,N-dimethylamino)-2-anthranil, 8-(N,N-dimethylamino)-2-anthranil, 9-(N,N-dimethylamino)-2-anthranil, 10-(N,N-dimethylamino)-2-anthranil, 1-(N,N-dimethylamino)-9-anthranil, 2-(N,N-dimethylamino)-9-anthranil, 3-(N,N-dimethylamino)-9-anthranil, 4-(N,N-dimethylamino)-9-anthranil, 10-(N,N-dimethylamino)-9-anthranil, 2-(N,N-diphenylamino)-1-anthranil, 3-(N,N-diphenylamino)-1-anthranil, 4-(N,N-diphenylamino)-1-anthranil, 5-(N,N-diphenylamino)-1-anthranil, 6-(N,N-diphenylamino)-1-anthranil, 7-(N,N-diphenylamino)-1-anthranil, 8-(N,N-diphenylamino)-1-anthranil, 9-(N,N-diphenylamino)-1-anthranil, 10-(N,N-diphenylamino)-1-anthranil, 1-(N,N-diphenylamino)-2-anthranil, 3-(N,N-diphenylamino)-2-anthranil, 4-(N,N-diphenylamino)-2-anthranil, 5-(N,N-diphenylamino)-2-anthranil, 6-(N,N-diphenylamino)-2-anthranil, 7-(N,N-diphenylamino)-2-anthranil, 8-(N,N-diphenylamino)-2-anthranil, 9-(N,N-diphenylamino)-2-anthranil, 10-(N,N-diphenylamino)-2-anthranil, 1-(N,N-diphenylamino)-9-anthranil, 2-(N,N-diphenylamino)-9-anthranil, 3-(N,N-diphenylamino)-9-anthranil, 4-(N,N-diphenylamino)-9-anthranil, 10-(N,N-diphenylamino)-9-anthranil and the like.

Of these substituent groups, it is preferred for $R^1$ and $R^2$ to use a hydrogen atom, a halogen atom such as a bromine atom, an iodine atom or the like, a trialkylstannyl group such as a tributylstannyl group $(Sn(Bu-n)_3)$, a trialkylsilyl group such as a trimethylsilyl group $(SiMe_3)$, and the like.

In the formula [1], $R^3$-$R^6$ each independently represent —$OR^7$, —$SR^8$ or —$NR^9{}_2$ wherein $R^7$-$R^9$ each independently represent a hydrogen atom, an alkyl group having 1-10 carbon atoms or a phenyl group which may be substituted with W.

It will be noted that specific examples of the alkyl group having 1-10 carbon atoms and the phenyl group which may be substituted with W are those as indicated above.

Among them, an alkyl group having 1-10 carbon atoms, preferably 1-5 carbon atoms or a phenyl group is preferred as $R^7$-$R^9$.

In the formula [2], $R^{10}$ represents a hydrogen atom, a halogen atom, a cyano group, a nitro group, a hydroxyl group, a mercapto group, an amino group, a formyl group, a carboxyl group, an alkyl group having 1-10 carbon atoms, a haloalkyl group having 1-10 carbon atoms, an alkenyl group having 1-10 carbon atoms, an alkynyl group having 1-10 carbon atoms, an alkoxy group having 1-10 carbon atoms, an alkylthio group having 1-10 carbon atoms, a monoalkylamino group having 1-10 carbon atoms, a dialkylamino group having 1-10 carbon atoms, or a phenyl group which may be substituted with W. Specific examples of these substituent groups are just as indicated above.

Of these, $R^{10}$ preferably includes a hydrogen atom and an alkyl group having 1-10 carbon atoms, of which a hydrogen atom is more preferred.

$R^{11}$ and $R^{12}$ represent —$SR^8$ or —$NR^9{}_2$ wherein $R^8$ and $R^9$ are preferably an alkyl group having 1-10 carbon atoms, more preferably 1-5 carbon atoms or a phenyl group, like the above case.

Specific examples of the compounds represented by the formulas [1] and [2] include those indicated below although not limited thereto.

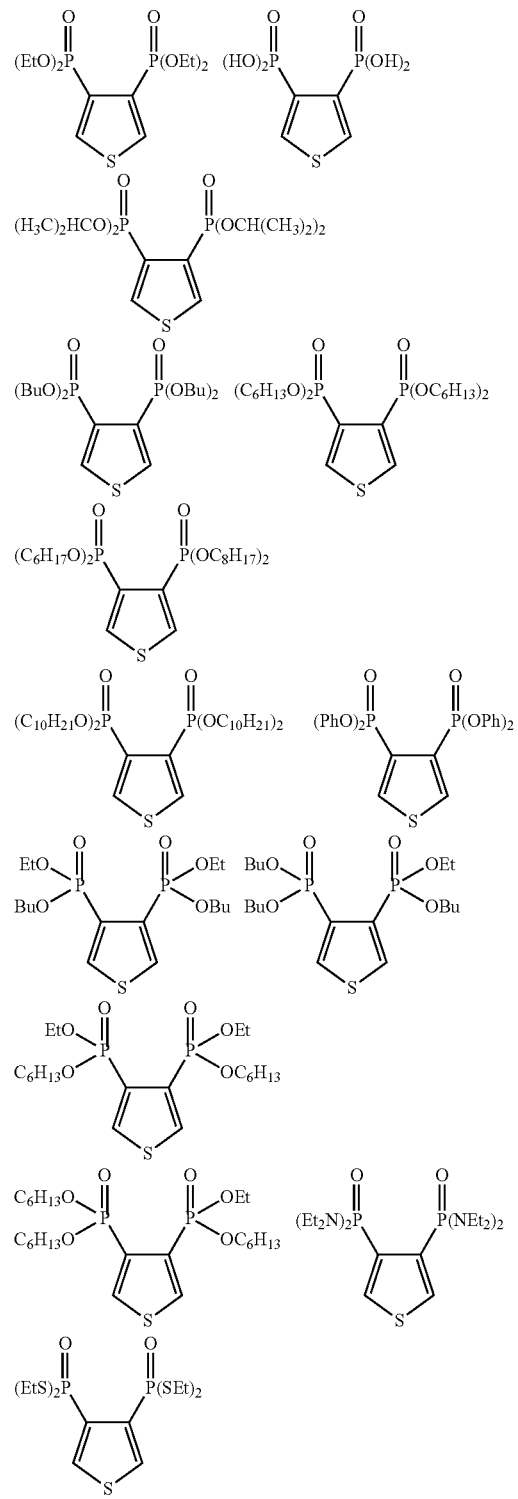

[Chemical Formula 34]

[Chemical Formula 35]

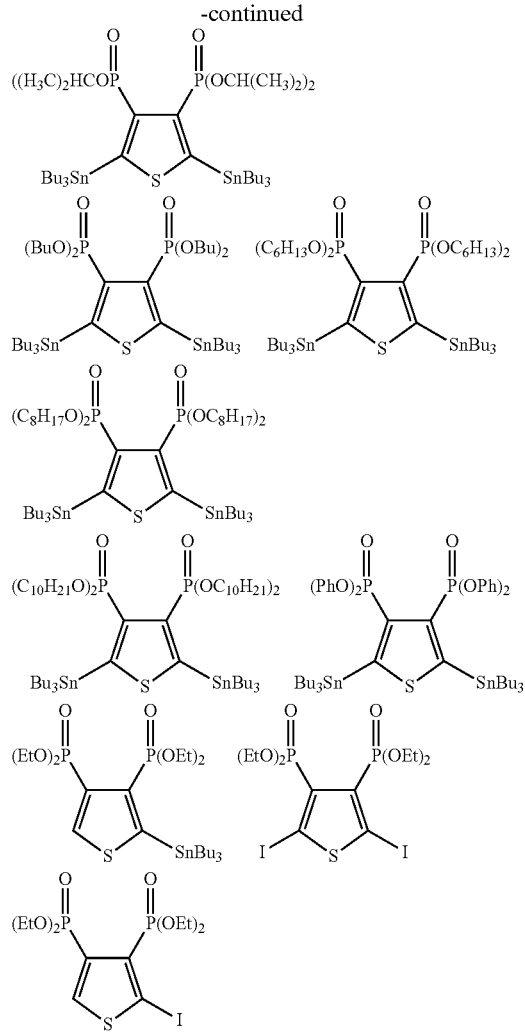
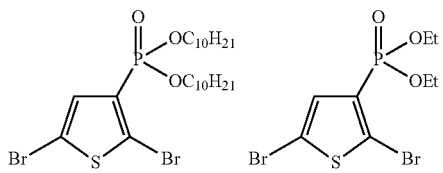
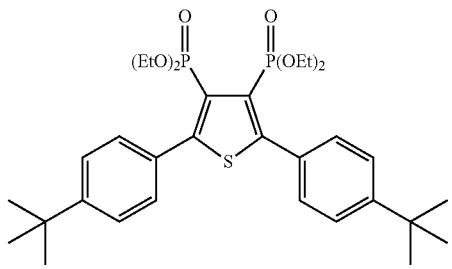

-continued
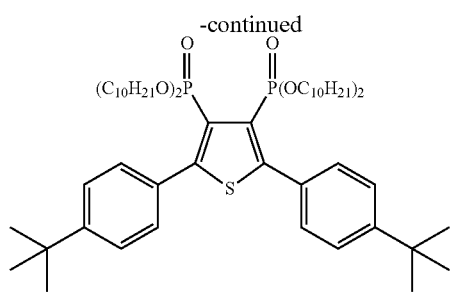
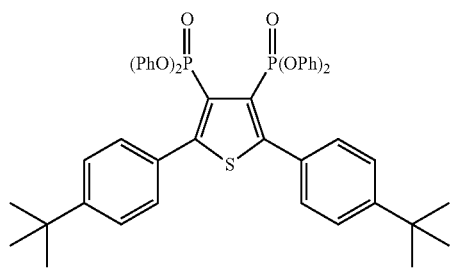
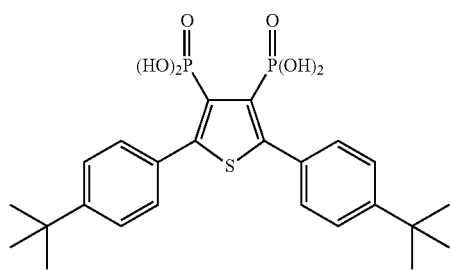
[Chemical Formula 39]
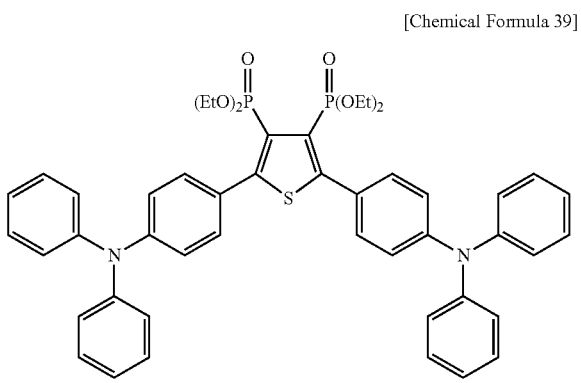
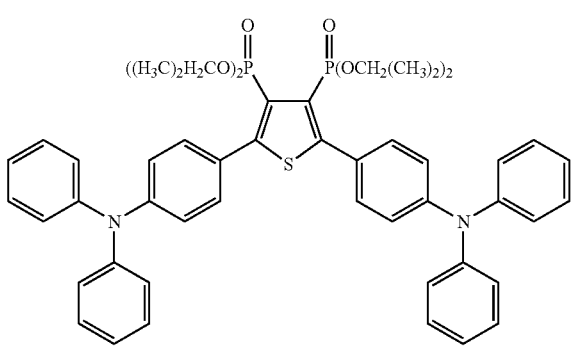
-continued
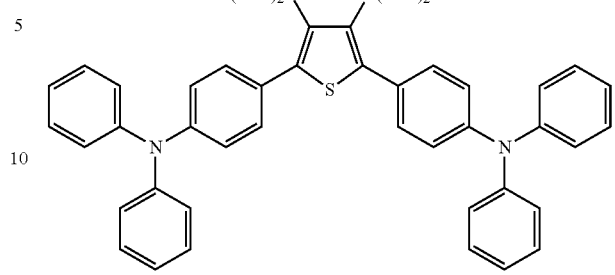
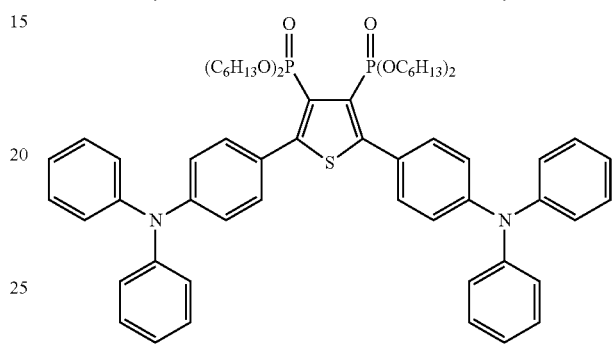
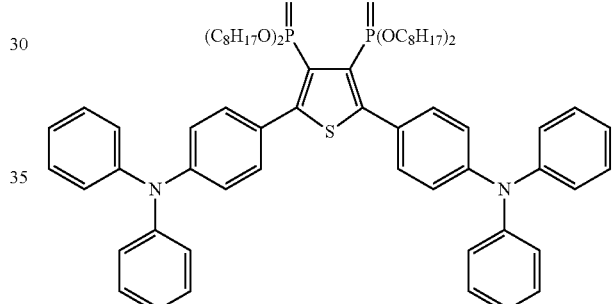
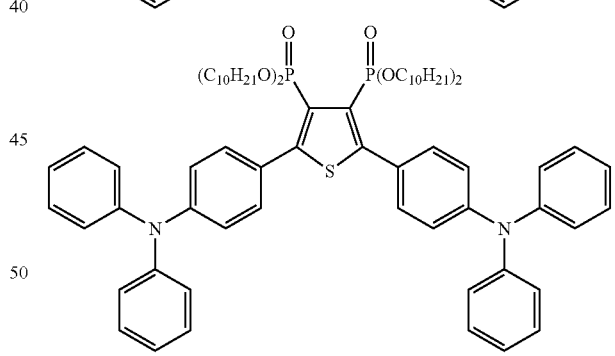
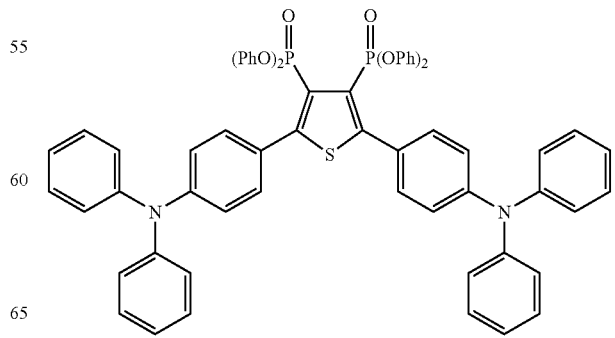

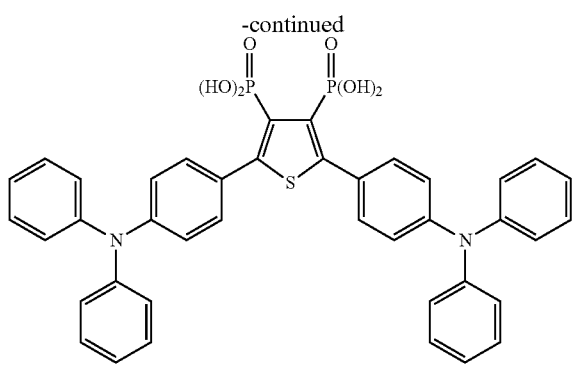
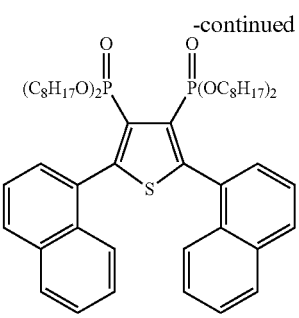
[Chemical Formula 40]
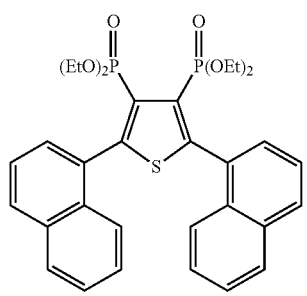
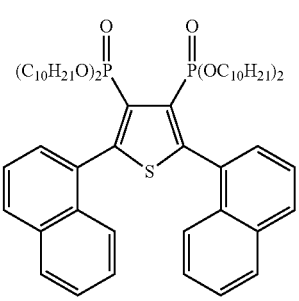
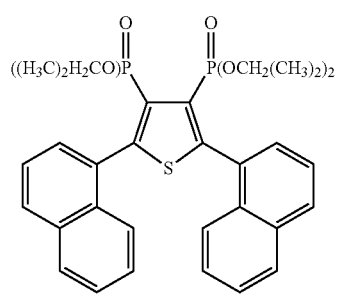
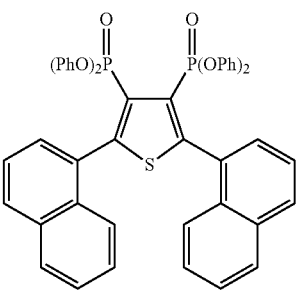
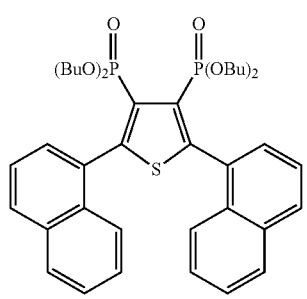
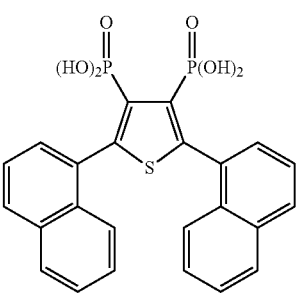
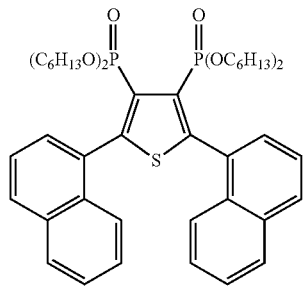
[Chemical Formula 41]
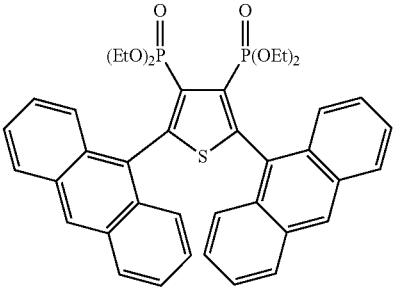

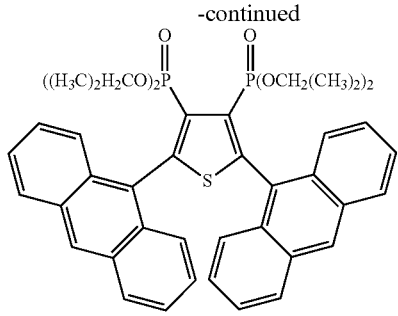
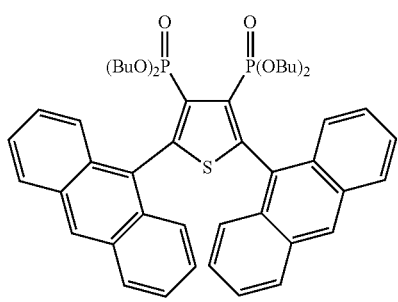
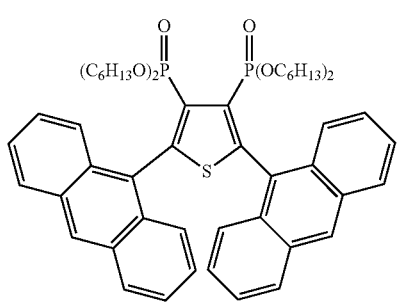
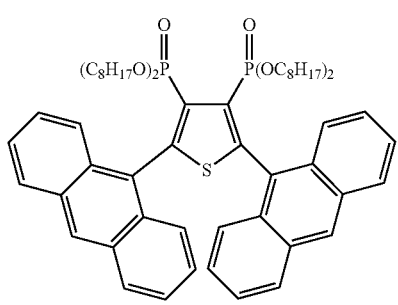
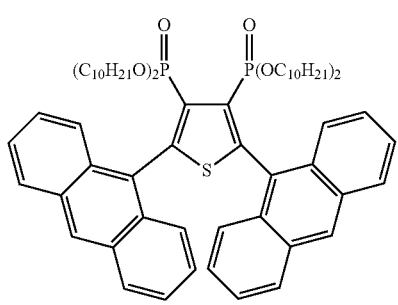
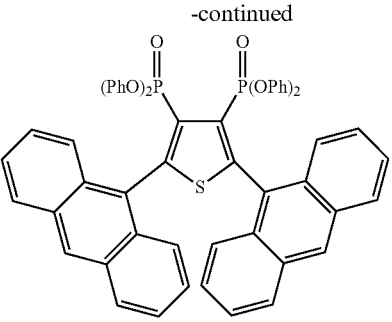
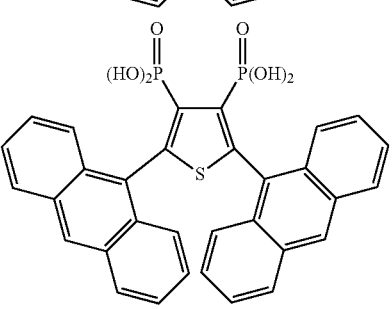
[Chemical Formula 42]
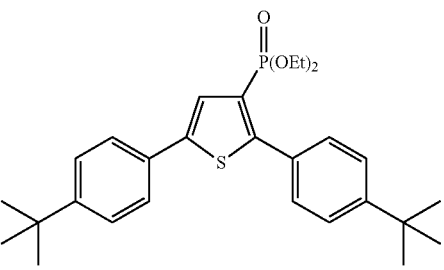
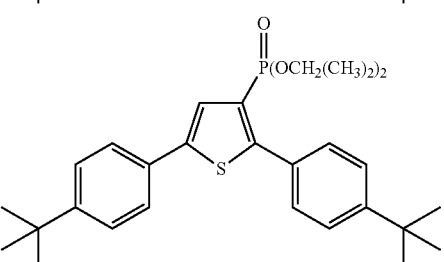
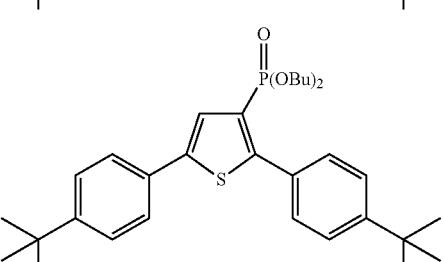
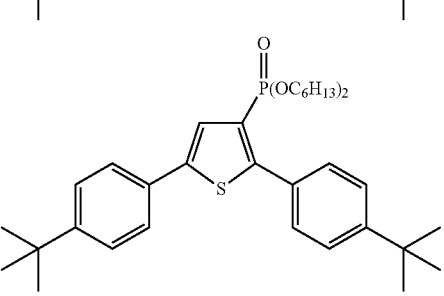

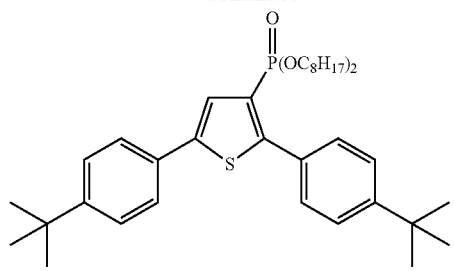
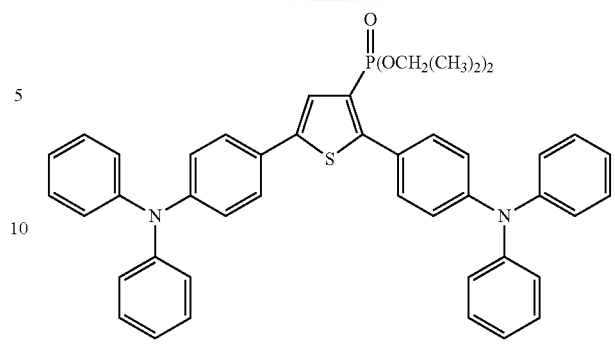
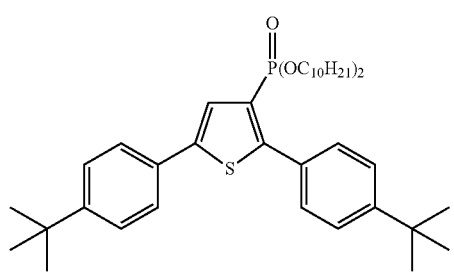
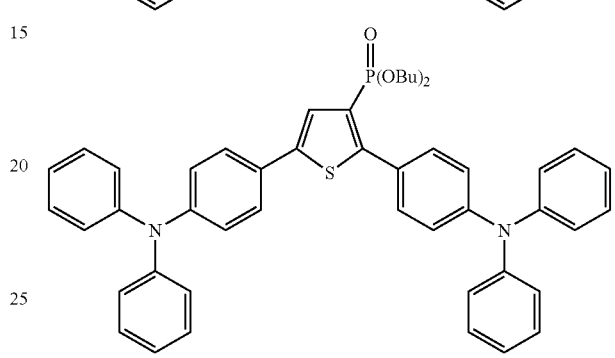
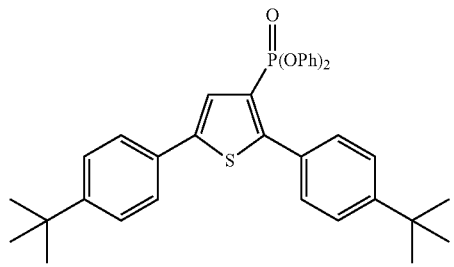
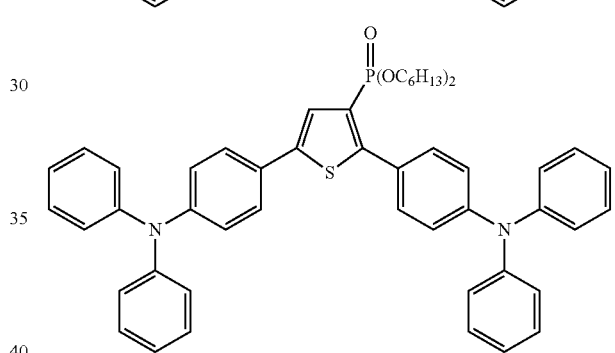
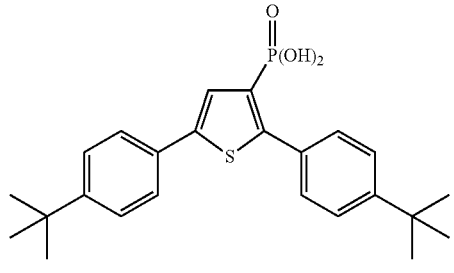
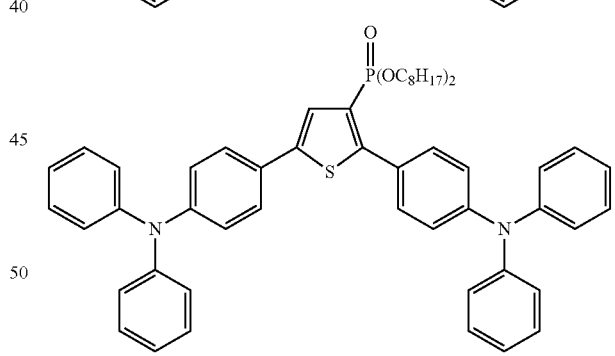
[Chemical Formula 43]
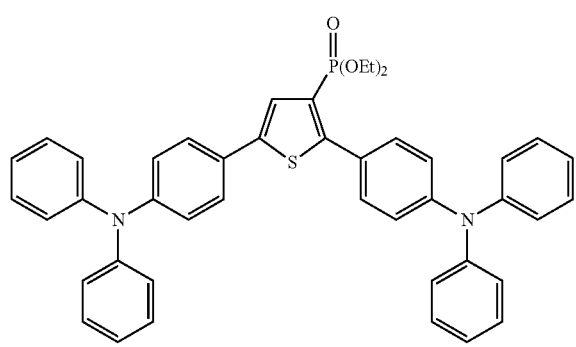
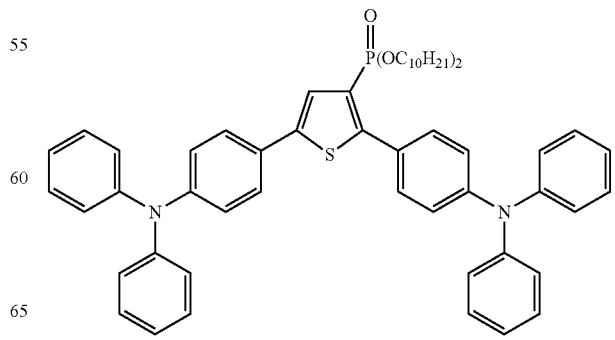

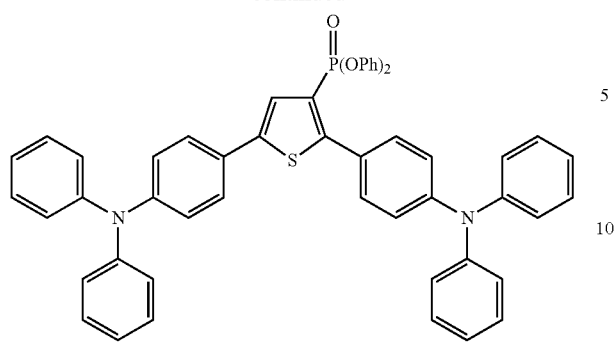
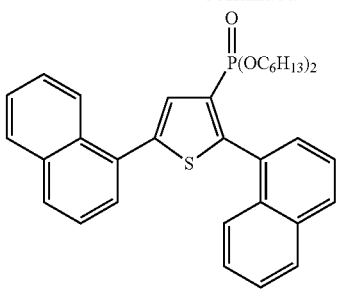
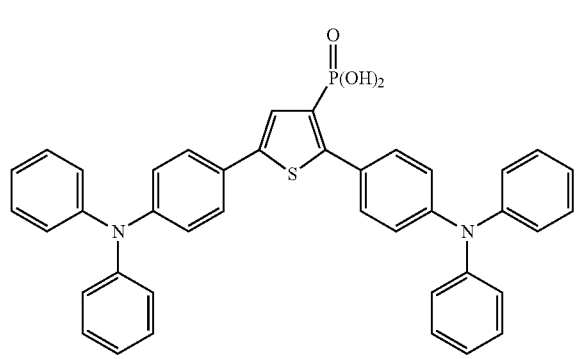
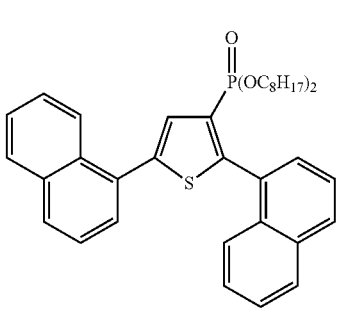
[Chemical Formula 44]
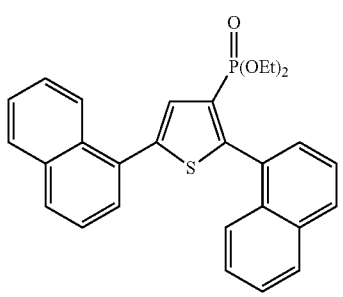
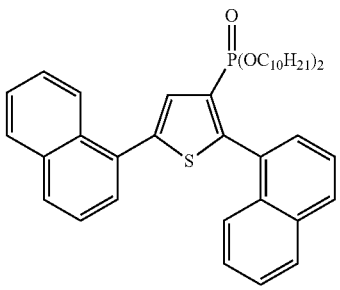
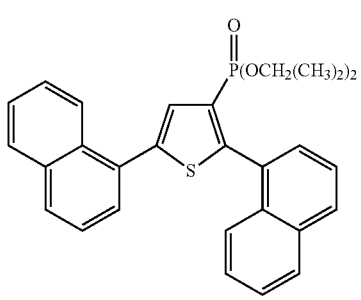
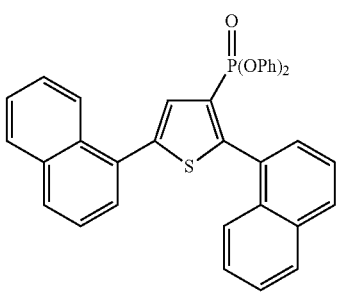
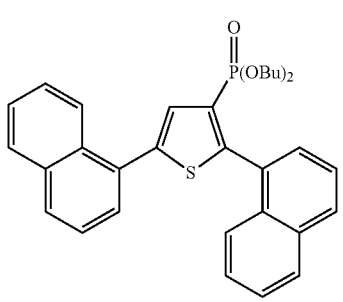
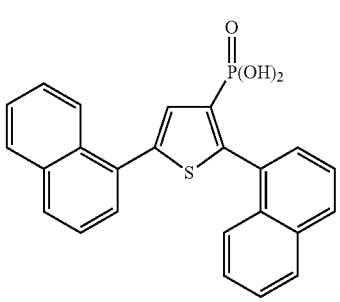

[Chemical Formula 45]

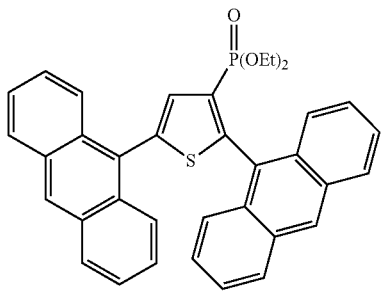

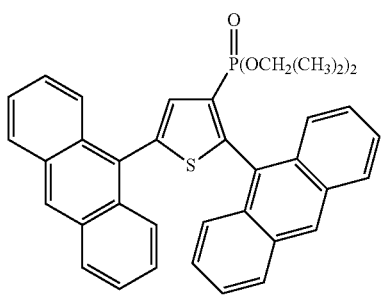

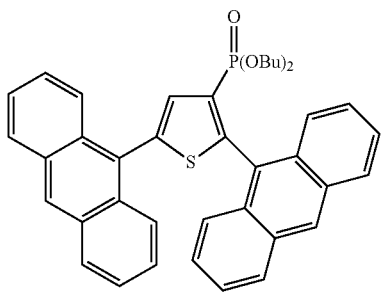

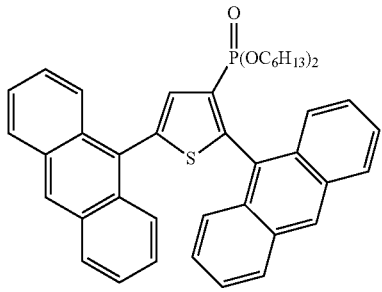

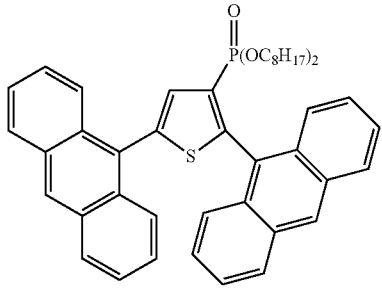

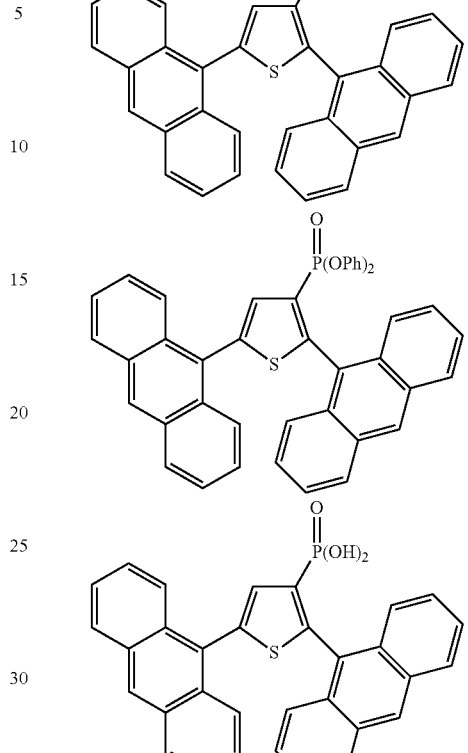

The phosphorylthiophene oligomer compounds of the invention are represented by the above formulas [3] and [13], and the phosphorylthiophene polymer compounds are represented by the above formulas [29] and [30].

In the phosphorylthiophene oligomer or polymer compounds of the invention, $R^3$-$R^6$ are as indicated in the above formula [1]. In this case, $R^7$-$R^9$ in the —$OR^7$, —$SR^8$ or —$NR^9{}_2$ are preferably an alkyl group having 1-10 carbon atoms, more preferably 1-5 carbon atoms, or a phenyl group, like the above case.

$R^{13}$-$R^{16}$ each independently represent —$OR^7$, —$SR^8$ or —$NR^9{}_2$ wherein $R^7$-$R^9$ are preferably an alkyl group having 1-10 carbon atoms, more preferably 1-5 carbon atoms, or a phenyl group, like the above case.

$R^{10}$ and $R^{17}$ each independently represent a hydrogen atom, a halogen atom, a cyano group, a nitro group, a hydroxyl group, a mercapto group, an amino group, a formyl group, a carboxyl group, an alkyl group having 1-10 carbon atoms, a haloalkyl group having 1-10 carbon atoms, an alkenyl group having 1-10 carbon atoms, an alkynyl group having 1-10 carbon atoms, an alkoxy group having 1-10 carbon atoms, an alkylthio group having 1-10 carbon atoms, a monoalkylamino group having 1-10 carbon atoms, a dialkylamino group having 1-10 carbon atoms, or a phenyl group which may be substituted with W. Specific examples of these substituent groups are just as those indicated above.

Of these, a hydrogen atom or an alkyl group having 1-10 carbon atoms is preferred as $R^{10}$ and $R^{17}$, of which a hydrogen atom is more preferred.

Z in the formulas [3] and [29] is at least one divalent organic group selected from those of the above formulas [4] to [12], of which a divalent organic group represented by the formula [4] is preferred. $R^{18}$-$R^{40}$ in the formulas [4] to [12] each independently represent a hydrogen atom, an alkyl group having 1-10 carbon atoms, a haloalkyl group having 1-10 carbon atoms, an alkoxy group having 1-10 carbon atoms, an alkylthio group having 1-10 carbon atoms, a dialkylamino group having 1-10 carbon atoms, or a phenyl group which may be substituted with W, wherein W has the same meaning as defined before. $R^{41}$ represents a hydrogen atom, an alkyl group having 1-10 carbon atoms, a haloalkyl group having a 1-10 carbon atoms, an alkoxy group having 1-10 carbon atoms or a phenyl group which may be substituted with W' wherein W'has the same meaning as defined before.

Specific examples of phenyl group which may be substituted with W' include phenyl, o-methylphenyl, m-methylphenyl, p-methylphenyl, o-trifluoromethylphenyl, m-trifluoromethylphenyl, p-trifluoromethylphenyl, p-ethylphenyl, p-i-propylphenyl, p-t-butylphenyl, o-methoxyphenyl, m-methoxyphenyl, o-trifluoromethoxyphenyl, p-trifluoromethoxyphenyl, 3,5-dimethylphenyl, 3,5-bistrifluoromethylphenyl, 3,5-dimethoxyphenyl, 3,5-bistrifluoromethoxyphenyl, 3,5-diethylphenyl, 3,5-di-i-propylphenyl, 2,4,6-trimethylphenyl, 2,4,6-tristrifluoromethylphenyl, 2,4,6-trimethoxyphenyl, 2,4,6-tristrifluoromethoxyphenyl and the like.

It will be noted that specific examples of other substituent groups of $R^{18}$-$R^{40}$ are those indicated before.

In the formula [3], m, n and o are each independently 0 or an integer of 1 or over, p is an integer of 1 or over provided that m+n+o≧1 and 2≦m+n+o≦50 are satisfied. Especially, it is preferred that 2≦m+n+o+p≦10 and any two of m, n and o are 0.

In the formula [13], m', n' and o' are each independently 0 or an integer of 1 or over and 2 μm'+n'+o'≦50 is satisfied. Especially, it is preferred that 2≦m'+n'+o'≦10 and any two of m', n' and o' are 0.

In the formula [29], m", n" and o" are each independently 0 or an integer of 1 or over, p' is 0 or an integer of 1 or over provided that m"+n"+o"≧2 and 50<m"+n"+o"+p'<5000 are satisfied. Especially, it is preferred that m"+n"+o"≧10 and 50<m"+n"+o"+p'<500.

In the formula [30], m'", n'" and o'" are each independently 0 or an integer of 1 or over and 50<m'"+n'"+o'"<5000 is satisfied. Especially, it is preferred that 50<m'"+n'"+o'"<500.

It will be noted that the opposite terminal ends of the respective phosphorylthiophene oligomer and polymer compounds are each independently a hydrogen atom, a halogen atom, a monoalkylamino group having 1-10 carbon atoms, a dialkylamino group having 1-10 carbon atoms, a phenyl group which may be substituted with W, a naphthyl group which may be substituted with W, an anthranil group which may be substituted with W, a trialkylstannyl group having 1-10 carbon atoms, or a trialkylsilyl group having 1-10 carbon atoms, of which a hydrogen atom, a bromine atom, an iodine atom or a tributylstannyl group is preferred.

The bisphosphorylthiophene compounds of the invention are represented by the above formulas [25] to [28].

In the formula [25], $R^{51}$, $R^{52}$, $R^{53}$ and $R^{54}$ are each independently a halogen atom, —$OR^7$, —$SR^8$ or —$NR^9{}_2$. $R^7$-$R^9$ are as defined before, for which an alkyl group having 1-10 carbon atoms, particularly, 1-5 carbon atoms and a phenyl group are preferred.

$R^{55}$ and $R^{56}$ are each independently represent a hydrogen atom, a halogen atom, a cyano group, a nitro group, a hydroxyl group, a mercapto group, an amino group, a formyl group, a carboxyl group, an alkyl group having 1-10 carbon atoms, a haloalkyl group having 1-10 carbon atoms, an alkenyl group having 1-10 carbon atoms, an alkynyl group having 1-10 carbon atoms, an alkoxy group having 1-10 carbon atoms, an alkylthio group having 1-10 carbon atoms, a monoalkylamino group having 1-10 carbon atoms, a dialkylamino group having 1-10 carbon atoms, or a phenyl group which may be substituted with W. Specific examples of these substituent groups are as defined before, of which a hydrogen atom and an alkyl group having 1-10 carbon atoms are preferred as $R^{55}$ and $R^{56}$, of which a hydrogen atom is more preferred.

Specific examples of the thiophene compounds represented by the formulas [3], [13] and [25] to [28] are those indicated below although not limited thereto.

[Chemical Formula 46]

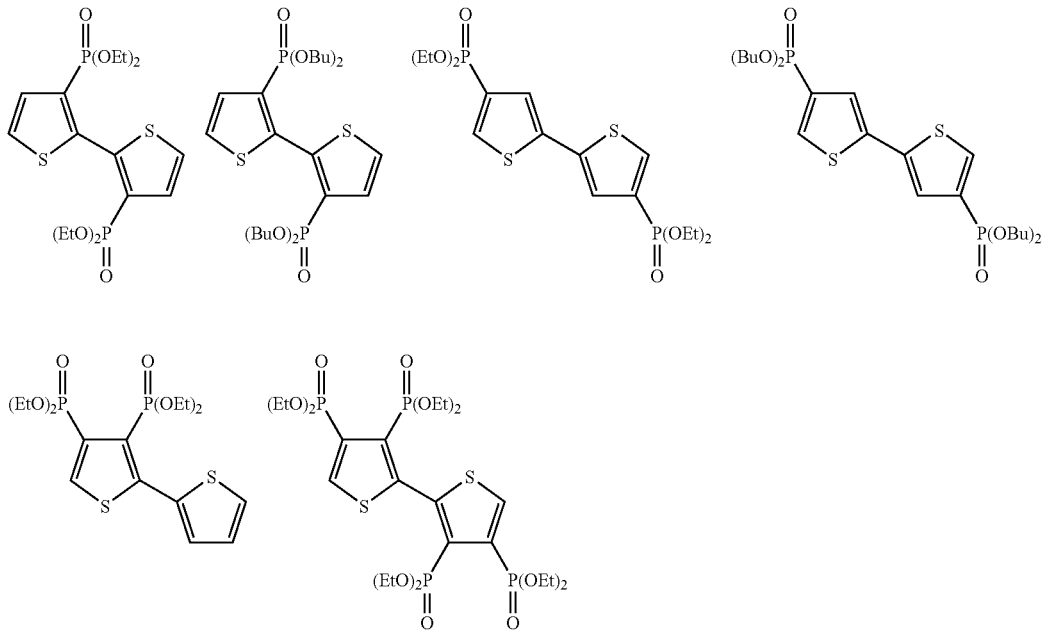

[Chemical Formula 47]
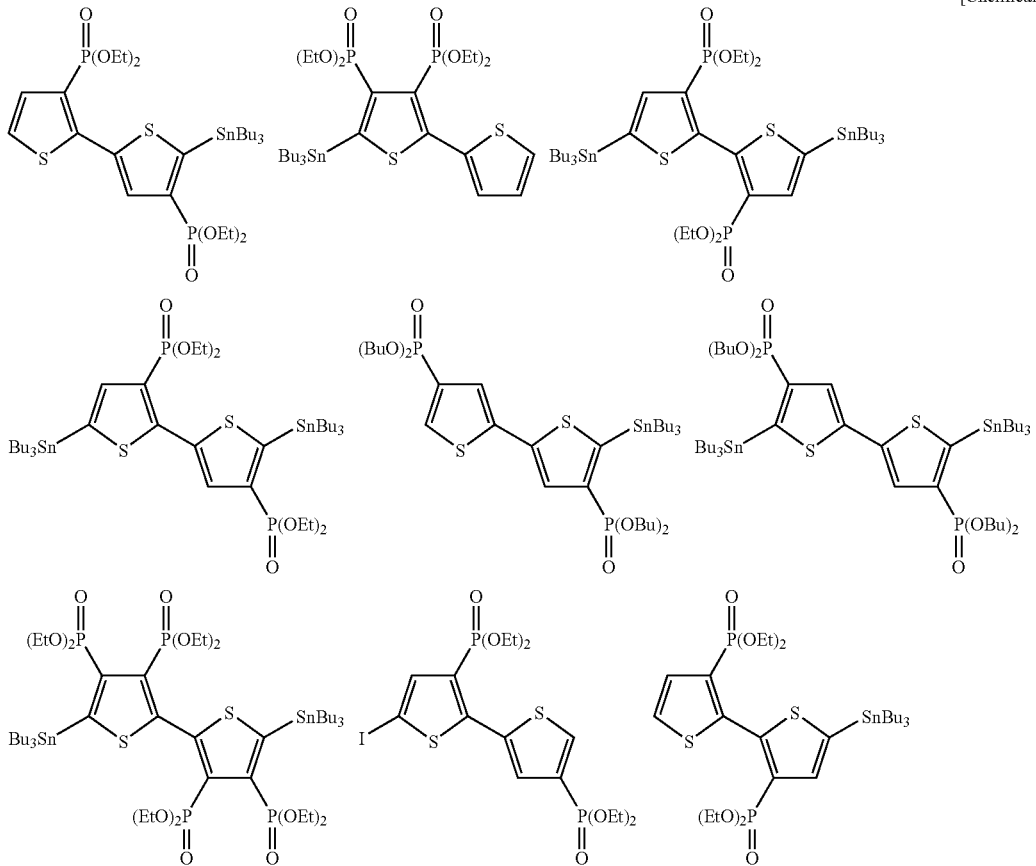
[Chemical Formula 48]
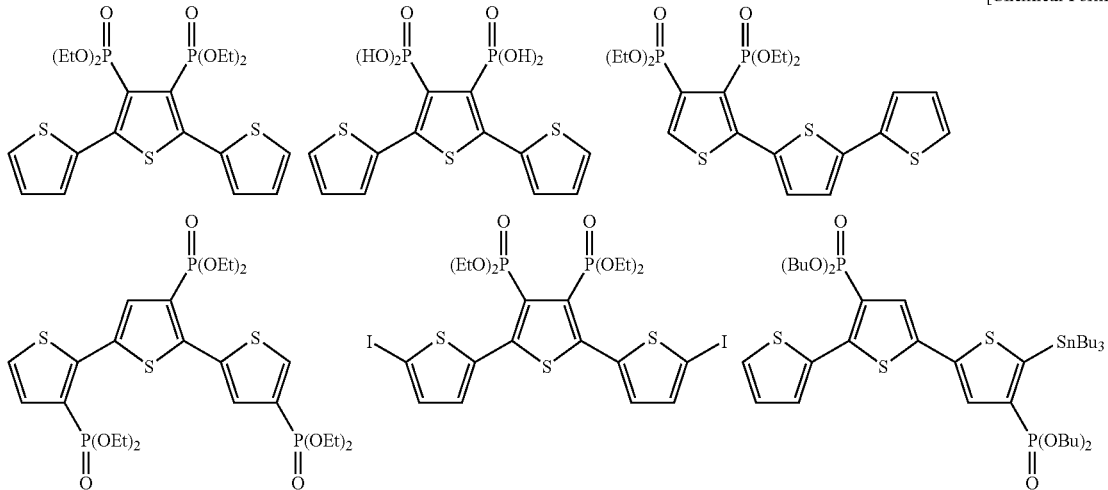
[Chemical Formula 49]
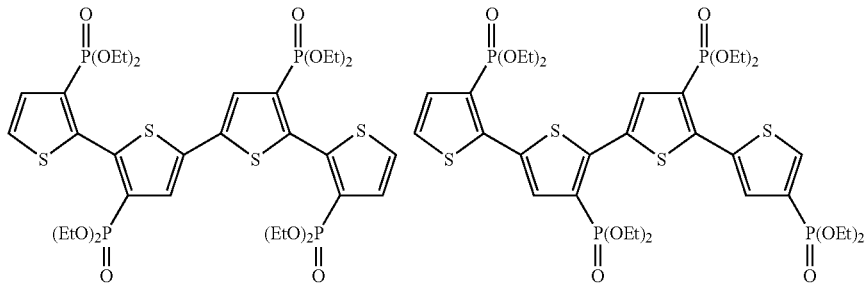

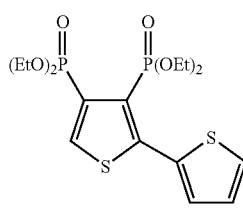
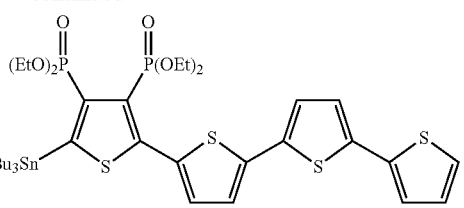
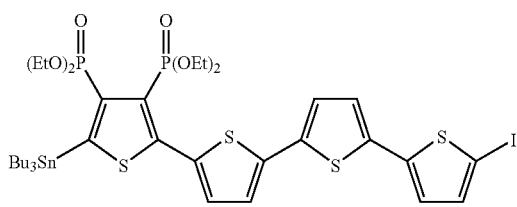
[Chemical Formula 50]
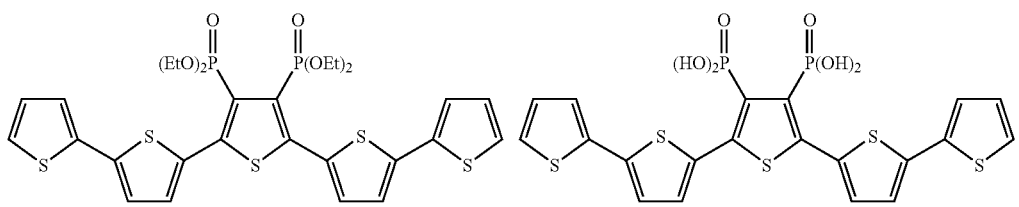
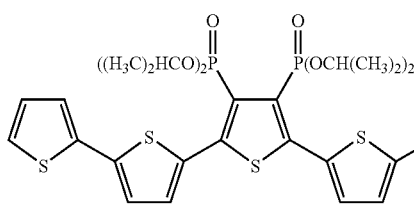
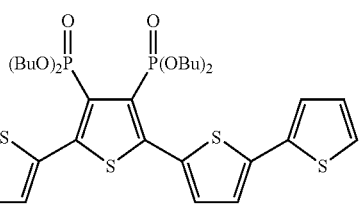
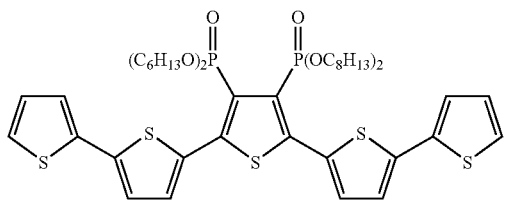
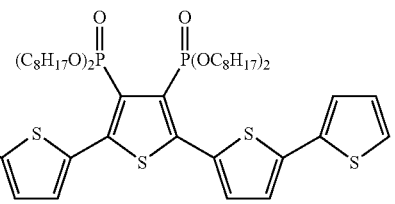
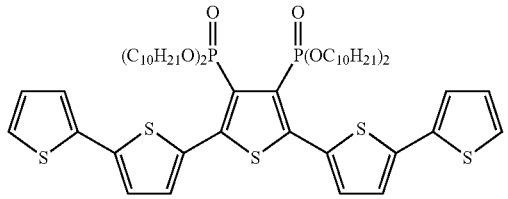
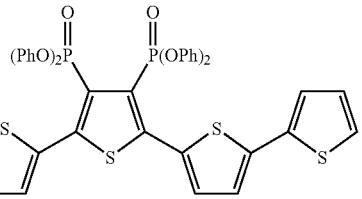
[Chemical Formula 51]
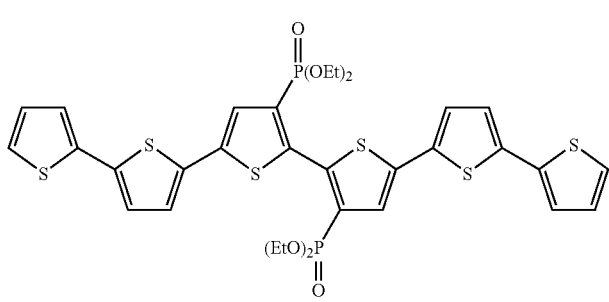

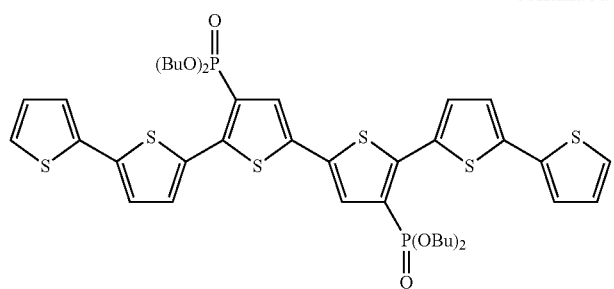
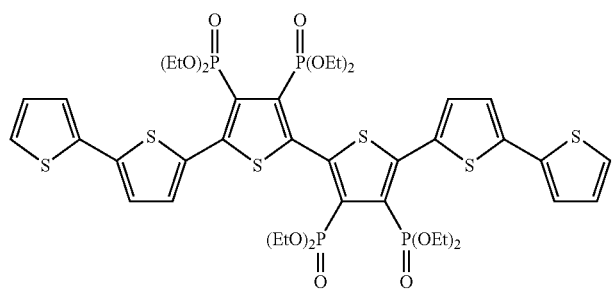
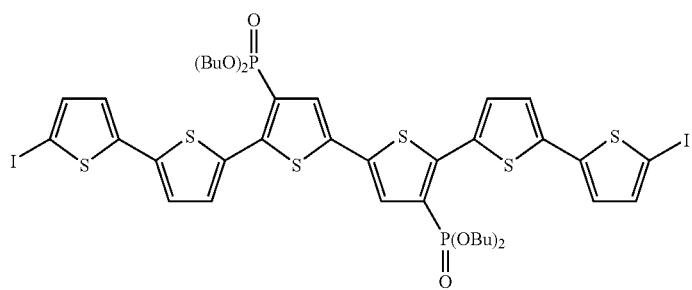
[Chemical Formula 52]
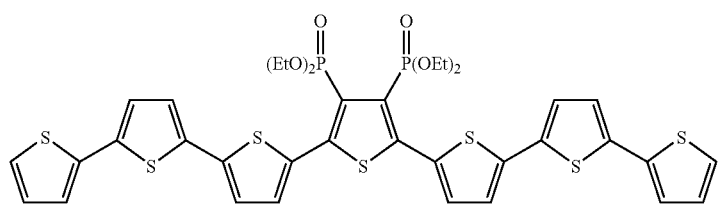
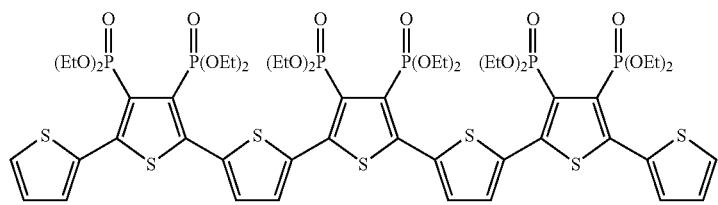
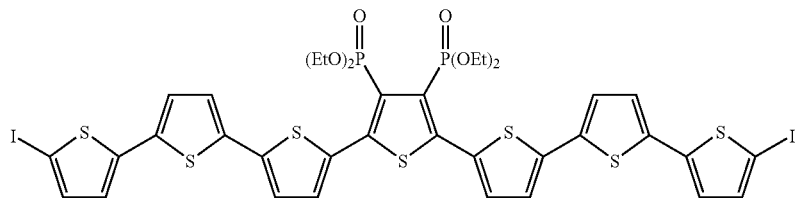

-continued
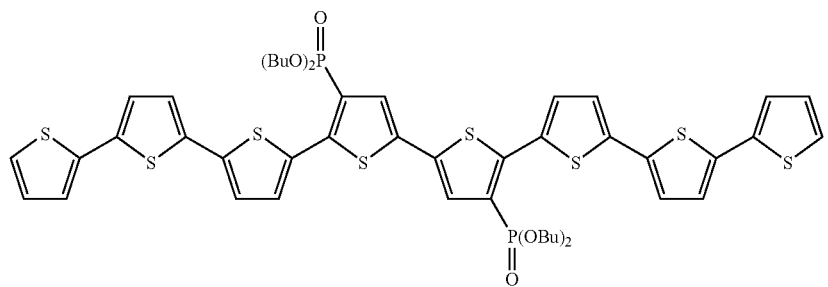
[Chemical Formula 53]
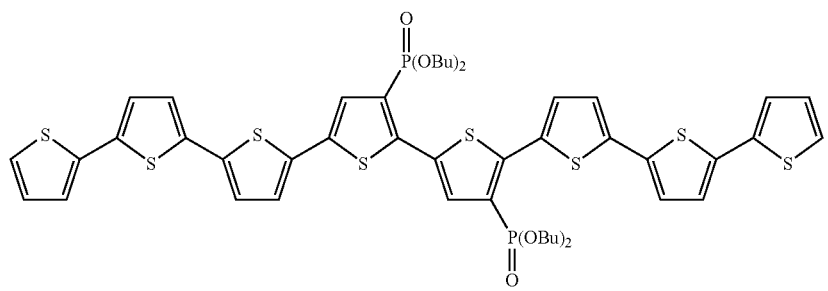
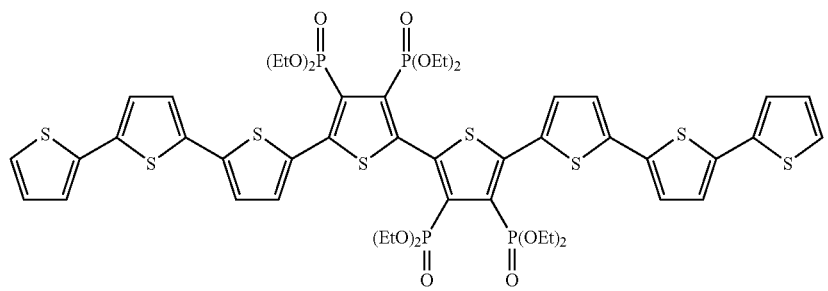
[Chemical Formula 54]
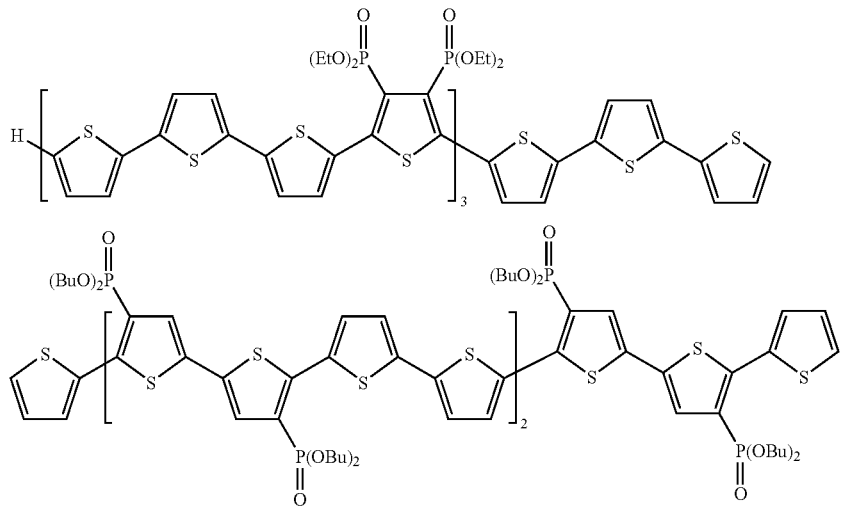
[Chemical Formula 55]
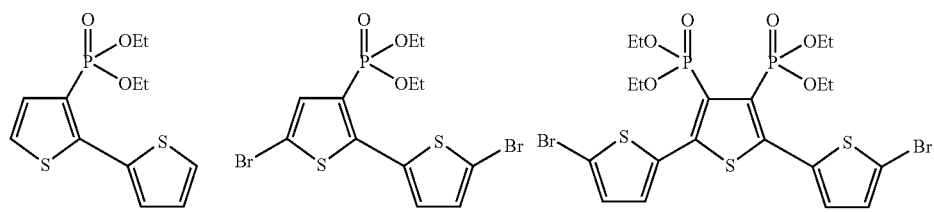

-continued
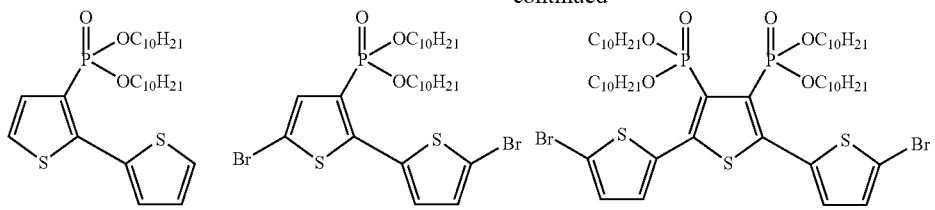
[Chemical Formula 56]
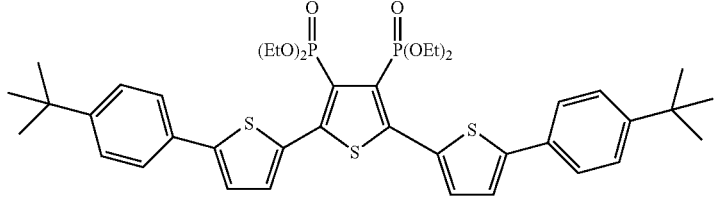
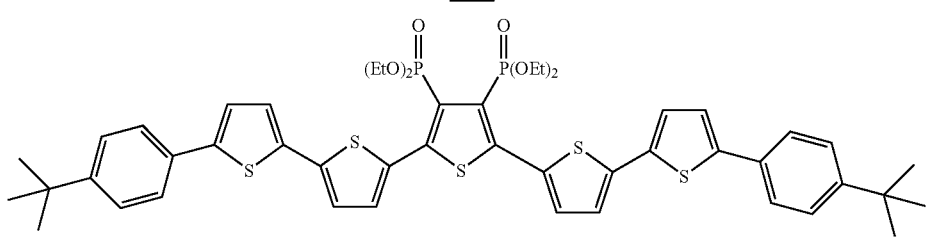
[Chemical Formula 57]
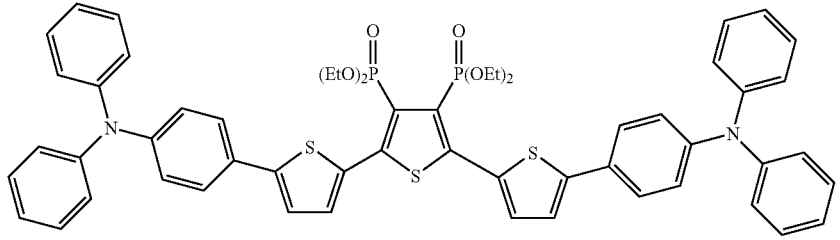
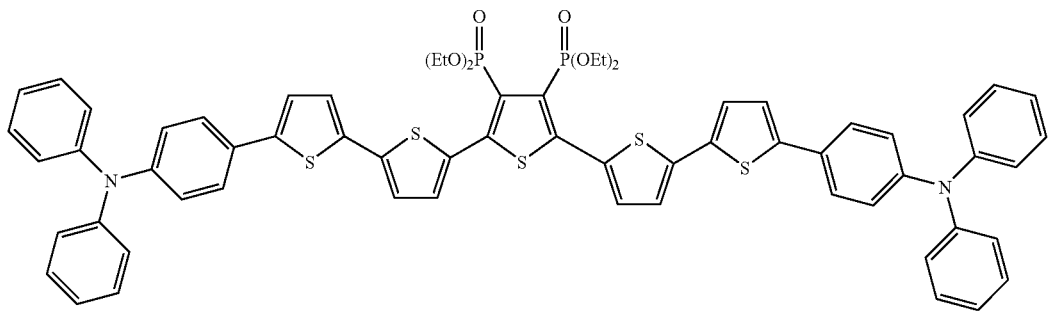
[Chemical Formula 58]
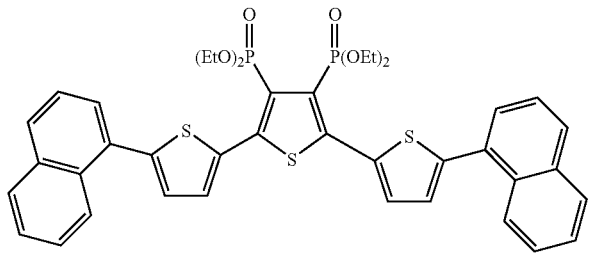
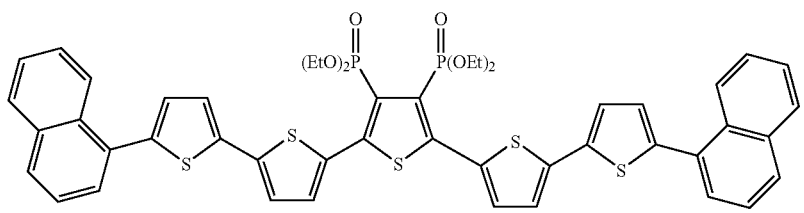

-continued
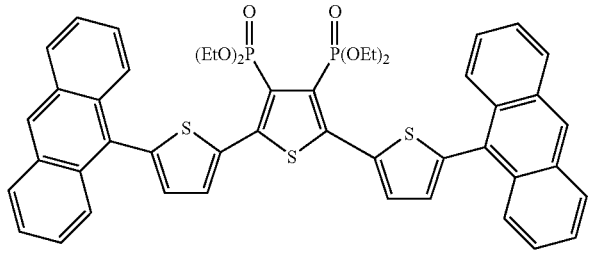
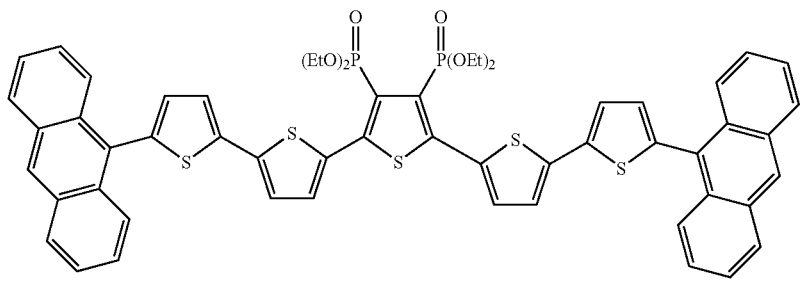
[Chemical Formula 59]
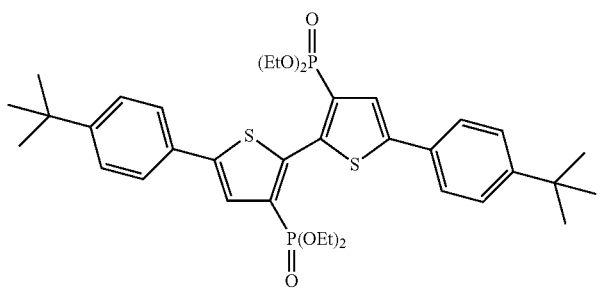
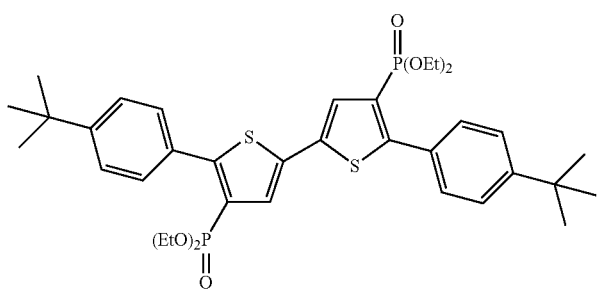
[Chemical Formula 60]
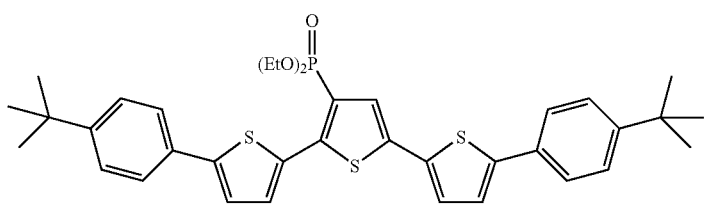
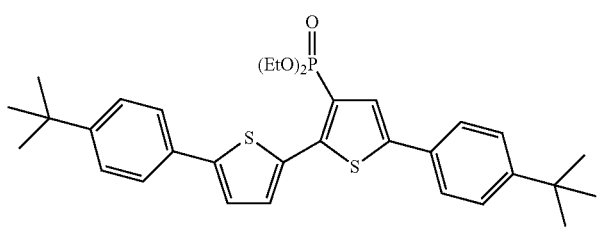

-continued
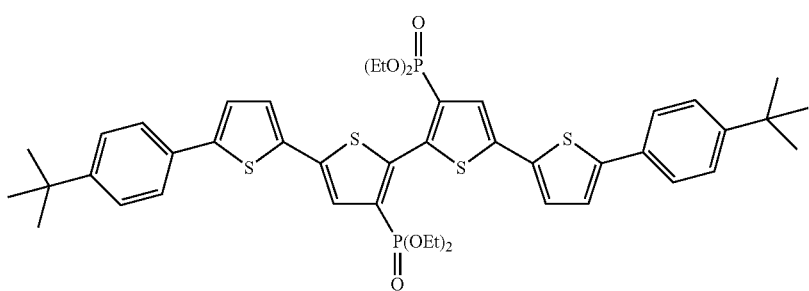
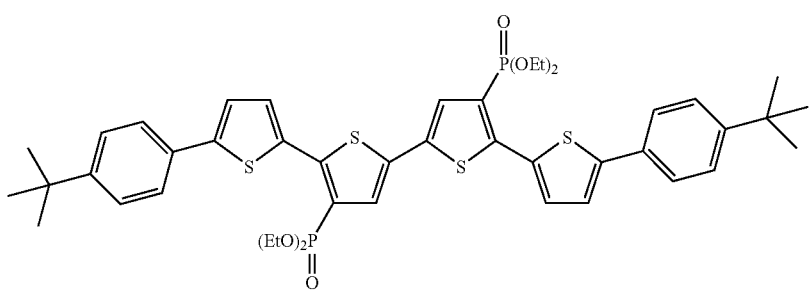
[Chemical Formula 61]
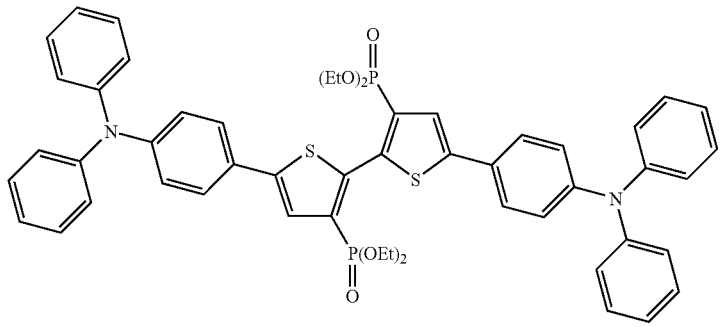
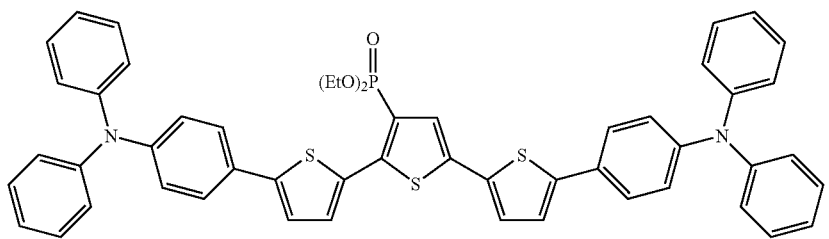
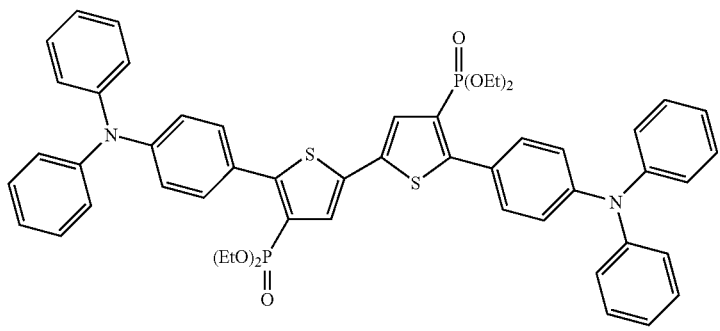

-continued
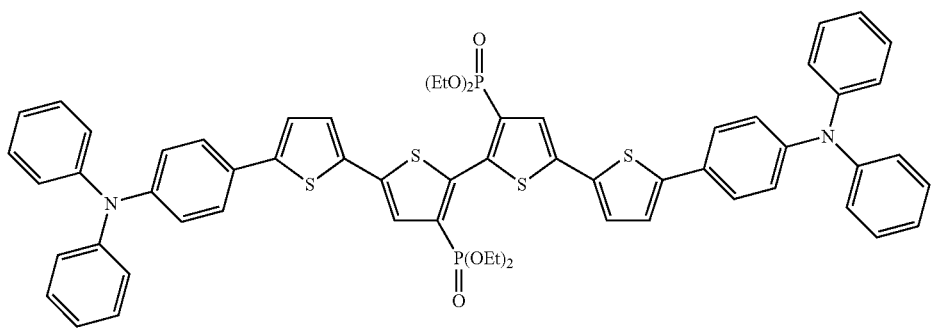
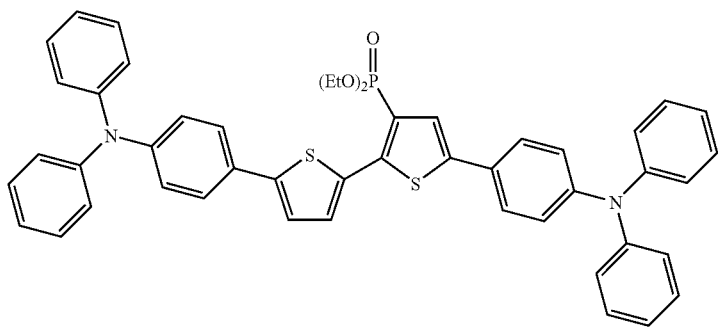
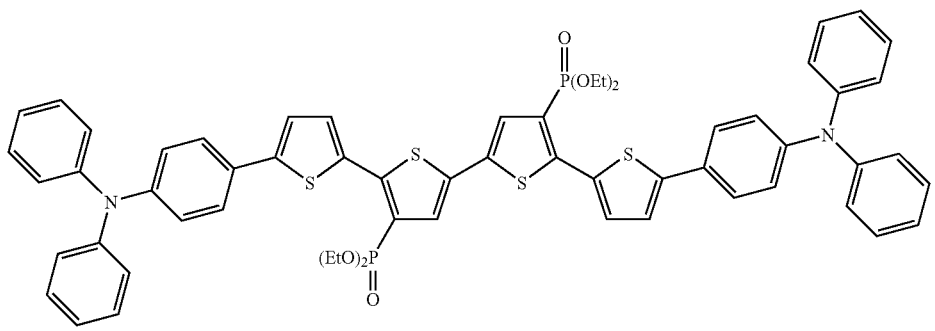
[Chemical Formula 62]
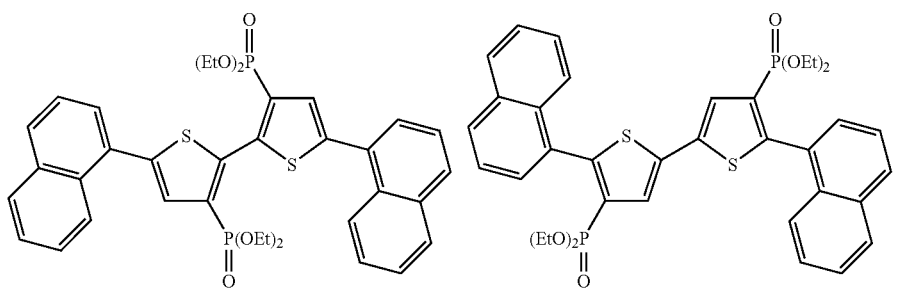
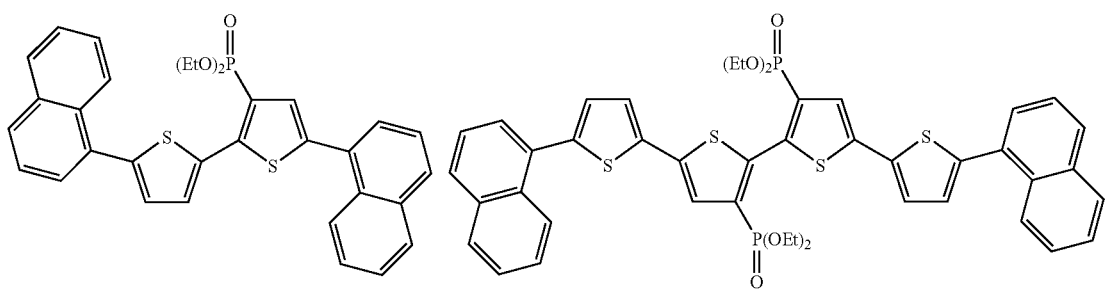

-continued
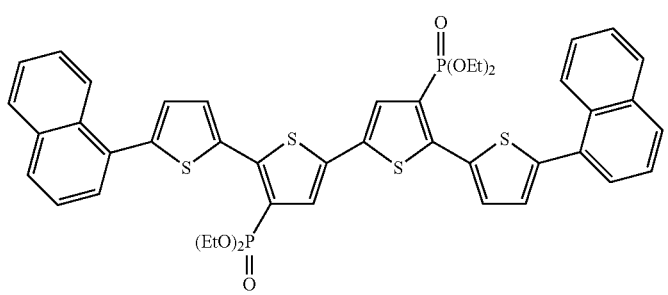
[Chemical Formula 63]
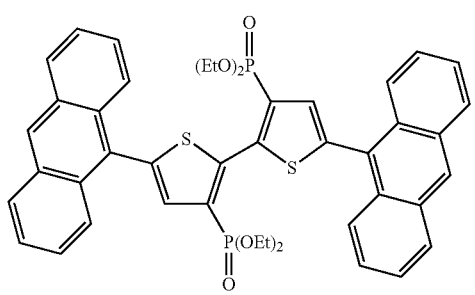
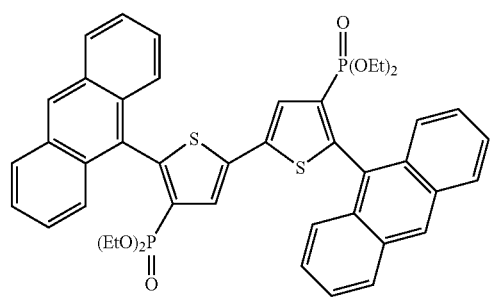
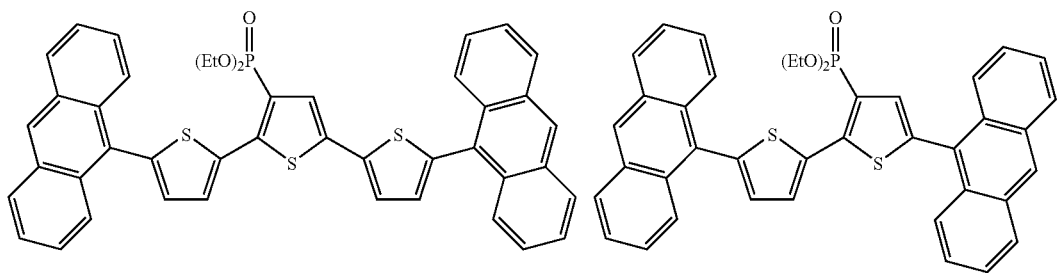
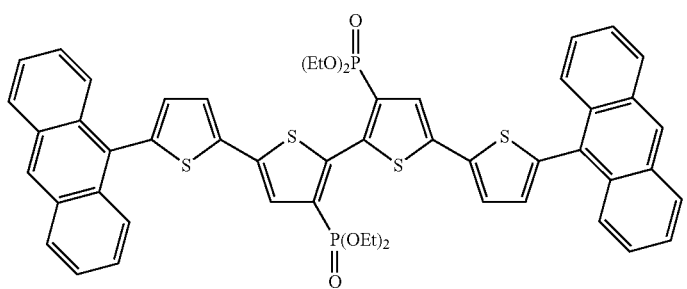
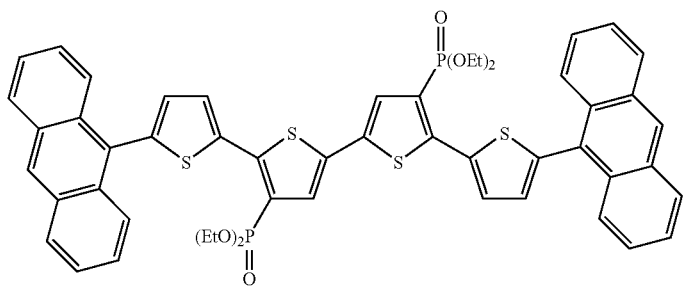

Next, the processes for producing the phosphorylthiophene compounds of the invention are illustrated using the compounds of the formulas [20] and [23] by way of example.

The compound of the formula [20] can be obtained according to a process (A) wherein a butynediol compound represented by the following formula [14] is used as a starting material as shown in the following scheme and cyclized.

[Chemical Formula 64]

First step

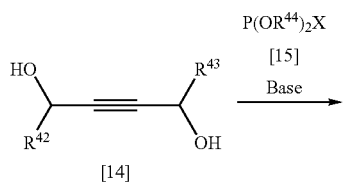

Second step

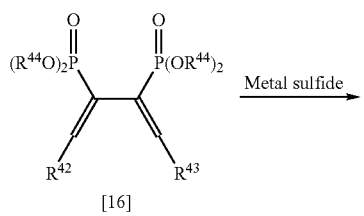

Third step

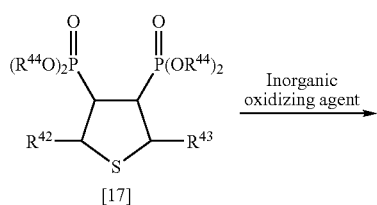

[Chemical Formula 65]

Fourth step

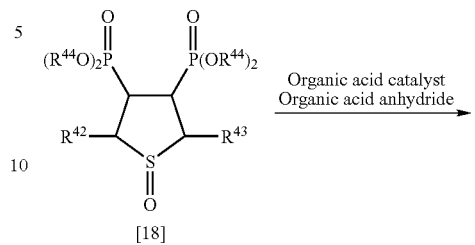

Fifth step

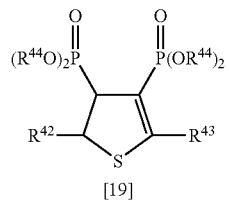

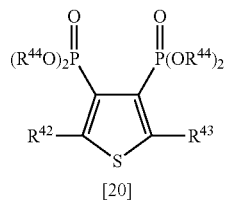

[1] First Step

This step is one wherein a butynediol compound represented by the formula [14] and a phosphate compound represented by the formula [15] are reacted in the presence of a base to prepare a bisphosphorylbutadiene compound represented by the formula [16].

For the phosphate compound, mention is made, for example, of phosphate compounds having an alkyl group having 1-10 carbon atoms such as chlorodimethyl phosphite, chlorodiethyl phosphate, chlorodi-n-propyl phosphate, chlorodi-n-butyl phosphate and the like, and phosphite compounds having a phenyl group such as chlorodiphenyl phosphite and the like. Of these, chlorodimethyl phosphite and chlorodiethyl phosphate are preferred from an economical standpoint.

The amount of the phosphate compound preferably ranges 0.1 to 5 times by mole, more preferably 1.8 to 2.2 times by mole, relative to the butynediol compound serving as a substrate.

This reaction should preferably be carried out in the presence of a base. Usable bases include, for example, alkylamines such as diethylamine, triethylamine, diisopropylamine, diisopropylethylamine, di-n-butylamine and the like, aromatic amines such as pyridine, picoline and the like, and inorganic bases such as potassium carbonate and the like. Of these, triethylamine is preferred.

The amount of the base is preferably in the range of 1 to 10 times by mole, more preferably 1.8 to 2.2 times by mole, relative to the butynediol compound serving as a substrate.

Various types of solvents may be used as a reaction solvent so far as they do not influence the reaction. In particular, halogenated hydrocarbons such as methylene chloride, chloroform, 1,2-dichloroethane and the like, and ether compound such as tetrahydrofuran (THF), 1,4-dioxane, 1,2-dimethoxyethane, diethylene glycol dimethyl ether and the like are preferred, of which methylene chloride is most preferred.

The amount of the solvent is preferably in the range of 1 to 100 times by weight, more preferably 20 to 50 times by weight, relative to the butynediol compound serving as a substrate.

The reaction temperature generally at −100 to 100° C., preferably −100 to 30° C.

The progress of the reaction can be confirmed by thin-layer chromatography or gas chromatography.

After completion of the reaction, ordinary after-treatments are carried out, followed by purification, if necessary, to obtain an intended substance.

[2] Second step

This step is one wherein a bisphosphorylbutadiene compound represented by the formula [16] and a metal sulfide are reacted to prepare a 3,4-bisphosphorylthiolane compound represented by the formula [17].

Examples of the metal sulfide include sodium sulfide, potassium sulfide and the like, of which sodium sulfide is preferred in view of the reactivity thereof.

The amount of a metal sulfide is preferably in the range of 0.8 to 3 times by mole, more preferably 1.0 to 1.3 times by mole, relative to the bisphosphorylbutadiene compound serving as a substrate.

For the reaction solvent, alcohol solvents are preferred including, for example, alkyl alcohols having 1-10 carbon atoms such as methanol, ethanol, n-propanol, i-propanol, n-octanol, n-decanol and the like, of which ethanol is preferred.

The amount of the solvent is in the range of 1 to 100 times by weight, preferably 20 to 50 times by weight, relative to the bisphosphorylbutadiene serving as a substrate.

The reaction temperature generally ranges −100 to 100° C., preferably 0 to 40° C.

The progress of the reaction can be confirmed by thin-layer chromatography.

After completion of the reaction, ordinary after-treatments are carried out, followed by purification, if necessary, to obtain an intended substance.

[3] Third step

This step is one wherein a 3,4-bishosphorylthiolane compound represented by the formula [17] and an inorganic oxidizing agent are reacted to prepare a 3,4-bisphorphorylsulfirane represented by the formula [18].

For the inorganic oxidizing agent, mention is made, for example, of a permanganate and a periodate, of which a periodate is preferred in view of reactivity and sodium periodate is more preferred.

The amount of the inorganic oxidizing agent is in the range of 0.8 to 3 times by mole, preferably 1.0 to 1.3 times by mole, relative to the 3,4-bisphosphorylthiolane compound serving as a substrate.

An alcohol solvent or mixed solvent of an alcohol and water is preferred as a reaction solvent. Examples of the alcohol solvents include water-soluble alkyl alcohols having 1-4 carbon atoms such as methanol, ethanol, n-propanol, i-propanol, n-butanol, t-butanol and the like. Of these, methanol is preferred. If a mixed solvent of an alcohol and water is used, a ratio between an alcohol and water is not critical and is favorably at about 5:1 to 15:1 on the weight basis.

The amount of the solvent is preferably 1 to 100 times by weight, more preferably 20 to 50 times by weight, relative to the 3,4-bisphosphorylthiolane compound serving as a substrate.

The progress of the reaction can be confirmed by thin-layer chromatography.

After completion of the reaction, ordinary after-treatments are carried out, followed by purification, if necessary, to obtain an intended substance.

[4] Fourth step

This step is one wherein the bisphosphorylsulfurane compound represented by the formula [18] and an organic acid anhydride are reacted in the presence of an organic acid catalyst to prepare a 3,4-bisphosphoryldihydrothiophene compound represented by the formula [19].

For the organic acid anhydride, aliphatic carboxylic acid anhydrides, and aromatic carboxylic acid anhydrides are used, of which more inexpensive aliphatic carboxylic acid anhydrides are preferred and more preferably, acetic acid anhydride is used.

The amount of the organic acid anhydride is preferably 0.8 to 5.0 times by mole, more preferably 1.0 to 1.3 times by mole, relative to the 3,4-bisphosphorylsulfurane compound used as a substrate.

For the organic acid catalyst, mention is made of aliphatic acids such as formic acid, acetic acid, propionic acid and the like, and sulfonic acids such as benzenesulfonic acid, p-toluenesulfonic acid, methanesulfonic acid, ethanesulfonic acid, trifluoromethansulfonic acid and the like, of which sulfonic acids are preferred and methanesulfonic acid is more preferred.

The amount of the organic acid catalyst is preferably 0.1 to 50 mol %, more preferably 10 to 30 mol %, relative to the 3,4-bisphosphorylsulfurane compound used as a substrate.

The reaction solvent may be an organic acid anhydride that is added in excess for use as a solvent, or may be an organic solvent that does not take direct part in the reaction. Such organic solvents include, for example, aromatic hydrocarbons such as toluene, xylene and the like, halogenated hydrocarbons such as methylene chloride, chloroform, 1,2-dichloroethane, 1,2-dichloropropane and the like, of which halogenated hydrocarbons are preferred and, especially, methylene chloride is more preferred.

The amount of the solvent is preferably at 1 to 100 times by weight, more preferably 20 to 50 times by weight, relative to the 3,4-bisphosphorylsulfurane compound serving as a substrate.

The reaction temperature is generally at −100 to 100° C., preferably −20 to 40° C.

The progress of the reaction can be confirmed by thin-layer chromatography.

After completion of the reaction, ordinary after-treatments are carried out, followed by purification, if necessary, to obtain an intended substance.

[5] Fifth step

This step is one wherein the 3,4-bisphosphoryldihydrothiophene compound represented by the formula [19] and an inorganic oxidizing agent are reacted to prepare a. 3,4-bisphosphorylthiophene compound represented by the formula [20].

For the inorganic oxidizing agent, mention is made, for example, of manganese oxide, a permanganate, a periodate and the like, of which manganese oxide is preferred.

The amount of the inorganic oxidizing agent is preferably at 0.8 to 30 times by mole, more preferably 2 to 22 times by mole, relative to the 3,4-bisphosphoryldihydrothiophene compound serving as a substrate.

As a reaction solvent, mention is made of, for example, aromatic hydrocarbons such as benzene, toluene, xylene and the like, and halogenated hydrocarbons such as methylene chloride, chloroform, 1,2-dichloroethane, 1,2-dichloropropane and the like, of which aromatic hydrocarbons are preferred and benzene is more preferred.

The reaction temperature generally ranges −100 to 100° C., preferably 50 to 100° C.

The progress of the reaction can be confirmed by thin-layer chromatography.

After completion of the reaction, ordinary after-treatments are carried out, followed by purification, if necessary, to obtain an intended substance.

The respective reactions of the first to fifth steps having illustrated hereinabove may be carried out in a batchwise or continuous manner and may be performed under a normal pressure or under pressure.

The substituent groups of the compounds of the above formulas [14] to [20] are now described.

In the respective formulas, $R^{42}$ and $R^{43}$ each independently represent a hydrogen atom, a halogen atom, a cyano group, a phenyl group which may be substituted with W″, an alkyl group having 1-10 carbon atoms or an haloalkyl group having 1-10 carbon atoms, $R^{44}$ represents a hydrogen atom, an alkyl group having 1-10 carbon atoms, or a phenyl group which may be substituted with W″, and W″ represents a halogen atom, a cyano group, a nitro group, an alkyl group having 1-10 carbon atoms, a haloalkyl group having 1-10 carbon atoms, an alkenyl group having 1-10 carbon atoms, an alkynyl group having 1-10 carbon atoms, an alkoxy group having 1-10 carbon atoms, or a phenyl group.

It will be noted that specific examples of the halogen atom, alkyl group having 1-10 carbon atoms, haloalkyl group having 1-10 carbon atoms, alkenyl group having 1-10 carbon atoms, alkynyl group having 1-10 carbon atoms and alkoxy group having 1-10 carbon atoms are those indicated hereinbefore.

Specific examples of the phenyl group which may be substituted with W″ include phenyl, o-methylphenyl, m-methylphenyl, p-methylphenyl, o-trifluoromethylphenyl, m-trifluoromethylphenyl, p-trifluoromethylphenyl, p-ethylphenyl, p-i-propylphenyl, p-t-butylphenyl, o-chlorophenyl, m-chlorophenyl, p-chlorophenyl, o-bromophenyl, m-bromophenyl, p-bromophenyl, o-fluorophenyl, p-fluorophenyl, o-methoxyphenyl, m-methoxyphenyl, p-methoxyphenyl, o-trifluoromethoxyphenyl, p-trifluoromethoxyphenyl, o-nitrophenyl, m-nitrophenyl, p-nitrophenyl, o-dimethylaminophenyl, m-dimethylaminophenyl, p-dimethylaminophenyl, p-cyanophenyl, 3,5-dimethylphenyl, 3,5-bistrifluoromethylphenyl, 3,5-dimethoxyphenyl, 3,5-bistrifluoromethoxyphenyl, 3,5-diethylphenyl, 3,5-di-i-propylphenyl, 3,5-dichlorophenyl, 3,5-dibromophenyl, 3,5-difluorophenyl, 3,5-dinitrophenyl, 3,5-dicyanophenyl, 2,4,6-trimethylphenyl, 2,4,6-tristrifluoromethylphenyl, 2,4,6-trimethoxyphenyl, 2,4,6-tristrifluoromethoxylphenyl, 2,4,6-trichlorophenyl, 2,4,6-tribromophenyl, 2,4,6-trifluorophenyl, o-biphenylyl, m-biphenylyl, p-biphenylyl and the like.

For $R^{42}$ and $R^{43}$, a substituent group whose influence on the steric hindrance is small is favorable and preferably includes a hydrogen atom, a halogen atom, a cyano group, an alkyl group having 1-3 carbon atoms (e.g. methyl, ethyl, n-propyl or the like), a haloalkyl group having 1-3 carbon atoms ($CF_3$, $CH_2CF_3$, $CH_2CH_2CF_3$ or the like), a phenyl group, a phenyl group substituted with a halogen atom (p-chlorophenyl, p-bromophenyl, p-fluorophenyl or the like) or the like, of which a hydrogen atom is more preferred.

For $R^{44}$, a substituent group whose influence on steric hindrance is small is favorable and preferably includes a hydrogen atom, an alkyl group having 1-3 carbon atoms (methyl, ethyl, n-propyl group or the like), a phenyl group substituted with an alkyl group having 1-3 carbon atoms (o-methylphenyl, m-methylphenyl, p-methylphenyl group or the like), or the like.

Especially, the process (A) consisting of the first to fifth steps as stated above is an optimum process of preparing compounds of the following formulas wherein $R^{42}$ and $R^{43}$ are a hydrogen atom and $R^{44}$ is an ethyl group.

[Chemical Formula 66]

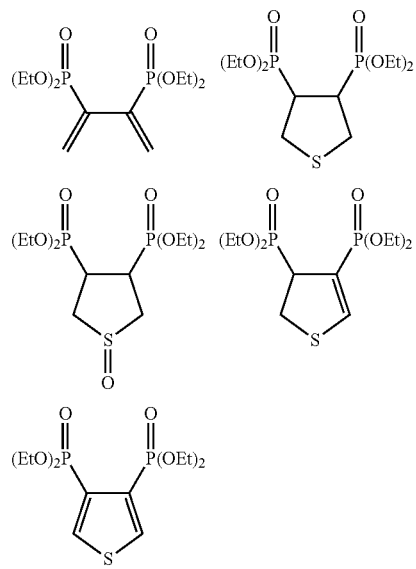

Further, a process of producing a phosphorylthiophene compound of the invention is illustrated using a phosphorylthiophene compound represented by the following formula [23].

The compound of the formula [23] can be obtained by a coupling process (B) of a halogenated thiophene compound and a phosphate shown by the following scheme. It will be noted that in the formula [23], where $R^{50}$ is a phosphoryl group, a bisphosphoryl compound similar to the compound of the afore-indicated formula [20] is obtainable.

This process (B) can make use of the following two reactions (B-1) and (B-2) indicated below.

[Chemical Formula 67]

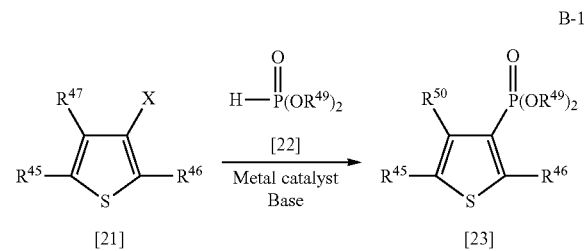

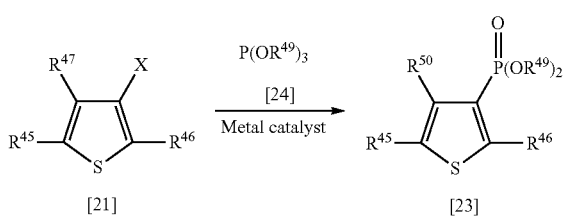

[1] Process (B-1)

This process is one wherein a halogenated thiophene compound represented by the formula [21] and a phosphite compound represented by the formula [22] are reacted in the presence of a metal catalyst and a base to provide a mono or bisphosphorylbutadiene compound represented by the formula [23].

For the phosphite compound, mention is made, for example, of phosphate compounds having an alkyl group having 1-10 carbon atoms such as dimethyl phosphate, diethyl phosphate, di-n-propyl phosphate, di-n-butyl phosphate and the like, and phosphate compounds having a phenyl group such as diphenyl phosphite. Of these, economical dimethyl phosphite and diethyl phosphite are preferred.

The amount of the phosphate compound is preferably at 0.1 to 5 times by mole, more preferably 1.0 to 1.5 times by mole, relative to the halogen atom of the halogenated thiophene compound serving as a substrate.

For a metal catalyst, mention is made of a palladium catalyst and the like. Specific examples include palladium(0) complexes such as tetrakistriphenylphosphine-palladium, tetrakistributylphosphine-palladium, $Pd_2(dba)_3$ and $Pd(dppf)_2Cl_2$ and combinations of palladium (II) complexes such as palladium acetate and palladium chloride, and various types of ligands such as triphenylphosphine and tributylphosphine. Of these, tetrakistriphenylphosphine-palladium and a combination of palladium acetate and triphenylphosphine are preferred from an economical standpoint.

The amount of the metal catalyst is preferably at 0.1 to 50 mol %, more preferably 2 to 30 mol %, relative to the halogen atom of the halogenated thiophene compound serving as a substrate.

In this process, the presence of a base is important. Examples of the base include alkylamines such as diethylamine, triethylamine, diisopropylamine, diisopropylethylamine, di-n-butylamine and the like, aromatic amines such as pyridine, picoline and the like, and inorganic amines such as sodium hydrogen carbonate, potassium carbonate and the like, of which alkylamines, particularly, diisopropylethylamine, are preferred.

The amount of the base is preferably at 0.5 to 5 times by mole, more preferably 1.0 to 1.5 times by mole, relative to the halogen atom of the halogenated thiophene compound serving as a substrate.

The reaction solvents preferably include amide compounds such as N,N-dimethylformamide, N,N-dimethylacetamide and the like, aromatic hydrocarbons such as benzene, toluene, xylene and the like, and ether compounds such as tetrahydrofuran (THF), 1,4-dioxane, 1,2-dimethoxyethane, diethylene glycol dimethyl ether and the like. Of these N-N-dimethylformamide and toluene are more preferred.

The amount of the solvent is preferably at 1 to 100 times by weight, more preferably 5 to 20 times by weight, relative to the halogen atom of the halogenated thiophene compound serving as a substrate.

The reaction temperature is generally at −100 to 100° C., preferably 40 to 80° C.

The progress of the reaction can be confirmed by gel permeation chromatography.

After completion of the reaction, ordinary after-treatments are carried out, followed by purification, if necessary, to obtain an intended substance.

[2] (B-2) Process

This process is one wherein a halogenated thiophene compound represented by the formula [21] and a phosphite compound represented by the formula [22] are reacted in the presence of a metal catalyst to prepare a mono or bisphosphorylbutadiene compound represented by the formula [23].

For the phosphate compound, mention is made of phosphite compounds having an alkyl group having 1-10 carbon atoms such as trimethyl phosphate, triethyl phosphate, tri-n-propyl phosphate, tri-n-butyl phosphite and the like, and phosphate compounds having a phenyl group such as triphenyl phosphate. Of these, economical trimethyl phosphite and triethyl phosphate are preferred.

The amount of the phosphite compound is preferably at 0.1 to 5 times by mole, more preferably 1.0 to 1.5 times by mole, relative to the halogen atom of the halogenated thiophene compound serving as a substrate.

For the metal catalyst, mentions is made of palladium catalysts, nickel catalysts and the like, and specific examples include palladium catalysts mentioned in (B-1) and nickel complexes such as $Ni(PPh_3)_2Cl_2$. Economical tetrakistriphenylphosphine-palladium and a combination of palladium acetate and triphenylphosphine are preferred.

The amount of the metal catalyst is at 0.1 to 50 mol %, more preferably 2 to 30 mol %, relative to the halogen atom of the halogenated thiophene compound serving as a substrate.

Various types of solvents can be used as a reaction solvent and include, for example, amide compounds such as N,N-dimethylformamide, N,N-dimethylacetamide and the like, aromatic hydrocarbons such as benzene, toluene, xylene and the like, and ether compounds such as tetrahydrofuran (THF), 1,4-dioxane, 1,2-dimethoxyethane, diethylene glycol dimethyl ether and the like. Of these, N,N-dimethylformamide and toluene are preferred.

The amount of the solvent is at 1 to 100 times by weight, preferably 20 to 50 times by weight, relative to the halogenated thiophene compound serving as a substrate.

The reaction temperature is generally at −100 to 100° C., preferably −100 to 120° C.

The progress of the reaction can be confirmed by thin-layer chromatography or high pressure liquid phase chromatography.

After completion of the reaction, ordinary after-treatments are carried out, followed by purification, if necessary, to obtain an intended substance.

It will be noted that the reactions in (B-1) and (B-2) may be carried out in a batchwise manner or continuously, and may be effected under a normal pressure or under pressure.

The substituent groups of the compounds of the formulas. [21] to [24] are illustrated.

In the respective formulas, X represents a halogen atom, and $R^{45}$ and $R^{46}$ each independently represent a hydrogen atom, a cyano group, a phenyl group which may be substituted with W''', a hydroxyl group, an amino group, a formyl group, a carboxyl group, an alkyl group having 1-10 carbon atoms, a haloalkyl group having 1-10 carbon atoms, a monoalkylamino group having 1-10 carbon atoms, or a dialkylamino group having 1-10 carbon atoms.

$R^{47}$ represents a hydrogen atom, a halogen atom, a cyano group, a nitro group, a phenyl group which may be substituted with W''', a hydroxyl group, a mercapto group, an amino group, a formyl group, a carboxyl group, an alkyl group having 1-10 carbon atoms, a haloalkyl group having 1-10 carbon atoms, a monoalkylamino group having 1-10 carbon atoms, a dialkylamino group having 1-10 carbon atoms or —P(O)(OR$^{48}$)$_2$ wherein R$^{48}$ represents a hydrogen atom, an alkyl group having 1-10 carbon atoms or a phenyl group which may be substituted with W'''. R$^{49}$ represents an alkyl group having 1-10 carbon atoms or a phenyl group which may be substituted with W'''.

$R^{50}$ represents a hydrogen atom, a halogen atom, a cyano group, a nitro group, a phenyl group which may be substituted with W''', a hydroxyl group, a mercapto group, an amino group, a formyl group, a carboxyl group, an alkyl group having 1-10 carbon atoms, a haloalkyl group having 1-10 carbon atoms, a monoalkyl group having 1-10 carbon atoms, a dialkylamino group having 1-10 carbon atoms, —P(O)(OR$^{48}$)$_2$ or —P(O)(OR$^{49}$)$_2$ wherein W''', R$^{48}$ and R$^{49}$ have the same meanings as defined above.

W''' represents a cyano group, a nitro group, a hydroxyl group, a mercapto group, an amino group, a formyl group, a carboxyl group, an alkyl group having 1-10 carbon atoms, a haloalkyl group having 1-10 carbon atoms, an alkenyl group having 1-10 carbon atoms, an alkynyl group having 1-10 carbon atoms, an alkoxy group having 1-10 carbon atoms, an alkylthio group having 1-10 carbon atoms, a monoalkylamino group having 1-10 carbon atoms, a dialkylamino group having 1-10 carbon atoms, an alkylcarbonyl group having 1-10 carbon atoms, an alkoxycarbonyl group having 1-10 carbon atoms, or a phenyl group.

Specific examples of the halogen atom, alkyl group having 1-10 carbon atoms, haloalkyl group having 1-10 carbon atoms, monoalkylamino group having 1-10 carbon atoms, dialkylamino group having 1-10 carbon atoms, alkenyl group having 1-10 carbon atoms, alkynyl group having 1-10 carbon atoms, alkoxy group having 1-10 carbon atoms, alkylthio group having 1-10 carbon atoms, alkylcarbonyl group having 1-10 carbon atoms, and an alkoxycarbonyl group having 1-10 carbon atoms are those as mentioned hereinbefore.

Specific examples of the phenyl group which may be substituted with W''' include phenyl, o-methylphenyl, m-methylphenyl, p-methylphenyl, o-trifluoromethylphenyl, m-trifluoromethylphenyl, p-trifluoromethylphenyl, p-ethylphenyl, p-i-propylphenyl, o-methoxyphenyl, m-methoxyphenyl, p-methoxyphenyl, o-trifluoromethoxyphenyl, p-trifluoromethoxyphenyl, o-nitrophenyl, m-nitrophenyl, p-nitrophenyl, o-dimethylaminophenyl, m-dimethylaminophenyl, p-dimethylaminophenyl, p-cyanophenyl, 3,5-dimethylphenyl, 3,5-bistrifluoromethylphenyl, 3,5-dimethoxyphenyl, 3,5-bistrifluoromethoxyphenyl, 3,5-diethylphenyl, 3,5-di-i-propylphenyl, 3,5-dinitrophenyl, 3,5-dicyanophenyl, 2,4,6-trimethylphenyl, 2,4,6-tristrifluoromethylphenyl, 2,4,6-trimethoxyphenyl, 2,4,6-tristrifluoromethoxylphenyl, o-biphenylyl, m-biphenylyl, p-biphenylyl and the like.

Of these, groups whose influence on steric hindrance is small are favorable as R$^{45}$-R$^{47}$ and preferably include a hydrogen atom, a halogen atom, an alkyl group having 1-5 carbon atoms (methyl, ethyl, n-propyl, i-propyl, n-butyl, i-butyl, s-butyl, t-butyl, c-butyl, n-pentyl group or the like), especially, an alkyl group having 1-3 carbon atoms (methyl, ethyl, n-propyl group or the like), a haloalkyl group having 1-3 carbon atoms (CF$_3$, CH$_2$CF$_3$, CH$_2$CH$_2$CF$_3$ or the like), a monoalkylamino group having 1-3 carbon atoms (NHEt, NHPr-n, NHPr-i or the like), a dialkylamino group having 1-3 carbon atoms (NMe$_2$, NEt$_2$, N(Pr-n)$_2$, N(Pr-i)$_2$ or the like), phenyl, and a phenyl group substituted with an alkyl group having 1-3 carbon atoms (o-methylphenyl, m-methylphenyl, p-methylphenyl or the like), among which a hydrogen atom is more preferred.

For R$^{48}$ and R$^{49}$, those groups whose influence on steric hindrance is small are favorable and preferably include an alkyl group having 1-5 carbon atoms (methyl, ethyl, n-propyl, i-propyl, n-butyl, i-butyl, s-butyl, t-butyl, c-butyl, n-pentyl group or the like), particularly, an alkyl group having 1-3 carbon atoms (methyl, ethyl, n-propyl group or the like), phenyl, and a phenyl group substituted with an alkyl group having 1-3 carbon atoms (o-methylphenyl, m-methylphenyl, p-methylphenyl group or the like).

For R$^{50}$, a group whose influence on steric hindrance is small is favorable and preferably includes a hydrogen atom, an alkyl group having 1-5 carbon atoms (methyl, ethyl, n-propyl, i-propyl, n-butyl, i-butyl, s-butyl, t-butyl, c-butyl, n-pentyl group or the like), particularly, an alkyl group having 1-3 carbon atoms (methyl, ethyl, n-propyl group or the like), a haloalkyl group having 1-3 carbon atoms (CF$_3$, CH$_2$CF$_3$, CH$_2$CH$_2$CF$_3$ or the like), a monoalkylamino group having 1-3 carbon atoms (NHEt, NHPr-n, NHPr-i or the like), a dialkylamino group having 1-3 carbon atoms (NMe$_2$, NEt$_2$, N(Pr-n)$_2$, N(Pr-i)$_2$ or the like), phenyl, and a phenyl group substituted with an alkyl group having 1-3 carbon atoms (o-methylphenyl, m-methylphenyl, p-methylphenyl or the like).

Especially, the process (B) is a preferable process of synthesizing a compound wherein R$^{45}$-R$^4$ are each a hydrogen atom.

The processes for producing phosphorylthiophene oligomer compounds represented by the formulas [3] and [13] and bisphosphorylthiophene compounds represented by the formulas [25] to [28] are not critical, and such compounds can be obtained by converting a terminal substituent group of the phosphorylthiophene compounds represented by the formulas [1] and [2] to an appropriate substituent group and coupling by an arbitrary method as will be described hereinafter. Alternatively, after obtaining the resulting compounds represented by the formulas [3] and [13], a terminal substituent group of the thiophene ring (or other spacers represented by the formulas (4) to (12)) may be converted to an appropriate substituent group, followed by coupling according to an arbitrary method.

The coupling methods are not critical and there can be used, for example, biaryl coupling, Stille coupling, Suzuki coupling, Ullmann coupling, Heck reaction, Sonogashira coupling, Grignard reaction and the like.

There are set out hereinbelow instances of a method of altering a substituent group at terminals of the phosphorylthiophene compounds of the formulas [1] and [2] ([3] and [13]) for the purpose of coupling.

The halogenation method in case where a terminal substituent group of a phosphorylthiophene compound is converted to a halogen is not critical, for which there can be used the processes described in Heterocycles, 1996, p. 1927 and Journal of Organic Chemistry (J. Org. Chem.), 1993, p. 3072.

For a trialkylsilylizing method where a terminal substituent group of a phosphorylthiophene compound is converted to a trialkylsilyl group, no specific limitation is placed thereon and such a method may be based on a method described, for example, in Journal of Organic Chemistry (J. Org. Chem.), 1993, p. 3072 may be used.

For the biaryl coupling method, no specific limitation is placed thereon and a method described, for example, in Tetrahedron, 1980, p. 3327 may be used.

The Stille coupling method is not critical and may be based on a method described, for example, in Journal of Organic Synthesis (J. Org. Synth.) 1998, p. 553. It will be noted that a copper reagent is added to a reaction system, if necessary, to improve a yield.

The Suzuki coupling method is not critical and may be based on a method described, for example, in Tetrahedron (Tetrahedron.), 1994, p. 8301.

The Ullmann coupling method is also not critical and may be based on a method described, for example, in *Organic Reactions*, 1944, p. 224.

The coupling method using the Heck reaction is not critical and may be based on a method described, for example, in *Organic Reactions*, 1982, page 345.

The Sonogashira coupling method is not critical and may be based on a method described, for example, in Tetrahedron Letter (Tetrahedron. Lett.), 1975, p. 4467.

The coupling method using the Grignard reaction is not critical and may be based on a method described, for example, in Organic Synthesis (J. Org. Synth.), 1988, p. 407. Description is now made on a method of converting an alkoxy moiety of a phosphoric acid ester group in the phosphorylthiophene compounds of the formulas [1] to [3] and [13].

When the phosphoric acid ester group of the phosphorylthiophene compound is subjected to solvolysis with water or an alcohol, the alkoxy moiety can be converted.

The solvolytic method is not critical and may be based on methods described, for example, in Journal of Chemical Society (J. Chem. Soc.), 1959, p. 3950 and Journal of American Chemical Society (J. Am. Chem. Soc.), 1953, p. 3379.

For a method of converting a phosphoric acid ester group to an amido or thioester in the phosphorylthiophene compounds of the formulas [1] to [3] and [13], no limitation is placed thereon and such a method may be based on methods described, for example, in Organic Phosphorus Compounds (Organic Phosphorus Compounds), Vol. 4, published by Wiley-Interscience, 1972, Chapter 9, pp. 155 to 253, Organic Phosphorus Compounds (Organic Phosphorus Compounds), Vol. 6, published by Wiley-Interscience, 1973, Chapter 14, pp. 1 to 209, and Organic Phosphorus Compounds (Organic Phosphorus Compounds), Vol. 7, published by Wiley-Interscience, 1976, Chapter 18, pp. 1 to 486.

When the phosphorylthiophene (monomer or oligomer) compounds of the above formulas [1], [2], [3] and [13] are polymerized, a phosphorylthiophene polymer compound represented by the above formula [29] or [30] is obtained.

The molecular weight of the phosphorylthiophene polymer compound is not critical and preferably has a weight average molecular weight of 9,000 to 100,000, more preferably 10,000 to 50,000. It will be noted that the weight average molecular weight is a value calculated as polystyrene by gel permeation chromatography.

Specific examples of the phosphorylthiophene polymer compound include those indicated below although not limited thereto. It will be noted that k is an integer of 50 to 5000 and is favorably a value capable of giving such a weight average molecular weight as indicated above.

[Chemical Formula 68]

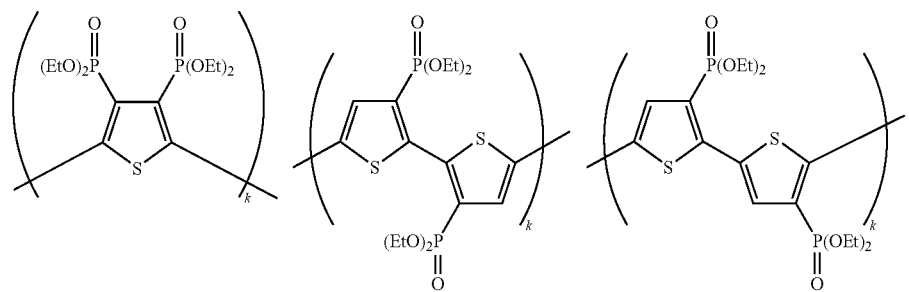

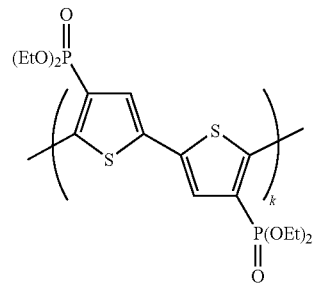

[Chemical Formula 69]

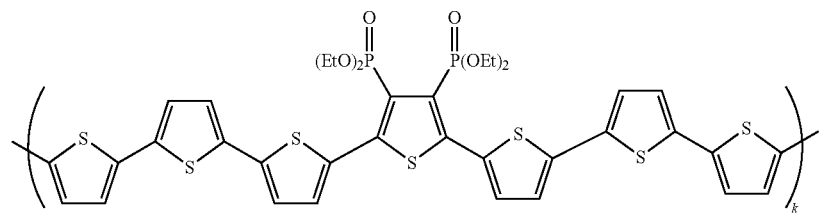

-continued
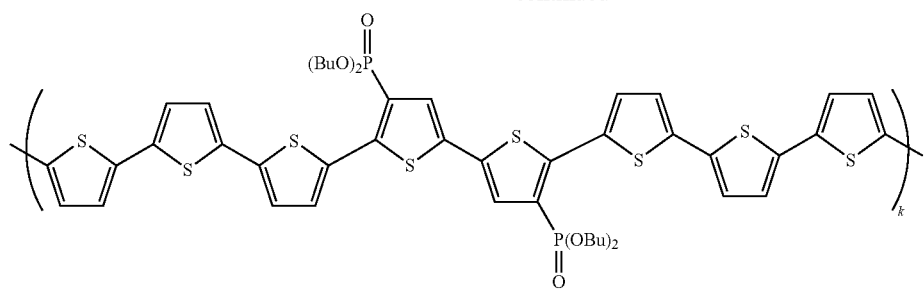
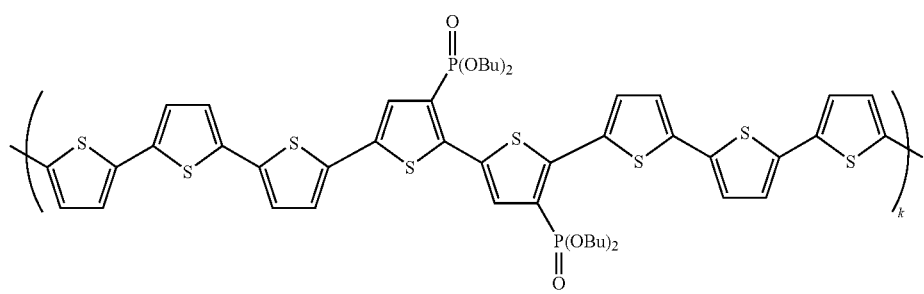
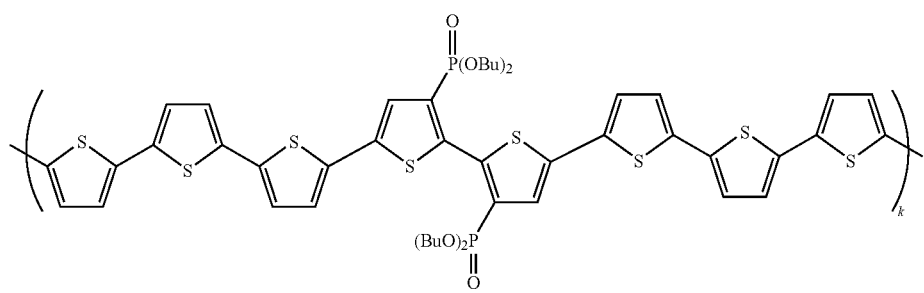
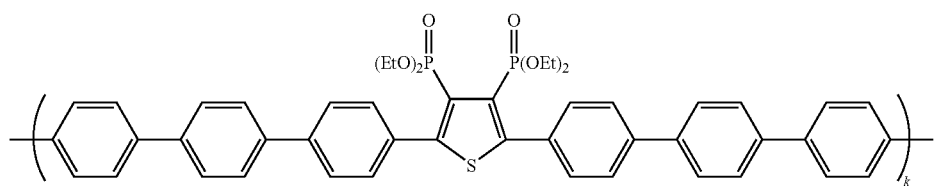
[Chemical Formula 70]
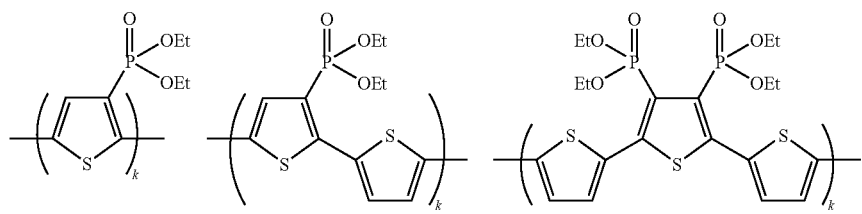
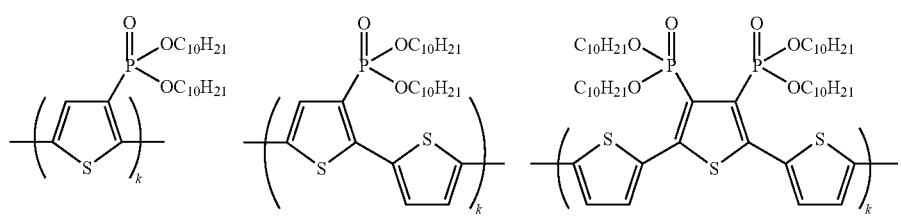

The polymerization method is not critical so far as it is able to polymerize a phosphorylthiophene compound and there can be used, for example, chemical oxidation polymerization, electrolytic oxidation polymerization and catalytic polymerization and the like. Where a polymer is formed on an electrode surface by polymerization reaction on the electrode surface, chemical oxidation polymerization and electrolytic oxidation polymerization are preferred, of which electrolytic oxidation polymerization is more preferred.

The oxidizing agent used for chemical oxidation polymerization is not critical, for which mention is made, for example, of ammonium persulfate, tetraammonium peroxide, iron chloride, cerium sulfate and the like.

The electrolytic oxidation polymerization is carried out, for example, by adding an oxidizing agent to a phosphorylthiophene compound and well stirring, after which an organic solvent is added to prepare a homogenous solution and a three-electrode beaker cell equipped with a platinum mesh counter electrode and the like is used. More particularly, for instance, a platinum plate scratched with emery paper on the surface thereof is used as a test electrode substrate and $Ag/Ag^+$ is used as a reference electrode, under which polymerization is carried out according to a potential sweep method, a constant potential method or the like using a electrochemical measuring system. In this way, an intended thiophene polymer is deposited on the electrode in the form of a film.

The oxidizing agent used for the electrolytic oxidation polymerization includes, for example, hydrochloric acid, sulfuric acid, perchloric acid, trifluoromethanesulfonic acid, paratoluenesulfonic acid, of which perchloric acid is preferred.

The organic solvent includes, for example, N,N-dimethylformamide, tetrahydrofuran, acetonitrile, dichloromethane, dimethylsulfoxide, methanol, ethanol and the like, of which acetonitrile and N,N-dimethylformamide are preferred.

The catalytic polymerization is a process wherein at least one selected form the phosphorylthiophene compounds of the formulas [1], [2], [3] and [13] is reacted in the presence of a metal catalyst to provide a phosphorylthiophene polymer compound.

The phosphorylthiophene compound to be used for the catalytic polymerization is not critical in type, however, a phosphorylthiophene compound whose terminal substituent group is a halogen atom is preferred. Especially, a bromine atom is more preferred.

The metal catalyst includes nickel complexes and the like. Specific examples include nickel(0) complexes such as bis(1,5-cyclooctadiene)nickel(0), tetrakis(triphenylphosphine)nickel(0) and the like, or combinations of nickel chloride or nickel(II) complexes such as bis(triphenylphosphine)nickel(II) dichloride, [1,2-bis(diphenylphosphino)ethane]nickel(II) dichloride, [1,3-bis(diphenylphosphino)propane]nickel(II) dichloride, tris(2,2'-bipyridyl)nickel(II) dibromide and the like and various types of ligands such as 1,5-cyclooctadiene, 2,2'-bipyridine and triphenylphosphine. Of these, a combination of bis(1,5-cyclooctadiene)nickel and 1,5-cyclooctadiene and 2,2'-bipyridine is preferred in view of a high degree of polymerization of a produced polymer.

The amount of the metal catalyst is preferably at 0.05 to 2.0 times by mole, more preferably 0.5 to 0.8 times by mole, relative to the halogen atom of the phosphorylthiophene compound serving as a substrate.

The amount of the ligand is preferably at 0.05 to 2.0 times by mole, preferably 0.5 to 0.8 times by mole, relative to the halogen atom of the phosphorylthiophene compound serving as a substrate.

The reaction solvents preferably include, for example, amide compounds such as N,N-dimethylformamide, N,N-dimethylacetamide and the like; aromatic hydrocarbons such as benzene, toluene, xylene and the like, and ether compounds such as tetrahydrofuran (THF), 1,4-dioxane, 1,2-dimethoxyethane, diethylene glycol dimethyl ether and the like. Of these, 1,4-dioxane is more preferred in view of the high degree of polymerization of a produced polymer.

Using excellent characteristic properties, the phosphorylthiophene compound of the invention stated hereinabove can be utilized as a film, an electrochromic device, a semiconductor, a cell, a solar cell, an organic electroluminescent device, an active substance and an electrode of non-linear materials and the like. The phosphorylthiophene compound has electric conductivity in itself and can be utilized as an n-type semiconductor by reduction with a reducing agent or by electrochemical doping.

It will be noted that the when molded as a film or other types of moldings, the phosphoryl compound may be appropriately formulated with additives such as a heat stabilizer, a light stabilizer, a filler, a reinforcing agent and the like.

EXAMPLES

The invention is more particularly described by way of examples, which should not be construed as limiting the invention thereto.

It is to be noted that analyzers and conditions used in the examples are as shown below.

[1] Gas Chromatography (GC)
  Model: Hewlett Packard: HP6800, Column: DB-624 (30 m×0.53 mm$\phi$×3 µm), column temperature: 40 (0-minute retention) to 290° C. (0-minute retention), 10° C./minute (rate of temperature rise), charge port temperature: 180° C., detector temperature: 250° C., carrier gas: helium, detection method: FID method

[2] Mass Spectrography (MASS)
  Model: LX-1000 (JEOL Ltd.), detection method: FAB method
  Model: JMS-SX102A (JEOL Ltd.), detection method: FAB method

[3] $^1$H NMR
  Model: JNM-A500 (JEOL Ltd.), solvent for measurement: $CDCl_3$, DMSO-$d_6$
  Model: AVANCE 400S (Bruker), solvent for measurement: $CDCl_3$, DMSO-$d_6$

[4] $^{13}$C NMR
  Model: JNM-A500 (JEOL Ltd.), solvent for measurement: $CDCl_3$, DMSO-$d_6$
  Model: AVANCE 400S (Bruker), solvent for measurement: $CDCl_3$, DMSO-$d_6$

[5] IR
  Model: BIORAD FTS-40, KBr tablet method
  Model: JIR-Winspec 50 (JEOL Ltd.), neat method

[6] High Pressure Liquid Phase Chromatography (LC)
  Model: Hewlett Packard: HP1100, Column: Inertsil ODS-3 (5 µm, 250 mm×46 mm$\phi$+guard column 10 mm×4.0 mm$\phi$), column temperature: 40° C., detector: UV 220 nm, eluant: $H_2O/CH_3CN$=6/4 gradation (45-minutes retention) to $CH_3CN$ in 15 minutes from (0-minute retention), 10° C./minute, flow rate: 2.0 ml/minute

[7] Thin-Layer Chromatography (TLC)
  Using a MERCK silica gel plate, UV 254 nm, confirmed by baking with phosphomolybdic acid

[8] Cyclic Voltanmetry (CV)
  Model: Electrochemical Analyzer Model 660B (ALC/HCH Instruments)

[9] Gel Permeation Chromatography (GPC)
  Model: TOSOH: HLC-8220GPC, column: SHODEX GPC KF-804L+GPC KF-805L, column temperature: 40° C., detector: UV detector (254 nm) and RI detector, eluant: THF, column flow rate: 1.0 ml/minute

Example 1

Synthesis of 3,4-bis(diethoxyphosphoryl)thiophene

Synthesis was carried out according to the following processes (1) to (5).

(1) Synthesis of 2,3-bis(diethoxyphosphoryl)-1,3-butadiene

[Chemical Formula 71]

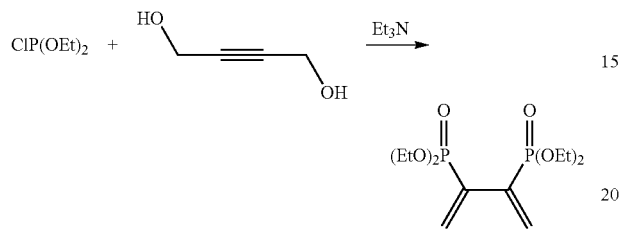

In 25 ml of methylene chloride, 1.00 g (11.6 mmols) of commercially available 2-butyne-1,4-diol was dissolved, to which 2.37 g (23.2 mmols) of commercially available triethylamine was added, followed by stirring at room temperature until complete dissolution. This solution was cooled down to −78° C., then 0.303 g (19.4 mmols) of chlorodiethyl phosphite was slowly dropped to the solution with a dropping funnel. After completion of the dropping, the reaction temperature was gently raised to room temperature, followed by stirring for 19 hours. A disodium hydrogen phosphate/sodium dihydrogen phosphate buffer solution, adjusted to pH=7, was added to the reaction mixture to complete the reaction, followed by extraction with ethyl acetate. The organic phase was washed with a saturated saline solution and dried over anhydrous sodium sulfate. The solvent was removed and the resulting crude product was purified with a silica gel column (ethyl acetate:chloroform=1:2) to obtain the specified substance in the form of a yellow oil at a yield of 2.63 g (yield: 83.0%).

$^1$H-NMR (CDCl$_3$): 1.33 (12H, t, J=7.0 Hz), 4.07-4.17 (8H, m), 6.43 (2H, d, $^2$J$_{P-H}$=20.4 Hz), 6.51 (2H, d, $^2$J$_{P-H}$=44.9 Hz) ppm.
$^{13}$C-NMR (CDCl$_3$): 16.2 (t, $^3$J$_{P-C}$=3.1 Hz), 61.2 (t, $^2$J$_{P-C}$=3.1 Hz), 133.3 (d, $^1$J$_{P-C}$=187.3 Hz), 134.7 (t, $^2$J$_{P-C}$=5.2 Hz) ppm.

(2) Synthesis of 3,4-bis(diethoxyphosphoryl)thiolane

[Chemical Formula 72]

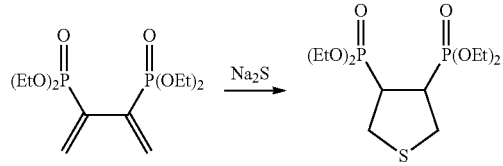

In ethanol, 2.02 g (6.19 mmols) of 2,3-bis(diethoxyphosphoryl)-1,3-butadiene was dissolved, to which 1.63 g (6.81 mmols) of commercially available sodium sulfide nonahydrate was added, followed by stirring at room temperature for 3 days. After completion of the reaction, the reaction mixture was dried over anhydrous sodium sulfate for 1 hour. Ethyl acetate was added to and the resulting mixture was charged into a silica gel column to dissolve out the specified substance with ethyl acetate. Thereafter, the solvent was removed, and the resulting crude product was purified with a silica gel column (ethyl acetate:chloroform=1:2) to obtain the specified substance in the form of a yellow oil at a yield of 1.88 g (yield: 84.3%).

$^1$H-NMR (CDCl$_3$): 1.32-1.36 (12H, m), 2.93 (2H, dd, $^1$J$_{P-H}$=5.0 Hz, J=5.0 Hz), 3.18-3.24 (4H, m), 4.12-4.20 (8H, m) ppm.
$^{13}$C-NMR (CDCl$_3$): 16.0 (t, $^3$J$_{P-C}$=27.7 Hz), 32.4 (d, $^2$J$_{P-C}$=36.1 Hz), 40.5 (dd, $^3$J$_{P-C}$=141.8 Hz, $^2$J$_{P-C}$=12.6 Hz), 61.6-62.3 (m) ppm.

(3) Synthesis of 3,4-bis(diethoxyphosphoryl)sulfurane

[Chemical Formula 73]

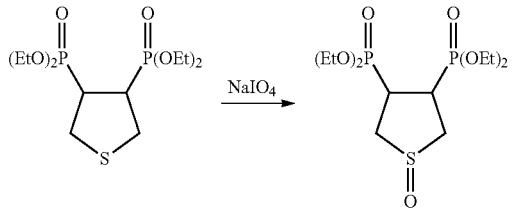

In a solvent of methanol/water=10:1, 3.260 g (9.05 mmols) of 3,4-bis(diethoxyphosphoryl)thiolane was dissolved, to which 2.12 g (9.96 mmols) of commercially available sodium periodide was added at room temperature, followed by stirring for 21 hours. Thereafter, the reaction mixture was poured into and diluted with methylene chloride and stirred for 1 hour, followed by removing the precipitate of sodium iodide by filtration. The filtrate was extracted with methylene chloride and the resulting organic phase was dried over anhydrous sodium sulfate. The crude product obtained by removal of the solvent was purified with a silica gel column to obtain the specified substance on the form of a brown oil at a yield of 3.30 g (96.9%).

$^1$H-NMR (CDCl$_3$): 1.32-1.38 (12H, m), 2.85-3.50 (6H, m), 4.12-4.22 (8H, m) ppm.
$^{13}$C-NMR (CDCl$_3$): 16.1 (t, $^3$J$_{P-C}$=28.9 Hz), 36.5 (dd, $^1$J$_{P-C}$=145.2 Hz, $^2$J$_{P-C}$=23.1 Hz), 55.0(s), 62.3-62.9 (m) ppm.

(4) Synthesis of 3,4-bis(diethoxyphosphoryl)-2,3-dihydrothiophene

[Chemical Formula 74]

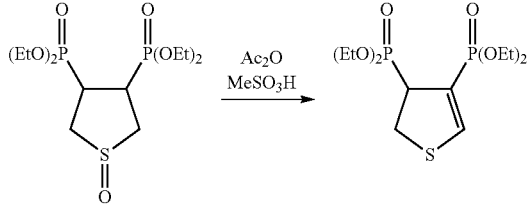

In methylene chloride, 2.19 g (5.82 mmols) of 3,4-bis(diethoxyphosphoryl)sulfurane was dissolved, to which 0.714 g (6.99 mmols) of commercially available acetic anhydride and 0.140 g (1.46 mmols) of methanesulfonic acid were added at room temperature, followed by stirring for 6 hours. Thereafter, 0.967 g (7.00 mmols) of potassium carbonate was added to the reaction solution to complete the reaction and the solid was removed by filtration. The filtrate was distilled off under reduced pressure to remove the solvent and acetic acid. The resulting crude product was purified with a silica gel column (ethyl acetate:methanol=15:1) to obtain the specified substance in the form of a brown oil at a yield of 2.010 g (yield: 96.4%).

$^1$H-NMR (CDCl$_3$): 1.31-1.37 (12H, m), 3.66-3.74 (3H, m), 4.11-4.19 (8H, m), 7.29 (1H, dd, $^2J_{P-H}$=9.8 Hz, $^1J_{P-H}$=5.7 Hz) ppm.
$^{13}$C-NMR (CDCl$_3$): 16.2 (t, $^3J_{P-C}$=6.2 Hz), 36.1(s), 46.1 (d, $^2J_{P-C}$=133.3 Hz), 62.0-62.5 (m), 120.3 (dd, $^1J_{P-C}$=190.1 Hz, $^2J_{P-C}$=7.14 Hz), 148.7 (m) ppm.

(5) Synthesis of 3,4-bis(diethoxyphosphoryl)thiophene

[Chemical Formula 75]

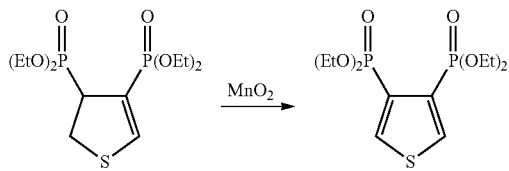

In benzene, 9.740 g (112 mmols) of commercially available manganese (IV) oxide was dissolved, to which 2.010 g (5.60 mmols) of 3,4-bis(diethoxyphosphoryl)-2,3-dihydrothiophene was added at room temperature. Thereafter, the reaction mixture was heated and stirred under reflux for 29 hours. After the reaction, the reaction mixture was cooled down to room temperature and the solid was removed by celite filtration. The filtrate was distilled off under reduced pressure to remove the solvent, and the resulting crude product was purified with a silica gel column (ethyl acetate:methanol=15:1) to obtain the specified substance in the form of a brown solid at a yield of 1.700 g (yield: 85.4%).

m/z (FAB+): 357 (calculated: 356.06).
$^1$H-NMR (CDCl$_3$): 1.20-1.33 (12H, m), 4.05-4.19 (8H, m), 8.15 (2H, dd, $^2J_{P-H}$=7.3 Hz, $^3J_{P-H}$=3.9 Hz) ppm.
$^{13}$C-NMR (CDCl$_3$): 16.2 (d, $^3J_{P-C}$=7.0 Hz), 62.4 (d, $^2J_{P-C}$=6.0 Hz), 131.0 (dd, $^2J_{P-C}$=197.0 Hz, $^1J_{P-C}$=18.0 Hz), 140.1 (dd, $^2J_{P-C}$=18.0 Hz, $^3J_{P-C}$=18.0 Hz) ppm.

Example 2

Synthesis of 3,4-bis(diethoxyphosphoryl)thiophene

Synthesis was carried out according to the following processes (1) and (2).

(1) Synthesis of 3-bromo-4-(diethoxyphosphoryl)thiophene

[Chemical Formula 76]

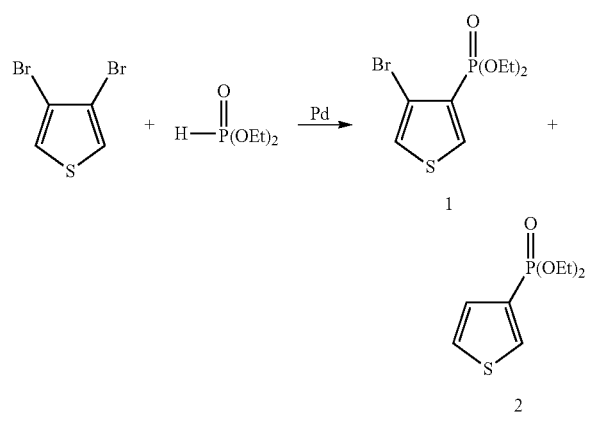

Under nitrogen, 0.0968 g (0.4 mmols) of 3,4-dibromothiophene and 0.0131 g (0.016 mmols) of commercially available Pd(dppf)$_2$Cl$_2$ were added to DMF (4 ml) and were dissolved under stirring at room temperature for 5 minutes. To the thus obtained solution, 0.1326 g (0.96 mmols) of commercially available diethyl phosphate and 0.1241 g (0.96 mmols) of diisopropylethylamine were added at room temperature. Thereafter, the reaction mixture was heated to 110° C. and stirred for 4 hours. After the reaction, the reaction mixture was cooled down to room temperature, to which a disodium hydrogen phosphate/sodium dihydrogen phosphate buffer solution, adjusted to pH=7.0, was added, followed by extraction with ethyl acetate. The resulting organic phase was washed with a saturated saline and dried over anhydrous sodium sulfate. The solvent was removed by distilling off under reduced pressure, and the resulting crude product was purified with a PTLC plate (developed with ethyl acetate: hexane=1:1) to obtain a specified substance 1 in the form of a brown solid and the specified substance 2 in the form of a yellow oil. The thus obtained substances were used for the reaction of Example 2(2) as they are. The yields of the compounds 1 and 2 are shown in Table 1.

TABLE 1

| Yield (%) | |
|---|---|
| 1 | 2 |
| 63 | 6 |

(a) 3-bromo-4-(diethoxyphosphoryl)thiophene 1

$^1$H-NMR (CDCl$_3$): 1.20-1.33 (12H, m), 4.05-4.19 (8H, m), 8.15 (2H, dd, $^2J_{P-H}$=7.3 Hz, $^3J_{P-H}$=3.9 Hz) ppm.
$^{13}$C-NMR (CDCl$_3$): 16.2 (d, $^3J_{P-C}$=7.0 Hz), 62.4 (d, $^2J_{P-C}$=6.0 Hz), 131.0 (dd, $^2J_{P-C}$=197.0 Hz, $^1J_{P-C}$=18.0 Hz), 140.1 (dd, $^2J_{P-C}$=18.0 Hz, $^3J_{P-C}$=18.0 Hz) ppm.

(b) 3-(diethoxyphosphoryl)thiophene 2 m/z (FAB+): 221 (calculated: 220.03).
$^1$H-NMR (CDCl$_3$): 1.33 (6H, t, J=7.1 Hz), 4.06-4.18 (4H, m), 7.32-7.35 (1H, m), 7.42-7.45 (1H, m), 7.98-8.01 (1H, m) ppm.
$^{13}$C-NMR (CDCl$_3$): 16.2 (d, $^3J_{P-C}$=6.4 Hz), 62.0 (d, $^2J_{P-C}$=5.4 Hz), 127.1 (d, $^2J_{P-C}$=19.4 Hz), 128.8 (d, $^3J_{P-C}$=16.8 Hz), 129.3 (d, $^1J_{P-C}$=201.2 Hz), 135.2 (d, $^2J_{P-C}$=19.8 Hz) ppm.

(2) Synthesis of 3,4-bis(diethoxyphosphoryl)thiophene

[Chemical Formula 77]

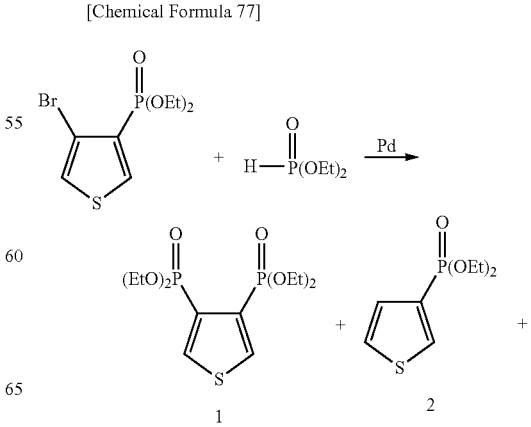

-continued

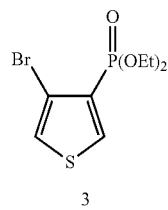

3

Under nitrogen, 0.1196 g (0.4 mmols) of 3-bromo-4-(diethoxyphosphoryl)thiophene and 0.0185 g (0.016 mmols) of commercially available tetrakistriphenylphosphine palladium were added to DMF (4 ml) and were dissolved under stirring at room temperature for 5 minutes. To the thus obtained solution, 0.0663 g (0.48 mmols) of commercially available diethyl phosphate and 0.0621 g (0.48 mmols) of diisopropylethylamine were added at room temperature. Thereafter, the reaction mixture was heated to 110° C. and stirred for 5 hours. After the reaction, the reaction mixture was cooled down to room temperature, to which a disodium hydrogen phosphate/sodium dihydrogen phosphate buffer solution, adjusted to pH=7.0, was added at room temperature, followed by extraction with ethyl acetate. The resulting organic phase was washed with a saturated saline and dried over anhydrous sodium sulfate. The solvent was removed by distilling off under reduced pressure and the resulting crude product was purified with a PTLC plate (developed with ethyl acetate:hexane=1:1) to obtain the specified substance 1 in the form of a white solid, a compound 2 in the form of a yellow oil and a compound 3 in the form of a brown solid. The yields of the compounds 1, 2, and 3 are shown in Table 2.

TABLE 2

| | Yield (%) | |
|---|---|---|
| 1 | 2 | 3 |
| 9 | 9 | 45 |

Example 3

Synthesis of 3,4-bis(diethoxyphosphoryl)thiophene

[Chemical Formula 78]

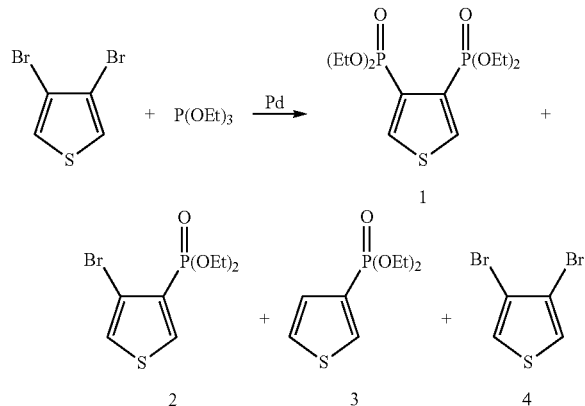

Under nitrogen, 0.500 g (2.07 mmols) of 3,4-dibromothiophene and 0.009 g (0.1035 mmols) of commercially available palladium dichloride were added to DMF (2 ml), followed by dissolution under stirring at room temperature for 5 minutes. To the thus obtained solution, 0.841 g (4.968 mmols) of commercially available triethyl phosphate and 0.031 g (0.207 mmols) of sodium iodide were added at room temperature. Thereafter, the reaction mixture was heated to 110° C. and stirred for 16 hours, followed by further heating to 150° C. and stirred for 2 hours. After the reaction, the reaction mixture was cooled down to room temperature and subjected to analysis with HPLC. The results of the analysis are shown in Table 3.

TABLE 3

| HPLC Area (%) | | | |
|---|---|---|---|
| 1 | 2 | 3 | 4 |
| 12 | 71 | 3 | 14 |

(a) 3,4-bis(diethoxyphosphoryl)thiophene 1

Retention time: 2.9 minutes (b) 3-bromo-4-(diethoxyphosphoryl)thiophene 2

Retention time: 7.5 minutes (c) 3-(diethoxyphosphoryl)thiophene 3

Retention time: 4.6 minutes

Example 4

Synthesis of 3,4-bis(diethoxyphosphoryl)-2-iodothiophene

[Chemical Formula 79]

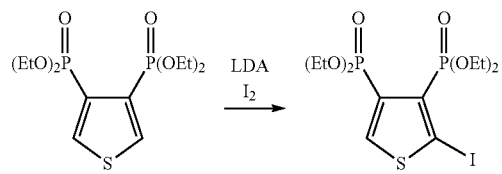

Commercially available n-butyllithium (1.58 M hexane solution, 8.420 mmols) was slowly dropped in a THF solution cooled to −78° C., of 0.852 g (8.420 mmols) of commercially available diisopropylamine. After stirring for 1 hour, a THF solution of 3.000 g (8.420 mmols) of 3,4-bis(diethoxyphosphoryl)thiophene obtained above was added to. After stirring for further 1 hour while keeping the temperature, a THF solution of 2.7781 g (10.946 mmols) of commercially available iodine was dropped, followed by stirring for still further 1 hour. After completion of the reaction, sodium thiosulfate was added, followed by extraction with ethyl acetate. The organic phase was washed with sodium thiosulfate and a saturated saline solution and dried over anhydrous sodium sulfate. The solvent was removed and the resulting crude product was purified with a silica gel column (ethyl acetate:methanol=15:1) to obtain the specified substance in the form of a white solid at a yield of 3.26 g (yield: 80%).

$^1$H-NMR (CDCl$_3$): 1.32 (6H, t, J=7.1 Hz), 1.35 (6H, t, J=7.0 Hz), 4.11-4.21 (8H, m), 8.21 (1H, dd, $^3$J$_{P-H}$=2.7 Hz, $^2$J$_{P-H}$=9.4 Hz) ppm.

Example 5

Synthesis of 2-tributylstannyl-3,4-bis(diethoxyphosphoryl)-thiophene

[Chemical Formula 80]

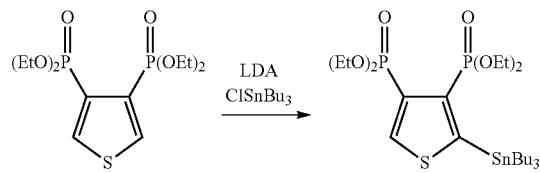

Commercially available n-butyllithium (1.58 M hexane solution, 9.262 mmols) was slowly dropped in a THF solution cooled to −78° C., of 0.9386 g (9.276 mmols) of commercially available diisopropylamine. After stirring for 1 hour, a THF solution of 3.000 g (8.420 mmols) of 3,4-bis(diethoxyphosphoryl)thiophene obtained above was added thereto. After stirring for further 1 hour while keeping the temperature, a THF solution of 4.1109 g (12.63 mmols) of commercially available tributylstannyl chloride was dropped, followed by stirring for still further 1 hour. After completion of the reaction, a disodium hydrogen phosphate/sodium dihydrogen phosphate buffer solution, adjusted to pH=7, was added thereto to complete the reaction, followed by extraction with ethyl acetate. The organic phase was washed with a saturated saline solution and dried over anhydrous sodium sulfate. The solvent was removed, and the resulting crude product was purified with a silica gel column (ethyl acetate) to obtain the specified substance in the form of a transparent oil at a yield of 2.4852 g (yield: 46%).

$^1$H-NMR (CDCl$_3$): 0.77-0.85 (12H, m), 1.11-1.56 (27H, m), 4.00-4.13 (8H, m), 8.34 (1H, dd, $^3$J$_{P-H}$=2.5 Hz, $^2$J$_{P-H}$=7.9 Hz) ppm.
$^{13}$C-NMR (CDCl$_3$): 12.7, 13.0, 16.2 (m), 29.4, 61.8 (m), 132.2 (dd, $^2$J$_{P-C}$=22.4 Hz, $^1$J$_{P-C}$=192.9 Hz), 135.2 (dd, $^2$J$_{P-C}$=17.6 Hz, $^1$J$_{P-C}$=182.1 Hz), 145.5 (d, $^2$J$_{P-C}$=19.5 Hz), 161.6 (dd, $^3$J$_{P-C}$=12.7 Hz, $^2$J$_{P-C}$=32.2 Hz) ppm.

Example 6

Synthesis of a phosphorylthiophene compound derived from 2-iodo-3,4-bis(diethoxyphosphoryl)thiophene and 2-tributylstannyl-3,4-bis(diethoxyphosphoryl)thiophene Synthesized according to the following processes (1) to (12).

(1) Synthesis of 3,4-bis(diethoxyphosphoryl)-[2,2']-bithiophene

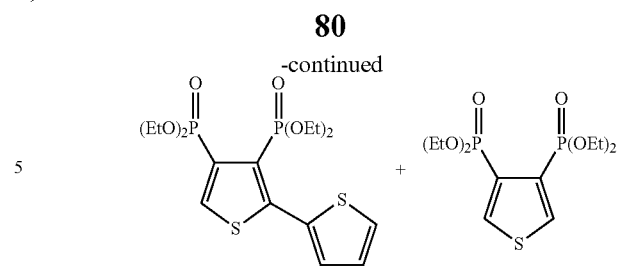

The 2-tributylstannyl-3,4-bis(diethoxyphosphoryl)-thiophene obtained above, different types of palladium catalysts (0.05 equivalents, commercially available products) indicated in the following Table 4 and copper(I) cyanide (0 or 0.10 equivalents, a commercial product) were dissolved in solvents indicated in Table 4, to which 2-iodothiophene (1.2 equivalents) was added. Thereafter, the reaction mixture was heated to 70° C. and stirred for 2 to 12 hours. After the reaction, the reaction mixture was cooled down to room temperature, to which a potassium fluoride aqueous solution was added, followed by stirring for 2 hours. Subsequently, the resulting solid was removed by celite filtration and the filtrate was extracted with ethyl acetate. The organic phase was washed with a saturated saline solution and dried over anhydrous sodium sulfate. The solvent was removed by distilling off under reduced pressure, and the resulting crude product was purified with a silica gel column (ethyl acetate:methanol=15:1) to obtain the specified substance 1 in the form of a transparent oil and a white solid compound 2, respectively.

TABLE 4

| Entry | Pd cat. | Additive | Solvent | Time (h) | Yield (%) 1 | 2 |
|---|---|---|---|---|---|---|
| 1 | Pd(OAc)$_2$4PPh$_3$ | CuCN | toluene | 2 | 5 | 90 |
| 2 | Pd(PPh$_3$)$_4$ | — | toluene | 10 | 17 | 60 |
| 3 | Pd(PPh$_3$)$_4$ | CuCN | toluene | 7 | 86 | 8 |
| 4 | Pd(PPh$_3$)$_4$ | CuCN | DMF | 12 | — | 80 |

3,4-bis(diethoxyphosphoryl)-[2,2']-bithiophene 1 m/z (FAB+): 439 (calculated: 438.05).
$^1$H-NMR (CDCl$_3$): 1.18 (6H, t, J=7.1 Hz), 1.39 (6H, t, J=7.0 Hz), 3.90-4.00 (2H, m), 4.05-4.15 (2H, m), 4.21-4.24 (4H, m), 7.08-7.09 (1H, m), 7.38 (1H, m), 7.42 (1H, m), 8.15 (1H, dd) ppm.

(2) Synthesis of 3,4-bis(diethoxyphosphoryl)-[2,2']-bithiophene

[Chemical Formula 81]

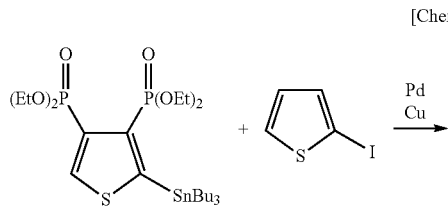

[Chemical Formula 82]

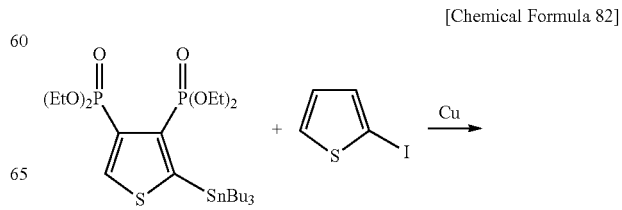

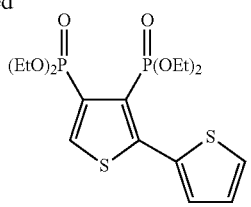

In THF, 0.600 g (0.930 mmols) of 2-tributylstannyl-3,4-bis(diethoxyphosphoryl)thiophene and 0.1013 g (1.023 mmols) of commercially available copper(I) chloride were dissolved, to which 0.2344 g (1.116 mmols) of 2-iodothiophene was added at room temperature. Thereafter, the reaction mixture was heated and stirred under reflux for 4 hours. After the reaction, the reaction mixture was cooled down to room temperature, to which a potassium fluoride aqueous solution was added, followed by stirring for 2 hours. Subsequently, the resulting solid was removed by celite filtration and the filtrate was extracted with ethyl acetate. The organic phase was washed with a saturated saline solution and dried over anhydrous sodium sulfate. The solvent was removed by distilling off under reduced pressure, and the resulting crude product was purified with a silica gel column (ethyl acetate:methanol=15:1) to obtain the specified substance at a yield of 0.3595 g (yield: 88%).

(3) Synthesis of 3,4-bis(diethoxyphosphoryl)-[2,2'] bithiophene

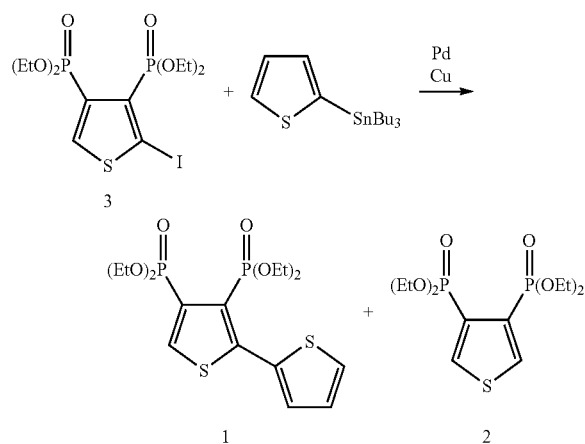

[Chemical Formula 83]

3,4-bis(diethoxyphosphoryl)-2-iodothiophene, different types of palladium catalysts (0.05 equivalents, commercially available products) indicated in the following Table 5 and commercially available copper(I) cyanide (0.20 equivalents) were dissolved in toluene, to which 2-tributylstannylthiophene (1.2 equivalents) was added at room temperature. Thereafter, the reaction mixture was heated to 70° C. and stirred for 8.5 to 10 hours. After the reaction, the reaction mixture was cooled down to room temperature, to which a potassium fluoride aqueous solution was added, followed by stirring for 2 hours. The resulting solid was removed by celite filtration and the filtrate was extracted with ethyl acetate. The organic phase was washed with a saturated saline solution and dried over anhydrous sodium sulfate. The solvent was removed by distilling off under reduced pressure, and the resulting crude product was purified with a silica gel column (ethyl acetate:methanol=15:1) to obtain the specified substances.

TABLE 5

| | | Time | Yield (%) | | |
| --- | --- | --- | --- | --- | --- |
| Entry | Pd cat. | (h) | 1 | 2 | 3 |
| 1 | Pd(PPh$_3$)$_4$ | 9 | 70 | 20 | — |
| 2 | Pd(PPh$_3$)$_2$Cl$_2$ | 8.5 | trace | 82 | — |
| 3 | Pd$_2$(dba)$_3$ | 9 | 41 | 39 | — |
| 4 | Pd(OAc)$_2$2dppe | 10 | — | 31 | 63 |

(4) Synthesis of 3,4-bis(diethoxyphosphoryl)-[2,2']-bithiophene

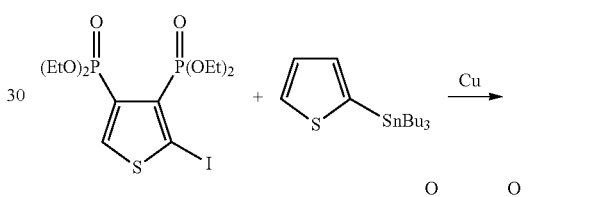

[Chemical Formula 84]

3,4-bis(diethoxyphosphoryl)-2-iodothiophene and different equivalents of copper(I) chloride (commercially available product) indicated in Table 6 were dissolved in DMF, to which 2-tributylstannylthiophene (1.2 equivalents) was added at room temperature. Thereafter, the reaction mixture was heated to 80° C. and stirred for 8.5 to 11 hours. After the reaction, the reaction mixture was cooled down to room temperature, to which a 0.6 M hydrochloric acid aqueous solution was added, followed by extraction of the resulting product with ethyl acetate. The organic phase was washed with a saturated saline solution and dried over anhydrous sodium sulfate. The solvent was removed by distilling off under reduced pressure and the resulting crude product was purified with a silica gel column (ethyl acetate:methanol=15:1) to obtain the specified substance.

TABLE 6

| Entry | CuCl (eq.) | Time (h) | Yield (%) |
| --- | --- | --- | --- |
| 1 | 1.1 | 10 | 85 |
| 2 | 2.2 | 8.5 | 80 |
| 3 | 4.2 | 11 | 19 |

(5) Synthesis of 5-tributylstannyl-3,4-bis(diethoxyphosphoryl)-[2,2']-bithiophene

[Chemical Formula 85]

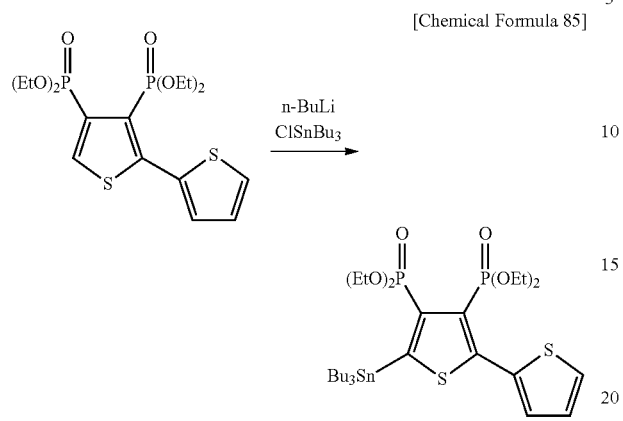

In THF, 0.3595 g (0.820 mmols) of 3,4-bis(diethoxyphosphoryl)-[2,2']-bithiophene obtained above was dissolved and cooled down to −78° C. Commercially available n-butyllithium (1.58 M hexane solution, 0.984 mmols) was slowly dropped in the solution and stirred for 1 hour while keeping the temperature. Thereafter, 0.400 g (1.23 mmols) of commercially available tributylstannyl chloride was dropped and stirred for 4 hours. After completion of the reaction, a disodium hydrogen phosphate/sodium dihydrogen phosphate buffer solution, adjusted to pH=7.0, was added to complete the reaction, followed by extraction with ethyl acetate. The solvent was removed, and the resulting crude product was purified with a silica gel column to obtain the specified substance in the form of an oil at a yield of 0.3757 g (yield: 63%). The thus obtained substance was used as it is for reaction in Example 9(5).

(6) Synthesis of 3,4-bis(diethoxyphosphoryl)-[2,2';5',2";5",2'"]-quaterthiophene

[Chemical Formula 86]

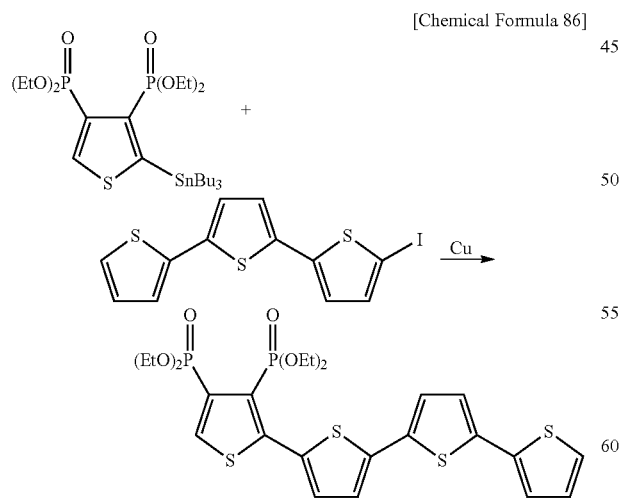

In THF, 0.200 g (0.310 mmols) of 2-tributylstannyl-3,4-bis(diethoxyphosphoryl)thiophene obtained above and 0.0338 g (0.341 mmols) of commercially available copper(I) chloride were dissolved, to which 0.128 g (0.341 mmols) of 2-iodoterthiophene was added at room temperature. Thereafter, the reaction mixture was heated and stirred under reflux for 10 hours. After the reaction, the reaction mixture was cooled down to room temperature, to which a potassium fluoride aqueous solution was added, followed by stirring for 1 hour. The resulting solid was removed by celite filtration and the filtrate was extracted with ethyl acetate. The organic phase was washed with a saturated saline solution and dried over anhydrous sodium sulfate. The solvent was removed by distilling off under reduced pressure, and the resulting crude product was purified with a silica gel column to obtain the specified substance in the form of a yellow solid at a yield of 0.158 g (yield: 85%). The thus obtained substrate was used as it is for reaction in Example 6(7).

(7) Synthesis of 2-tributylstannyl-3,4-bis(diethoxyphosphoryl)-[2,2';5',2";5",2'"]-quaterthiophene

[Chemical Formula 87]

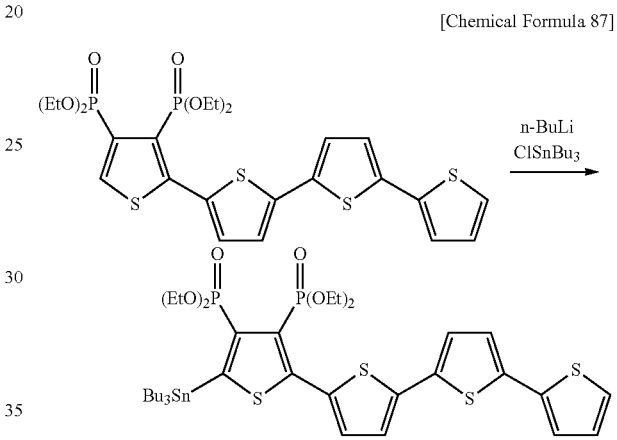

In THF, 0.1507 g (0.250 mmols) of 3,4-bis(diethoxyphosphoryl)-[2,2';5',2";5",2'"]-quaterthiophene obtained above was dissolved and cooled down to −78° C. Commercially available n-butyl lithium (1.58 M hexane solution, 0.250 mmols) was slowly dropped, followed by stirring for 1 hour at a standing temperature. Thereafter, 0.0814 g (0.250 mmols) of commercially available tributylstannyl chloride was dropped and stirred for 4 hours. After completion of the reaction, a disodium hydrogen phosphate/sodium dihydrogen sulfate buffer solution, adjusted to pH=7, was added to complete the reaction, followed by extraction with ethyl acetate. The solvent was removed and the resulting crude product was purified with a silica gel column to obtain the specified substance in the form of a yellow oil at a yield of 0.1271 g (yield: 57%). The thus obtained substance was used as it is for reaction in Example 9(11).

(8) Synthesis of 3,3',4,4'-tetrakis(diethoxyphosphoryl)-[2,2']-bithiophene

[Chemical Formula 88]

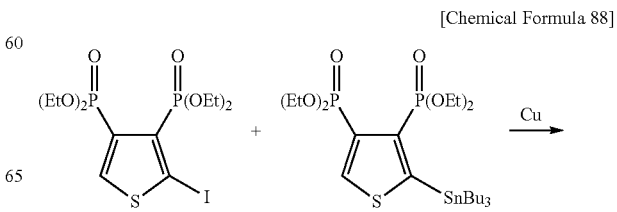

-continued

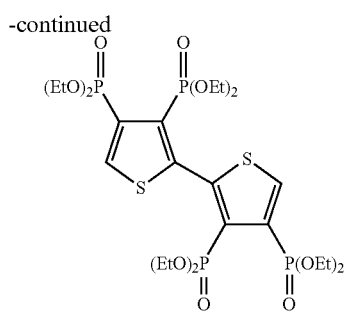

In THF, 0.037 g (0.076 mmols) of the 2-iodo-3,4-bis(diethoxyphosphoryl)thiophene obtained in Example 4 and 0.049 g (0.076 mmols) of the 2-tributylstannyl-3,4-bis(diethoxyphosphoryl)thiophene obtained in Example 5 were dissolved, to which 0.009 g (0.091 mmols) of commercially available copper(I) chloride was added at room temperature. Thereafter, the reaction mixture was heated and stirred for 4 hours under reflux. After the reaction, the reaction mixture was cooled down to room temperature and the resulting solid was removed by celite filtration. The filtrate was distilled off under reduced pressure to remove the solvent, and the resulting crude product was purified with a silica gel column (ethyl acetate:methanol=15:1 to ethyl acetate:methanol=5:1) to obtain the specified substance in the form of a transparent oil at a yield of 0.049 g (yield: 91%).

m/z (FAB+): 711 (calculated: 710.11).

$^1$H-NMR (CDCl$_3$): 1.22 (12H, tq, J=7.4 Hz, J=7.4 Hz), 1.37 (12H, tq, J=7.1 Hz, J=7.1 Hz), 3.99-4.16 (8H, m), 4.17-4.25 (8H, m), 8.24 (2H, dd, $^3J_{P-H}$=3.0 Hz, $^2J_{P-H}$=9.2 Hz) ppm.

$^{13}$C-NMR (CDCl$_3$): 16.1 (dd, J=10.9 Hz, J=6.7 Hz), 16.3 (d, $^2J_{P-C}$=4.1 Hz), 62.3 (d, $^2J_{P-C}$=9.3 Hz), 62.6 (dd, J=30.0 Hz, J=5.2 Hz), 130.7 (dd, $^2J_{P-C}$=22.4 Hz, $^1J_{P-C}$=195.9 Hz), 132.6 (dd, $^2J_{P-C}$=17.6 Hz, $^1J_{P-C}$=197.4 Hz), 140.0 (dd, $^3J_{P-C}$=14.4 Hz, $^2J_{P-C}$=18.6 Hz), 145.5 (dd, $^3J_{P-C}$=13.1, $^2J_{P-C}$=18.1 Hz) ppm.

(9) Synthesis of 3,3',4,4'-tetrakis(diethoxyphosphoryl)-[2,2']-bithiophene

[Chemical Formula 89]

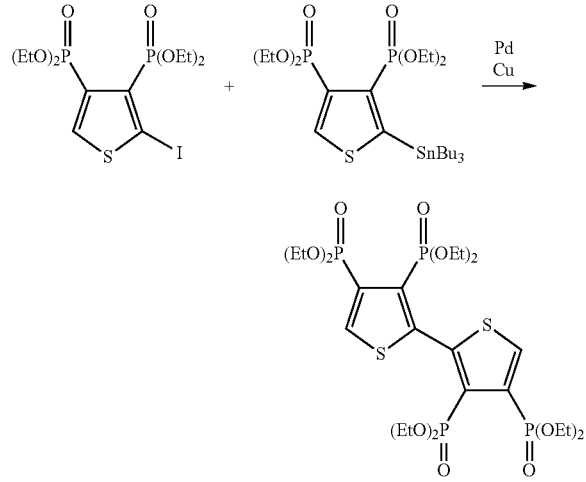

In THF, 0.082 g (0.171 mmols) of the 2-iodo-3,4-bis(diethoxyphosphoryl)thiophene obtained in Example 4 and 0.009 g (0.00775 mmols) of commercially available tetrakistriphenylphosphine palladium, and 0.0014 g (0.0155 mmols) of commercially available copper(I) chloride were dissolved, to which 0.100 g (0.155 mmols) of the 2-tributylstannyl-3,4-bis(diethoxyphosphoryl)thiophene obtained in Example 5 was added at room temperature. Thereafter, the reaction mixture was heated to 70° C. and stirred for 11 hours. After the reaction, the reaction mixture was cooled down to room temperature, followed by distilling off under reduced pressure to remove the solvent, and the resulting crude product was purified with a silica gel column (ethyl acetate:methanol=15:1 to ethyl acetate:methanol=5:1) to obtain the specified substance at a yield of 0.046 g (yield: 38%).

(10) Synthesis of 5,5'-bis(tributylstannyl)-3,3',4,4'-tetrakis(diethoxyphosphoryl)-[2,2']-bithiophene

[Chemical Formula 90]

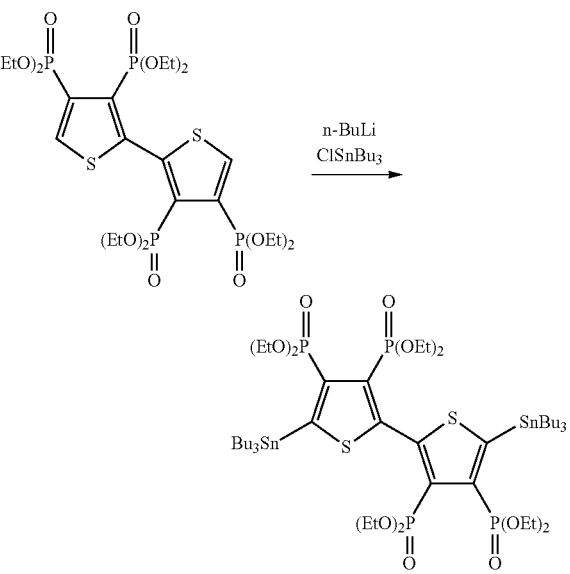

In 25 ml of THF, 0.952 g (1.34 mmols) of the 3,3',4,4'-tetrakis(diethoxyphosphoryl)-[2,2']-bithiophene obtained in Example 6(8) or (9) was dissolved, and cooled down to −78° C. Commercially available n-butyl lithium (1.59 M hexane solution, 5.34 mmols) was slowly dropped, followed by stirring for 3 hours at a standing temperature. Thereafter, 1.956 g (6.01 mmols) of commercially available tributylstannyl chloride was dropped and stirred for 4 hours. After completion of the reaction, a disodium hydrogen phosphate/sodium dihydrogen sulfate buffer solution, adjusted to pH=7, was added to complete the reaction, followed by extraction with ethyl acetate. The organic phase was washed with a saturated saline solution and dried over anhydrous sodium sulfate. The solvent was removed, and the resulting crude product was purified with a silica gel column (ethyl acetate) to obtain the specified substance in the form of a transparent oil at a yield of 1.174 g (yield: 68%). The thus obtained substance was used as it is for reaction in Example 6(11).

(11) Synthesis of 3'',3''',4'',4'''-tetrakis(diethoxyphosphoryl)-[2,2';5',2'';5'',2''';5''',2'''';5'''',2''''']-sexithiophene

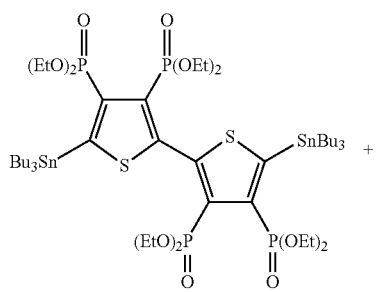

[Chemical Formula 91]

0.0170 g (0.172 mmols) of copper(I) chloride was added at room temperature. Thereafter, the reaction mixture was heated and stirred for 11 hours under reflux. After the reaction, the reaction mixture was cooled down to room temperature and the solvent was removed by distilling off under reduced pressure, and the resulting crude product was purified with a silica gel column (ethyl acetate:methanol=5:1) to obtain the specified substance in the form of a yellow oil at a yield of 0.0809 g (yield: 99%).

m/z (FAB+): 1038 (calculated 1038.06).

$^1$H-NMR (CDCl$_3$): 1.19-1.26 (24H, m), 4.05-4.22 (16H, m), 7.03-7.05 (2H, m), 7.15 (2H, d, J=3.7 Hz), 7.22 (2H, d, J=3.4 Hz), 7.26-7.29 (4H, m) ppm.

(12) Synthesis of 3''',3'''',4''',4''''-tetrakis(diethoxyphosphoryl)-[2,2';5',2'';5'',2''';5''',2'''';5'''',2''''';5''''',2'''''';5'''''',2''''''']-octithiophene

[Chemical Formula 92]

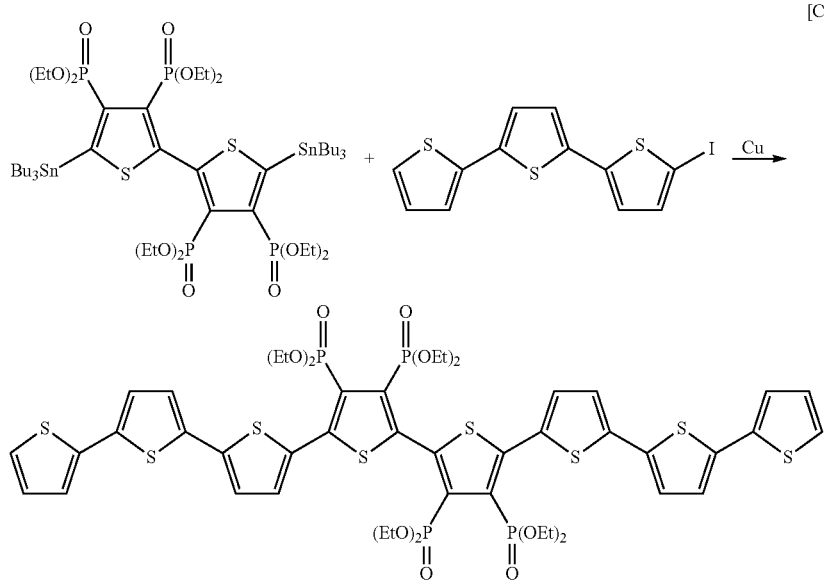

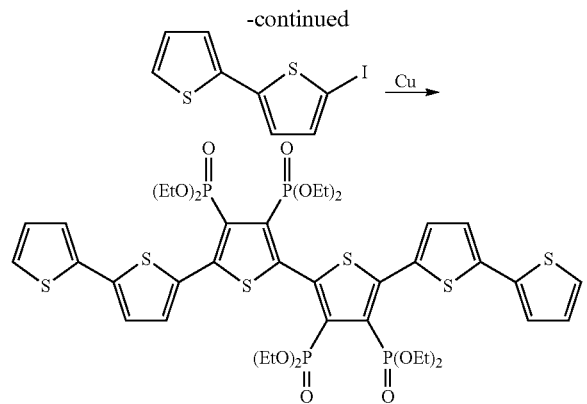

In THF, 0.101 g (0.0781 mmols) of the 5,5'-bis(tributylstannyl)-3,3',4,4'-tetrakis(diethoxyphosphoryl)-[2,2']-bithiophene obtained in (10) above and 0.0503 g (0.172 mmols) of 2-iodo-bithiophene were dissolved, to which In THF (4.0 ml), 0.200 g (0.155 mmols) of 5,5'-bis(tributylstannyl)-3,3',4,4'-tetrakis(diethoxyphosphoryl)-[2,2']-bithiophene obtained in Example 6(10) above and 0.128 g (0.341 mmols) of 2-iodo-terthiophene were dissolved, to which 0.034 g (0.341 mmols) of commercially available copper(I) chloride was added at room temperature. Thereafter, the reaction mixture was heated and stirred for 13 hours under reflux. After the reaction, the reaction mixture was cooled down to room temperature, to which a potassium fluoride aqueous solution was added, followed by stirring for 1 hour. Thereafter, the solid was removed by celite filtration and the filtrate was extracted with ethyl acetate. The resulting organic phase was washed with a saturated saline solution and dried over anhydrous sodium sulfate. The solvent was removed by distilling off under reduced pressure, and the resulting crude product was purified with a silica gel column (ethyl acetate: methanol=5:1) to obtain 0.157 g (yield: 84%) of the specified substance in the form of a yellow solid.

m/z (FAB+): 1202 (calculated 1202.03)

$^1$H-NMR (CDCl$_3$): 1.20-1.27 (24H, m), 4.02-4.21 (18H, m), 7.03-7.30 (14H, m) ppm.

Example 7

Synthesis of 3,4-bis(diethoxyphosphoryl)-2,5-diiodothiophene

[Chemical Formula 93]

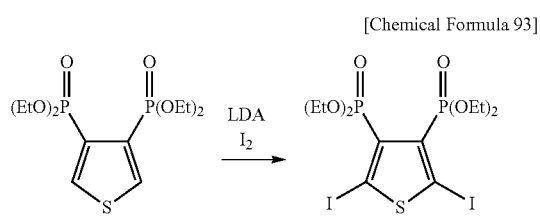

A THF solution of 0.300 g of the 3,4-bis(diethoxyphosphoryl)thiophene obtained in Example 1 was cooled down to −78° C., in which commercially available n-butyl lithium (1.59 M hexane solution, 1.852 mmols) was slowly dropped. After stirring for 1 hour at a standing temperature, a THF solution of 0.6411 g (2.526 mmols) of commercially available iodine was dropped, followed by stirring for 4 hours. After completion of the reaction, sodium thiosulfate was added, followed by extraction with ethyl acetate. The resulting organic phase was washed with sodium thiosulfate and a saturated saline solution, and dried over anhydrous sodium sulfate. The solvent was removed, and the resulting crude product was purified with a silica gel column (ethyl acetate:methanol=15:1) to obtain the specified substance in the form of a white solid at a yield of 0.3884 g (yield: 76%).

m/z (EI): 608 (calculated 607.85).

$^1$H-NMR (CDCl$_3$): 1.36 (12H, t, J=7.1 Hz), 4.13-4.23 (8H, m) ppm.

$^{13}$C-NMR (CDCl$_3$): 16.2 (d, $^3J_{P-C}$=6.0 Hz), 62.8 (d, $^2J_{P-C}$=5.9 Hz), 93.6 (dd, $^3J_{P-C}$=12.2 Hz, $^2J_{P-C}$=18.6 Hz), 136.8 (dd, $^2J_{P-C}$=17.4 Hz, $^1J_{P-C}$=195.5 Hz) ppm.

Example 8

Synthesis of 2,5-bis(tributylstannyl)-3,4-bis(diethoxyphosphoryl)thiophene

[Chemical Formula 94]

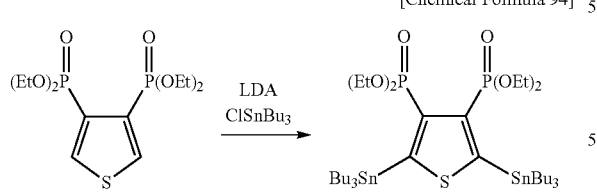

Commercially available n-butyl lithium (2.6 M hexane solution, 21.0 mmols) was slowly dropped in a THF solution cooled to −78° C., of 2.14 g (21.0 mmols) of commercially available diisopropylamine. After stirring for 1 hour, a THF solution of 3.00 g (8.41 mmols) of 3,4-bis(diethoxyphosphoryl)thiophene obtained in Example 1 was added. After stirring for further 1 hour at a standing temperature, 8.20 g (25.2 mmols) of commercially available tributylstannyl chloride was dropped, followed by stirring for 4 hours. After completion of the reaction, a disodium hydrogen phosphate/sodium dihydrogen phosphate buffer solution, adjusted to pH=7, was added so as to complete the reaction, followed by extraction with ethyl acetate. The organic phase was washed with a saturated saline solution and dried over anhydrous sodium sulfate. The solvent was removed, and the resulting crude product was purified with a silica gel column (ethyl acetate) to obtain the specified substance in the form of a transparent oil at a yield of 5.58 g (yield: 100%).

IR (neat): 2956, 1390 cm$^{-1}$.

Anal. calculated for C$_{36}$H$_{74}$O$_6$P$_2$SSn$_2$ C, 7.98; H, 46.27. Found C, 7.99; H, 46.43.

$^1$H-NMR (CDCl$_3$): 0.88 (18H, t, J=7.3 Hz), 1.19 (12H, q, J=7.0 Hz), 1.29-1.36 (24H, m), 1.57 (12H, t, J=7.2 Hz), 4.00-4.15 (8H, m) ppm.

$^{13}$C-NMR (CDCl$_3$): 11.4, 13.6, 16.3 (d, $^3J_{P-C}$=4.2 Hz), 27.3 (t, $^1J_{Sn-C}$=33.2 Hz), 29.1 (t, $^2J_{Sn-C}$=9.7 Hz), 61.6 (d, $^2J_{P-C}$=5.4 Hz), 136.6 (dd, $^2J_{P-C}$=22.1 Hz, $^1J_{P-C}$=192.36 Hz), 167.3 (dd, $^3J_{P-C}$=11.5 Hz, $^2J_{P-C}$=32.5 Hz) ppm.

Example 9

Synthesis of phosphorylthiophene compounds derived from 2,5-diiodo-3,4-bis(diethoxyphosphoryl)thiophene and 2,5-bis(tributylstannyl)-3,4-bis(diethoxyphosphoryl)-thiophene According to the following processes (1) to (11), the respective compounds were prepared.

(1) Synthesis of 3',4'-bis(diethoxyphosphoryl)-[2,2'; 5',2"]-terthiophene

[Chemical Formula 95]

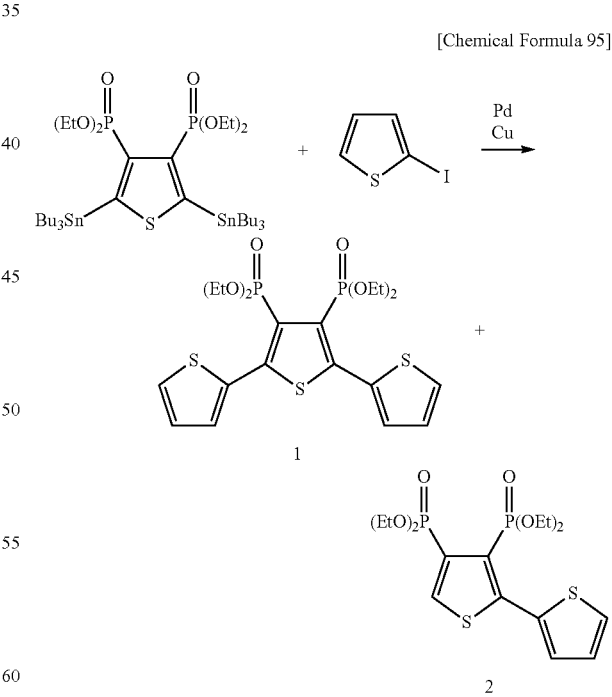

2,5-bis(tributylstannyl)-3,4-bis(diethoxyphosphoryl)-thiophene obtained in Example 8, commercially available tetrakistriphenylphosphine palladium (0.10 equivalent) and copper reagents (0.40 to 0.50 equivalents) indicated in Table 7 were dissolved in THF, to which 2-iodothiophene (2.4 equivalents) was added at room temperature. Thereafter, the reaction mixture was heated to 70° C. and stirred for 15 to 24 hours. After the reaction, the reaction mixture was cooled down to room temperature, to which a potassium fluoride aqueous solution was added, followed by stirring for 2 hours. Thereafter, the solid was removed by celite filtration and the filtrate was extracted with ethyl acetate. The organic phase was washed with a saturated saline solution and dried over anhydrous sodium sulfate. The solvent was removed by distilling off under reduced pressure, and the resulting product was purified with a silica gel column (ethyl acetate:ethanol=15:1) to obtain the specified substance in the form of a transparent oil.

TABLE 7

| Entry | CuX | (eq.) | Time (h) | Yield (%) 1 | 2 |
|---|---|---|---|---|---|
| 1 | CuCl | 40 mol % | 18 | 48 | 10 |
| 2 | CuCN | 40 mol % | 15 | 70 | trace |
| 3 | CuCN | 50 mol % | 16 | 82 | trace |
| 4 | CuI | 50 mol % | 24 | 30 | 14 | m/z (FAB+): 521 (calculated: 520.04).
$^1$H-NMR (CDCl$_3$): 1.08 (12H, t, J=7.1 Hz), 3.84-3.88 (4H, m), 4.01-4.07 (4H, m), 7.00-7.02 (2H, m), 7.30 (2H, d, J=3.4 Hz), 7.35 (2H, d, J=5.1 Hz) ppm.
$^{13}$C-NMR (CDCl$_3$): 16.0 (d, $^3J_{P-C}$=8.3 Hz), 62.7 (d, $^2J_{P-C}$=14.6 Hz), 127.8 (d, $^1J_{P-C}$=42.2 Hz), 128.8 (d, J=16.7 Hz), 130.0, 130.4 (d, J=19.9 Hz), 133.2 (d, J=5.2 Hz), 146.1 (dd, $^3J_{P-C}$=9.4 Hz, $^2J_{P-C}$=17.2 Hz) ppm.

(2) Synthesis of 3,4-bis(ethoxyphosphoryl)-[2,2']-bithiophene

[Chemical Formula 96]

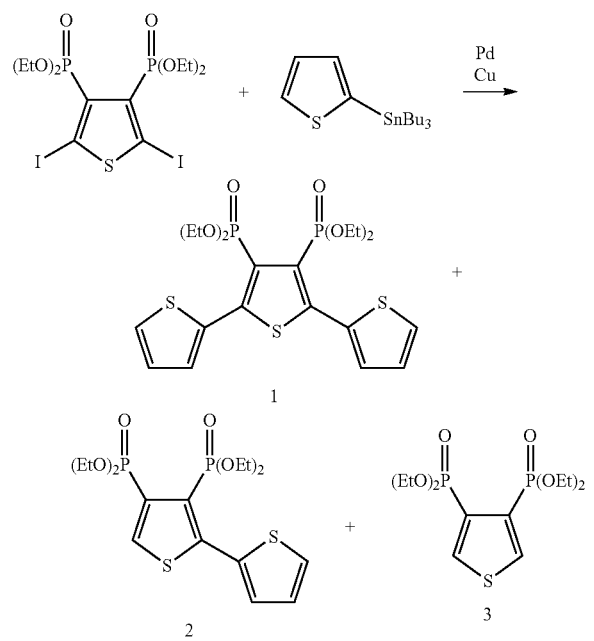

3,4-bis(diethoxyphosphoryl)-2,5-diiodothiophene obtained in Example 7, commercially available tetrakistriphenylphosphine palladium (0.10 equivalent) and copper(I) cyanide (commercial product) in amounts indicated in Table 8 were dissolved in different types of solvents indicated in Table 8, to which 2-tributylstannylthiophene (2.2 equivalents) was added at room temperature. Thereafter, the reaction mixture was heated to 70° C. and stirred for 6 to 20 hours. After the reaction, the reaction mixture was cooled down to room temperature, to which a potassium fluoride aqueous solution was added, followed by stirring for 2 hours. Thereafter, the solid was removed by celite filtration and the filtrate was extracted with ethyl acetate. The organic phase was washed with a saturated saline solution and dried over anhydrous sodium sulfate. The solvent was removed by distilling off under reduced pressure, and the resulting product was purified with a silica gel column (ethyl acetate:methanol=15:1).

TABLE 8

| | CuCN | | Time | Yield (%) | | |
|---|---|---|---|---|---|---|
| Entry | (eq.) | Solvent | (h) | 1 | 2 | 3 |
| 1 | 20 mol % | toluene/THF = 5/1 | 6 | — | 40 | — |
| 2 | 20 mol % | toluene/DMF = 5/1 | 9 | — | — | 70 |
| 3 | 40 mol % | toluene/DMF = 5/1 | 9 | — | — | 60 |
| 4 | 40 mol % | toluene | 20 | trace | 38 | 40 |

(3) Synthesis of 3',4'-bis(diethoxyphosphoryl)-[2,2': 5',2"]-terthiophene

[Chemical Formula 97]

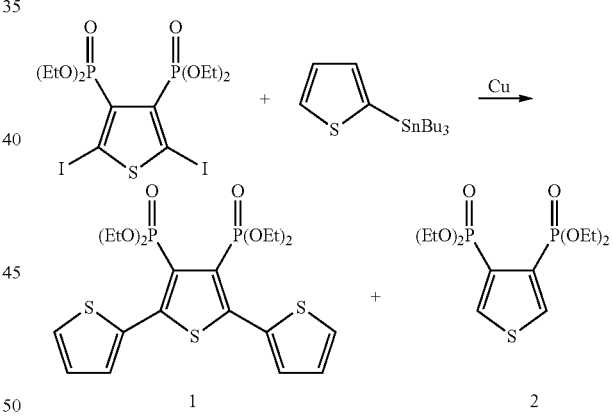

3,4-bis(diethoxyphosphoryl)-2,5-diiodothiophene obtained in Example 7, and different types of copper reagents (2.2 equivalents, commercial products) indicated in Table 9 were dissolved in DMF, to which 2-tributylstannylthiophene (2.2 equivalents) was added at room temperature. Thereafter, the reaction mixture was heated to 80° C. and stirred for 11 to 13 hours. After the reaction, the reaction mixture was cooled down to room temperature, to which a 0.6 M hydrochloric acid aqueous solution was added, followed by extraction of the resulting product with ethyl acetate. The organic phase was washed with a saturated saline solution and dried over anhydrous sodium sulfate. The solvent was removed by distilling off under reduced pressure, and the resulting product was purified with a silica gel column (ethyl acetate:methanol=15:1) to obtain the specified substance.

TABLE 9

| Entry | CuX | Time (h) | Yield (%) 1 | Yield (%) 2 |
|---|---|---|---|---|
| 1 | CuCl | 11 | 80 | trace |
| 2 | CuI | 13 | complex | mixture |
| 3 | CuCN | 11 | trace | — |

(4) Synthesis of 5,5"-Diiodo-3',4'-bis(diethoxyphosphoryl)-[2,2';5',2"]-terthiophene

[Chemical Formula 98]

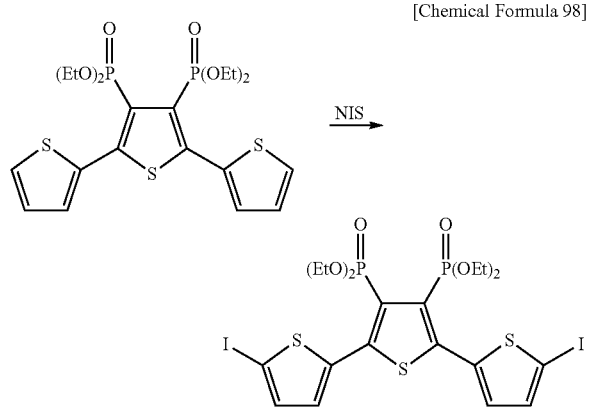

In a mixed solvent of chloroform and acetic acid at 1:1, 0.137 g (0.264 mmols) of the 3',4'-bis(diethoxyphosphoryl)-[2,2';5',2"]-terthiophene obtained in Example 7(1) or (3) was dissolved, to which 0.125 g (0.554 mmols) of commercially available N-iodosuccinimide was added at room temperature. Thereafter, the reaction mixture was stirred at room temperature for 24 hours. After the reaction, a sodium thiosulfate aqueous solution was added, followed by extraction with methylene chloride. The solvent was removed by distilling off under reduced pressure, and the resulting crude product was purified with a silica gel column to obtain the specified substance in the form of a yellow solid at a yield of 0.165 g (yield: 81%). The thus obtained product was used for reaction in Example 9(5).

(5) Synthesis of 3',3''',3'''''',4',4''',4'''''-hexakis(diethoxyphosphoryl)-[2,2';5',2'';5'',2''';5''',2'''';5'''',2''''';5''''',2'''''']-septithiophene

[Chemical Formula 99]

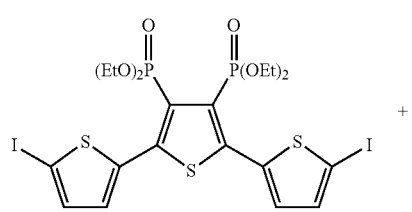

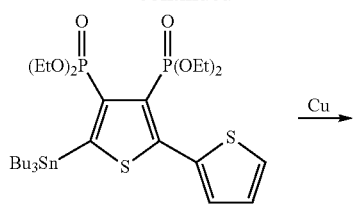

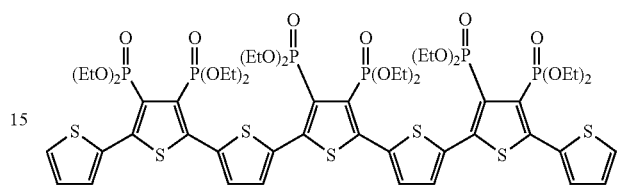

In THF, 0.155 g (0.201 mmols) of the 5,5"-diiodo-3',4'-bis(diethoxyphosphoryl)-[2,2';5',2"]-terthiophene obtained in Example 7(4) and 0.307 g (0.422 mmols) of 5-tributylstannyl-3,4-bis(diethoxyphosphoryl)-[2,2']-bithiophene obtained in Example 6(5) were dissolved, to which 0.0438 g (0.442 mmols) of commercially available copper(I) chloride was added at room temperature. Thereafter, the reaction mixture was heated and stirred under reflux for 18 hours. After the reaction, the reaction mixture was cooled down to room temperature, to which a potassium fluoride aqueous solution was added, followed by stirring for 1 hour. Subsequently, the solid was removed by celite filtration and the filtrate was extracted with ethyl acetate. The organic phase was washed with a saturated saline solution and dried over anhydrous sodium sulfate. The solvent was removed by distilling off under reduced pressure, and the resulting crude product was purified with a silica gel column to obtain the specified substance in the form of a yellow oil at a yield of 0.216 g (yield: 77%).

m/z (FAB+): 1392 (calculated: 1392.10).

$^1$H-NMR (CDCl$_3$): 1.12-1.40 (36H, m), 3.93-4.23 (24H, m), 7.10-7.12 (2H, m), 7.34-7.46 (2H, m) ppm.

(6) Synthesis of 3'',4''-bis(diethoxyphosphoryl)-[2,2';5',2'';5'',2''';5''',2'''']-quinquethiophene and 3,4-bis(diethoxyphosphoryl)-2,2';5',2'')-terthiophene

[Chemical formula 100]

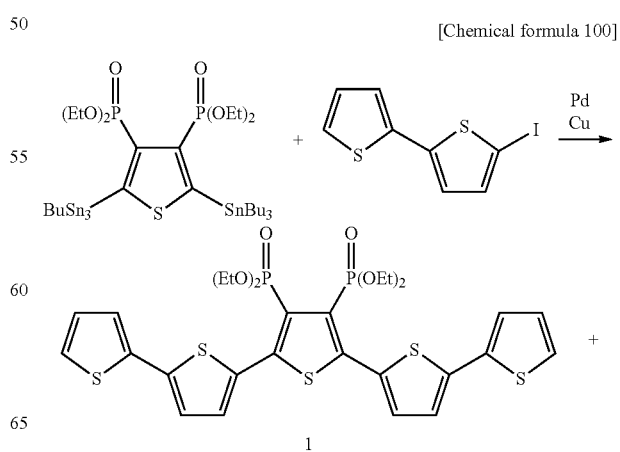

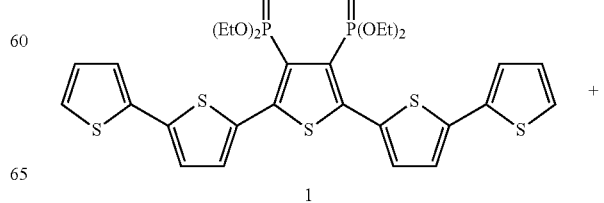

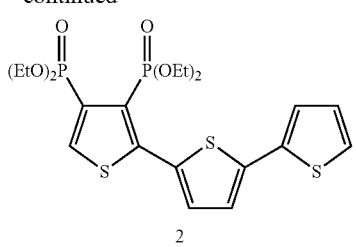

2

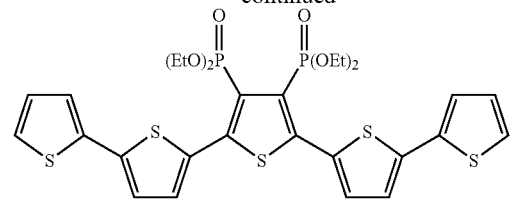

1

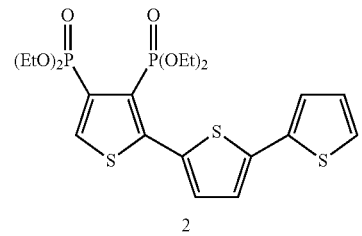

2

In THF, 2,5-bis(tributylstannyl)-3,4-bis(diethoxyphosphoryl)thiophene, commercially available tetrakistriphenylphosphine palladium (0.10 equivalent) and copper(I) cyanide (commercial product) in different amounts indicated in Table 10 were dissolved, to which 2-iodobithiophene (2.2 equivalents) was added at room temperature. Thereafter, the reaction mixture was heated to 70° C. and stirred for 4 to 22 hours. After the reaction, the reaction mixture was cooled down to room temperature, to which a potassium fluoride aqueous solution was added, followed by stirring for 2 hours. Thereafter, the solid was removed by celite filtration and the filtrate was extracted with ethyl acetate. The organic phase was washed with a saturated saline solution and dried over anhydrous sodium sulfate. The solvent was removed by distilling off under reduced pressure, and the resulting product was purified with a silica gel column (ethyl acetate:methanol=15:1) to obtain the specified substances 1, 2 in the form of a yellow solid.

TABLE 10

| Entry | CuCN (eq.) | Solvent | Temp. (° C.) | Time (h) | Yield (%) 1 | 2 |
|---|---|---|---|---|---|---|
| 1 | 0.5 | toluene | 70 | 10 | 56 | 38 |
| 2 | 1.0 | toluene | 70 | 20 | 67 | 30 |
| 3 | 1.0 | toluene | reflux | 16 | 48 | 21 |
| 4 | 1.0 | benzene | reflux | 22 | 5 | 48 |
| 5 | 1.0 | o-xylene | reflux | 4 | 60 | 23 |
| 6 | 1.0 | o-xylene | reflux | 8 | 59 | 23 |

(a) 3''',4''-bis(diethoxyphosphoryl)-[2,2';5',2'';5'',2''';5''',2'''']-quinquethiophene m/z (FAB+): 685 (calculated: 684.01).

$^1$H-NMR (CDCl$_3$): 1.20 (12H, t, J=7.1 Hz), 3.99-4.02 (4H, m), 4.12-4.18 (4H, m), 7.03 (2H, dd, J=5.0, 5.0 Hz), 7.15 (2H, d, J=3.7 Hz), 7.21-7.22 (2H, m), 7.32 (2H, d, J=3.8 Hz) ppm.

(7) Synthesis of 3'',4''-bis(diethoxyphosphoryl)-[2,2';5',2'';5'',2''';5''',2'''']-quinquethiophene

[Chemical Formula 101]

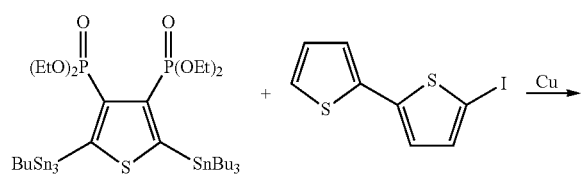

2,5-bis(tributylstannyl)-3,4-bis(diethoxyphosphoryl)-thiophene and commercially available copper(I) cyanide (2.2 equivalents) were dissolved in solvents indicated in the following Table 11, to which 2-iodobithiophene (2.2 equivalents) was added at room temperature. Thereafter, the reaction mixture was heated to 70° C. and stirred for 4 to 22 hours. After the reaction, the reaction mixture was cooled down to room temperature, to which a 0.6M hydrochloric acid aqueous solution was added, followed by extraction of the resulting product with ethyl acetate. The organic phase was washed with a saturated saline solution and dried over anhydrous sodium sulfate. The solvent was removed by distilling off under reduced pressure, and the resulting product was purified with a silica gel column (ethyl acetate:methanol=15:1) to obtain the specified substance 1.

TABLE 11

| Entry | CuCN (eq.) | Solvent | Temp. (° C.) | Time (h) | Yield (%) 1 | 2 |
|---|---|---|---|---|---|---|
| 1 | 2.2 | DMF/toluene = 3/1 | 80 | 10 | 10 | 30 |
| 2 | 2.2 | THF | reflux | 9 | 70 | 18 |

(8) Synthesis of 3'',4''-bis(diethoxyphosphoryl)-[2,2';5',2'';5'',2''';5''',2'''']-quinquethiophene

[Chemical Formula 102]

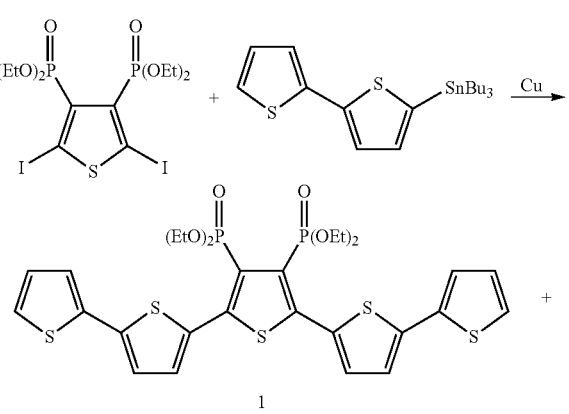

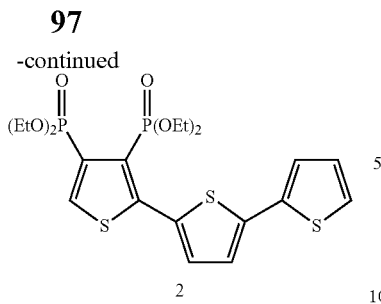

In DMF, 0.0971 g (0.159 mmols) of 2,5-diiodo-3,4-bis(diethoxyphosphoryl)thiophene and 0.0346 g (0.349 mmols) of commercially available copper(I) chloride were dissolved, to which 0.1744 g (0.383 mmols) of tributylstannylbithiophene was added at room temperature. Thereafter, the reaction mixture was heated to 80° C. and stirred for 12 hours. After the reaction, the reaction mixture was cooled down to room temperature, to which a 0.6 M hydrochloric acid aqueous solution was added, followed by extraction of the resulting product with ethyl acetate. The organic phase was washed with a saturated saline solution and dried over anhydrous sodium sulfate. The solvent was removed by distilling off under reduced pressure, and the resulting product was purified with a silica gel column (ethyl acetate:methanol=15:1) to obtain the specified substance 1. The results are shown in Table 12.

TABLE 12

| Entry | CuCL (eq.) | Solvent | Temp. (° C.) | Time (h) | Yield (%) 1 | 2 |
|---|---|---|---|---|---|---|
| 1 | 2.2 | DMF | 80 | 10 | 31 | 21 |

(9) Synthesis of 3''',4'''-bis(diethoxyphosphoryl)-[2,2';5',2'';5'',2''';5''',2'''';5'''',2''''';5''''',2'''''']-septithiophene

[Chemical Formula 103]

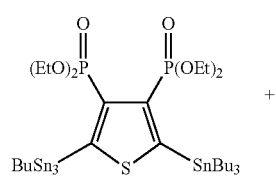

+

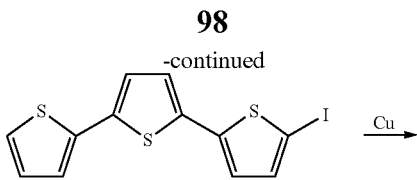

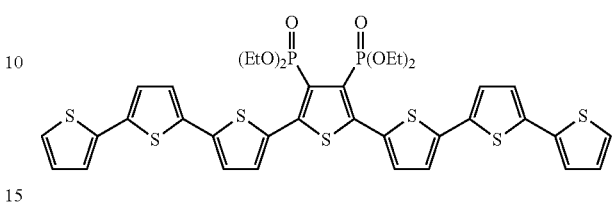

In THF, 0.200 g (0.214 mmols) of 2,5-bis(tributylstannyl)-3,4-bis(diethoxyphosphoryl)thiophene and 0.0466 g (0.471 mmols) of commercially available copper(I) chloride were dissolved, to which 0.168 g (0.449 mmols) of 2-iodotrithiophene was added at room temperature. Thereafter, the reaction mixture was heated and stirred under reflux for 15 hours. After the reaction, the reaction mixture was cooled down to room temperature, to which a potassium fluoride aqueous solution was added, followed by stirring for 1 hour. Subsequently, the solid was removed by celite filtration and the filtrate was extracted with ethyl acetate. The organic phase was washed with a saturated saline solution and dried over anhydrous sodium sulfate. The solvent was removed by distilling off under reduced pressure, and the resulting crude product was purified with a silica gel column to obtain the specified substance in the form of a yellow solid at a yield of 0.1499 g (yield: 77%).

m/z (FAB+): 849 (calculated: 847.99).

$^1$H-NMR (CDCl$_3$): 1.20-1.25 (12H, m), 3.99-4.19 (8H, m), 7.04-7.33 (14H, m) ppm.

$^{13}$C-NMR (CDCl$_3$): 16.0 (d, $^3J_{P-C}$=6.9 Hz), 62.7 (d, $^2J_{P-C}$=6.3 Hz), 123.9, 124.0, 124.4, 124.8, 124.9, 127.9, 131.0, 131.9, 135.1, 136.8, 137.1, 139.7, 145.4) ppm.

(10) Synthesis of 5,5''''''-diiodo-3''',4'''-bis(diethoxyphosphoryl)-[2,2';5',2'';5'',2''';5''',2'''';5'''',2''''';5''''',2'''''']-septithiophene

[Chemical Formula 104]

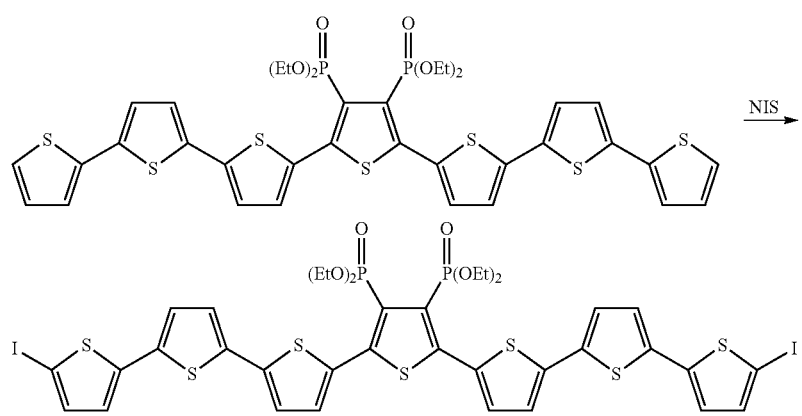

In a mixed solvent of chloroform and acetic acid at 1:1, 0.0600 g (0.0707 mmols) of the 3''',4'''-bis(diethoxyphosphoryl)-[2,2';5',2'';5'',2''';5''',2'''';5'''',2''''';5''''',2'''''']-septithiophene obtained in (9) above was dissolved, to which 0.0333 g (0.148 mmols) of commercially available N-iodosuccinimide was added at room temperature. Thereafter, the reaction mixture was stirred at room temperature for 20 hours. After the reaction, a sodium thiosulfate aqueous solution was added, followed by extraction with methylene chloride. The solvent was removed by distilling off under reduced pressure, and the resulting crude product was purified with a silica gel column to obtain the specified substance in the form of an orange solid at a yield of 0.0682 g (yield: 83%). The thus obtained substance was used as it is for reaction in the following (11).

(11) Synthesis of 3''',3'''''''',3''''''''''''',4''',4'''''''',4'''''''''''''-hexakis-(diethoxyphosphoryl)-[2,2';5',2'''';5',2''';5''', 2'''';5'''',2'''';5'''',2''''';5''''',2''''';5''''',2'''''';5'''''', 2''''''';5''''''',2''''''';5''''''',2'''''''';5'''''''',2''''''''; 5''''''''',2''''''''';5''''''''',2''''''''']-pentadecithiophene

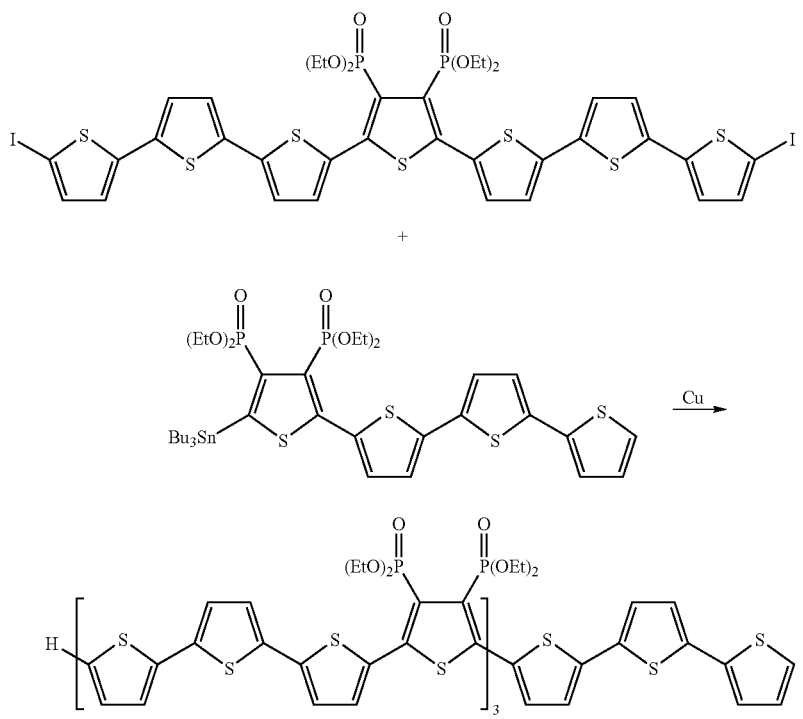

In THF, 0.0682 g (0.0619 mmols) of 5,5'''''''-diiodo-3''',4'''-bis(diethoxyphosphoryl)-[2,2';5',2'';5'',2''';5''',2''''; 5'''',2''''';5''''',2'''''']-septithiophene and 0.116 g (0.130 mmols) of 5-tributylstannyl-3,4-bis(diethylphosphono)-[2,2';5',2'';5'', 2''']quaterthiophene derived from 2,5-bis(tributylstannyl)-3, 4-bis(diethoxyphosphoryl)thiophene were dissolved, to which 0.0135 g (0.136 mmols) of commercially available copper(I) chloride was added at room temperature. Thereafter, the reaction mixture was heated and stirred under reflux for 34 hours. After the reaction, the reaction mixture was cooled down to room temperature, to which a potassium fluoride aqueous solution was added, followed by stirring for 1 hour. Subsequently, the solid was removed by celite filtration and the filtrate was extracted with ethyl acetate. The organic phase was washed with a saturated saline solution and dried over anhydrous sodium sulfate. The solvent was removed by distilling off under reduced pressure, and the resulting crude product was purified with a silica gel column to obtain the specified substance in the form of an orange solid at a yield of 0.0392 g (yield: 31%).

m/z (FAB+): 2049 (calculated: 2048.01).

$^1$H-NMR (CDCl$_3$): 1.18-1.28 (36H, m), 4.00-4.21 (24H, m), 7.04-7.35 (26H, m) ppm.

Example 10

Synthesis of Phosphorylthiophene Compounds Derived by Conversion of the Phosphoryl Group The respective compounds were synthesized according to the following processes (1) to (12).

(1) Synthesis of 3,4-diphosphonothiophene

[Chemical Formula 106]

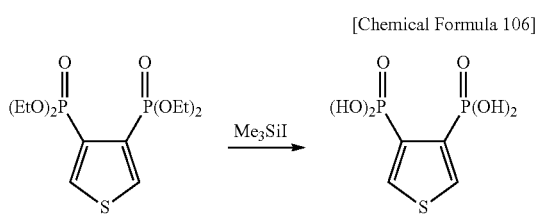

In acetonitrile, 0.200 g (0.561 mmols) of 3,4-bis(diethoxyphosphoryl)thiophene was dissolved, to which 0.5613 g (2.805 mmols) of commercially available iodotrimethylsilane was added at room temperature. Thereafter, the mixture was stirred at room temperature for 12 hours. After the reaction, the solvent was removed by distilling off under reduced pressure, followed by addition of methanol and stirring at room temperature for further 12 hours. The methanol was removed by distilling off under reduced pressure, followed by addition of distilled water under stirring and separation of an aqueous phase. The thus separated aqueous phase was washed several times with chloroform and the aqueous phase was concentrated and evaporated to dryness to obtain the specific substance of white crystals at a yield of 0.1333 g (yield: 97%).

m/z (FAB+): 245 (calculated: 243.94).

$^1$H-NMR (CDCl$_3$): 4.81 (4H, m), 7.81 (2H, s) ppm.

$^{13}$C-NMR (CDCl$_3$): 135.0 (dd, $^2J_{P-C}$=19.6 Hz, $^1J_{P-C}$=187.1 Hz), 138.3 (dd, $^3J_{P-C}$=17.2 Hz, $^2J_{P-C}$=17.2 Hz) ppm.

(2) Synthesis of 3',4'-diphosphono-[2,2';5',2"]-terthiophene

[Chemical Formula 107]

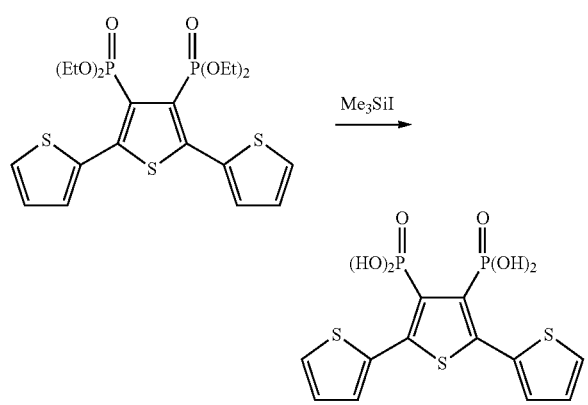

In acetonitrile, 0.2478 g (0.476 mmols) of 3',4'-bis(diethoxyphosphoryl)-[2,2';5',2"]-terthiophene was dissolved, to which 0.4762 g (2.380 mmols) of commercially available iodotrimethylsilane was added at room temperature. Thereafter, the mixture was stirred at room temperature for 12 hours. After the reaction, the solvent was removed by distilling off under reduced pressure, followed by addition of methanol and stirring at room temperature for further 12 hours. The methanol was removed by distilling off under reduced pressure, followed by addition of distilled water under stirring and separation of an aqueous phase. The thus separated aqueous phase was washed several times with chloroform and the aqueous phase was concentrated and evaporated to dryness to obtain the specified substance in the form of yellow crystals at a yield of 0.1742 g (yield: 90%).

m/z (FAB+): 409 (calculated: 407.91).

$^1$H-NMR (CDCl$_3$): 4.91 (4H, s), 7.10-7.12 (2H, m), 7.40 (2H, d, J=0.7 Hz), 7.21-7.22 (2H, m), 7.55 (2H, d, J=1.3H) ppm.

$^{13}$C-NMR (CDCl$_3$): 128.7 (d, $^1J_{P-C}$=86.8 Hz), 129.0, 131.1, 131.4, 133.9, 146.5 (dd, $^3J_{P-C}$=11.9 Hz, $^2J_{P-C}$=19.1 Hz) ppm.

(3) Synthesis of 3'',4''-diphosphono-[2,2';5',2'';5'',2''';5''',2'''']-quinquethiophene

[Chemical Formula 108]

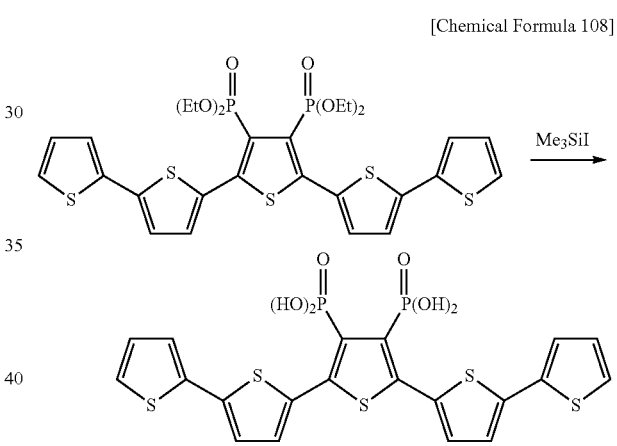

In 4.0 ml of acetonitrile, 0.2746 g (0.401 mmols) of 3'',4''-bis(diethoxyphosphoryl)-[2,2';5',2'';5'',2''';5''',2'''']-quinquethiophene was dissolved, to which 0.4012 g (2.005 mmols) of commercially available iodotrimethylsilane was added at room temperature. Thereafter, the mixture was stirred at room temperature for 12 hours. After the reaction, the solvent was removed by distilling off under reduced pressure, followed by addition of methanol and stirring at room temperature for further 12 hours. A sodium thiosulfate aqueous solution was added, followed by stirring, filtration of the precipitated crystals, washing with distilled water, methanol, chloroform and diethyl ether and drying to obtain the specified substance in the form of a yellow powder at a yield of 0.1630 g (yield: 71%).

m/z (FAB+): 573 (calculated: 571.89).

$^1$H-NMR (CDCl$_3$): 1.18-1.25 (4H, br), 6.96-6.97 (2H, m), 7.10-7.11 (2H, m), 7.18 (2H, s), 7.22 (2H, s), 7.27-7.28 (2H, m) ppm.

$^{13}$C-NMR (DMSO-d$_6$): 125.0 (d, $^1J_{P-C}$=201.5 Hz), 124.3, 128.4, 130.9, 133.7, 136.0, 136.6 (d, $J_{P-C}$=17.5 Hz), 137.7, 137.9 (d, $J_{P-C}$=19.6 Hz), 139.9 (dd, $^3J_{P-C}$=15.0 Hz, $^2J_{P-C}$=15.0 Hz) ppm.

(4) Synthesis of 3,4-bis(dibutoxyphosphoryl)thiophene and 3,4-bis(butoxy-ethoxyphosphoryl)thiophene

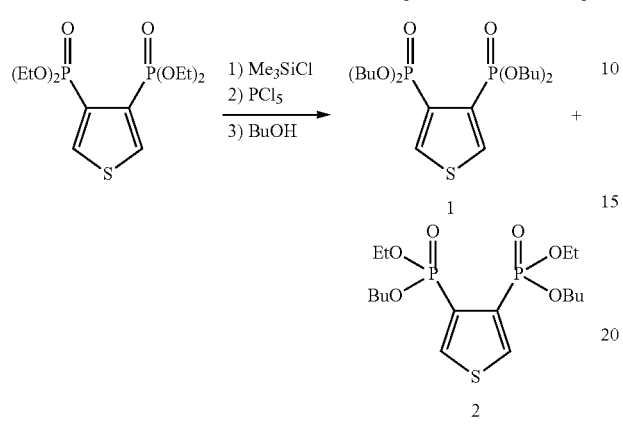

[Chemical Formula 109]

3,4-bis(diethoxyphosphoryl)thiophene was dissolved in acetonitrile under nitrogen, to which different types of halogenated trimethylsilanes (4.5 equivalents, commercial products) indicated in Table 13 were dropwise added at room temperature, followed by stirring at room temperature for 24 hours. After the reaction, the solvent was removed by distilling off under reduced pressure, followed by addition of a solution of commercially available phosphorus pentachloride (4.5 equivalents) dissolved in carbon tetrachloride at room temperature. Thereafter, the reaction mixture was heated and stirred under reflux for 4 hours. After the reaction, the reaction mixture was cooled down to 0° C., to which a solution of commercially available 1-butanol (30 equivalents) and triethylamine (30 equivalents) dissolved in methylene chloride was gently added, followed by stirring at room temperature for 14 hours. A disodium hydrogen phosphate/sodium dihydrogen phosphate buffer solution, adjusted to pH=7, was added so as to complete the reaction, followed by extraction with ethyl acetate. The organic phase was washed with a saturated saline solution and dried over anhydrous sodium sulfate. The solvent was removed, and the resulting crude product was purified with a silica gel column (ethyl acetate: hexane=1:1) to obtain the specified substances 1, 2 in the form of a yellow oil.

TABLE 13

| Entry | Me₃SiX | Yield (%) 1 | Yield (%) 2 |
|---|---|---|---|
| 1 | Me₃SiCl | — | 67 |
| 2 | Me₃SiBr | 8 | — |
| 3 | Me₃SiI | 18 | — |

(a) 3,4-bis(dibutoxyphosphoryl)thiophene 1 m/z (FAB+): 469 (calculated: 468.19).

$^1$H-NMR (CDCl$_3$): 0.92 (12H, t, J=7.4 Hz), 1.40 (8H, m, J=7.5 Hz), 1.69 (8H, m), 4.02-4.16 (8H, m), 8.17 (2H, dd, $^2J_{P-H}$=4.6 Hz, $^3J_{P-H}$=2.7 Hz) ppm.

$^{13}$C-NMR (CDCl$_3$): 13.5 (s), 18.6 (s), 32.4 (d, $^3J_{P-C}$=6.1 Hz), 66.2 (d, $^2J_{P-C}$=6.0 Hz), 131.1 (dd, $^2J_{P-C}$=18.0 Hz, $^1J_{P-C}$=180.0 Hz), 140.0 (dd, $^2J_{P-C}$=17.4 Hz, 3J$_{P-C}$=18.1 Hz) ppm.

(b) 3,4-bis(butoxy-ethoxyphosphoryl)thiophene 2

Yellow Oil $^1$H-NMR (CDCl$_3$): 0.93 (12H, t, J=7.4 Hz), 1.36-1.46 (10H, m), 1.66-1.73 (4H, m), 4.05-4.22 (8H, m), 8.18 (2H, dd, $^2J_{P-H}$=4.6 Hz, $^3J_{P-H}$=2.7 Hz) ppm.

(5) Synthesis of 3,4-bis(dibutoxyphosphoryl)thiophene

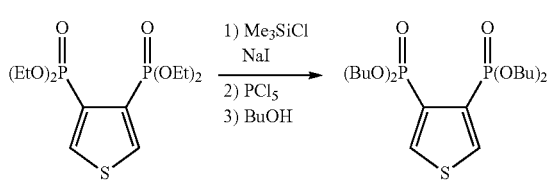

[Chemical Formula 110]

3,4-bis(diethoxyphosphoryl)thiophene and commercially available sodium iodide or bromide (4.5 equivalents) were dissolved in acetonitrile under nitrogen, to which commercially available iodotrimethylsilane (4.5 equivalents) as dropwise added at room temperature, followed by stirring at room temperature for 24 hours. After the reaction, the solvent was removed by distilling off under reduced pressure, to which a solution of commercially available phosphorus pentachloride (4.5 equivalents) dissolved in carbon tetrachloride was added at room temperature. Thereafter, the mixture was heated and stirred under reflux for 4 hours. After the reaction, the mixture was cooled down to 0° C., to which a solution of commercially available 1-butanol (30 equivalents) and triethylamine (30 equivalents) dissolved in methylene chloride was added slowly. Thereafter, the mixture was stirred at room temperature for 14 hours. A disodium hydrogen phosphate/sodium dihydrogen phosphate buffer solution, adjusted to pH=7, was added so as to complete the reaction, followed by extraction with ethyl acetate. The organic phase was washed with a saturated saline solution and dried over anhydrous sodium sulfate. The solvent was removed, and the resulting crude product was purified with a silica gel column (ethyl acetate: hexane=1:1) to obtain the specified substance in the form of a yellow oil.

TABLE 14

| Entry | Me₃SiCl | NaX | PCl₅ | BuOH | Et₃N | Yield (%) |
|---|---|---|---|---|---|---|
| 1 | 4.5 eq. | NaBr 4.5 eq. | 4.5 eq. | 30 eq. | 30 eq. | 25 |
| 2 | 4.5 eq. | NaI 4.5 eq. | 4.5 eq. | 30 eq. | 30 eq. | 47 |
| 3 | 4.5 eq. | NaI 4.5 eq. | 4.5 eq. | 30 eq. | 30 eq. | 18 |
| 4 | 5.0 eq. | NaI 5.0 eq. | 5.0 eq. | 35 eq. | 35 eq. | 61 |

(6) Synthesis of 3,4-bis(dibutoxyphosphoryl)thiophene, 3,4-bis(dibutoxy-ethoxyphosphoryl)thiophene and 3-(butoxy-ethoxyphosphoryl)-4-(dibutoxyphosphoryl)thiophene

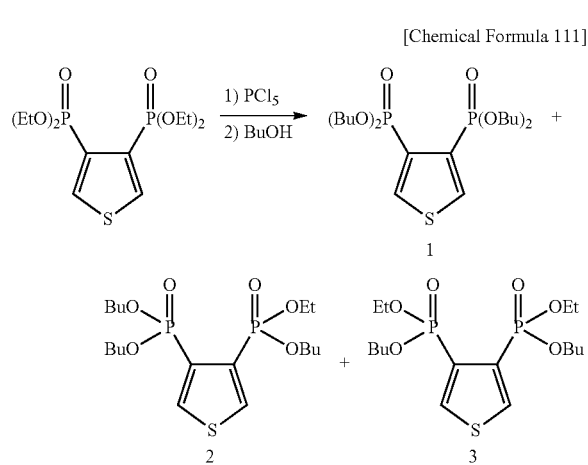

[Chemical Formula 111]

Under nitrogen, 1.000 g (2.807 mmols) of 3,4-bis(diethoxyphosphoryl)thiophene was dissolved in carbon tetrachloride, to which a solution of 2.630 g (12.63 mmols) of commercially available phosphorus pentachloride dissolved in carbon tetrachloride was added at room temperature. Thereafter, the mixture was heated and stirred under reflux for 4 hours. After the reaction, the mixture was cooled down to 0° C., to which a solution of 6.242 g (84.21 mmols) of commercially available 1-butanol and 8.521 g (84.21 mmols) triethylamine dissolved in methylene chloride was added slowly. Thereafter, the mixture was stirred at room temperature for 14 hours. A disodium hydrogen phosphate/sodium dihydrogen phosphate buffer solution, adjusted to pH=7, was added so as to complete the reaction, followed by extraction with ethyl acetate. The organic phase was washed with a saturated saline solution and dried over anhydrous sodium sulfate. The solvent was removed, and the resulting crude product was purified with a silica gel column (ethyl acetate:hexane=1:1) to obtain the specified substances 1, 2, 3 in the form of a yellow oil at yields indicated in Table 15, respectively.

TABLE 15

| Yield (%) | | |
| --- | --- | --- |
| 1 | 2 | 3 |
| 4 | 30 | 47 |

3-(dibutoxy-ethoxyphosphoryl)-4-(dibutoxyphosphoryl)thiophene 2

$^1$H-NMR (CDCl$_3$): 0.93 (9H, t, J=7.4 Hz), 1.34-1.45 (9H, m), 1.66-1.73 (6H, m), 4.04-4.19 (8H, m), 8.14-8.19 (2H, m) ppm.

(7) Synthesis of 3-(ethoxy-hexyloxyphosphoryl)-4-(dihexyloxyphosphoryl)thiophene and 3,4-bis(ethoxy-hexyloxyphosphoryl)-thiophene

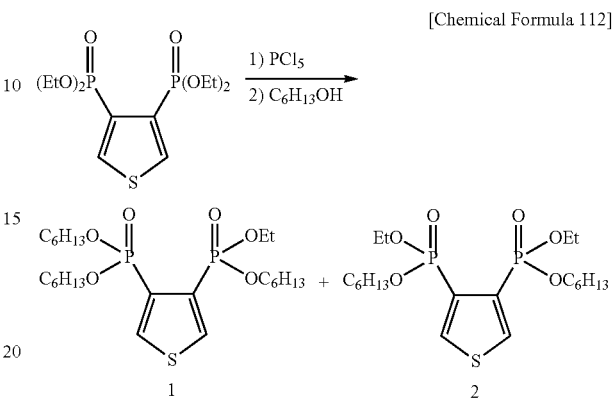

[Chemical Formula 112]

Under nitrogen, 0.3500 g (0.9823 mmols) of 3,4-bis(diethoxyphosphoryl)thiophene was dissolved in carbon tetrachloride, to which a solution of 0.9204 g (4.420 mmols) of commercially available phosphorus pentachloride dissolved in carbon tetrachloride was added at room temperature. Thereafter, the mixture was heated and stirred under reflux for 4 hours. After the reaction, the mixture was cooled down to 0° C., to which a solution of 3.011 g (29.47 mmols) of commercially available 1-hexanol and 2.982 g (29.47 mmols) triethylamine dissolved in methylene chloride was slowly added. Thereafter, the mixture was stirred at room temperature for 14 hours. A disodium hydrogen phosphate/sodium dihydrogen phosphate buffer solution, adjusted to pH=7, was added so as to complete the reaction, followed by extraction with ethyl acetate. The organic phase was washed with a saturated saline solution and dried over anhydrous sodium sulfate. The solvent was removed, and the resulting crude product was purified with a silica gel column (ethyl acetate:hexane=1:1) to obtain the specified substances 1, 2 in the form of a yellow oil at yields indicated in Table 16, respectively.

TABLE 16

| Yield (%) | |
| --- | --- |
| 1 | 2 |
| 37 | 17 |

(a) 3-(ethoxy-hexyloxyphosphoryl)-4-(dihexyloxyphosphoryl)-thiophene 1

$^1$H-NMR (CDCl$_3$): 0.81 (9H, m), 1.01-1.30 (22H, m), 1.60-1.65 (6H, m), 3.90-4.13 (8H, m), 8.11 (2H, m) ppm.

(b) 3,4-bis(ethoxy-hexyloxyphosphoryl)thiophene 2

$^1$H-NMR (CDCl$_3$): 0.80 (6H, t, J=6.8 Hz), 1.21-1.30 (18H, m), 1.60-1.67 (4H, m), 3.96-4.13 (8H, m), 8.11 (2H, dd, $^2J_{P-H}$=4.5 Hz, $^3J_{P-H}$=2.3 Hz) ppm.

(8) Synthesis of 3,4-bis(alkoxyphosphoryl)thiophene and 3,4-bis(phenoxyphosphoryl)thiophene

[Chemical Formula 113]

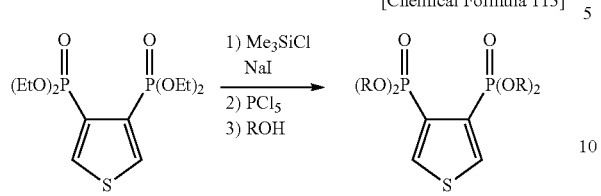

3,4-bis(diethoxyphosphoryl)thiophene and commercially available sodium iodide (5.0 equivalents) were dissolved in acetonitrile under nitrogen, to which commercially available iodotrimethylsilane (5.0 equivalents) was dropwise added at room temperature. Thereafter, the mixture was stirred at room temperature for 24 hours. After the reaction, the solvent was removed by distilling off under reduced pressure, to which a solution of commercially available phosphorus pentachloride (5.0 equivalents) dissolved in carbon tetrachloride was added at room temperature. Thereafter, the mixture was heated and stirred under reflux for 4 hours. After the reaction, the mixture was cooled down to 0° C., to which different types of alcohols indicated in Table 17 or phenol (35 equivalents), or triethylamine (35 equivalents) dissolved in methylene chloride was slowly added, followed by stirring at room temperature for 14 hours. A disodium hydrogen phosphate/sodium dihydrogen phosphate buffer solution, adjusted to pH=7, was added so as to complete the reaction, followed by extraction with ethyl acetate. The organic phase was washed with a saturated saline solution and dried over anhydrous sodium sulfate. The solvent was removed, and the resulting crude product was purified with a silica gel column (ethyl acetate:hexane=1:1) to obtain the respective specified substances in the form of a yellow oil.

TABLE 17

| Entry | R | Yield (%) |
|---|---|---|
| 1 | $C_6H_{13}$ | 79 |
| 2 | $C_8H_{17}$ | 80 |
| 3 | $C_{10}H_{21}$ | 73 |
| 4 | $CH(CH_3)_2$ | 79 |
| 5 | Ph | 95 |

(a) 3,4-bis(dihexyloxyphosphoryl)thiophene $^1$H-NMR (CDCl$_3$): 0.88 (12H, t, J=6.9 Hz), 1.26-1.39 (24H, m), 1.66-1.74 (8H, m), 4.02-4.13 (8H, m), 8.16 (2H, dd, $^2J_{P-H}$=4.6 Hz, $^3J_{P-H}$=2.7 Hz) ppm.

(b) 3,4-bis(dioctyloxyphosphoryl)thiophene $^1$H-NMR (CDCl$_3$): 0.88 (12H, t, J=6.9 Hz), 1.26-1.37 (40H, m), 1.66-1.73 (8H, m), 4.02-4.13 (8H, m), 8.16 (2H, dd, $^2J_{P-H}$=4.7 Hz, $^3J_{P-H}$=2.7 Hz) ppm.

(c) 3,4-bis(didecyloxyphosphoryl)thiophene $^1$H-NMR (CDCl$_3$): 0.88 (12H, t, J=6.7 Hz), 1.25-1.35 (56H, m), 1.66-1.73 (8H, m), 4.02-4.13 (8H, m), 8.16 (2H, dd, $^2J_{P-H}$=4.6 Hz, $^3J_{P-H}$=2.7 Hz) ppm.

(d) 3,4-bis(diisopropoxyphosphoryl)thiophene $^1$H-NMR (CDCl$_3$): 1.27 (12H, d, J=6.2 Hz), 1.39 (12H, d, J=6.2 Hz), 4.77-4.82 (4H, m), 8.16 (2H, dd, $^2J_{P-H}$=4.6 Hz, $^3J_{P-H}$=2.6 Hz) ppm.

(e) 3,4-bis(diphenoxyphosphoryl)thiophene $^1$H-NMR (CDCl$_3$): 7.10-7.13 (8H, m), 7.19-7.26 (12H, m), 8.44 (2H, dd, $^2J_{P-H}$=4.9 Hz, $^3J_{P-H}$=2.9 Hz) ppm.

(9) Synthesis of 3,4-bis(diethylaminophosphono)thiophene

[Chemical Formula 114]

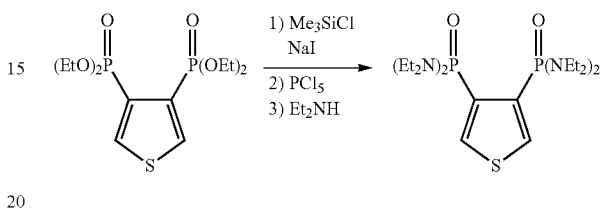

Under nitrogen, 0.050 g (0.1403 mmols) of 3,4-bis(diethoxyphosphoryl)thiophene and 0.1052 g (0.7016 mmols) of commercially available sodium iodide were dissolved in acetonitrile, to which 0.0762 g (0.7016 mmols) of commercially available chlorotrimethylsilane was dropwise added at room temperature, followed by stirring at room temperature for 24 hours. After the reaction, the solvent was removed by distilling off under reduced pressure, to which a solution of 0.1462 g (0.7016 mmols) of commercially available phosphorus pentachloride dissolved in carbon tetrachloride was added at room temperature. Subsequently, the reaction mixture was heated and stirred under reflux for 4 hours.

After the reaction, the reaction mixture was cooled down to 0° C., to which a solution of 0.3592 g (4.911 mmols) of commercially available diethylamine and 0.4969 g (4.911 mmols) of triethylamine dissolved in methylene chloride was slowly added, followed by stirring at room temperature for 14 hours. A disodium hydrogen phosphate/sodium dihydrogen phosphate buffer solution, adjusted to pH=7, was added so as to complete the reaction, followed by extraction with ethyl acetate. The organic phase was washed with a saturated saline solution and dried over anhydrous sodium sulfate. The solvent was removed, and the resulting crude product was purified with a silica gel column (ethyl acetate:hexane=1:1) to obtain the specified substance in the form of a yellow oil at a yield of 0.030 g (yield: 46%).

$^1$H-NMR (CDCl$_3$): 1.04 (24H, t, J=7.1 Hz), 3.00-3.08 (8H, m), 3.16-3.24 (8H, m), 7.68 (2H, dd, $^2J_{P-H}$=3.8 Hz, 3J$_{P-H}$=2.8 Hz) ppm.

(10) Synthesis of 3,4-bis(diethylsulfanylphosphoryl)thiophene

[Chemical Formula 115]

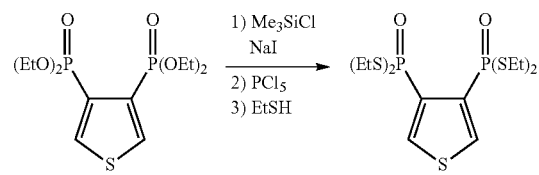

Under nitrogen, 0.2000 g (0.5613 mmols) of 3,4-bis(diethoxyphosphoryl)thiophene and 0.4207 g (2.807 mmols) of commercially available sodium iodide were dissolved in acetonitrile, to which 0.3050 g (2.807 mmols) of commercially available chlorotrimethylsilane was dropwise added at room temperature. Thereafter, the reaction mixture was stirred at room temperature for 24 hours. After the reaction, the solvent was removed by distilling off under reduced pressure, to which a solution of 0.5845 g (2.907 mmols) of commercially available phosphorus pentachloride dissolved in carbon tetrachloride was added at room temperature.

Subsequently, the reaction mixture was heated and stirred under reflux for 4 hours. After the reaction, the reaction mixture was cooled down to 0° C., to which a solution of 1.221 g (19.65 mmols) of commercially available ethylthiol and 1.988 g (19.65 mmols) of triethylamine dissolved in methylene chloride was slowly added. Thereafter, the mixture was stirred at room temperature for 14 hours. A disodium hydrogen phosphate/sodium dihydrogen phosphate buffer solution, adjusted to pH=7, was added so as to complete the reaction, followed by extraction with ethyl acetate. The organic phase was washed with a saturated saline solution and dried over anhydrous sodium sulfate. The solvent was removed, and the resulting crude product was purified with a silica gel column (ethyl acetate:hexane=1:1) to obtain the specified substance in the form of a yellow oil at a yield of 0.0895 g (yield: 38%).

$^1$H-NMR (CDCl$_3$): 1.36 (12H, t, J=7.4 Hz), 2.95-3.04 (8H, m), 8.26 (2H, dd, $^2$J$_{P-H}$=4.1 Hz, $^3$J$_{P-H}$=3.3 Hz) ppm.

(11) Synthesis of 2,5-bis(tributylstannyl)-3,4-bis(alkoxyphosphoryl)thiophene and 2,5-bis(tributylstannyl)-3,4-bis(phenoxyphosphoryl)thiophene

[Chemical Formula 116]

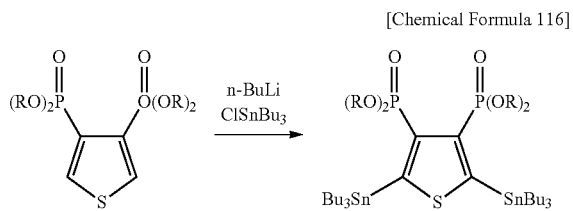

Different types of 3,4-bis(dialkoxyphosphoryl)thiophenes obtained above were dissolved in THF and cooled down to −78° C. Commercially available n-butyl lithium (1.59 M hexane solution, 2.5 equivalents) was slowly dropped, followed by stirring for 1 hour while keeping the temperature. Commercially available tributylstannyl chloride (3.0 equivalents) was dropped, followed by stirring for 4 hours. After completion of the reaction, a disodium hydrogen phosphate/sodium dihydrogen phosphate buffer solution, adjusted to pH=7, was added so as to complete the reaction, followed by extraction with ethyl acetate. The organic phase was washed with a saturated saline solution and dried over anhydrous sodium sulfate. The solvent was removed, and the resulting crude product was purified with a silica gel column (ethyl acetate:hexane=1:7) to obtain the specified substances in the form of a transparent oil. The results are shown in Table 18.

TABLE 18

| Entry | R | Yield (%) |
|---|---|---|
| 1 | C$_4$H$_9$ | 72 |
| 2 | C$_6$H$_{13}$ | 86 |
| 3 | C$_8$H$_{17}$ | 79 |

TABLE 18-continued

| Entry | R | Yield (%) |
|---|---|---|
| 4 | C$_{10}$H$_{21}$ | 62 |
| 5 | CH(CH$_3$)$_2$ | 84 |
| 6 | Ph | 75 |

(a) 2,5-bis(tributylstannyl)-3,4-bis(dibutoxyphosphoryl)-thiophene $^1$H-NMR (CDCl$_3$): 0.86-0.92 (30H, m), 1.17-1.21 (12H, m), 1.30-1.39 (20H, m), 1.54-1.56 (12H, m), 1.63-1.65 (8H, m), 3.89-4.01 (8H, m) ppm.

(b) 2,5-bis(tributylstannyl)-3,4-bis(dihexyloxyphosphoryl)-thiophene $^1$H-NMR (CDCl$_3$): 0.85-0.92 (30H, m), 1.17-1.21 (12H, m), 1.27-1.35 (36H, m), 1.54-1.56 (12H, m), 1.65 (8H, m), 3.85-4.01 (8H, m) ppm.

(c) 2,5-bis(tributylstannyl)-3,4-bis(dioctyloxyphosphoryl)-thiophene $^1$H-NMR (CDCl$_3$): 0.85-0.90 (30H, m), 1.16-1.21 (12H, m), 1.25-1.35 (52H, m), 1.54-1.58 (12H, m), 1.66 (8H, m), 3.86-3.99 (8H, m) ppm.

(d) 2,5-bis(tributylstannyl)-3,4-bis(didecyloxyphosphoryl)-thiophene $^1$H-NMR (CDCl$_3$): 0.86-0.90 (30H, m), 1.17-1.35 (80H, m), 1.55 (12H, m), 1.66 (8H, m), 3.86-3.99 (8H, m) ppm.

(e) 2,5-bis(tributylstannyl)-3,4-bis(diisopropoxyphosphoryl)-thiophene $^1$H-NMR (CDCl$_3$): 0.85-0.89 (18H, m, J=6.2 Hz), 1.13 (12H, d, J=6.2 Hz), 1.17-1.34 (12H, m), 1.37 (12H, d, J=6.2 Hz), 1.50-1.57 (12H, m), 4.64-4.69 (4H, m) ppm.

(f) 2,5-bis(tributylstannyl)-3,4-bis(diphenoxyphosphoryl)-thiophene $^1$H-NMR (CDCl$_3$): 0.84 (18H, t, J=7.3 Hz), 1.07-1.12 (12H, m), 1.22-1.27 (12H, m), 1.45-1.50 (12H, m), 7.06-7.08 (12H, m), 7.16-7.20 (8H, m) ppm.

(12) Synthesis of 3",4"-bis(alkoxyphosphoryl)-[2,2'; 5',2"; 5"',2"';5"'',2""]-quinquethiophene and 3",4"-bis(diphenoxyphosphoryl)-[2,2';5',2";5",2"';5"'',2""]-quinquethiophene

[Chemical Formula 117]

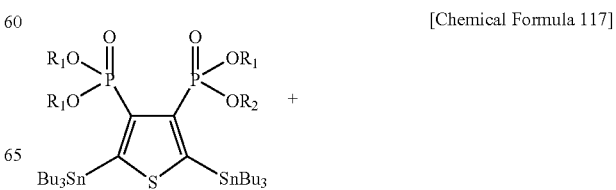

-continued

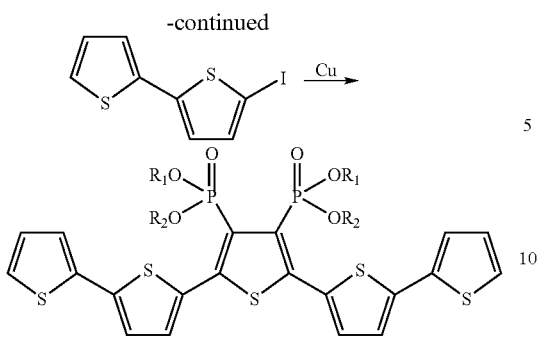

The respective 2,5-bis(tributylstannyl)-3,4-bis(dibutoxyphosphoryl)thiophenes obtained above and commercially available copper(I) chloride (2.2 equivalents) were dissolved in THF, to which 2-iodobithiophene (2.1 equivalents) was added at room temperature. Thereafter, the reaction mixture was heated and stirred under reflux for 4 to 22 hours. After the reaction, the reaction mixture was cooled down to room temperature, to which a potassium fluoride aqueous solution was added, followed by stirring for 1 hour. The solid was removed by celite filtration and the filtrate was extracted with ethyl acetate. The organic phase was washed with a saturated saline solution and dried over anhydrous sodium sulfate. The solvent was removed by distilling off under reduced pressure, and the resulting crude product was purified with a silica gel column (ethyl acetate:methanol=15:1) to obtain the specified substances. The results are shown in Table 19.

TABLE 19

| Entry | $R_1$ | $R_2$ | Yield (%) |
| --- | --- | --- | --- |
| 1 | $C_4H_9$ | $C_4H_9$ | 77 |
| 2 | $C_6H_{13}$ | $C_6H_{13}$ | 84 |
| 3 | $C_8H_{17}$ | $C_8H_{17}$ | 78 |
| 4 | $C_{10}H_{21}$ | $C_{10}H_{21}$ | 69 |
| 5 | $CH(CH_3)_2$ | $CH(CH_3)_2$ | 76 |
| 6 | Ph | Ph | 76 |
| 7 | $C_2H_5$ | $C_4H_9$ | 63 |

(a) 3″,4″-bis(butoxyphosphoryl)-[2,2′;5′,2″;5″,2‴;5‴,2″″]-quinquethiophene (Entry 1)

Yellow Oil m/z (FAB+): 797 (calculated: 796.14).

$^1$H-NMR (CDCl$_3$): 0.85 (12H, t, J=7.4 Hz), 1.25-1.34 (8H, m), 1.47-1.55 (8H, m), 3.90-3.97 (4H, m), 4.07-4.15 (4H, m), 7.04 (2H, dd, J=3.7 Hz, 1.24 Hz), 7.14 (2H, d, J=3.8 Hz), 7.20 (2H, d, J=3.6 Hz), 7.26 (2H, d, J=5.0 Hz), 7.31 (2H, d, J=3.8 Hz) ppm.

$^{13}$C-NMR (CDCl$_3$): 13.6 (s), 18.7 (s), 32.3 (d, $^3J_{P-C}$=6.9 Hz), 66.4 (d, $^2J_{P-C}$=6.7 Hz), 124.0 (s), 124.2 (s), 125.1 (s), 127.9 (s), 129.9 (dd, $^2J_{P-C}$=18.2 Hz, $^1J_{P-C}$=179.1 Hz), 130.7 (s), 132.0 (s), 136.4 (s), 140.0 (s), 145.1 (dd, $^2J_{P-C}$=6.4 Hz, $^3J_{P-C}$=13.2 Hz) ppm.

(b) 3″,4″-bis(dihexyloxyphosphoryl)-[2,2′;5′,2″;5″,2‴;5‴,2″″]-quinquethiophene (Entry 2)

Yellow Oil m/z (FAB+): 909 (calculated: 908.26).

$^1$H-NMR (CDCl$_3$): 0.83 (12H, t, J=6.8 Hz), 1.16-1.31 (24H, m), 1.48-1.55 (8H, m), 3.88-3.96 (4H, m), 4.06-4.14 (4H, m), 7.03 (2H, dd, J=3.7 Hz, 1.4 Hz), 7.16 (2H, d, J=3.8 Hz), 7.22 (2H, d, J=3.5 Hz), 7.27 (2H, d, J=4.2 Hz), 7.32 (2H, d, J=3.8 Hz) ppm.

$^{13}$C-NMR (CDCl$_3$): 14.0 (s), 22.5 (s), 25.2 (s), 32.3 (d, $^3J_{P-C}$=6.8 Hz), 31.4 (s), 66.8 (d, $^2J_{P-C}$=6.6 Hz), 123.9 (s), 124.2 (s), 125.0 (s), 127.8 (s), 129.8 (dd, $^2J_{P-C}$=18.4 Hz, $^1J_{P-C}$=176.4 Hz), 130.7 (s), 131.8 (s), 136.4 (s), 140.0 (s), 145.0 (dd, $^2J_{P-C}$=5.9 Hz, $^3J_{P-C}$=13.5 Hz) ppm.

(c) 3″,4″-bis(dioctyloxyphosphoryl)-[2,2′;5′,2″;5″,2‴;5‴,2″″]-quinquethiophene (Entry 3)

Yellow Oil m/z (FAB+): 1021 (calculated: 1020.39).

$^1$H-NMR (CDCl$_3$): 0.85 (12H, t, J=6.8 Hz), 1.25 (40H, m), 1.49-1.54 (8H, m), 3.88-3.96 (4H, m), 4.06-4.14 (4H, m), 7.03 (2H, dd, J=3.8 Hz, 1.2 Hz), 7.14 (2H, d, J=3.8 Hz), 7.20 (2H, d, J=3.6 Hz), 7.26 (2H, d, J=5.1 Hz), 7.31 (2H, d, J=3.8 Hz) ppm.

$^{13}$C-NMR (CDCl$_3$): 14.0 (s), 22.6 (s), 25.6 (s), 29.1 (s), 29.2 (s), 30.3 (d, $^3J_{P-C}$=6.8 Hz), 31.8 (s), 66.8 (d, $^2J_{P-C}$=6.6 Hz), 123.9 (s), 124.2 (s), 125.1 (s), 127.9 (s), 130.0 (dd, $^2J_{P-C}$=17.8 Hz, $^1J_{P-C}$=181.1 Hz), 130.8 (s), 132.0 (s), 136.5 (s), 140.0 (s), 145.1 (dd, $^2J_{P-C}$=6.1 Hz, $^3J_{P-C}$=13.4 Hz) ppm.

(d) 3″,4″-bis(didecyloxyphosphoryl)-[2,2′;5′,2″;5″,2‴;5‴,2″″]-quinquethiophene (Entry 4)

Yellow Oil m/z (FAB+): 1133 (calculated: 1132.51).

$^1$H-NMR (CDCl$_3$): 0.87 (12H, t, J=6.9 Hz), 1.20 (56H, m), 1.48-1.54 (8H, m), 3.88-3.96 (4H, m), 4.06-4.14 (4H, m), 7.03 (2H, dd, J=3.7 Hz, 1.3 Hz), 7.13 (2H, d, J=3.8 Hz), 7.20 (2H, d, J=3.6 Hz), 7.25 (2H, d, J=5.1 Hz), 7.31 (2H, d, J=3.8 Hz) ppm.

$^{13}$C-NMR (CDCl$_3$): 14.1 (s), 22.6 (s), 25.6 (s), 29.2 (s), 29.5 (s), 30.3 (d, $^3J_{P-C}$=6.7 Hz), 31.9 (s), 66.8 (d, $^2J_{P-C}$=6.7 Hz), 124.0 (s), 124.2 (s), 125.1 (s), 127.9 (s), 130.0 (dd, $^2J_{P-C}$=18.0 Hz, $^1J_{P-C}$=181.1 Hz), 130.8 (s), 132.0 (s), 136.5 (s), 140.0 (s), 145.1 (dd, $^2J_{P-C}$=6.2 Hz, $^3J_{P-C}$=13.4 Hz) ppm.

(e) 3″,4″-bis(diisopropoxyphosphoryl)-[2,2′;5′,2″;5″,2‴;5‴,2″″]-quinquethiophene (Entry 5)

Yellow Amorphous m/z (FAB+): 741 (calculated: 740.07).

$^1$H-NMR (CDCl$_3$): 1.23 (12H, d, J=6.2 Hz), 1.25 (12H, d, J=6.2 Hz), 4.89-4.93 (4H, m), 7.03 (2H, t, J=4.2 Hz), 7.13 (2H, d, J=3.9 Hz), 7.20 (2H, d, J=3.6 Hz), 7.25 (2H, d, J=5.9 Hz), 7.25 (2H, d, J=4.8 Hz) ppm.

$^{13}$C-NMR (CDCl$_3$): 23.7 (d, $^3J_{P-C}$=5.2 Hz) 23.9 (d, $^3J_{P-C}$=3.7 Hz), 71.1 (d, $^2J_{P-C}$=6.0 Hz), 123.8 (s), 124.1 (s), 124.9 (s), 127.9 (s), 130.6 (s), 131.9 (dd, $^2J_{P-C}$=19.4 Hz, $^1J_{P-C}$=177.4 Hz), 132.8 (s), 136.7 (s), 139.4 (s), 144.4 (dd, $^2J_{P-C}$=8.7 Hz, $^3J_{P-C}$=11.6 Hz) ppm.

(f) 3″,4″-bis(diphenoxyphosphoryl)-[2,2′;5′,2″;5″,2‴;5‴,2″″]-quinquethiophene (Entry 6)

Yellow Amorphous m/z (FAB+): 877 (calculated: 876.01).

$^1$H-NMR (CDCl$_3$): 7.04 (2H, dd, J=3.7 Hz, 1.42 Hz), 7.01-7.17 (24H, m), 7.23 (2H, dd, J=4.1 Hz, 1.0 Hz), 7.25 (2H, d, J=3.8 Hz) ppm.

$^{13}$C-NMR (CDCl$_3$): 120.4 (s), 120.5 (s), 124.2 (s), 124.5 (s), 124.7 (s), 125.3 (s), 127.7 (dd, $^2J_{P-C}$=18.5 Hz, $^1J_{P-C}$=187.1 Hz), 127.9 (s), 129.3 (s), 130.7 (d, J=3.2 Hz), 131.4 (s), 136.2 (s), 140.8 (s), 147.4 (dd, $^2J_{P-C}$=5.3 Hz, $^3J_{P-C}$=14.7 Hz), 150.4 (d, J=8.6 Hz) ppm.

(g) 3",4"-bis(butoxy-ethoxyphosphoryl)-[2,2';5',2"; 5",2'";5'",2""]-quinquethiophene (Entry 7)

Yellow Amorphous m/z (FAB+): 741 (calculated: 740.07).

$^1$H-NMR (CDCl$_3$): 0.82-0.87 (6H, m), 1.20-1.30 (10H, m), 1.46-1.51 (4H, m), 3.90-3.93 (2H, m), 4.03-4.12 (4H, m), 4.17-4.22 (2H, m), 7.01-7.03 (2H, m), 7.14 (2H, d, J=3.8 Hz), 7.20 (2H, d, J=3.4 Hz), 7.25 (2H, d, J=5.1 Hz), 7.30-7.32 (2H, m) ppm.

Example 11

Synthesis of 3-(diethoxyphosphoryl)thiophene

[Chemical formula 118]

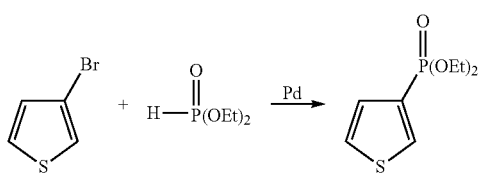

Under nitrogen, 0.0815 g (0.5 mmols) of 3-bromothiophene and 0.0231 g (0.02 mmols) of commercially available tetrakistriphenylphosphine palladium were dissolved in DMF, to which 0.0829 g (0.6 mmols) of commercially available diethyl phosphite and 0.0776 g (0.6 mmols) of diisopropylethylamine were added at room temperature. Thereafter, the reaction mixture was heated to 110° C. and stirred for 4 hours. After the reaction, the reaction mixture was cooled down to room temperature, to which a disodium hydrogen phosphate/sodium dihydrogen phosphate buffer solution, adjusted to pH=7, was added to the reaction mixture, followed by extraction with ethyl acetate. The organic phase was washed with a saturated saline solution and dried over anhydrous sodium sulfate. The solvent was removed by distilling off under reduced pressure, and the resulting crude product was purified with a silica gel column (ethyl acetate: hexane=1:1) to obtain the specified substance in the form of a yellow oil at a yield of 0.0782 g (yield: 71%).

m/z (FAB+): 221 (calculated: 220.03).

$^1$H-NMR (CDCl$_3$): 1.33 (6H, t, J=7.1 Hz), 4.06-4.18 (4H, m), 7.32-7.35 (1H, m), 7.42-7.45 (1H, m), 7.98-8.01 (1H, m) ppm.

$^{13}$C-NMR (CDCl$_3$): 16.2 (d, $^3J_{P-C}$=6.4 Hz), 62.0 (d, $^2J_{P-C}$=5.4 Hz), 127.1 (d, $^2J_{P-C}$=19.4 Hz), 128.8 (d, $^3J_{P-C}$=16.8 Hz), 129.3 (d, $^1J_{P-C}$=201.2 Hz), 135.2 (d, $^2J_{P-C}$=19.8 Hz) ppm.

Example 12

Synthesis of compounds derived from 3-(diethoxyphosphoryl)-thiophene

These compounds were synthesized according to the following processes (1) to (26).

(1) Synthesis of 3-diethoxyphosphoryl)-2-iodothiophene

[Chemical Formula 119]

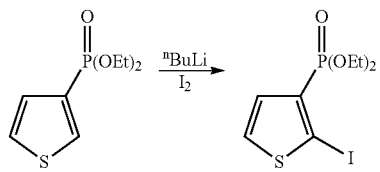

In THF, 1.38 g (6.30 mmols) of 3-(diethoxyphosphoryl) thiophene was dissolved and cooled down to −78° C. Commercially available n-butyl lithium (1.59 M hexane solution, 6.30 mmols) was slowly dropped and stirred for 3 hours at a standing temperature. Thereafter, a THF solution of 1.76 g (6.90 mmols) of commercially available iodine was dropped, followed by stirring for 1 hour. Thereafter, the reaction mixture was returned to room temperature and stirred for further 13 hours. After completion of the reaction, sodium thiosulfate was added to the reaction mixture, followed by extraction with ethyl acetate. The resulting organic phase was washed with a sodium thiosulfate aqueous solution and a saturated saline solution and dried over anhydrous sodium sulfate. The solvent was removed, and the resulting crude product was purified with a silica gel column (ethyl acetate:hexane=1:1) to obtain 1.86 g (yield: 85%) of the specified substance in the form of a brown solid. The thus obtained substance was used as it is for reaction in Example 12(3).

(2) Synthesis of 2-(tributylstannyl)-3-(diethoxyphosphoryl)-thiophene

[Chemical Formula 120]

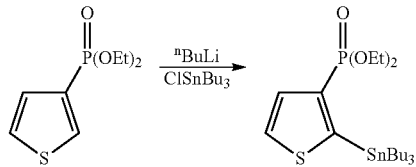

In THF, 1.96 g (8.90 mmols) of 3-(diethoxyphosphoryl) thiophene was dissolved and cooled down to −78° C. Commercially available n-butyl lithium (1.59 M hexane solution, 8.90 mmols) was slowly dropped, followed by stirring for 3 hours at a standing temperature. Thereafter, 3.19 g (9.80 mmols) of commercially available tributylstannyl chloride was dropped and stirred for 1.5 hours. After completion of the reaction, a disodium hydrogen phosphate/sodium dihydrogen phosphate buffer solution, adjusted to pH=7, was added so as to complete the reaction, followed by extraction with ethyl acetate. The organic phase was washed with a saturated saline solution and dried over anhydrous sodium sulfate. The solvent was removed, and the resulting crude product was purified with a silica gel column (ethyl acetate:hexane=1:2) to obtain the specified substance in the form of a transparent oil at a yield of 4.35 g (yield: 96%). The thus obtained substance was used as it is for reaction in Example 12(3).

(3) Synthesis of 3,3'-bis(diethoxyphosphoryl)-[2,2']-bithiophene

[Chemical Formula 121]

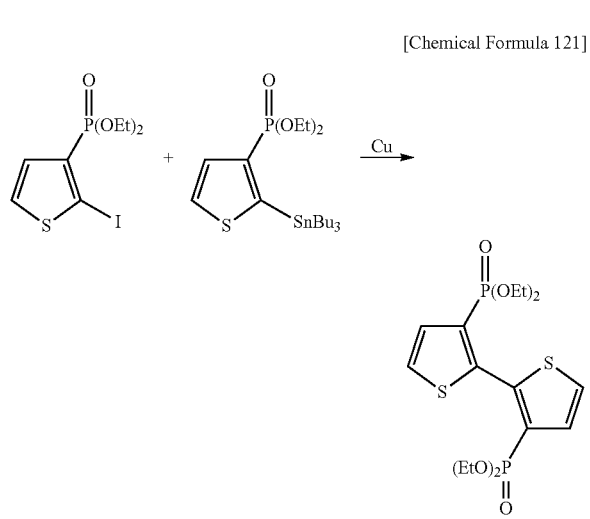

At room temperature, 0.6790 g (1.96 mmols) of the 3-(diethoxyphosphoryl)-2-iodothiophene obtained in Example 12(1) and 0.9982 g (1.96 mmols) of the 2-(tributylstannyl)-3-(diethoxyphosphoryl)thiophene obtained in Example 12(2) were dissolved in DMF, to which 0.2326 g (2.35 mmols) of commercially available copper(I) chloride was added at room temperature. Thereafter, the reaction mixture was heated to 80° C. and stirred for 10 hours. After the reaction, the reaction mixture was cooled down to room temperature, to which a 10% hydrochloric acid aqueous solution, followed by extraction of the resulting product with ethyl acetate. The organic phase was washed with a saturated saline solution and dried over anhydrous sodium sulfate. The solvent was removed by distilling off under reduced pressure, and the resulting crude product was purified with a silica gel column (gradiated from ethyl acetate:hexane=1:1 with acetone) to obtain the specified substance in the form of white crystals at a yield of 0.6101 g (yield: 71%).

m/z (FAB+): 439 (calculated: 438.05).

$^1$H-NMR (CDCl$_3$): 1.21 (12H, t, J=7.1 Hz), 3.98-4.09 (8H, m), 7.40 (2H, dd, J=4.8, 4.8 Hz), 7.47 (2H, dd, J=5.3, 3.0 Hz) ppm.

$^{13}$C-NMR (CDCl$_3$): 16.2 (d, $^3J_{P-C}$=6.8 Hz), 62.0 (d, $^2J_{P-C}$=5.7 Hz), 127.4 (d, $^3J_{P-C}$=19.8 Hz), 129.7 (d, $^1J_{P-C}$=194.7 Hz), 131.1 (d, $^2J_{P-C}$=16.1 Hz), 141.1 (dd, $^3J_{P-C}$=3.2 Hz, $^2J_{P-C}$=15.4 Hz) ppm.

(4) Synthesis of 3,3'-bis(dibutoxyphosphoryl)-[2,2']-bithiophene

[Chemical Formula 122]

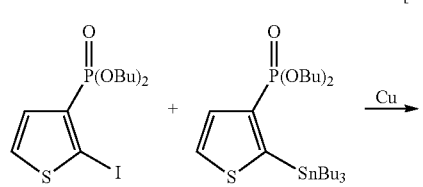

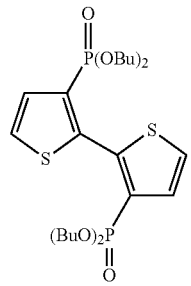

At room temperature, 0.8045 g (2.00 mmols) of 3-(dibutoxyphosphoryl)-2-iodothiophene and 1.1308 g (2.00 mmols) of 2-(tributylstannyl)-3-(dibutoxyphosphoryl)thiophene were dissolved in DMF, to which 0.2376 g (2.40 mmols) of commercially available copper(I) chloride was added at room temperature. Thereafter, the reaction mixture was heated to 80° C. and stirred for 10 hours. After the reaction, the reaction mixture was cooled down to room temperature, to which a 10% hydrochloric acid aqueous solution, followed by extraction of the resulting product with ethyl acetate. The organic phase was washed with a saturated saline solution and dried over anhydrous sodium sulfate. The solvent was removed by distilling off under reduced pressure, and the resulting crude product was purified with a silica gel column (gradiated from ethyl acetate:hexane=1:1 with acetone) to obtain the specified substance in the form of white crystals at a yield of 1.6012 g (yield: 55%).

m/z (FAB+): 550 (calculated: 550.17).

$^1$H-NMR (CDCl$_3$): 0.88 (12H, t, J=7.4 Hz), 1.30 (8H, qt, J=7.5 Hz, J=7.5 Hz), 1.49-1.57 (8H, m), 3.87-4.03 (8H, m), 7.38 (2H, dd, J=4.8, 4.8 Hz), 7.45 (2H, dd, J=5.2, 3.0 Hz) ppm.

$^{13}$C-NMR (CDCl$_3$): 13.5, 18.6, 32.3 (d, $^3J_{P-C}$=6.7 Hz), 65.7 (d, $^2J_{P-C}$=6.0 Hz), 127.3 (d, $^3J_{P-C}$=19.7 Hz), 129.7 (d, $^1J_{P-C}$=195.0 Hz), 131.1 (d, $^2J_{P-C}$=15.9 Hz), 141.1 (dd, $^3J_{P-C}$=3.1 Hz, $^2J_{P-C}$=15.4 Hz) ppm.

(5) Synthesis of 3,3'-bis(diethoxyphosphoryl)-5,5'-bis(tributylstannyl)-[2,2']-bithiophene and 3,3'-bis(diethoxyphosphoryl)-5-(tributylstannyl)-[2,2']-bithiophene

[Chemical Formula 123]

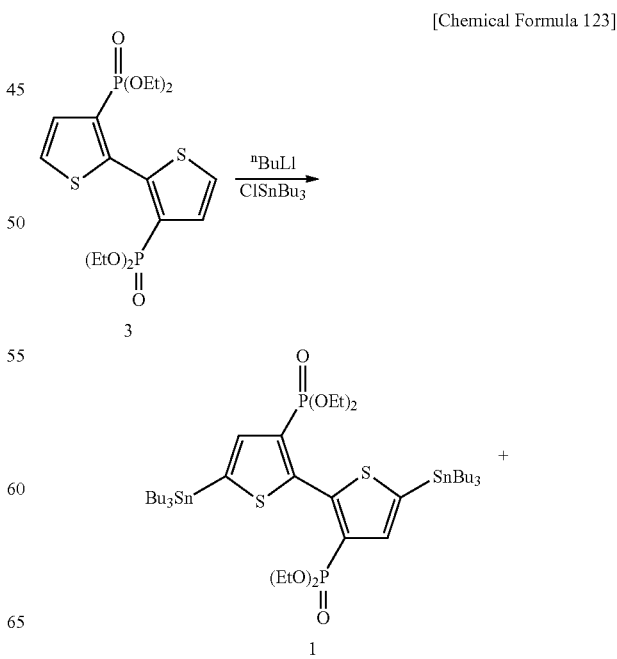

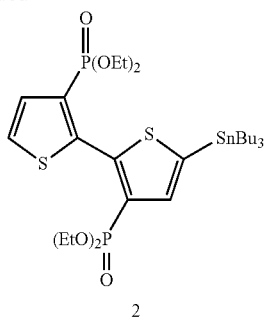

2

3,3'-bis(diethoxyphosphoryl)-[2,2']-bithiophene was dissolved in THF and cooled down to −78° C. Commercially available n-butyl lithium (1.59 M hexane solution) was slowly dropped in amounts indicated in the following Table 20, followed by stirring for 2 hours at a standing temperature. Thereafter, commercially available tributylstannyl chloride was dropped in amounts indicated in Table 20 and stirred for 1.5 hours. After completion of the reaction, a disodium hydrogen phosphate/sodium dihydrogen phosphate buffer solution, adjusted to pH=7, was added so as to complete the reaction, followed by extraction with ethyl acetate. The organic phase was washed with a saturated saline solution and dried over anhydrous sodium sulfate. The solvent was removed, and the resulting crude product was purified with a silica gel column (gradiated from ethyl acetate:hexane=1:5 with acetone) to obtain the captioned specified substances in the form of a yellow solid. The thus obtained substances were used as they are for reaction in Example 12(6) or (7).

TABLE 20

| Entry | $^n$BuLi | ClSnBu$_3$ | Temp. | Time (h) | Yield (%) 1 | 2 | 3 |
|---|---|---|---|---|---|---|---|
| 1 | 1.0 eq. | 1.1 eq. | −78° C. to rt | 18 | — | 69 | 22 |
| 2 | 2.5 eq. | 2.5 eq. | −78° C. | 3 | 74 | — | — |

(6) Synthesis of 3''',4''-bis(diethoxyphosphoryl)-[2,2';5',2'';5'',2''';5''',2'''';5'''',2''''']-sexithiophene

[Chemical Formula 124]

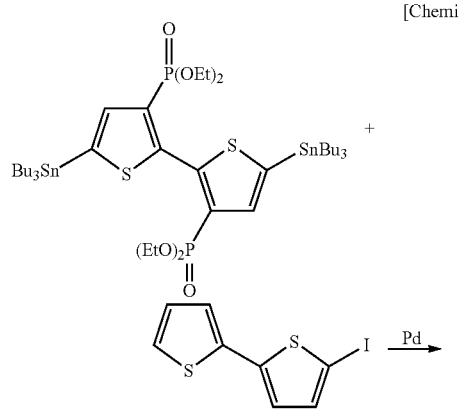

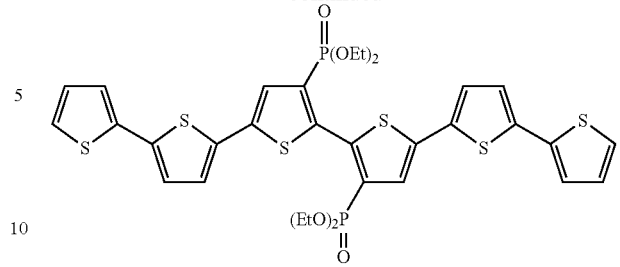

At room temperature, 0.0065 g (0.0056 mmols) of commercially available tetrakistriphenylphosphine palladium and 0.0818 g (0.28 mmols) of 2-iodobithiophene were dissolved in DMF. Thereafter, 0.1345 g (0.14 mmols) of 3,3'-bis(diethoxyphosphoryl)-5,5'-bis(tributylstannyl)-[2,2']-bithiophene was added at room temperature. The reaction mixture was heated and stirred under reflux for 5 hours. After the reaction, the reaction mixture was cooled down to room temperature, to which a potassium fluoride aqueous solution was added, followed by stirring for 2 hours. Thereafter, the solid was removed by celite filtration and the filtrate was extracted with ethyl acetate. The organic phase was washed with a saturated saline solution and dried over anhydrous sodium sulfate. The solvent was removed by distilling off under reduced pressure, and the resulting crude product was purified with a PTLC plate (developed with ethyl acetate:hexane=1:5 and ethyl acetate:hexane=1:1) to obtain the specified substance in the form of a yellow solid at a yield of 0.0451 g (yield: 42%).

m/z (FAB+): 766 (calculated: 766.00)
$^1$H-NMR (CDCl$_3$): 1.27 (12H, t, J=7.1 Hz), 4.07-4.15 (8H, m), 7.03-7.04 (2H, m), 7.09-7.12 (4H, m), 7.19-7.20 (2H, m), 7.24-7.27 (2H, m), 7.44 (2H, d, J=4.9 Hz) ppm.

(7) Synthesis of 3,3',4'',3'''-tetrakis(diethoxyphosphoryl)-[2,2';5',2'';5'',2''']-quaterthiophene

[Chemical Formula 125]

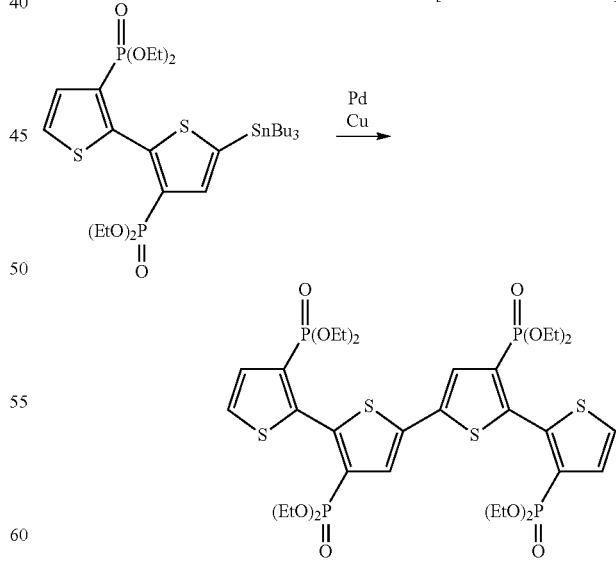

At room temperature, 0.1045 g (0.15 mmols) of 3,3'-bis(diethoxyphosphoryl)-5-(tributylstannyl)-[2,2']-bithiophene, 0.0034 g (0.015 mmols) of commercially available palladium acetate and 0.0403 g (0.3 mmols) of commercially available copper(II) chloride were dissolved in THF, followed by stirring the reaction mixture at room temperature for 7 hours. After the reaction, a disodium hydrogen phosphate/sodium dihydrogen phosphate buffer solution, adjusted to pH=7, was added, followed by extraction with ethyl acetate. The organic phase was washed with a 10% hydrochloric acid aqueous solution and dried over anhydrous sodium sulfate. The solvent was removed, and the resulting crude product was purified with a PTLC plate (developed with ethyl acetate:hexane=30:1 and ethyl acetate:hexane=15:1) to obtain the specified substance in the form of light brown crystals at a yield of 0.0407 g (yield: 62%).

m/z (FAB+): 874 (calculated: 874.08)

$^1$H-NMR (CDCl$_3$): 1.25 (12H, m), 4.00-4.14 (8H, m), 7.40-4.43 (2H, m), 7.47-7.49 (2H, m), 7.50-7.52 (2H, m) ppm.

$^{13}$C-NMR (CDCl$_3$): 16.4 (d, $^3J_{P\text{-}C}$=6.5 Hz), 16.4 (d, $^3J_{P\text{-}C}$=6.2 Hz), 62.3 (d, $^2J_{P\text{-}C}$=5.7 Hz), 62.4 (d, $^2J_{P\text{-}C}$=5.7 Hz), 128.1 (d, $^3J_{P\text{-}C}$=19.8 Hz), 128.3 (d, $^3J_{P\text{-}C}$=16.1 Hz), 130.2 (d, $^1J_{P\text{-}C}$=194.9 Hz), 131.2 (d, $^1J_{P\text{-}C}$=194.2 Hz), 131.3 (d, $^2J_{P\text{-}C}$=16.1 Hz), 137.5 (d, $^2J_{P\text{-}C}$=20.2 Hz), 140.4 (dd, $^3J_{P\text{-}C}$=3.4 Hz, $^2J_{P\text{-}C}$=15.3 Hz), 140.6 (dd, $^3J_{P\text{-}C}$=3.8 Hz, $^2J_{P\text{-}C}$=15.0 Hz) ppm.

(8) Synthesis of 5-iodo-3-(diethoxyphosphoryl)thiophene

[Chemical Formula 126]

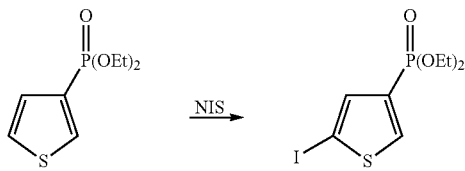

In 5 ml of a mixed solvent of chloroform:acetic acid=1:1, 0.1101 g (0.5 mmols) of 3-(diethoxyphosphoryl)thiophene was dissolved, to which 0.2362 g (1.05 mmols) of commercially available N-iodosuccinimide was added at room temperature. Thereafter, the reaction mixture was stirred at room temperature for 4 days. After the reaction, a disodium hydrogen phosphate/sodium dihydrogen phosphate buffer solution, adjusted to pH=7, was added, followed by extraction with chloroform. The organic phase was washed with a 0.2N sodium hydroxide aqueous solution and dried over anhydrous sodium sulfate. The solvent was removed, and the resulting crude product was purified with a PTLC plate (developed with ethyl acetate:hexane 1:1) to obtain the specified substance in the form of a yellow oil at a yield of 0.1263 g (yield: 73%). The thus obtained substance was used as it is for reaction in Example 12(9).

(9) Synthesis of 4,3'-bis(diethoxyphosphoryl)-[2,2']-bithiophene

[Chemical Formula 127]

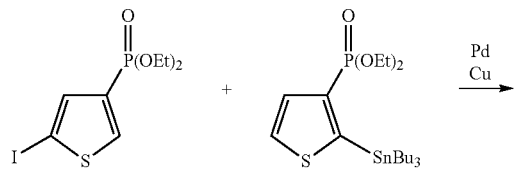

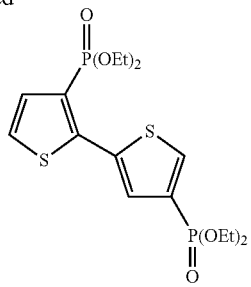

At room temperature, 1.4875 g (4.3 mmols) of 5-iodo-3-(diethoxyphosphoryl)thiophene and 0.0994 g (0.086 mmols) of commercially available tetrakistriphenylphosphine palladium were dissolved in 43 ml of toluene, to which 2.1899 g (4.3 mmols) of 2-tributylstannyl-3-(diethoxyphosphoryl)thiophene and 0.0347 g (0.39 mmols) of commercially available copper(I) chloride were added at room temperature. Thereafter, the reaction mixture was heated and stirred under reflux for 3.5 hours. After the reaction, the reaction mixture was cooled down to room temperature, to which a potassium fluoride aqueous solution was added, followed by stirring for 1 hour. Thereafter, the solid was removed by celite filtration and the filtrate was extracted with ethyl acetate. The resulting organic phase was washed with a saturated saline solution and dried over anhydrous sodium sulfate. The solvent was removed by distilling off under reduced pressure, and the resulting crude product was purified with a silica gel column (gradiated with acetone from ethyl acetate) to obtain the specified substance in the form of a yellow oil at a yield of 1.5836 g (yield: 84%).

$^1$H-NMR (CDCl$_3$): 1.23 (t, 6H, J=7.08 Hz), 1.35 (t, 6H, J=7.04 Hz), 4.03-4.18 (m, 8H), 7.34 (dd, 1H, J=5.24, 2.96 Hz), 7.44 (t, 1H, J=4.82 Hz), 7.63 (dd, 1H, J=4.26, 0.96 Hz), 8.02 (dd, 1H, J=8.66, 1.0 Hz) ppm.

$^{13}$C-NMR (CDCl$_3$): δ=16.0 (d, $^3J_{P\text{-}C}$=6.8 Hz), 16.2 (d, $^3J_{P\text{-}C}$=6.5 Hz), 62.1 (d, $^2J_{P\text{-}C}$=5.1 Hz), 62.2 (d, $^2J_{P\text{-}C}$=4.9 Hz), 125.6 (d, $^3J_{P\text{-}C}$=19.4 Hz), 126.3 (d, $^1J_{P\text{-}C}$=194.6 Hz), 130.0 (d, $^1J_{P\text{-}C}$=197.0 Hz), 130.1 (d, $^2J_{P\text{-}C}$=16.7 Hz), 133.1 (d, $^2J_{P\text{-}C}$=16.0 Hz), 135.9 (dd, $^2J_{P\text{-}C}$=20.5, 3.1 Hz), 136.6 (d, $^2J_{P\text{-}C}$=16.8 Hz), 142.6 (d, $^2J_{P\text{-}C}$=15.4 Hz) ppm.

UV λmax: 247.8 nm

(10) Synthesis of 5-(tributylstannyl)-4,3'-bis(diethoxyphosphoryl)-[2,2']-bithiophene and 5,5'-bis(tributylstannyl)-4,3'-bis(diethoxyphosphoryl)-[2,2']-bithiophene

[Chemical Formula 128]

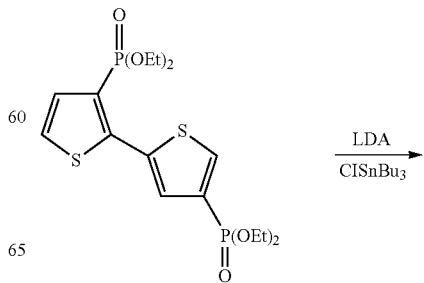

121
-continued

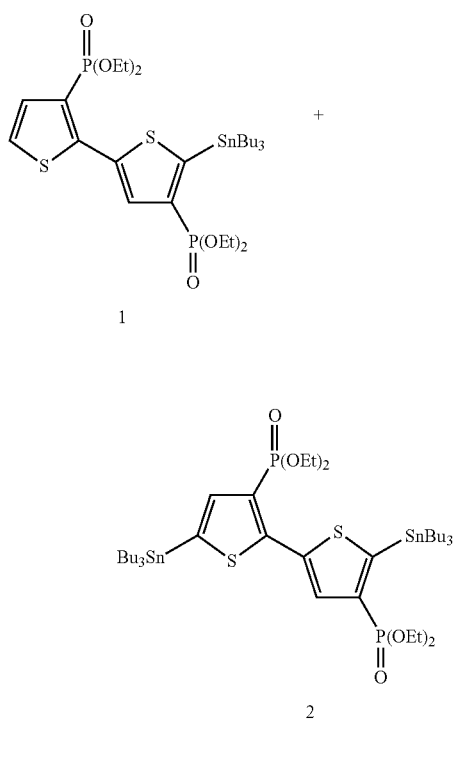

Commercially available n-butyl lithium (1.59 M hexane solution, 0.49 mmols) was gradually dropped in a THF solution of 0.0505 g (0.49 mmols) of commercially available diisopropylamine cooled to −78° C. After stirring for 1 hour, a THF solution of 0.0877 g (0.2 mmols) of 4,3'-bis(diethylphosphono)-[2,2']-bithiophene was slowly added. After stirring for 2 hours at a standing temperature, 0.1595 g (0.49 mmols) of commercially available tributyltin chloride was dropped, followed by stirring for 1 hour. After completion of the reaction, a disodium hydrogen phosphate/sodium dihydrogen phosphate buffer solution, adjusted to pH=7, was added, followed by extraction with ethyl acetate. The organic phase was washed with a saturated saline solution and dried over anhydrous sodium sulfate. The solvent was removed by distilling off under reduced pressure, and the resulting crude product was purified with a PTLC plate (developed with ethyl acetate:hexane=1:5 and ethyl acetate:hexane=1:3) to obtain the respective captioned substances in the form of a yellow oil at yields indicated in Table 21. The thus obtained substances were used as they are for reaction in Example 12(11).

TABLE 21

| Yield (%) | |
|---|---|
| 1 | 2 |
| 32 | 44 |

122

(11) Synthesis of 4,3'-bis(diethoxyphosphoryl)-5'-iodo-[2,2']-bithiophene

[Chemical Formula 129]

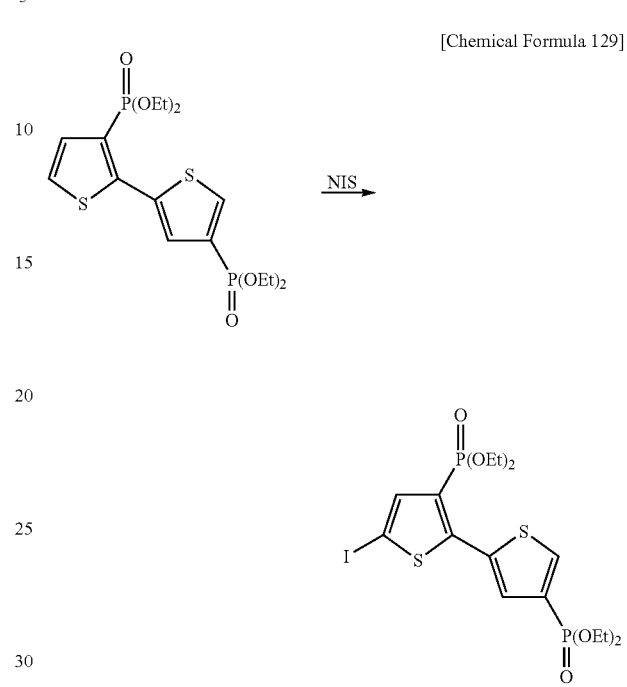

In a mixed solvent of chloroform and acetic acid at 1:1, 0.0877 g (0.2 mmols) of 4,3'-bis(diethoxyphosphoryl)-[2,2']-bithiophene was dissolved, to which 0.2250 g (1.0 mmol) of commercially available N-iodosuccinimide was added at room temperature. Thereafter, the reaction mixture was stirred at room temperature for 8 hours. After the reaction, a sodium thiosulfate aqueous solution was added, followed by extraction with chloroform. The organic phase was washed with a 0.2 N sodium hydroxide aqueous solution and dried over anhydrous sodium sulfate. The solvent was removed by distilling off under reduced pressure, and the resulting crude product was purified with a PTLC plate (developed with ethyl acetate:hexane=2:1) to obtain the specified substance in the form of a yellow solid at a yield of 0.0880 g (yield: 78%). The thus obtained product was used as it is for reaction in Example 12(12).

(12) Synthesis of 3,4',4''-tri(diethoxyphosphoryl)-[2,2';5',2'']-terthiophene

[Chemical Formula 130]

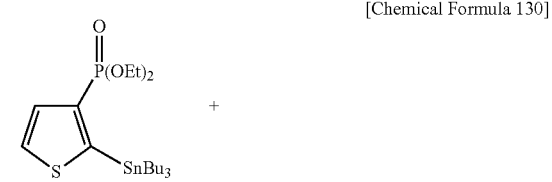

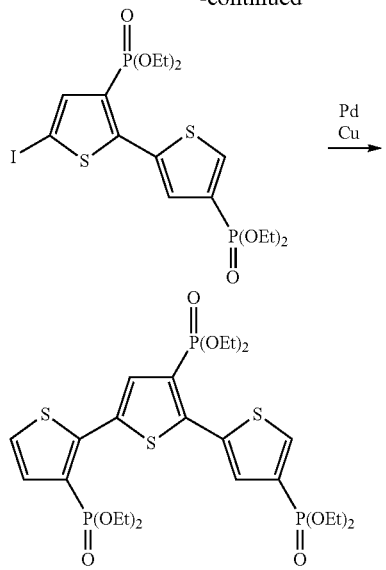

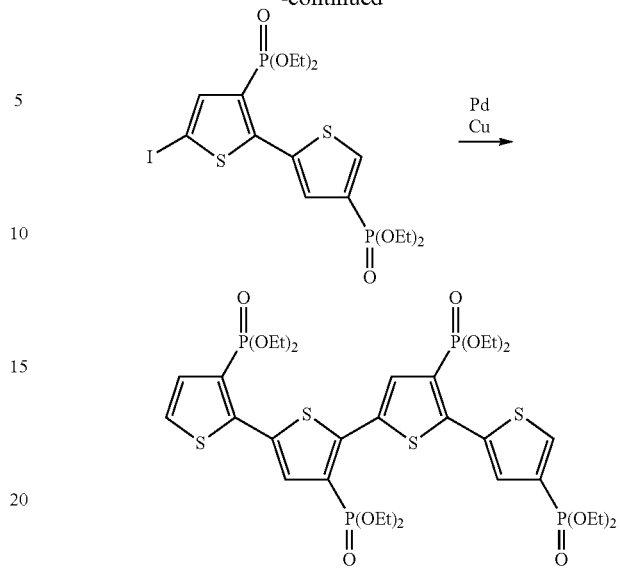

At room temperature, 0.1129 g (0.2 mmols) of 4,3'-bis(diethoxyphosphoryl)-5'-iodo-[2,2']-bithiophene and 0.0092 g (0.008 mmols) of commercially available tetrakistriphenylphosphine palladium were dissolved in 2 ml of toluene, to which 0.1018 g (0.2 mmols) of 2-(tributylstannyl)-3-(diethoxyphosphoryl)thiophene and 0.0036 g (0.04 mmols) of commercially available copper(I) cyanide were added at room temperature. Thereafter, the reaction mixture was heated and stirred under reflux for 2.5 hours. After the reaction, the reaction mixture was cooled down to room temperature, to which a potassium fluoride aqueous solution added, followed by stirring for 1 hour. The resulting solid was removed by celite filtration and the filtrate was extracted with ethyl acetate. The organic phase was washed with a saturated saline solution and dried over anhydrous sodium sulfate. The solvent was removed by distilling off under reduced pressure, and the resulting crude product was purified with a PTLC plate (developed with ethyl acetate:hexane=1:2 and ethyl acetate:hexane=1:1) to obtain the specified substance in the form of a yellow oil at a yield of 0.0919 g (yield: 70%).

m/z (FAB+): 656 (calculated: 656.07).

$^1$H-NMR (CDCl$_3$): 1.26-1.38 (18H, m), 4.09-4.17 (12H, m), 7.38 (1H, s), 7.44 (1H, s), 7.72 (1H, d, J=4.3 Hz), 7.75 (1H, d, J=4.9 Hz), 8.05 (1H, d, J=8.6 Hz) ppm.

(13) Synthesis of 3,4',4'',4'''-tetrakis(diethoxyphosphoryl)-[2,2';5',2'';5'',2''']-quaterthiophene

[Chemical Formula 131]

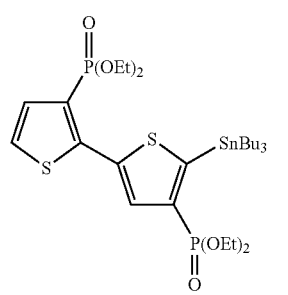

+

At room temperature, 0.0564 g (0.1 mmol) of 4,3'-bis(diethoxyphosphoryl)-5'-iodo-[2,2']-bithiophene and 0.0092 g (0.008 mmols) of commercially available tetrakistriphenylphosphine palladium were dissolved in 2 ml of toluene, to which 0.0709 g (0.1 mmol) of 5-(tributylstannyl)-4,3'-bis(diethoxyphosphoryl)-[2,2']-bithiophene and 0.0018 g (0.02 mmols) of commercially available copper(I) cyanide were added at room temperature. Thereafter, the reaction mixture was heated and stirred under reflux for 2.5 hours. After the reaction, the reaction mixture was cooled down to room temperature, to which a potassium fluoride aqueous solution added, followed by stirring for 1 hour. The resulting solid was removed by celite filtration and the filtrate was extracted with ethyl acetate. The organic phase was washed with a saturated saline solution and dried over anhydrous sodium sulfate. The solvent was removed by distilling off under reduced pressure, and the resulting crude product was purified with a PTLC plate (developed with ethyl acetate and ethyl acetate:hexane=15:1) to obtain the specified substance in the form of an orange oil at a yield of 0.0717 g (yield: 82%).

m/z (FAB+): 875 (calculated: 874.08).

$^1$H-NMR (CDCl$_3$): 1.15-1.29 (24H, m), 3.98-4.13 (18H, m), 7.29-7.31 (1H, m), 7.35-7.37 (1H, m), 7.64 (1H, d, J=4.3 Hz), 7.67 (1H, d, J=4.9 Hz), 7.73 (1H, d, J=4.9 Hz), 7.97 (1H, d, J=8.6 Hz) ppm.

(14) Synthesis of 3-(dibutoxyphosphoryl)-2,5-diiodothiophene

[Chemical Formula 132]

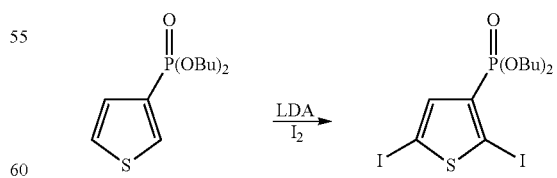

Commercially available n-butyl lithium (1.59 M hexane solution, 39.6 mmols) was slowly dropped in a THF solution of 4.01 g (39.6 mmols) of commercially available diisopropylamine, cooled to −78° C. After stirring for 1 hour, this solution was slowly dropped in a separately prepared solution, cooled to −78° C., of 4.97 g (18.0 mmols) of 3-(dibutoxyphosphoryl)thiophene dissolved in THF, followed by stirring for 2 hours at a standing temperature. Thereafter, a THF solution of 10.1 g (39.6 mmols) of commercially available iodine was dropped, followed by stirring for 1.5 hours, returning to room temperature and stirring for further 13 hours. After completion of the reaction, a sodium thiosulfate aqueous solution was added, followed by extraction with ethyl acetate. The organic phase was washed with a sodium thiosulfate aqueous solution and a saturated saline solution and dried over anhydrous sodium sulfate. The solvent was removed by distilling off under reduced pressure, and the resulting crude product was purified with a silica gel column (ethyl acetate:hexane=1:2) to obtain the specified substance in the form of a brown oil at a yield of 7.90 g (yield: 83%). The thus obtained substance was used as it is for reaction in Example 12(16).

(15) Synthesis of 3-(dibutoxyphosphoryl)-2,5-bis (tributylstannyl)thiophene

[Chemical Formula 133]

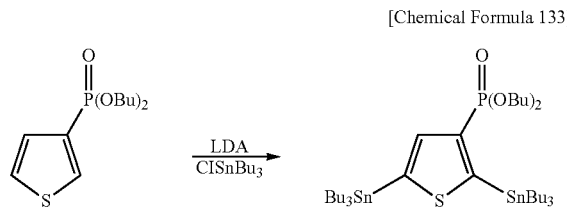

Commercially available n-butyl lithium (1.59 M hexane solution, 45.0 mmols) was slowly dropped in a THF solution of 4.55 g (45.0 mmols) of commercially available diisopropylamine, cooled to −78° C. After stirring for 1 hour, this solution was slowly dropped in a separately prepared solution, cooled to −78° C., of 4.97 g (18.0 mmols) of 3-(dibutoxyphosphoryl)thiophene dissolved in THF, followed by stirring for 2 hours at a standing temperature. Thereafter, 14.6 g (45.0 mmols) of commercially available tributylstannyl chloride was dropped, followed by stirring for 4.5 hours. After completion of the reaction, a disodium hydrogen phosphate/sodium dihydrogen phosphate buffer solution, adjusted to pH=7, was added so as to complete the reaction, followed by extraction with ethyl acetate. The organic phase was washed with a saturated saline solution and dried over anhydrous sodium sulfate. The solvent was removed by distilling off under reduced pressure, and the resulting crude product was purified with a silica gel column (gradiated from hexane with ethyl acetate:hexane=1:10) to obtain the specified substance in the form of a transparent oil at a yield of 12.35 g (yield: 80%). The thus obtained substance was used as it is for reaction in Example 12(17).

(16) Synthesis of 3-(dibutoxyphosphoryl)-5-iodothiophene

[Chemical Formula 134]

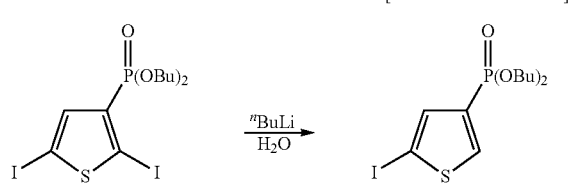

In THF, 3.10 g (5.9 mmols) of 3-(dibutoxyphosphoryl)-2,5-diiodothiophene was dissolved and cooled down to −78° C. Commercially available n-butyl lithium (1.59 M hexane solution, 6.2 mmols) was slowly dropped, followed by stirring for 1 hour at a standing temperature. Thereafter, a disodium hydrogen phosphate/sodium dihydrogen phosphate buffer solution, adjusted to pH=7, was added, followed by extraction with ethyl acetate. The organic phase was washed with a saturated saline solution and dried over anhydrous sodium sulfate. The solvent was removed by distilling off under reduced pressure, and the resulting crude product was purified with a silica gel column (ethyl acetate:hexane=1:1) to obtain the specified substance in the form of a brown oil at a yield of 1.88 g (yield: 79%). The thus obtained substance was used as it is for reaction in Example 12(18).

(17) Synthesis of 3-(butoxyphosphoryl)-5-(tributylstannyl)-thiophene

[Chemical Formula 135]

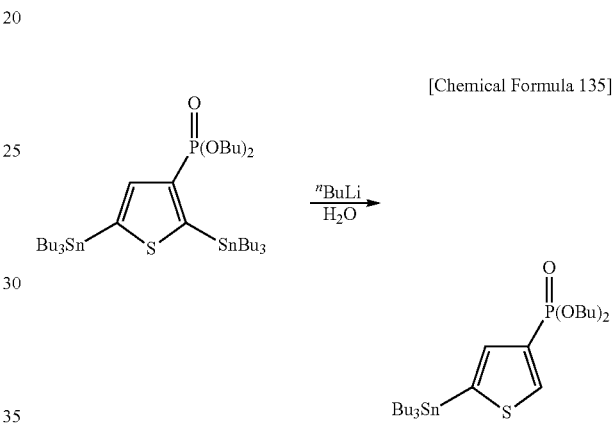

In THF, 8.48 g (9.90 mmols) of 3-(dibutoxyphosphoryl)-2,5-bis(tributylstannyl)thiophene was dissolved and cooled down to −78° C. Commercially available n-butyl lithium (1.59 M hexane solution, 10.9 mmols) was slowly dropped, followed by stirring for 1 hour at a standing temperature. Thereafter, a disodium hydrogen phosphate/sodium dihydrogen phosphate buffer solution, adjusted to pH=7, was added, followed by extraction with ethyl acetate. The organic phase was washed with a saturated saline solution and dried over anhydrous sodium sulfate. The solvent was removed by distilling off under reduced pressure, and the resulting crude product was purified with a silica gel column (gradiated from ethyl acetate:hexane=1:10 with ethyl acetate:hexane=1:2) to obtain the specified substance in the form of a transparent oil at a yield of 4.64 g (yield: 83%). The thus obtained substance was used as it is for reaction in Example 12(18).

(18) Synthesis of 4,4'-bis(dibutoxyphosphoryl)-[2.2']-bithiophene

[Chemical Formula 136]

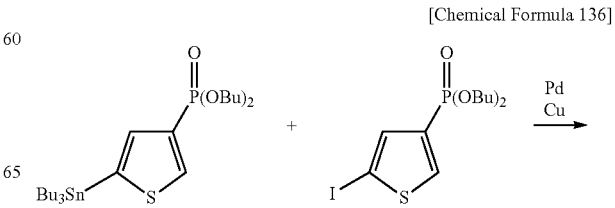

-continued

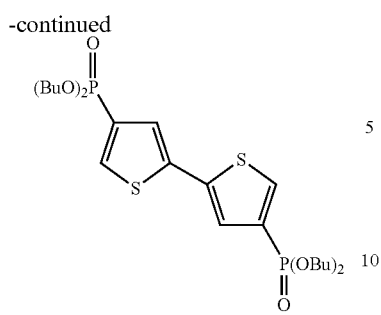

At room temperature, 0.0804 g (0.2 mmols) of 3-(dibutoxyphosphoryl)-5-iodothiophene and 0.0092 g (0.008 mmols) of commercially available tetrakistriphenylphosphine palladium were dissolved in 2 ml of toluene, to which 0.1131 g (0.2 mmols) of 3-(dibutoxyphosphoryl)-5-(tributylstannyl)-thiophene and 0.0036 g (0.04 mmols) of commercially available copper(I) cyanide were added at room temperature. Thereafter, the reaction mixture was heated and stirred under reflux for 2 hours. After the reaction, the reaction mixture was cooled down to room temperature, to which a potassium fluoride aqueous solution was added, followed by stirring for 1 hour. Thereafter, the solid was removed by celite filtration and the filtrate was extracted with ethyl acetate. The organic phase was washed with a saturated saline solution and dried over anhydrous sodium sulfate. The solvent was removed by distilling off under reduced pressure, and the resulting crude product was purified with a PTLC plate (developed with ethyl acetate:hexane=1:2 and ethyl acetate:hexane=1:1) to obtain the specified substance in the form of a white solid at a yield of 0.0881 g (yield: 80%).

$^1$H-NMR (CDCl$_3$): 0.93 (t, 12H, J=7.44 Hz), 1.41 (sex, 8H, J=7.28 Hz), 1.68 (sex, 8H, J=6.64 Hz), 4.02-4.12 (m, 8H), 7.38 (dd, 2H, J=4.20, 1.12 Hz), 7.86 (dd, 2H, J=8.58, 1.16 Hz) ppm.

$^{13}$C-NMR (CDCl$_3$): δ=13.5, 18.7, 32.3 (d, $^3J_{P-C}$=6.4 Hz), 66.0 (d, $^2J_{P-C}$=5.6 Hz), 126.0 (d, $^2J_{P-C}$=16.5 Hz), 130.8 (d, $^1J_{P-C}$=197.1 Hz), 134.5 (d, $^2J_{P-C}$=16.4 Hz), 137.9 (d, $^3J_{P-C}$=19.9 Hz) ppm.

UV λmax=300.5 nm

(19) Synthesis of 4,4'-bis(dibutoxyphosphoryl)-5'-(tributylstannyl)-[2,2']-bithiophene and 4,4'-bis(dibutoxyphosphoryl)-5,5'-bis(tributylstannyl)-[2,2']-bithiophene

[Chemical Formula 137]

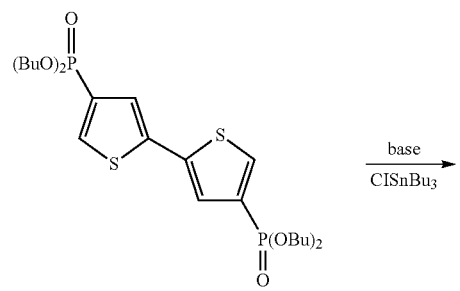

-continued

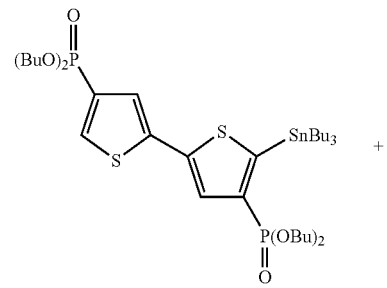

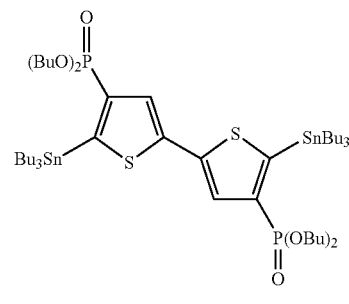

In THF, 4,4'-tetra(dibutylstannylphosphono)-[2,2']-bithiophene was dissolved and cooled to −78° C., to which 1.0 equivalent of commercially available n-butyl lithium (1.59 M hexane solution), or 2.5 equivalents of an LDA solution prepared from commercially available butyl lithium (1.59 M hexane solution) and commercially available diisopropylamine was slowly dropped and stirred for 2 hours at a standing temperature. Thereafter, commercially available tributylstannyl chloride was dropped in amounts indicated in the following Table 22, respectively, followed by stirring for 2 to 3 hours. A disodium hydrogen phosphate/sodium dihydrogen phosphate buffer solution, adjusted to pH=7, was added, followed by extraction with chloroform. The organic phase was washed with a saturated saline solution and dried over anhydrous sodium sulfate. The solvent was removed by distilling off under reduced pressure, and the resulting crude product was purified with a silica gel column (gradiated from ethyl acetate:hexane=1:20 with ethyl acetate:hexane=1:2) to obtain the specified substance 1 in the form of a transparent oil and the specified substance 2 in the form of colorless crystals, respectively. The thus obtained substances were used as they are for reaction in Example 12(20).

TABLE 22

| | | | | | Yield (%) | | |
|---|---|---|---|---|---|---|---|
| Entry | base | ClSnBu$_3$ | Temp. | Time | 1 | 2 | 3 |
| 1 | $^n$BuLi 1.0 eq. | 1.0 eq. | −78° C. | 2 h | 55 | 4 | 3 |
| 2 | LDA 2.5 eq. | 2.5 eq. | −78° C. | 3 h | — | 69 | — |

(20) Synthesis of 3",4'''-bis(dibutoxyphosphoryl)-[2,2';5',2'';5'',2''';5''',2'''']-sexithiophene

[Chemical Formula 138]

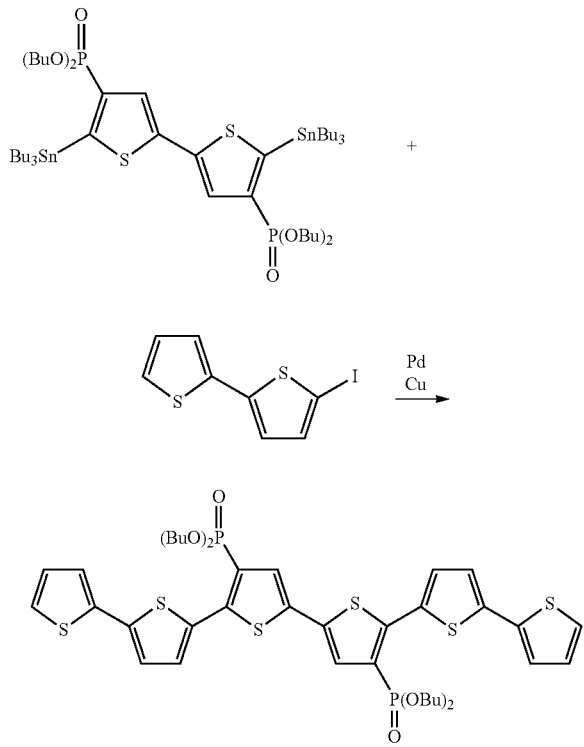

At room temperature, 0.5785 g (2.0 mmols) of 2-iodoterthiophene, 0.0330 g (0.036 mmols) of commercially available tris(dibenzylideneacetone)dipalladium and 0.0378 g (0.14 mmols) of triphenylphosphine were dissolved in 9 mL of toluene, to which 1.0159 g (0.9 mmols) of 4,4'-bis(dibutoxyphosphoryl)-5,5'-bis(tributylstannyl)-[2,2']-bithiophene and 0.0161 g (0.18 mmols) of commercially available copper (I) chloride were added at room temperature. Thereafter, the reaction mixture was heated and stirred under reflux for 2 hours. After the reaction, the reaction mixture was cooled down to room temperature, to which a potassium fluoride aqueous solution was added, followed by stirring for 1 hour. Subsequently, the solid was removed by celite filtration and the filtrate was extracted with ethyl acetate. The organic phase was washed with a saturate saline solution and dried over anhydrous sodium sulfate. The solvent was removed by distilling off under reduced pressure, and the resulting crude product was purified with a silica gel column (gradiated from ethyl acetate:hexane=1:5 with ethyl acetate:hexane=3:1) to obtain the specified substance in the form of a red solid at a yield of 0.5460 g (yield: 69%).

m/z (FAB+): 878 (calculated: 878.13).

$^1$H-NMR (CDCl$_3$): 0.86-0.90 (12H, m), 1.30-1.37 (8H, m), 1.58-1.65 (8H, m), 4.01-4.11 (8H, m), 7.01-7.04 (2H, m), 7.14-7.15 (2H, m), 7.21-7.25 (4H, m), 7.50-7.54 (4H, m) ppm.

$^{13}$C-NMR (CDCl$_3$): 13.4, 18.5, 32.1 (d, $^3J_{P-C}$=6.6 Hz), 66.0 (d, $^2J_{P-C}$=5.8 Hz), 124.1, 124.2, 124.6, 125.0, 126.5, 127.8, 129.7, 130.1 (d, J=15.6 Hz), 131.9 (d, J=3.2 Hz), 134.2 (d, J=19.8 Hz), 137.9 (d, $^1J_{P-C}$=313.2 Hz), 143.0 (d, J=14.8 Hz) ppm.

(21) Synthesis of 3''',4''''-bis(dibutoxyphosphoryl)-[2,2';5',2'';5'',2''';5''',2'''';5'''',2''''';5''''',2'''''';5'''''',2''''''']-octithiophene

[Chemical Formula 139]

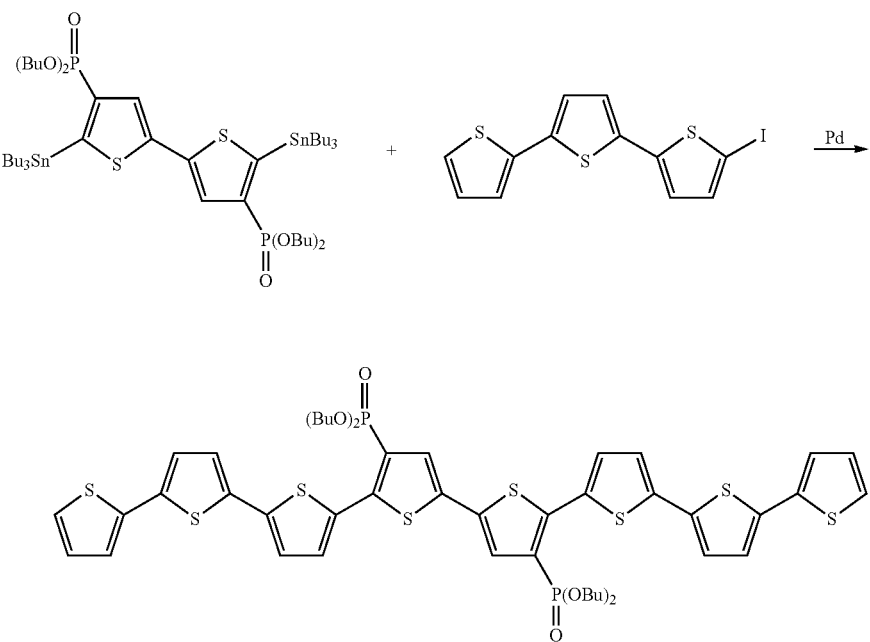

At room temperature, 0.1235 g (0.33 mmols) of 2-iodoterthiophene and 0.0069 g (0.006 mmols) of commercially available tetrakistriphenylphosphine palladium were dissolved in 2 ml of toluene, to which 0.1693 g (0.15 mmols) of 4,4'-bis(dibutoxyphosphoryl)-5,5'-bis(tributylstannyl)-[2,2']-bithiophene was added at room temperature. Thereafter, the reaction mixture was heated and stirred under reflux for 2 hours. After the reaction, the reaction mixture was cooled down to room temperature, to which a potassium fluoride aqueous solution was added, followed by stirring for 1 hour. Subsequently, the solid was removed by celite filtration and the filtrate was extracted with ethyl acetate. The organic phase was washed with a saturate saline solution and dried over anhydrous sodium sulfate. The solvent was removed by distilling off under reduced pressure, and the resulting crude product was purified with a PTLC plate (developed with ethyl acetate:hexane=1:10) to obtain the specified substance in the form of a red solid at a yield of 0.1143 g (yield: 73%).

m/z (FAB+): 1042 (calculated: 1042.10).

$^1$H-NMR (CDCl$_3$): 0.89 (t, 12H, J=7.40 Hz), 1.35 (sex, 8H, J=7.30 Hz), 1.62 (sex, 8H, J=6.67 Hz), 4.02-4.12 (m, 8H), 7.00 (dd, 2H, J=4.95, 3.74 Hz), 7.08 (d, J=3.75 Hz), 7.11 (d, 2H, J=3.77 Hz), 7.13 (d, 2H, J=3.85 Hz), 7.17 (d, 2H, J=3.46 Hz), 7.21 (d, 2H, J=5.12 Hz), 7.50 (d, 2H, J=4.79 Hz), 7.54 (d, 2H, J=3.86 Hz) ppm.

$^{13}$C-NMR (CDCl$_3$): δ=13.5, 18.6, 32.2 (d, $^3J_{P-C}$=6.6 Hz), 66.0 (d, $^2J_{P-C}$=5.8 Hz), 123.7, 124.2, 124.2, 124.6, 124.7, 125.6 (d, $^1J_{P-C}$=195.3 Hz), 127.8, 129.9, 130.2 (d, $^2J_{P-C}$=15.4 Hz), 132.1 (d, 3J$_{P-C}$=3.3 Hz), 134.2 (d, $^3J_{P-C}$=19.9 Hz), 135.0, 136.7, 136.9, 139.1, 143.0 (d, $^2J_{P-C}$=14.6 Hz) ppm.

UV λmax=428.5 nm

(22) Synthesis of 4'',4'''-bis(dibutoxyphosphoryl)-[2,2';5',2'';5'',2''';5''',2'''']-sexithiophene At room temperature, 0.0643 g (0.220 mmols) of 2-iodobithiophene and 0.0046 g (0.00398 mmols) of commercially available tetrakistriphenylphosphine palladium were dissolved in toluene, to which 0.113 g (0.100 mmol) of 5,5'-bis(tributylstannyl)-4,3'-bis(dibutoxyphosphoryl)-[2,2']-bithiophene and 0.0018 g (0.020 mmols) of commercially available copper(I) cyanide were added at room temperature. Thereafter, the reaction mixture was heated and stirred under reflux for 3 hours. After the reaction, the reaction mixture was cooled down to room temperature, to which a potassium fluoride aqueous solution was added, followed by stirring for 1 hour. Subsequently, the solid was removed by celite filtration and the filtrate was extracted with ethyl acetate. The organic phase was washed with a saturate saline solution and dried over anhydrous sodium sulfate. The solvent was removed by distilling off under reduced pressure, and the resulting crude product was purified with a PTLC plate (developed with ethyl acetate:hexane=1:10) to obtain the specified substance in the form of a red solid at a yield of 0.0345 g (yield: 39%).

m/z (FAB+): 878 (calculated: 878.13).

$^1$H-NMR (CDCl$_3$): 0.86-1.67 (12H, m), 1.32-1.40 (8H, m), 1.59-1.67 (8H, m), 4.02-4.14 (8H, m), 7.02-7.03 (2H, m), 7.09-7.10 (2H, m), 7.15-7.29 (5H, m), 7.50-7.51 (1H, m), 7.58-7.59 (1H, m), 7.74-7.76 (1H, m) ppm.

(23) Synthesis of 4''',4''''-bis(dibutoxyphosphoryl)-[2,2';5',2'';5'',2''';5''',2'''';5'''',2''''';5''''',2'''''';5'''''',2''''''']-octithiophene

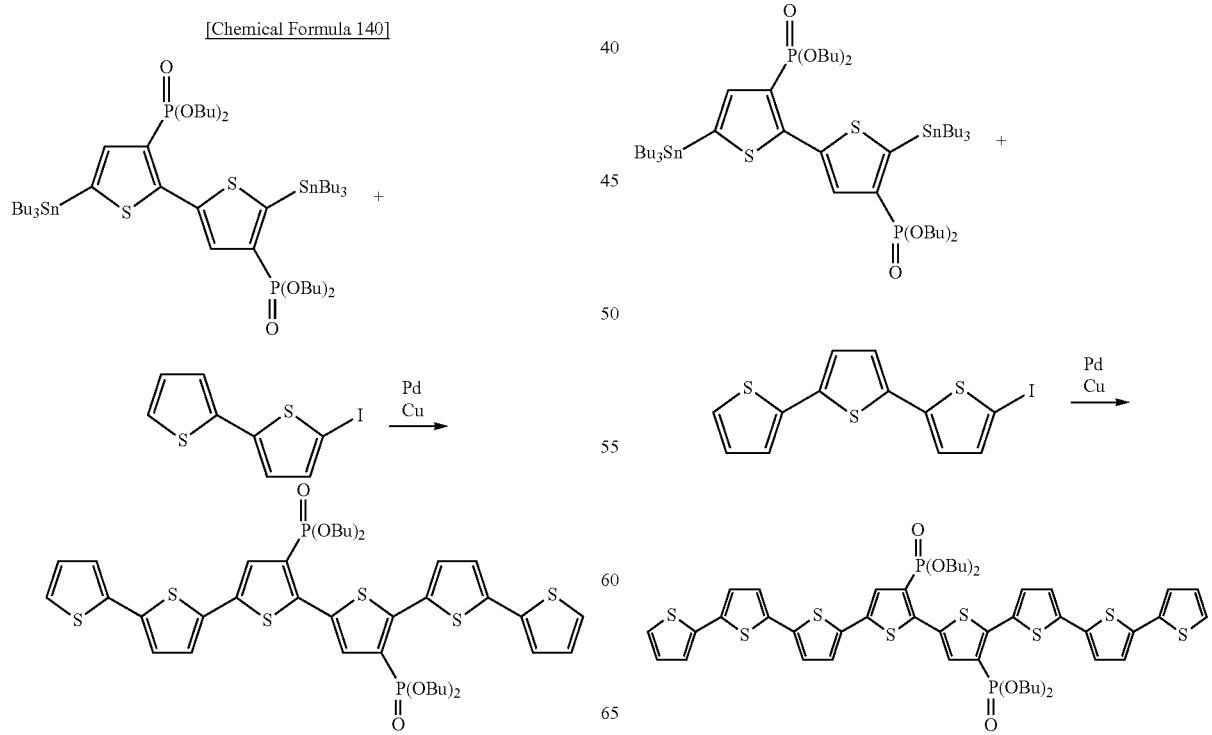

[Chemical Formula 140]

[Chemical Formula 141]

At room temperature, 0.1235 g (0.33 mmols) of 2-iodoterthiophene and 0.0069 g (0.006 mmols) of commercially available tetrakistriphenylphosphine palladium were dissolved in toluene, to which 0.1693 g (0.15 mmols) of 5,5'-bis(tributylstannyl)-4,3'-bis(dibutoxyphosphoryl)-[2,2']-bithiophene and 0.0027 g (0.03 mmols) of commercially available copper(I) cyanide were added at room temperature. Thereafter, the reaction mixture was heated and stirred under reflux for 3 hours. After the reaction, the reaction mixture was cooled down to room temperature, to which a potassium fluoride aqueous solution was added, followed by stirring for 1 hour. Subsequently, the solid was removed by celite filtration and the filtrate was extracted with ethyl acetate. The organic phase was washed with a saturate saline solution and dried over anhydrous sodium sulfate. The solvent was removed by distilling off under reduced pressure, and the resulting crude product was purified with a PTLC plate (developed with ethyl acetate:chloroform=1:10) to obtain the specified substance in the form of a red solid at a yield of 0.0642 g (yield: 41%).

m/z (FAB+): 1042 (calculated: 1042.10).

$^1$H-NMR (CDCl$_3$): 0.90 (sep, 12H), 1.29-1.38 (m, 8H), 1.63 (q, 8H, J=7.77 Hz), 4.03-4.12 (m, 8H), 7.01 (d, 1H, J=5.04 Hz), 7.01 (dd, 1H, J=7.32, 5.08 Hz), 7.07-7.12 (m, 6H), 7.15 (d, 1H, J=3.85 Hz), 7.18 (t, 2H, J=3.65 Hz), 7.22 (t, 2H, J=3.85 Hz), 7.49 (d, 1H, J=4.88 Hz), 7.58 (d, 1H, J=3.90 Hz), 7.75 (d, 1H, J=4.84 Hz) ppm.

UV λmax=427.5 nm

(24) Synthesis of 3",4'''-bis(dibutoxyphosphoryl)-5,5''''-diiodo-[2,2';5',2'';5'',2''';5''',2'''';5'''',2''''']-sexithiophene

[Chemical Formula 142]

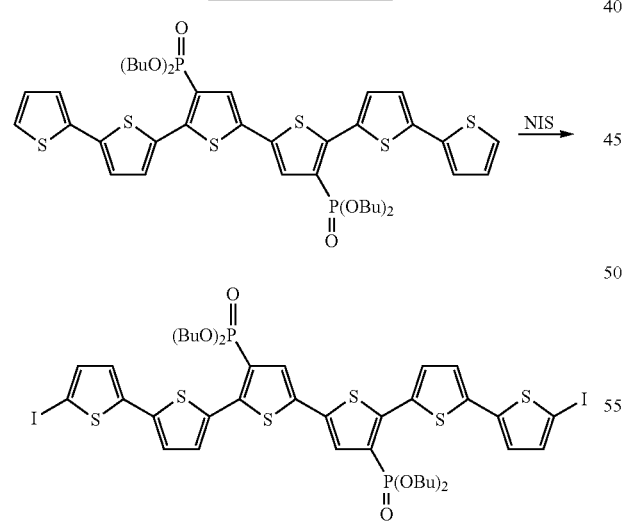

In 5 mL of a mixed solvent of chloroform and acetic acid at 1:1, 0.2208 g (0.25 mmols) of 3",4'''-bis(dibutoxyphosphoryl)-[2,2';5',2'';5'',2''';5''',2'''';5'''',2''''']-sexithiophene was dissolved, to which 0.1413 g (0.63 mmols) of commercially available N-iodosuccinimide was added at room temperature. Thereafter, the reaction mixture was heated to 50° C. and stirred for 20 hours. After the reaction, a disodium hydrogen phosphate/sodium dihydrogen phosphate buffer solution, adjusted to pH=7, was added, followed by extraction with ethyl acetate. The organic phase was washed with a 0.2 N sodium hydroxide aqueous solution and dried over anhydrous sodium sulfate. The solvent was removed by distilling off under reduced pressure, and the resulting crude product was purified with a PTLC plate (developed with ethyl acetate:chloroform=1:10) to obtain the specified substance in the form of an orange solid. The thus obtained substance was used as it is for reaction in Example 12(26).

(25) Synthesis of 3',4''-bis(dibutoxyphosphoryl)-5''-(tributylstannyl)-[2,2';5',2'']-terthiophene

[Chemical Formula 143]

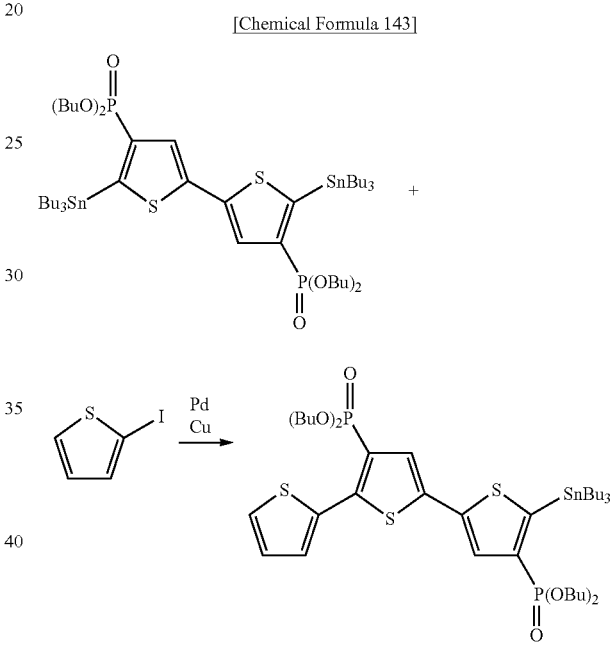

At room temperature, 0.1285 g (0.44 mmols) of 2-iodothiophene and 0.0092 g (0.008 mmols) of commercially available tetrakistriphenylphosphine palladium were dissolved in toluene, to which 0.1961 g (0.200 mmols) of 4,4'-bis(dibutoxyphosphoryl)-5,5'-bis(tributylstannyl)-[2,2']-bithiophene was added at room temperature. Thereafter, the reaction mixture was heated and stirred under reflux for 2 hours. After the reaction, the reaction mixture was cooled down to room temperature, to which a potassium fluoride aqueous solution was added, followed by stirring for 1 hour. Thereafter, the solid was removed by celite filtration and the filtrate was extracted with ethyl acetate. The organic phase was washed with a saturated saline solution and dried over anhydrous sodium sulfate. The solvent was removed by distilling off under reduced pressure, and the resulting crude product was purified with a silica gel column to obtain the specified substance in the form of a red solid at a yield of 0.0634 g (yield: 53%). The thus obtained substance was used as it is for reaction in Example 12(26).

(26) Synthesis of 3',4",3'''',4'''''',3'''''''',4''''''''''-hexakis(dibutoxyphosphoryl)-[2,2';5',2'';5'',2''';5''',2'''';5'''',2''''';5''''',2'''''';5'''''',2''''''';5''''''',2'''''''';5'''''''',2''''''''';5''''''''',2'''''''''']-dodecithiophene

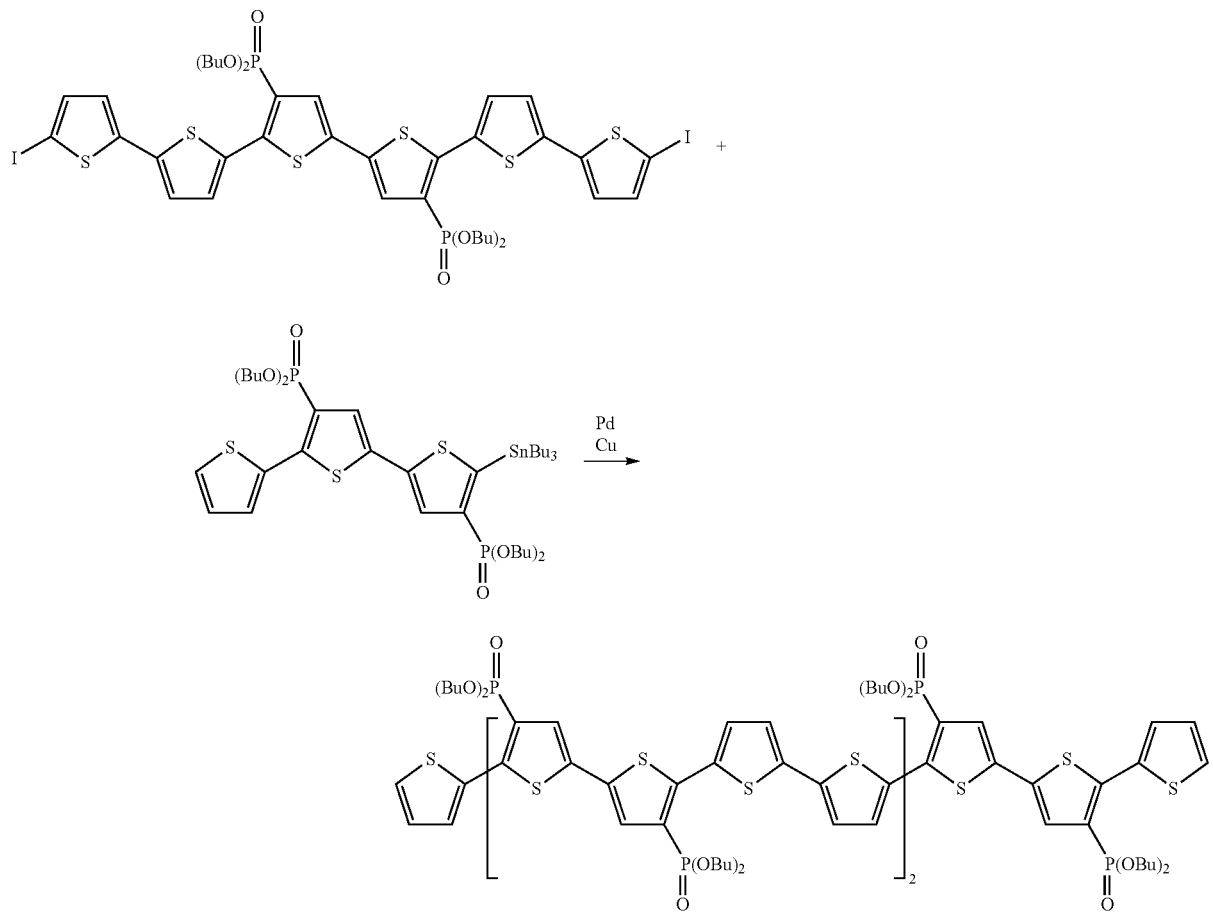

[Chemical Formula 144]

At room temperature, 0.0925 g (0.082 mmols) of 3",4"'-bis(dibutoxyphosphoryl)-5,5''''-diiodo-[2,2';5',2''; 5'',2''';5''', 2'''';5'''',2''''']-sexithiophene and 0.0076 g (0.0065 mmols) of commercially available tetrakistriphenylphosphine palladium were dissolved in 3 mL of toluene, to which 0.1508 g (0.16 mmols) of 3',4"-bis(dibutoxyphosphoryl)-5"-(tributylstannyl)-[2,2';5',2"]-terthiophene and 0.0029 g (0.032 mmols) of commercially available copper(I) chloride were added at room temperature. Thereafter, the reaction mixture was heated and stirred under reflux for 2 hours. After the reaction, the reaction mixture was cooled down to room temperature, to which a potassium fluoride aqueous solution was added, followed by stirring for 1 hour. Subsequently, the solid was removed by celite filtration and the filtrate was extracted with ethyl acetate. The organic phase was washed with a saturated saline solution and dried over anhydrous sodium sulfate. The solvent was removed by distilling off under reduced pressure, and the resulting crude product was purified with a PTLC plate (developed with ethyl acetate:hexane=2:1 and ethyl acetate:hexane=3:1) to obtain the specified substance in the form of a red solid at a yield of 0.0720 g (yield: 41%).

m/z (FAB+): 2140.6 (calculated: 2138.42).

$^1$H-NMR (CDCl$_3$): 0.89 (sex, 18H), 1.34 (sep, 12H, J=15.5, 7.52 Hz), 1.60 (o, 12H, J=6.64 Hz), 3.97-4.12 (m, 12H), 7.10 (dd, 2H, J=4.96, 3.78 Hz), 7.21 (d, 4H, J=3.85 Hz), 7.41 (d, 2H, J=5.13 Hz), 7.50 (quin, 6H), 7.58 (quin, 6H) ppm.

UV λmax=437.0 nm

Example 13

Synthesis of poly{3",4"-bis(diethylphosphono)-[2,2'; 5',2";5",2''';5''',2'''']-pentathiophene}

Using a three-electrode beaker cell equipped with a platinum mesh counter electrode, electrolytic oxidation was carried out according to a potential sweep method to prepare the above-specified substance. More particularly, a solution of 6.2 mg (0.073 mmols) of 3",4"-bis(diethylphosphono)-[2,2'; 5',2";5",2''';5''',2'''']-pentathiophene and 1.727 g (5.05 mmols) of commercially available tetrabutylammonium perchlorate dissolved in 50 mL of acetonitrile was used. Using a platinum plate (with one surface of 1.0 cm²) as a test electrode substrate and Ag/Ag⁺ as a reference electrode, electrolytic polymerization was carried out by use of an electrochemical measuring system (BSS Co., Ltd.) for potential sweep of 520 cycles within a potential range of 600 to 1500 mV at a sweep rate of 50 mVsec⁻¹. As a result, a dark blue solid polymer which was the specified compound was deposited on the electrode.

IR (KBr) of Specified Substance:
576, 625, 637, 739, 795, 978, 1022, 1045, 1088, 1109, 1122, 1145, 1224, 1274, 1350, 1363, 1392, 1441, 1635, 2963, 3066 cm⁻¹.

IR (KBr) of Starting Material:
554, 577, 693, 796, 837, 867, 978, 1026, 1048, 1098, 1163, 1260, 1391, 1475, 1635, 2902, 2981, 3069 cm⁻¹.

Example 14

Measurement by Cyclic Voltanmetry

Using a three-electrode beaker cell equipped with a platinum counter electrode, cyclic voltanmetry measurement was carried out by a potential sweep method. Solutions of the respective thiophene derivatives indicated in the following Table 23 (concentration: 0.0003 to 0.002 N) and commercially available tetrabutylammonium perchlorate (concentration; 0.1N) dissolved in acetonitrile were used. Using a glassy carbon electrode as a test electrode substrate and Ag/Ag⁺ as a reference electrode, the potential sweep measurement was carried out by use of an electrochemical measuring system (BSS Co., Ltd.) within a potential range of $-1000$ to 2500 mV at a scanning rate of 50 mVsec⁻¹.

TABLE 23

| Compound | First oxidation potential (mV) | Second oxidation potential (mV) | Third oxidation potential (mV) |
|---|---|---|---|
| (EtO)₂P(O)—thiophene—P(O)(OEt)₂ | 1540 | 2250 | 2450 |
| (i-PrO)₂P(O)—quinquethiophene—P(O)(Oi-Pr)₂ | 1000 | 2005 | — |
| (BuO)₂P(O)—quinquethiophene—P(O)(OBu)₂ | 1080 | 2100 | — |
| (EtO)(BuO)P(O)—quinquethiophene—P(O)(OBu)(OEt) | 1132 | 2074 | — |
| (C₆H₁₃O)₂P(O)—quinquethiophene—P(O)(OC₆H₁₃)₂ | 1088 | 2120 | — |

TABLE 23-continued
| Compound | First oxidation potential (mV) | Second oxidation potential (mV) | Third oxidation potential (mV) |
|---|---|---|---|
| 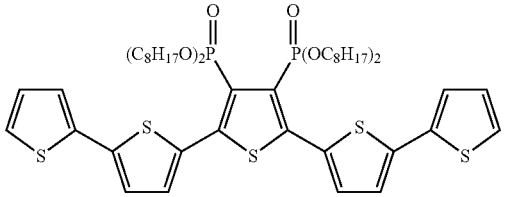 | 1084 | 1836 | 2054 |
| 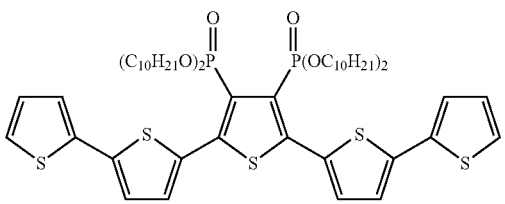 | 1024 | 2112 | — |
| 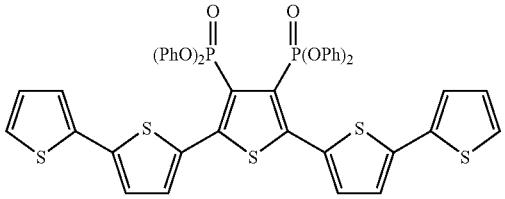 | 746 | 1184 | 2138 |
| 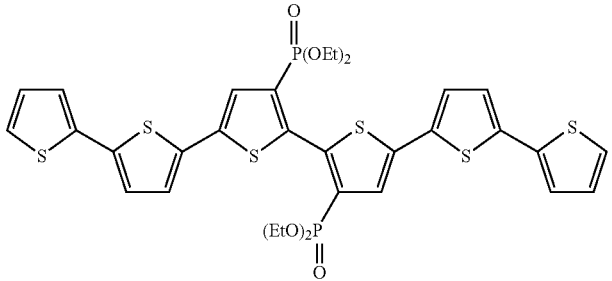 | 831 | 1131 | 1309 |
| 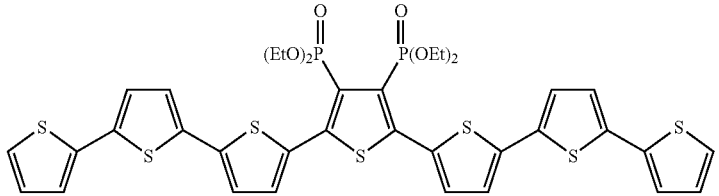 | 799 | 1222 | 1551 |
| 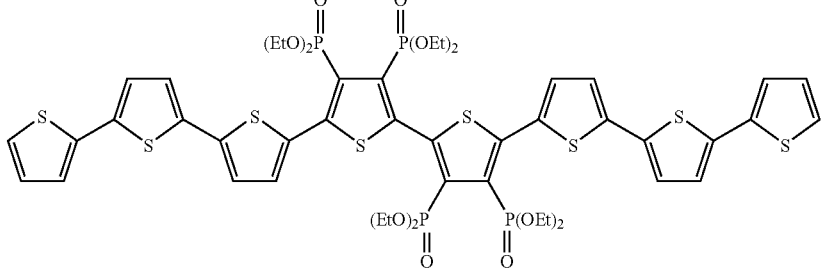 | 746 | 1184 | 2138 |

Example 15

Synthesis of 2,5-dibromo-3-diethoxyphosphorylthiophene

[Chemical Formula 145]

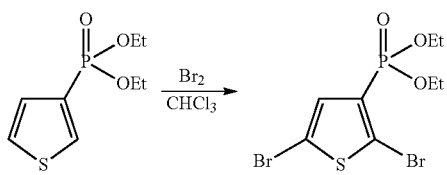

3-diethoxyphosphorylthiophene was charged into a reaction container, to which chloroform was added for dissolution under nitrogen atmosphere, followed by cooling to −5° C. Bromine (6 equivalents) diluted with chloroform was slowly dropped in the solution, followed by raising the temperature to room temperature after completion of the dropping and stirring for 23 hours. After completion of the reaction, a 1N sodium hydroxide aqueous solution was added to the reaction solution for quenching, followed by extraction with chloroform. The organic phase was washed with a 10% sodium thiosulfate aqueous solution and then with 10% saline solution, and was dried over anhydrous sodium sulfate. The solvent was distilled off and the resulting crude product was purified with a silica gel column (hexane:ethyl acetate=1:1) to obtain a white solid.

m/z (DI): 379 (calculated: 375.85)

$^1$H-NMR (CDCl$_3$): 1.36 (6H, t, J=6.6 Hz), 4.18 (4H, m, J=6.6 Hz), 7.21 (1H, d, J=4.3 Hz) ppm.

Example 16

Synthesis of 3-diethoxyphosphoryl-[2,2']-bithiophene

[Chemical Formula 146]

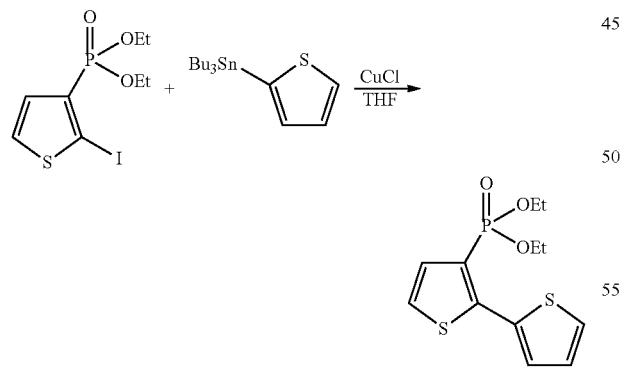

Copper(I) chloride (2.5 equivalents) was charged into a reaction container, to which 2-thienyltributyl tin (2.5 equivalents) and 2-iodo-3-diethoxyphosphorylthiophene were added under nitrogen atmosphere while being dissolved in tetrahydrofuran, followed by heating under reflux for 20 hours. After completion of the reaction, the reaction solution was filtered through celite and the resulting residue was washed with ethyl acetate. The filtrate was washed three times with a 1N hydrochloric acid aqueous solution and a 10% saline solution and dried over anhydrous sodium sulfate. The solvent was distilled off, and the resulting crude product was purified with a silica gel column (hexane:ethyl acetate=1:3) to obtain a colorless liquid.

$^1$H-NMR (CDCl$_3$): 1.22 (6H, t, J=7.1 Hz), 3.96-4.15 (4H, m), 7.19 (1H, m), 7.30 (1H, m), 7.36-7.41 (2H, m), 7.51 (1H, d) ppm.

Example 17

Synthesis of 5,5'-dibromo-3-diethoxyphosphoryl-[2,2']-bithiophene

[Chemical Formula 147]

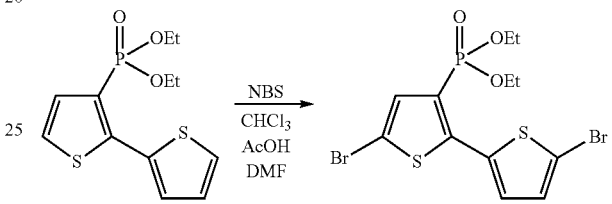

3-diethoxyphosphoryl-[2,2']-bithiophene was charged into a reaction container, which was dissolved by addition of chloroform, acetic acid and N,N-dimethylformamide, followed by addition of N-bromosuccinimide (2.2 equivalents) and stirring at room temperature for 24 hours. After the reaction, a disodium hydrogen phosphate/sodium dihydrogen phosphate buffer solution, adjusted to pH=7, was added so as to complete the reaction, followed by extraction with chloroform. The organic phase was washed with a 10% sodium thiosulfate aqueous solution and a 10% saline solution and dried over anhydrous sodium sulfate. The solvent was distilled off, and the resulting crude product was purified with a silica gel column (hexane:ethyl acetate=1:2) to obtain a green liquid.

$^1$H-NMR (CDCl$_3$): 1.26 (6H, t, J=7.1 Hz), 3.99-4.12 (4H, m), 7.04 (1H, d, J=4.6 Hz), 7.20 (1H, d, J=4.6 Hz), 7.33 (1H, d, J=4.7 Hz) ppm.

Example 18

Synthesis of 5,5''-dibromo-3',4'-bis(diethoxyphosphoryl)-[2,2';5',2'']-terthiophene

[Chemical Formula 148]

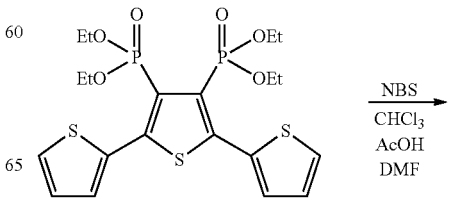

143
-continued

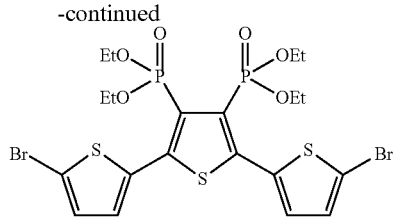

3',4'-bis(diethoxyphosphoryl-[2,2';5',2"]-terthiophene was charged into a reaction container, which was dissolved by addition of chloroform, acetic acid and N,N-dimethylformamide, followed by addition of N-bromosuccinimide (2.2 equivalents) and stirring at room temperature for 24 hours. After the reaction, a disodium hydrogen phosphate/sodium dihydrogen phosphate buffer solution, adjusted to pH=7, was added so as to complete the reaction, followed by extraction with chloroform. The organic phase was washed with a 10% sodium thiosulfate aqueous solution and a 10% saline solution and dried over anhydrous sodium sulfate. The solvent was distilled off, and the resulting crude product was purified with a silica gel column (ethyl acetate) to obtain a product.

m/z (DI): 678.53 (calculated: 675.86)

$^1$H-NMR (CDCl$_3$): 1.18 (12H, t, J=7.2 Hz), 3.93-4.04 (4H, m), 4.10-4.20 (4H, m), 7.05 (2H, d, J=3.8 Hz), 7.10 (2H, d, J=3.8 Hz) ppm.

Example 19

Synthesis of poly(3-diethoxyphosphorylthiophen-2,5-diyl)

[Chemical Formula 149]

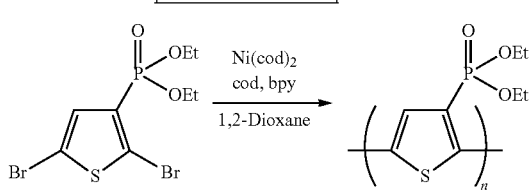

2,5-dibromo-3-diethoxyphosphorylthiophene, 2,2'-bipyridyl (1.2 equivalents), 1,5-cyclooctadiene (1.0 equivalent) and bis(1,5-cyclooctadiene)nickel(0) (1.2 equivalents) were charged into a reaction container, to which 1,4-dioxane was added under nitrogen atmosphere, followed by heating at 60° C. for 20 hours. After completion of the reaction, the reaction solution was filtered through celite and the resulting residue was washed with chloroform. The filtrate was washed twice with a 10% hydrochloric acid aqueous solution and five times with a 10% saline solution, and anhydrous sodium sulfate was added to the organic phase for drying, followed by distilling off the solvent therefrom. The resulting matter was dried by reducing the pressure by means of a vacuum pump to obtain an orange liquid.

Mw (GPC): 9700

$^1$H-NMR (CDCl$_3$): 1.20-1.29 (6H, m), 4.02-4.18 (4H, m), 6.91 (1H, s).

144
Example 20

Synthesis of poly(3-diethoxyphosphoryl-[2,2']-bithiophen-5,5'-diyl)

[Chemical Formula 150]

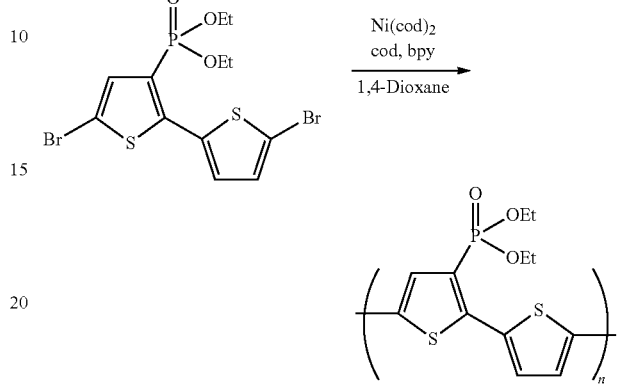

5,5'-dibromo-3-diethoxyphosphoryl-[2,2']-bithiophene, 2,2'-bipyridyl (1.2 equivalents), 1,5-cyclooctadiene (1.0 equivalent) and bis(1,5-cyclooctadiene)nickel(0) (1.2 equivalents) were charged into a reaction container, to which 1,4-dioxane was added under nitrogen atmosphere, followed by heating at 60° C. for 20 hours. After completion of the reaction, the reaction solution was filtered through celite and the resulting residue was washed with chloroform. The filtrate was washed twice with a 10% hydrochloric acid aqueous solution and five times with 10% saline solution, and anhydrous sodium sulfate was added to the organic phase for drying, followed by distilling off the solvent therefrom. The resulting matter was dried by reducing the pressure by means of a vacuum pump to obtain a red liquid.

Mw (GPC): 9800

$^1$H-NMR (CDCl$_3$): 1.20-1.34 (6H, m), 4.05-4.18 (4H, m), 7.02-7.56 (3H, m) ppm.

Example 21

Synthesis of poly{3,4-bis(diethoxyphosphoryl)-[2,2'; 5',2"]-terthiophen-5,5"-diyl}

[Chemical Formula 151]

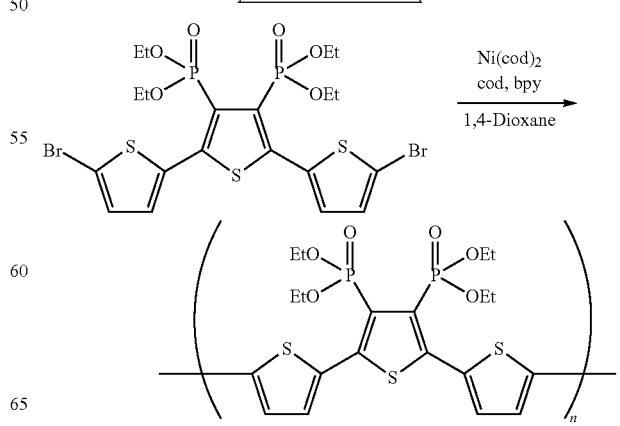

5,5"-dibromo-3',4'-bis(diethoxyphosphoryl)-[2,2';5',2"]-terthiophene, 2,2'-bipyridyl (1.2 equivalents), 1,5-cyclooctadiene (1.0 equivalent) and bis(1,5-cyclooctadiene)nickel(0) (1.2 equivalents) were charged into a reaction container, to which 1,4-dioxane was added under nitrogen atmosphere, followed by heating at 60° C. for 20 hours. After completion of the reaction, the reaction solution was filtered through celite and the resulting residue was washed with chloroform. The filtrate was washed twice with a 10% hydrochloric acid aqueous solution and five times with 10% saline solution, and anhydrous sodium sulfate was added to the organic phase for drying, followed by distilling off the solvent therefrom. The resulting matter was dried by reducing the pressure by means of a vacuum pump to obtain an orange solid.

Mw (GPC): 1500

$^1$H-NMR (CDCl$_3$): 1.15-1.32 (12H, t, J=6.5 Hz), 3.98-4.25 (8H, m), 7.20 (2H, m), 7.33 (2H, m) ppm.

Example 22

Synthesis of poly(3-phosphonothiophen-2,5-diyl)

[Chemical Formula 152]

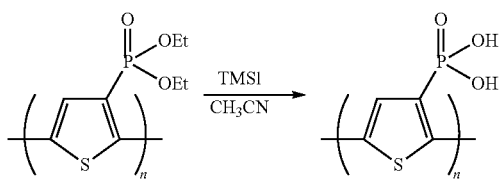

Poly(3-diethoxyphosphorylthiophen-2,5-diyl) was charged into a reaction container, to which acetonitrile was added so as to dissolve it under nitrogen atmosphere, followed by slowly dropping iodotrimethylsilane (3 equivalents) and stirring at room temperature for 20 hours after completion of the dropping. After the reaction, methanol was added and stirred for 1 hour, followed by vanishing excess iodotrimethylsilane and distilling off the solvent. The resulting crude product was dissolved in water, washed ten times with chloroform, and passed through an ion exchange resin (IR-120B, IRA-410), followed by distilling off the solvent and drying by means of a vacuum pump to obtain a red solid.

$^1$H-NMR (D$_2$O): 7.14 (1H, s)

$^{13}$C-NMR (D$_2$O): 112.7 (d, J=21.9 Hz), 117.9 (s, J=7.6 Hz), 135.1 (d, J=13.4 Hz), 138.8 (s, 187.5 Hz) ppm.

$^{31}$P-NMR (D$_2$O): 4.06 (s) ppm.

The invention claimed is:
1. A phosphorylthiophene oligomer compound, represented by the formula [3]

[Chemical Formula 3]

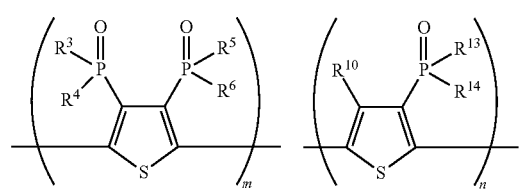

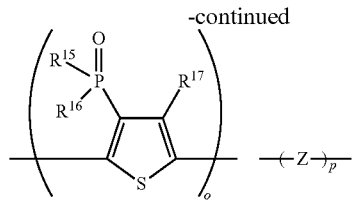

(wherein $R^3$-$R^6$, and $R^{13}$-$R^{16}$ each independently represent —OR$^7$, —SR$^8$ or —NR$^9_2$; R$^7$ represents an alkyl group having 1-10 carbon atoms or a phenyl group which may be substituted with W, and R$^8$-R$^9$ each independently represent a hydrogen atom, an alkyl group having 1-10 carbon atoms or a phenyl group which may be substituted with W;

$R^{10}$ and $R^{17}$ each independently represent a hydrogen atom, a halogen atom, a cyano group, a nitro group, a hydroxyl group, a mercapto group, an amino group, a formyl group, a carboxyl group, an alkyl group having 1-10 carbon atoms, a haloalkyl group having 1-10 carbon atoms, an alkenyl group having 1-10 carbon atoms, an alkynyl group having 1-10 carbon atoms, an alkoxy group having 1-10 carbon atoms, an akylthio group having 1-10 carbon atoms, a monoalkylamino group having 1-10 carbon atoms, a dialkylamino group having 1-10 carbon atoms, or a phenyl group which may be substituted with W;

W represents a halogen atom, a cyano group, a nitro group, a hydroxyl group, a mercapto group, an amino group, a formyl group, a carboxyl group, an alkyl group having 1-10 carbon atoms, a haloalkyl group having 1-10 carbon atoms, an alkenyl group having 1-10 carbon atoms, an alkynyl group having 1-10 carbon atoms, an alkoxy group having 1-10 carbon atoms, an alkylthio group having 1-10 carbon atoms, a monoalkylamino group having 1-10 carbon atoms, a dialkylamino group having 1-10 carbon atoms, a diphenylamino group which may be substituted with W', a dinaphthylamino group which may be substituted with W', a dianthranilamino group which may be substituted with W', an N-phenyl-N-napthylamino group which may be substituted with W', an N-phenyl-N-anthranilamino group which may be substituted with W', an N-naphthyl-N-anthranilamino group which may be substituted with W', a trialkylsilyl group having 1-10 carbon atoms, an alkylcarbonyl group having 1-10 carbon atoms, an alkoxycarbonyl group having 1-10 carbon atoms, or a phenyl group which may be substituted with W';

W' represents an alkyl group having 1-10 carbon atoms, a haloalkyl group having 1-10 carbon atoms or an alkoxy group having 1-10 carbon atoms;

m, n and o each independently represent 0 or an integer of 1 or over, p represents an integer of 1 or over provided that m+n+o≧1 and 2≦m+n+o+p≦50 are satisfied; and Z represents at least one divalent organic group selected from those of the following formulas [4] to [12]

[Chemical Formula 4]

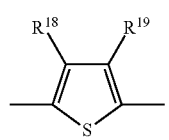

-continued

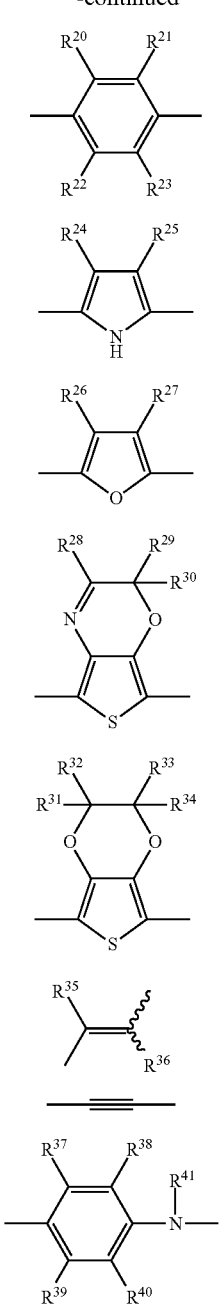

[5]
[6]
[7]
[8]
[9]
[10]
[11]
[12]

wherein $R^{18}$-$R^{40}$ each independently represent a hydrogen atom, an alkyl group having 1-10 carbon atoms, a haloalkyl group having 1-10 carbon atoms, an alkoxy group having 1-10 carbon atoms, an alkylthio group having 1-10 carbon atoms, a dialkylamino group having 1-10 carbon atoms, or a phenyl group which may be substituted with W; W has the same meaning as defined above; $R^{41}$ represents a hydrogen atom, an alkyl group having 1-10 carbon atoms, a haloalkyl group having 1-10 carbon atoms, an alkoxy group having 1-10 carbon atoms, or a phenyl group which may be substituted with W'; and W' has the same meaning as defined above;

opposite terminal ends of the phosphorylthiophene oligomer compound being each independently a hydrogen atom, a halogen atom, a monoalkylamino group having 1-10 carbon atoms, a dialkylamino group having 1-10 carbon atoms, a phenyl group which may be substituted with W, a naphthyl group which may be substituted with W, an anthranil group which may be substituted with W, a trialkylstannyl group having 1-10 carbon atoms or a trialkylsilyl group having 1-10 carbon atoms).

2. The phosphorylthiophene oligomer compound according to claim 1 wherein Z represents said formula [4].

3. A phosphorylthiophene polymer compound, represented by the formula [29]

[Chemical Formula 3]

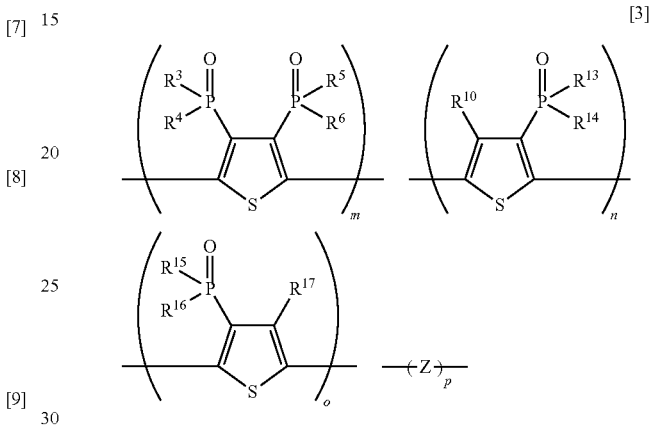

[3]

(wherein $R^3$-$R^6$ and $R^{13}$-$R^{16}$ each independently represent —$OR^7$, —$SR^8$ or —$NR^9{}_2$; and $R^7$ represents an alkyl group having 1-10 carbon atoms or a phenyl group which may be substituted with W, and $R^8$-$R^9$ each independently represent a hydrogen atom, an alkyl group having 1-10 carbon atoms or a phenyl group which may be substituted with W;

$R^{10}$ and $R^{17}$ each independently represent a hydrogen atom, a halogen atom, a cyano group, a nitro group, a hydroxyl group, a mercapto group, an amino group, a formyl group a carboxyl group, an alkyl group having 1-10 carbon atoms, a haloalkyl group having 1-10 carbon atoms, an alkenyl group having 1-10 carbon atoms, an alkynyl group having 1-10 carbon atoms an alkoxy group having 1-10 carbon atoms, an akylthio group having 1-10 carbon atoms, a monoalkylamino group having 1-10 carbon atoms, a dialkylamino group having 1-10 carbon atoms, or a phenyl group which may be substituted with W;

W represents a halogen atom, a cyano group, a nitro group, a hydroxyl group, a mercapto group, an amino group, a formyl group, a carboxyl group, an alkyl group having 1-10 carbon atoms, a haloalkyl group having 1-10 carbon atoms, an alkenyl group having 1-10 carbon atoms, an alkynyl group having 1-10 carbon atoms, an alkoxy group having 1-10 carbon atoms, an alkylthio group having 1-10 carbon atoms, a monoalkylamino group having 1-10 carbon atoms, a dialkylamino group having 1-10 carbon atoms, a diphenylamino group which may be substituted with W', a dinaphthylamino group which may be substituted with W', a dianthranilamino group which may be substituted with W', an N-phenyl-N-napthylamino group which may be substituted with W', an N-phenyl-N-anthranilamino group which may be substituted with W', an N-naphthyl-N-anthranilamino group which may be substituted with W', a trialkylsilyl group having 1-10 carbon atoms, an alkylcarbonyl group having 1-10 carbon atoms, an alkoxycarbonyl group having 1-10 carbon atoms, or a phenyl group which may be substituted with W';

W' represents an alkyl group having 1-10 carbon atoms, a haloalkyl group having 1-10 carbon atoms or an alkoxy group having 1-10 carbon atoms;

m", n" and o" each independently represent 0 or an integer of 1 or over, p' represents 0 or an integer of 1 or over provided that m"+n"+o"≧1 and 50<m"+n"+o"+p'<5000 are satisfied; and Z represents at least one divalent organic group selected from those of the following formulas [4] to [12]

[Chemical Formula 6]

[4]
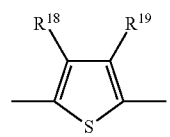

[5]
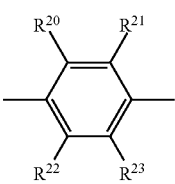

[6]
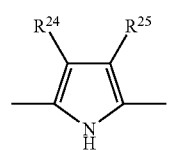

[7]
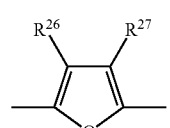

[8]
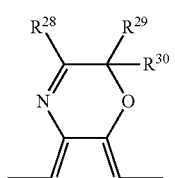

[9]
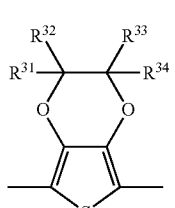

[10]
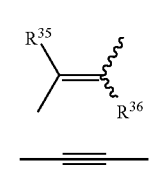

[11]
———≡———

[12]
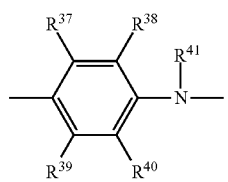

wherein $R^{18}$-$R^{40}$ each independently represent a hydrogen atom, an alkyl group having 1-10 carbon atoms, a haloalkyl group having 1-10 carbon atoms, an alkoxy group having 1-10 carbon atoms, an alkylthio group having 1-10 carbon atoms, a dialkylamino group having 1-10 carbon atoms, or a phenyl group which may be substituted with W; W has the same meaning as defined above; $R^{41}$ represents a hydrogen atom, an alkyl group having 1-10 carbon atoms, a haloalkyl group having 1-10 carbon atoms, an alkoxy group having 1-10 carbon atoms, or a phenyl group which may be substituted with W'; and W' has the same meaning as defined above;

opposite terminal ends of the phosphorylthiophene oligomer compound being each independently a hydrogen atom, a halogen atom, a monoalkylamino group having 1-10 carbon atoms, a dialkylamino group having 1-10 carbon atoms, a phenyl group which may be substituted with W, a naphthyl group which may be substituted with W, an anthranil group which may be substituted with W, a trialkylstannyl group having 1-10 carbon atoms or a trialkylsilyl group having 1-10 carbon atoms).

4. The sulfonylthiophene polymer compound according to claim 3, wherein Z is a divalent organic group represented by said formula [4].

5. A phosphorylthiophene oligomer compound, represented by the formula [13]

[Chemical Formula 7]

[13]
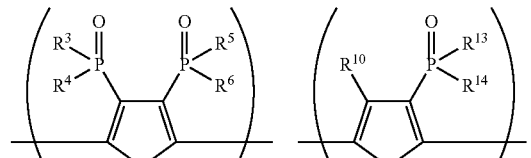

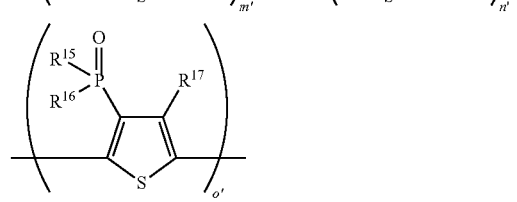

(wherein $R^3$-$R^6$ and $R^{13}$-$R^{16}$ each independently represent —$OR^7$, —$SR^8$ or —$NR^9{}_2$; and $R^7$ represents an alkyl group having 1-10 carbon atoms or a phenyl group which may be substituted with W, and $R^8$-$R^9$ each independently represent a hydrogen atom, an alkyl group having 1-10 carbon atoms or a phenyl group which may be substituted with W;

$R^{10}$ and $R^{17}$ each independently represent a hydrogen atom, a halogen atom, a cyano group, a nitro group, a hydroxyl group, a mercapto group, an amino group, a formyl group, a carboxyl group, an alkyl group having 1-10 carbon atoms, a haloalkyl group having 1-10 carbon atoms, an alkenyl group having 1-10 carbon atoms, an alkynyl group having 1-1carbon atoms, an alkoxy group having 1-10 carbon atoms, an alkylthio group having 1-10 carbon atoms, a monoalkylamino group having 1-10 carbon atoms, a dialkylamino group having 1-10 carbon atoms, or a phenyl group which may be substituted with W;

W represents a halogen atom, a cyano group, a nitro group, a hydroxyl group, a mercapto group, an amino group, a formyl group, a carboxyl group, an alkyl group having 1-10 carbon atoms, a haloalkyl group having 1-10 carbon atoms, an alkenyl group having 1-10 carbon atoms, an alkynyl group having 1-10 carbon atoms, an alkoxy group having 1-10 carbon atoms, an alkylthio group having 1-10 carbon atoms, a monoalkylamino group having 1-10 carbon atoms, a dialkylamino group having 1-10 carbon atoms, a diphenylamino group which may be substituted with W', a dinaphthylamino group which may be substituted with W', a dianthranilamino group which may be substituted with W', an N-phenyl-N-napthylamino group which may be substituted with W', an N-phenyl-N-anthranilamino group which may be substituted with W', an N-naphthyl-N-anthranilamino group which may be substituted with W', a trialkylsilyl group having 1-10 carbon atoms, an alkylcarbonyl group having 1-10 carbon atoms, an alkoxycarbonyl group having 1-10 carbon atoms, or a phenyl group which may be substituted with W;

W' represents an alkyl group having 1-10 carbon atoms, a haloalkyl group having 1-10 carbon atoms or an alkoxy group having 1-10 carbon atoms; and m',n' and o' each independently represent 0 or an integer of 1 or over provided that $2 \leqq m'+n'+o' \leqq 50$ is satisfied, opposite terminal ends of the phosphorylthiophene oligomer compound being each independently a hydrogen atom, a halogen atom, a monoalkylamino group having 1-10 carbon atoms, a dialkylamino group having 1-10 carbon atoms, a phenyl group which may be substituted with W, a naphthyl group which may be substituted with W, an anthranil group which may be substituted with W, a trialkylstannyl group having 1-10 carbon atoms or a trialkylsilyl group having 1-10 carbon atoms).

6. A phosphorylthiophene polymer compound, represented by the formula [30]

[Chemical Formula 8]

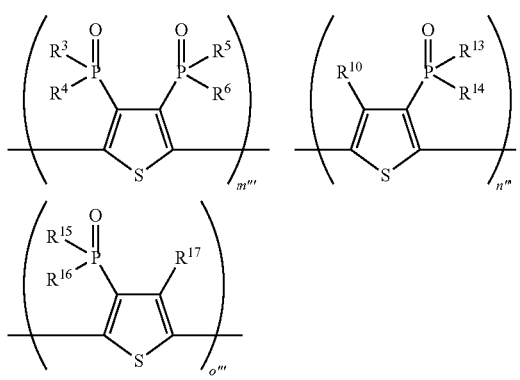

[30]

(wherein $R^3$-$R^6$ and $R^{13}$-$R^{16}$ each independently represent —$OR^7$, —$SR^8$ or —$NR^9_2$; and $R^7$ represents an alkyl group having 1-10 carbon atoms or a phenyl group which may be substituted with W, and $R^8$-$R^9$ each independently represent a hydrogen atom, an alkyl group having 1-10 carbon atoms or a phenyl group which may be substituted with W;

$R^{10}$ and $R^{17}$ each independently represent a hydrogen atom, a halogen atom, a cyano group, a nitro group, a hydroxyl group, a mercapto group, an amino group, a formyl group, a carboxyl group, an alkyl group having 1-10 carbon atoms, a haloalkyl group having 1-10 carbon atoms, an alkenyl group having 1-10 carbon atoms, an alkynyl group having 1-19 carbon atoms, an alkoxy group having 1-10 carbon atoms, an akylthio group having 1-10 carbon atoms, a monoalkylamino group having 1-10 carbon atoms, a dialkylamino group having 1-10 carbon atoms, or a phenyl group which may be substituted with W;

W represents a halogen atom, a cyano group, a nitro group, a hydroxyl group, a mercapto group, an amino group, a formyl group, a carboxyl group, an alkyl group having 1-10 carbon atoms, a haloalkyl group having 1-10 carbon atoms, an alkenyl group having 1-10 carbon atoms, an alkynyl group having 1-10 carbon atoms, an alkoxy group having 1-10 carbon atoms, an alkylthio group having 1-10 carbon atoms, a monoalkylamino group having 1-10 carbon atoms, a dialkylamino group having 1-10 carbon atoms, a diphenylamino group which may be substituted with W' , a dinaphthylamino group which may be substituted with W', a dianthranilamino group which may be substituted with W', an N-phenyl-N-napthylamino group which may be substituted with W', an N-phenyl-N-anthranilamino group which may be substituted with W', an N-naphthyl-N-anthranilamino group which may be substituted with W', a trialkylsilyl group having 1-10 carbon atoms, an alkylcarbonyl group having 1-10 carbon atoms, an alkoxycarbonyl group having 1-10 carbon atoms, or a phenyl group which may be substituted with W';

W' represents an alkyl group having 1-10 carbon atoms, a haloalkyl group having 1-10 carbon atoms or an alkoxy group having 1-10 carbon atoms; and m''', n''' and o''' each independently represent 0 or an integer of 1 or over provided that $50 < m'''+n'''+o''' < 5000$ is satisfied, opposite terminal ends of the phosphorylthiophene polymer compound being each independently a hydrogen atom, a halogen atom, a monoalkylamino group having 1-10 carbon atoms, a dialkylamino group having 1-10 carbon atoms, a phenyl group which may be substituted with W, a naphthyl group which may be substituted with W, an anthranil group which may be substituted with W, a trialkylstannyl group having 1-10 carbon atoms or a trialkylsilyl group having 1-10 carbon atoms).

7. A phosphorylthiophene polymer compound obtained by electrolytic oxidation polymerization or chemical oxidation polymerization of at least one selected from the phosphorylthiophene oligomer compounds defined in claims 1 and 5.

8. A process for producing a phosphorylthiophene polymner compound comprising electrolytic oxidation polymerization or chemical oxidation polymerization of at least one selected from the phosphorylthiophene oligomer compounds defined in claims 1 and 5.

9. A phosphorylthiophene polymer compound obtained by catalytic polymerization of the bisphosphorylthiophene compound defined in formula [1], the monophosphorylthiophene compound defined in formula [2], or at least one selected from the phosphorylthiophene oligomer compounds defined in claims 1 and 5,

[Chemical Formula 1]

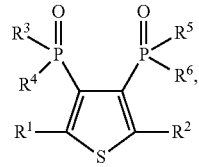

[1]

wherein $R^1$ and $R^2$ each independently represent a hydrogen atom, a halogen atom, a cyano group, a phenyl group optionally substituted with W, a naphthyl group optionally substituted with W, an anthranil group optionally substituted with W, a hydroxyl group, an amino group, a formyl group, a carboxyl group, an alkyl group having 1-10 carbon atoms, a haloalkyl group having 1-10 carbon atoms, a monoalkylamino group having 1-10 carbon atoms, a dialkylamino group having 1-10 carbon atoms, a trialkylstannyl group having 1-10 carbon atoms, or a trialkylsilyl group having 1-10 carbon atoms;

$R^3$-$R^6$ each independently represent —$OR^7$, —$SR^8$ or —$NR^9{}_2$;

$R^7$ represents an alkyl group having 1-10 carbon atoms or a phenyl group optionally substituted with W, and $R^8$-$R^9$ each independently represent a hydrogen atom, an alkyl group having 1-10 carbon atoms, or a phenyl group optionally substituted with W;

W represents a halogen atom, a cyano group, a nitro group, a hydroxyl group, a mercapto group, an amino group, a formyl group, a carboxyl group, an alkyl group having 1-10 carbon atoms, a haloalkyl group having 1-10 carbon atoms, an alkenyl group having 1-10 carbon atoms, an alkynyl group having 1-10 carbon atoms, an alkoxy group having 1-10 carbon atoms, an alkylthio group having 1-10 carbon atoms, a monoalkylamino group having 1-10 carbon atoms, a dialkylamino group having 1-10 carbon atoms, a diphenylamino group optionally substituted with W', a dinaphthylamino group optionally substituted with W', a dianthranilamino group optionally substituted with W', an N-phenyl-N-napthylamino group optionally substituted with W', an N-phenyl-N-anthranilamino group optionally substituted with W', an N-naphthyl-N-anthranilamino group optionally substituted with W', a trialkylsilyl group having 1-10 carbon atoms, an alkylcarbonyl group having 1-10 carbon atoms, an alkoxycarbonyl group having 1-10 carbon atoms, or a phenyl group optionally with W'; and W' represents an alkyl group having 1-10 carbon atoms, a haloalkyl group having 1-10 carbon atoms or an alkoxy group having 1-10 carbon atoms,

[Chemical Formula 2]

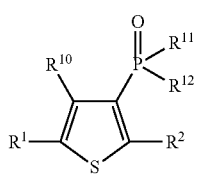

[2]

wherein $R^1$ and $R^2$ each independently represent a hydrogen atom, a halogen atom, a cyano group, a phenyl group optionally substituted with W, a naphthyl group optionally substituted with W, an anthranil group optionally substituted with W, a hydroxyl group, an amino group, a formyl group, a carboxyl group, an alkyl group having 1-10 carbon atoms, a haloalkyl group having 1-10 carbon atoms, a monoalkylamino group having 1-10 carbon atoms, a dialkylamino group having 1-10 carbon atoms, a trialkylstannyl group having 1-10 carbon atoms, or a trialkylsilyl group having 1-10 carbon atoms;

$R^{10}$ represents a hydrogen atom, a halogen atom, a cyano group, a nitro group, a hydroxyl group, a mercapto group, an amino group, a formyl group, a carboxyl group, an alkyl group having 1-10 carbon atoms, a haloalkyl group having 1-10 carbon atoms, an alkenyl group having 1-10 carbon atoms, an alkynyl group having 1-10 carbon atoms, an alkoxy group having 1-10 carbon atoms, an alkylthio group having 1-10 carbon atoms, a monoalkylamino group having 1-10 carbon atoms, a dialkylamino group having 1-10 carbon atoms, or a phenyl group optionally substituted with W;

$R^{11}$ and $R^{12}$ represent —$SR^8$ or —$NR^9{}_2$;

$R^8$ and $R^9$ each independently represent a hydrogen atom, an alkyl group having 1-10 carbon atoms, or a phenyl group optionally substituted with W;

W represents a halogen atom, a cyano group, a nitro group, a hydroxyl group, a mercapto group, an amino group, a formyl group, a carboxyl group, an alkyl group having 1-10 carbon atoms, a haloalkyl group having 1-10 carbon atoms, an alkenyl group having 1-10 carbon atoms, an alkynyl group having 1-10 carbon atoms, an alkoxy group having 1-10 carbon atoms, an alkylthio group having 1-10 carbon atoms, a monoalkylamino group having 1-10 carbon atoms, a dialkylamino group having 1-10 carbon atoms, a diphenylamino group optionally substituted with W', a dinaphthylamino group optionally substituted with W', a dianthranilamino group optionally substituted with W', an N-phenyl-N-napthylamino group optionally substituted with W', an N-phenyl-N-anthranilamino group optionally substituted with W', an N-naphthyl-N-anthranilamino group optionally substituted with W', a trialkylsilyl group having 1-10 carbon atoms, an alkylcarbonyl group having 1-10 carbon atoms, an alkoxycarbonyl group having 1-10 carbon atoms, or a phenyl group optionally substituted with W'; and W' represents an alkyl group having 1-10 carbon atoms, a haloalkyl group having 1-10 carbon atoms or an alkoxy group having 1-10 carbon atoms.

10. A process for producing a phosphorylthiophene polymer compound comprising catalytic polymerization of the bisphosphorylthiophene compound defined in formula [1], the monophosphorylthiophene compound defined in formula [2], or at least one selected from the phosphorylthiophene oligomer compounds defined in claims 1 and 5

[Chemical Formula 1]

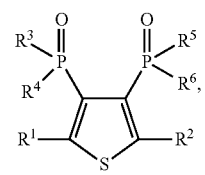

[1]

wherein $R^1$ and $R^2$ each independently represent a hydrogen atom, a halogen atom, a cyano group, a phenyl group optionally substituted with W, a naphthyl group optionally substituted with W, an anthranil group optionally substituted with W, a hydroxyl group, an amino group, a formyl group, a carboxyl group, an alkyl group having 1-10 carbon atoms, a haloalkyl group having 1-10 carbon atoms, a monoalkylamino group having 1-10 carbon atoms, a dialkylamino group having 1-10 carbon atoms, a trialkylstannyl group having 1-10 carbon atoms, or a trialkylsilyl group having 1-10 carbon atoms;

$R^3$-$R^6$ each independently represent —$OR^7$, —$SR^8$ or —$NR^9_2$;

$R^7$ represents an alkyl group having 1-10 carbon atoms or a phenyl group optionally substituted with W, and $R^8$-$R^9$ each independently represent a hydrogen atom, an alkyl group having 1-10 carbon atoms, or a phenyl group optionally substituted with W;

W represents a halogen atom, a cyano group, a nitro group, a hydroxyl group, a mercapto group, an amino group, a formyl group, a carboxyl group, an alkyl group having 1-10 carbon atoms, a haloalkyl group having 1-10 carbon atoms, an alkenyl group having 1-10 carbon atoms, an alkynyl group having 1-10 carbon atoms, an alkoxy group having 1-10 carbon atoms, an alkylthio group having 1-10 carbon atoms, a monoalkylamino group having 1-10 carbon atoms, a dialkylamino group having 1-10 carbon atoms, a diphenylamino group optionally substituted with W', a dinaphthylamino group optionally substituted with W', a dianthranilamino group optionally substituted with W', an N-phenyl-N-napthylamino group optionally substituted with W', an N-phenyl-N-anthranilamino group optionally substituted with W', an N-naphthyl-N-anthranilamino group optionally substituted with W', a trialkylsilyl group having 1-10 carbon atoms, an alkylcarbonyl group having 1-10 carbon atoms, an alkoxycarbonyl group having 1-10 carbon atoms, or a phenyl group optionally with W'; and W' represents an alkyl group having 1-10 carbon atoms, a haloalkyl group having 1-10 carbon atoms or an alkoxy group having 1-10 carbon atoms,

[Chemical Formula 2]

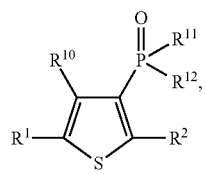

[2]

wherein $R^1$ and $R^2$ each independently represent a hydrogen atom, a halogen atom, a cyano group, a phenyl group optionally substituted with W, a naphthyl group optionally substituted with W, an anthranil group optionally substituted with W, a hydroxyl group, an amino group, a formyl group, a carboxyl group, an alkyl group having 1-10 carbon atoms, a haloalkyl group having 1-10 carbon atoms, a monoalkylamino group having 1-10 carbon atoms, a dialkylamino group having 1-10 carbon atoms, a trialkylstannyl group having 1-10 carbon atoms, or a trialkylsilyl group having 1-10 carbon atoms;

$R^{10}$ represents a hydrogen atom, a halogen atom, a cyano group, a nitro group, a hydroxyl group, a mercapto group, an amino group, a formyl group, a carboxyl group, an alkyl group having 1-10 carbon atoms, a haloalkyl group having 1-10 carbon atoms, an alkenyl group having 1-10 carbon atoms, an alkynyl group having 1-10 carbon atoms, an alkoxy group having 1-10 carbon atoms, an alkylthio group having 1-10 carbon atoms, a monoalkylamino group having 1-10 carbon atoms, a dialkylamino group having 1-10 carbon atoms, or a phenyl group optionally substituted with W;

$R^{11}$ and $R^{12}$ represent —$SR^8$ or —$NR^9_2$;

$R^8$ and $R^9$ each independently represent a hydrogen atom, an alkyl group having 1-10 carbon atoms, or a phenyl group optionally substituted with W;

W represents a halogen atom, a cyano group, a nitro group, a hydroxyl group, a mercapto group, an amino group, a formyl group, a carboxyl group, an alkyl group having 1-10 carbon atoms, a haloalkyl group having 1-10 carbon atoms, an alkenyl group having 1-10 carbon atoms, an alkynyl group having 1-10 carbon atoms, an alkoxy group having 1-10 carbon atoms, an alkylthio group having 1-10 carbon atoms, a monoalkylamino group having 1-10 carbon atoms, a dialkylamino group having 1-10 carbon atoms, a diphenylamino group optionally substituted with W', a dinaphthylamino group optionally substituted with W', a dianthranilamino group optionally substituted with W', an N-phenyl-N-napthylamino group optionally substituted with W', an N-phenyl-N-anthranilamino group optionally substituted with W', an N-naphthyl-N-anthranilamino group optionally substituted with W', a trialkylsilyl group having 1-10 carbon atoms, an alkylcarbonyl group having 1-10 carbon atoms, an alkoxycarbonyl group having 1-10 carbon atoms, or a phenyl group optionally substituted with W'; and W' represents an alkyl group having 1-10 carbon atoms, a haloalkyl group having 1-10 carbon atoms or an alkoxy group having 1-10 carbon atoms.

11. An active substance for cell comprising one selected from the phosphorylthiophene oligomer compound defined in any one of claims 1, 2 and 5 and the phosphorylthiophene polymer compounds defined in claims 3, 4 and 6.

12. An electrode material comprising one selected from the phosphorylthiophene oligomer compound defined in any one of claims 1, 2 and 5 and the phosphorylthiophene polymer compounds defined in claims 3, 4 and 6.

13. An organic electroluminescent material comprising one selected from the phosphorylthiophene oligomer compound defined in any one of claims 1, 2 and 5 and the phosphorylthiophene polymers defined in claims 3, 4 and 6.

14. A p-type semiconductor obtained by oxidizing at least one selected from the phosphorylthiophene oligomer compound defined in any one of claims 1, 2 and 5 and the phosphorylthiophene polymer compounds defined in claims 3, 4 and 6 with an oxidizing agent or by electrochemical doping.

15. An n-type semiconductor obtained by reducing at least one selected from the phosphorylthiophene oligomer compound defined in any one of claims 1, 2 and 5 and the phosphorylthiophene polymer compounds defined in claims 3, 4 and 6 with a reducing agent or by electrochemical doping.

16. A semiconductor device making use of at least one slected from the phosphorylthiophene oligomer compound defined in any one of claims 1, 2 and 5 and the phosphorylthiophene polymer compounds defined in claims 3, 4 and 6.

17. An organic electroluminescent device making use of at least one selected from the phosphorylthiophene oligomer compound defined in any one of claims 1, 2 and 5 and the phosphorylthiophene polymer compounds defined in claims 3, 4 and 6.

18. A total solid-state organic solar cell making use of at least one selected from the phosphorylthiophene oligomer compound defined in any one of claims 1, 2 and 5 and the phosphorylthiophene polymer compounds defined in claims 3, 4 and 6.

19. A dye-sensitized solar cell making use of at least ore selected from the phosphorylthiophene oligomer compound defined in any one of claims 1, 2 and 5 and the phosphorylthiophene polymer compounds defined in claims 3, 4 and 6.

20. A capacitor electrode comprising one selected from the phosphorylthiophene oligomer compound defined in any one of claims 1, 2 and 5 and the phosphorylthiophene polymer compounds defined in claims 3, 4 and 6.

21. An actuator making use of at least one selected from the phosphorylthiophene oligomer compound defined in any one of claims 1, 2 and 5 and the phosphorylthiophene polymer compounds defined in claims 3, 4 and 6.

22. A solid electrolyte for capacitor comprising one selected from the phosphorylthiophene oligomer compound defined in any one of claims 1, 2 and 5 and the phosphorylthiophene polymer compounds defined in claims 3, 4 and 6.

23. An antenna material comprising one selected from the phosphorylthiophene oligomer compound defined in any one of claims 1, 2 and 5 and the phosphorylthiophene polymer compounds defined in claims 3, 4 and 6.

24. A sensor making use of at least one sele cted from the phosphorylthiophene oligomer compound defined in any one of claims 1, 2 and 5 and the phosphorylthiophene polymer compounds defined in claims 3, 4 and 6.

25. A fuel cell separator comprising one selected from the phosphorylthiophene oligomer compound defined in any one of claims 1, 2 and 5 and the phosphorylthiophene polymer compounds defined in claims 3, 4 and 6.

\* \* \* \* \*